US012735743B2

(12) United States Patent
Lucero et al.

(10) Patent No.: US 12,735,743 B2
(45) **Date of Patent: *Sep. 15, 2026**

(54) RESOLVING SPATIAL ARRAYS

(71) Applicant: 10x Genomics, Inc., Pleasanton, CA (US)

(72) Inventors: Michael Ybarra Lucero, South San Francisco, CA (US); Michael Schnall-Levin, San Francisco, CA (US); Tarjei Sigurd Mikkelsen, Pleasanton, CA (US); Eswar Prasad Ramachandran Iyer, Pleasanton, CA (US); Paul Giresi, Palo Alto, CA (US); Benjamin Hindson, Pleasanton, CA (US)

(73) Assignee: 10x Genomics, Inc., Pleasanton, CA (US)

(*) Notice: Subject to any disclaimer, the term of this patent is extended or adjusted under 35 U.S.C. 154(b) by 1106 days.

This patent is subject to a terminal disclaimer.

(21) Appl. No.: 17/272,033

(22) PCT Filed: Aug. 27, 2019

(86) PCT No.: PCT/US2019/048428

§ 371 (c)(1),
(2) Date: Feb. 26, 2021

(87) PCT Pub. No.: WO2020/047005

PCT Pub. Date: Mar. 5, 2020

(65) Prior Publication Data

US 2021/0317524 A1 Oct. 14, 2021

Related U.S. Application Data

(60) Provisional application No. 62/860,993, filed on Jun. 13, 2019, provisional application No. 62/858,331, filed on Jun. 7, 2019, provisional application No. 62/842,463, filed on May 2, 2019, provisional application No. 62/839,346, filed on Apr. 26, 2019, provisional application No. 62/839,223, filed on Apr. 26, 2019, provisional application No. 62/839,320, filed on Apr. 26, 2019, provisional application No. 62/839,526, filed on Apr. 26, 2019, provisional application No. 62/822,627, filed on Mar. 22, 2019, provisional application No. 62/822,575, filed on Mar. 22, 2019, provisional application No. 62/822,565, filed on Mar. 22, 2019, provisional application No. 62/822,605, filed on Mar. 22, 2019, provisional application No. 62/822,632, filed on Mar. 22, 2019, provisional application No. 62/822,554, filed on Mar. 22, 2019, provisional application No. 62/822,649, filed on Mar. 22, 2019, provisional application No. 62/822,592, filed on Mar. 22, 2019, provisional application No. 62/822,618, filed on Mar. 22, 2019, provisional application No. 62/819,448, filed on Mar. 15, 2019, provisional application No. 62/819,486, filed on Mar. 15, 2019, provisional application No. 62/819,458, filed on Mar. 15, 2019, provisional application No. 62/819,456, filed on Mar. 15, 2019, provisional application No. 62/819,496, filed on Mar. 15, 2019, provisional application No. 62/819,478, filed on Mar. 15, 2019, provisional application No. 62/819,467, filed on Mar. 15, 2019, provisional application No. 62/819,468, filed on Mar. 15, 2019, provisional application No. 62/819,449, filed on Mar. 15, 2019, provisional application No. 62/812,219, filed on Feb. 28, 2019, provisional application No. 62/811,495, filed on Feb. 27, 2019, provisional application No. 62/788,905, filed on Jan. 6, 2019, provisional application No. 62/788,867, filed on Jan. 6, 2019, provisional application No. 62/788,885, filed (Continued)

(51) Int. Cl.
*C12Q 1/6874* (2018.01)

(52) U.S. Cl.
CPC .................................. *C12Q 1/6874* (2013.01)

(58) Field of Classification Search
None
See application file for complete search history.

(56) References Cited

U.S. PATENT DOCUMENTS 4,683,195 A 7/1987 Mullis
4,683,202 A 7/1987 Mullis (Continued)

FOREIGN PATENT DOCUMENTS

CA 2169928 4/2007
CN 1680604 10/2005

(Continued)

OTHER PUBLICATIONS

How DNA microarrays are built, Bitesize Bio (Year: 2011).*

(Continued)

*Primary Examiner* — Juliet C Switzer
*Assistant Examiner* — Brian Ellis Young
(74) *Attorney, Agent, or Firm* — Fish & Richardson P.C.

(57) ABSTRACT

Methods for determining a location of a feature in a spatial array of features include: providing a spatial array including a plurality of features on a substrate, where a feature of the plurality of features has a capture probe, and where the capture probe has a spatial barcode and a constant sequence; hybridizing a first sequencing probe to the spatial barcode, where the first sequencing probe has a first label and a first nucleotide sequence; obtaining a first image of the first label with the first sequencing probe hybridized to the spatial barcode; determining, based on the first image, a first portion of a sequence of the spatial barcode; and associating the feature with a location in the spatial array based on a location of the first label in the first image.

13 Claims, 28 Drawing Sheets

Specification includes a Sequence Listing.

Related U.S. Application Data on Jan. 6, 2019, provisional application No. 62/788,871, filed on Jan. 6, 2019, provisional application No. 62/788,897, filed on Jan. 6, 2019, provisional application No. 62/779,342, filed on Dec. 13, 2018, provisional application No. 62/724,561, filed on Aug. 29, 2018, provisional application No. 62/724,487, filed on Aug. 29, 2018, provisional application No. 62/724,483, filed on Aug. 29, 2018, provisional application No. 62/724,489, filed on Aug. 29, 2018, provisional application No. 62/723,970, filed on Aug. 28, 2018, provisional application No. 62/723,960, filed on Aug. 28, 2018, provisional application No. 62/723,972, filed on Aug. 28, 2018, provisional application No. 62/723,950, filed on Aug. 28, 2018, provisional application No. 62/723,957, filed on Aug. 28, 2018, provisional application No. 62/723,964, filed on Aug. 28, 2018.

(56) References Cited

U.S. PATENT DOCUMENTS 4,800,159 A 1/1989 Mullis
4,883,867 A 11/1989 Lee
4,965,188 A 10/1990 Mullis
5,002,882 A 3/1991 Lunnen
5,130,238 A 7/1992 Malek
5,308,751 A 5/1994 Ohkawa
5,321,130 A 6/1994 Yue
5,410,030 A 4/1995 Yue
5,436,134 A 7/1995 Haugland
5,455,166 A 10/1995 Walker
5,472,881 A 12/1995 Beebe et al.
5,494,810 A 2/1996 Barany et al.
5,503,980 A 4/1996 Cantor
5,512,439 A 4/1996 Hornes
5,512,462 A 4/1996 Cheng
5,582,977 A 12/1996 Yue
5,599,675 A 2/1997 Brenner
5,610,287 A 3/1997 Nikiforov et al.
5,641,658 A 6/1997 Adams
5,648,245 A 7/1997 Fire et al.
5,658,751 A 8/1997 Yue
5,750,341 A 5/1998 Macevicz
5,763,175 A 6/1998 Brenner
5,807,522 A 9/1998 Brown et al.
5,817,783 A 10/1998 Calabretta et al.
5,830,711 A 11/1998 Barany et al.
5,837,832 A 11/1998 Chee et al.
5,837,860 A 11/1998 Anderson et al.
5,854,033 A 12/1998 Lizardi
5,863,753 A 1/1999 Haugland
5,871,921 A 2/1999 Landegren et al.
5,912,148 A 6/1999 Eggerding
5,919,626 A 7/1999 Shi et al.
6,013,440 A 1/2000 Lipshutz
6,027,889 A 2/2000 Barany et al.
6,060,240 A 5/2000 Kamb et al.
6,130,073 A 10/2000 Eggerding
6,143,496 A 11/2000 Brown
6,153,389 A 11/2000 Haarer
6,165,714 A 12/2000 Lane et al.
6,172,218 B1 1/2001 Brenner
6,210,891 B1 4/2001 Nyren
6,210,894 B1 4/2001 Brennan
6,214,587 B1 4/2001 Dattagupta
6,258,568 B1 7/2001 Nyren
6,265,552 B1 7/2001 Schatz
6,266,459 B1 7/2001 Walt
6,274,320 B1 8/2001 Rothberg
6,300,063 B1 10/2001 Lipshutz et al.
6,306,597 B1 10/2001 Macevicz
6,309,824 B1 10/2001 Drmanac
6,344,316 B1 2/2002 Lockhart
6,355,431 B1 3/2002 Chee
6,368,801 B1 4/2002 Faruqi
6,391,937 B1 5/2002 Beuhler et al.
6,401,267 B1 6/2002 Drmanac
6,404,907 B1 6/2002 Gilchrist
6,432,360 B1 8/2002 Church et al.
6,503,713 B1 1/2003 Rana
6,506,561 B1 1/2003 Cheval et al.
6,544,732 B1 4/2003 Chee
6,620,584 B1 9/2003 Chee
6,632,641 B1 10/2003 Brennan
6,737,236 B1 5/2004 Pieken et al.
6,770,441 B2 8/2004 Dickinson
6,773,886 B2 8/2004 Kaufman
6,787,308 B2 9/2004 Balasubramanian
6,800,453 B2 10/2004 Labaer
6,812,005 B2 11/2004 Fan et al.
6,828,100 B1 12/2004 Ronaghi
6,833,246 B2 12/2004 Balasubramanian
6,859,570 B2 2/2005 Walt
6,864,052 B1 3/2005 Drmanac
6,867,028 B2 3/2005 Janulaitis
6,897,023 B2 5/2005 Fu
6,942,968 B1 9/2005 Dickinson et al.
6,969,488 B2 11/2005 Bridgham
7,001,792 B2 2/2006 Sauer et al.
7,057,026 B2 6/2006 Barnes
7,060,431 B2 6/2006 Chee et al.
7,115,400 B1 10/2006 Adessi
7,118,883 B2 10/2006 Inoue
7,166,431 B2 1/2007 Chee et al.
7,211,414 B2 5/2007 Hardin
7,255,994 B2 8/2007 Lao
7,258,976 B2 8/2007 Mitsuhashi
7,259,258 B2 8/2007 Kozlov et al.
7,264,929 B2 9/2007 Rothberg
7,297,518 B2 11/2007 Quake
7,329,492 B2 2/2008 Hardin
7,361,488 B2 4/2008 Fan et al.
7,375,234 B2 5/2008 Sharpless et al.
7,378,242 B2 5/2008 Hurt
7,393,665 B2 7/2008 Brenner
7,405,281 B2 7/2008 Xu
7,407,757 B2 8/2008 Brenner
7,427,678 B2 9/2008 Pieken et al.
7,537,897 B2 5/2009 Brenner
7,544,473 B2 6/2009 Brennan
7,563,576 B2 7/2009 Chee
7,582,420 B2 9/2009 Oliphant et al.
7,601,492 B2 10/2009 Fu et al.
7,601,498 B2 10/2009 Mao
7,635,566 B2 12/2009 Brenner
7,674,752 B2 3/2010 He
7,709,198 B2 5/2010 Luo et al.
7,754,429 B2 7/2010 Rigatti
7,776,567 B2 8/2010 Mao
7,803,943 B2 9/2010 Mao
7,910,304 B2 3/2011 Drmanac
7,955,794 B2 6/2011 Shen et al.
7,960,119 B2 6/2011 Chee
7,960,120 B2 6/2011 Rigatti
8,003,354 B2 8/2011 Shen et al.
8,148,068 B2 4/2012 Brenner
8,206,917 B2 6/2012 Chee
8,288,103 B2 10/2012 Oliphant
8,460,865 B2 6/2013 Chee
8,481,257 B2 7/2013 Van Eijk
8,481,292 B2 7/2013 Casbon
8,486,625 B2 7/2013 Gunderson
8,603,743 B2 12/2013 Liu et al.
8,604,182 B2 12/2013 Luo et al.
8,614,073 B2 12/2013 Van Eijk
8,685,889 B2 4/2014 Van Eijk
8,741,606 B2 6/2014 Casbon
8,785,353 B2 7/2014 Van Eijk
8,815,512 B2 8/2014 Van Eijk
8,835,358 B2 9/2014 Fodor
8,895,249 B2 11/2014 Shen

(56) References Cited

U.S. PATENT DOCUMENTS 8,911,945 B2 12/2014 Van Eijk
8,951,726 B2 2/2015 Luo et al.
9,023,768 B2 5/2015 Van Eijk
9,062,348 B1 6/2015 Van Eijk
9,080,210 B2 7/2015 Van Eijk
9,085,798 B2 7/2015 Chee
9,163,283 B2 10/2015 Chee et al.
9,194,001 B2 11/2015 Brenner
9,290,808 B2 3/2016 Fodor
9,290,809 B2 3/2016 Fodor
9,328,383 B2 5/2016 Van Eijk
9,330,295 B2 5/2016 Dunn
9,334,536 B2 5/2016 Van Eijk
9,371,598 B2 6/2016 Chec
9,376,716 B2 6/2016 Van Eijk
9,376,719 B2 6/2016 Eijk
9,447,459 B2 9/2016 Van Eijk
9,453,256 B2 9/2016 Van Eijk
9,493,820 B2 11/2016 Van Eijk
9,506,061 B2 11/2016 Brown et al.
9,512,422 B2 12/2016 Barnard et al.
9,574,230 B2 2/2017 Van Eijk
9,593,365 B2 3/2017 Frisen et al.
9,644,204 B2 5/2017 Hindson et al.
9,657,335 B2 5/2017 Van Eijk
9,670,542 B2 6/2017 Eijk
9,694,361 B2 7/2017 Bharadwaj
9,702,004 B2 7/2017 Van Eijk
9,727,810 B2 8/2017 Fodor et al.
9,745,627 B2 8/2017 Van Eijk
9,777,324 B2 10/2017 Van Eijk
9,783,841 B2 10/2017 Nolan et al.
9,834,814 B2 12/2017 Peter et al.
9,850,536 B2 12/2017 Oliphant et al.
9,868,979 B2 1/2018 Chee et al.
9,879,313 B2 1/2018 Chee et al.
9,889,422 B2 2/2018 Smith et al.
9,896,721 B2 2/2018 Van Eijk
9,898,576 B2 2/2018 Van Eijk
9,898,577 B2 2/2018 Van Eijk
10,002,316 B2 6/2018 Fodor et al.
10,011,872 B1 7/2018 Belgrader et al.
10,023,907 B2 7/2018 Van Eijk
10,030,261 B2 7/2018 Frisen et al.
10,041,949 B2 8/2018 Bendall et al.
10,059,990 B2 8/2018 Boyden et al.
10,095,832 B2 10/2018 Van Eijk
10,138,509 B2 11/2018 Church et al.
10,179,932 B2 1/2019 Church et al.
10,208,982 B2 2/2019 Bannish et al.
10,273,541 B2 4/2019 Hindson et al.
10,308,982 B2 6/2019 Chee
10,357,771 B2 7/2019 Bharadwaj
10,472,669 B2 11/2019 Chee
10,480,022 B2 11/2019 Chee
10,480,029 B2 11/2019 Bent et al.
10,494,667 B2 12/2019 Chee
10,550,429 B2 2/2020 Harada et al.
10,590,244 B2 3/2020 Delaney et al.
10,662,468 B2 5/2020 Chee
10,724,078 B2 7/2020 Van Driel et al.
10,725,027 B2 7/2020 Bell
10,774,372 B2 9/2020 Chee et al.
10,774,374 B2 9/2020 Frisen et al.
10,787,701 B2 9/2020 Chee
10,858,702 B2 12/2020 Lucero et al.
10,913,975 B2 2/2021 So et al.
10,914,730 B2 2/2021 Chee et al.
10,927,403 B2 2/2021 Chee et al.
10,961,566 B2 3/2021 Chee
11,001,879 B1 5/2021 Chee
11,008,607 B2 5/2021 Chee
11,046,996 B1 6/2021 Chee et al.
11,067,567 B2 7/2021 Chee
11,156,603 B2 10/2021 Chee
11,162,132 B2 11/2021 Frisen et al.
11,208,684 B2 12/2021 Chee
11,214,796 B2 1/2022 Shirai et al.
11,286,515 B2 3/2022 Chee et al.
11,293,917 B2 4/2022 Chee
11,299,774 B2 4/2022 Frisen et al.
11,313,856 B2 4/2022 Chee
11,332,790 B2 5/2022 Chell et al.
11,352,659 B2 6/2022 Frisen et al.
11,352,667 B2 6/2022 Hauling et al.
11,359,228 B2 6/2022 Chee et al.
11,365,442 B2 6/2022 Chee
11,371,086 B2 6/2022 Chee
11,384,386 B2 7/2022 Chee
11,390,912 B2 7/2022 Frisen et al.
11,401,545 B2 8/2022 Chee
11,407,992 B2 8/2022 Dadhwal
11,408,029 B2 8/2022 Katiraee et al.
11,434,524 B2 9/2022 Ramachandran Iyer et al.
11,459,607 B1 10/2022 Terry et al.
11,479,809 B2 10/2022 Frisen et al.
11,479,810 B1 10/2022 Chee
11,492,612 B1 11/2022 Dadhwal
11,501,440 B2 11/2022 Weisenfeld et al.
11,505,828 B2 11/2022 Chell et al.
11,512,308 B2 11/2022 Gallant et al.
11,519,022 B2 12/2022 Chee
11,519,033 B2 12/2022 Schnall-Levin et al.
11,519,138 B2 12/2022 Meier et al.
11,530,438 B2 12/2022 Persson et al.
11,535,887 B2 12/2022 Gallant et al.
11,542,543 B2 1/2023 Chee
11,560,587 B2 1/2023 Chee
11,560,592 B2 1/2023 Chew et al.
11,560,593 B2 1/2023 Chell et al.
11,592,447 B2 2/2023 Uytingco et al.
11,608,498 B2 3/2023 Gallant et al.
11,608,520 B2 3/2023 Galonska et al.
11,613,773 B2 3/2023 Frisen et al.
11,618,897 B2 4/2023 Kim et al.
11,618,918 B2 4/2023 Chee et al.
11,624,063 B2 4/2023 Dadhwal
11,624,086 B2 4/2023 Uytingco et al.
11,634,756 B2 4/2023 Chee
11,649,485 B2 5/2023 Yin et al.
11,661,626 B2 5/2023 Katiraee et al.
11,680,260 B2 6/2023 Kim et al.
11,692,218 B2 7/2023 Engblom et al.
11,702,693 B2 7/2023 Bharadwaj
11,702,698 B2 7/2023 Stoeckius
11,713,480 B2 8/2023 Lee
11,732,292 B2 8/2023 Chee
11,732,299 B2 8/2023 Ramachandran Iyer
11,732,300 B2 8/2023 Bava
11,733,238 B2 8/2023 Chee
11,739,372 B2 8/2023 Frisen et al.
11,739,381 B2 8/2023 Chew et al.
11,753,673 B2 9/2023 Chew et al.
11,753,674 B2 9/2023 Chee et al.
11,753,675 B2 9/2023 Ramachandran Iyer
11,761,030 B2 9/2023 Chee
11,761,038 B1 9/2023 Stoeckius
11,767,550 B2 9/2023 Chee
11,768,175 B1 9/2023 Kim et al.
11,773,433 B2 10/2023 Gallant et al.
11,781,130 B2 10/2023 Dadhwal
11,788,122 B2 10/2023 Frisen et al.
11,795,498 B2 10/2023 Frisen et al.
11,795,507 B2 10/2023 Chell et al.
11,808,769 B2 11/2023 Uytingco et al.
11,821,024 B2 11/2023 Chee et al.
11,821,035 B1 11/2023 Bent et al.
11,827,935 B1 11/2023 Ramachandran Iyer et al.
11,835,462 B2 12/2023 Bava
11,840,687 B2 12/2023 Gallant et al.
11,840,724 B2 12/2023 Chew et al.
11,845,979 B2 12/2023 Engblom et al.
11,859,178 B2 1/2024 Gallant et al.
11,866,767 B2 1/2024 Uytingco et al.

(56) References Cited

U.S. PATENT DOCUMENTS

| | | | |
|---|---|---|---|
| 11,866,770 | B2 | 1/2024 | Chee |
| 11,873,482 | B2 | 1/2024 | Kim et al. |
| 11,891,654 | B2 | 2/2024 | Alvarado Martinez et al. |
| 11,898,205 | B2 | 2/2024 | Bava |
| 11,926,822 | B1 | 3/2024 | Gohil et al. |
| 11,926,863 | B1 | 3/2024 | Boutet |
| 11,926,867 | B2 | 3/2024 | Yin et al. |
| 11,933,957 | B1 | 3/2024 | Tentori et al. |
| 11,952,627 | B2 | 4/2024 | Stoeckius |
| 11,959,076 | B2 | 4/2024 | Kim et al. |
| 11,959,130 | B2 | 4/2024 | Galonska et al. |
| 11,965,213 | B2 | 4/2024 | Williams |
| 11,970,739 | B2 | 4/2024 | Chew et al. |
| 11,981,958 | B1 | 5/2024 | Galonska |
| 11,981,960 | B1 | 5/2024 | Lin et al. |
| 11,981,965 | B2 | 5/2024 | Chell et al. |
| RE50,065 | E | 7/2024 | Frisen et al. |
| 12,024,741 | B2 | 7/2024 | Tentori et al. |
| 12,031,177 | B1 | 7/2024 | Tentori et al. |
| 12,060,604 | B2 | 8/2024 | Katiraee et al. |
| 12,071,655 | B2 | 8/2024 | Sukovich et al. |
| 12,076,701 | B2 | 9/2024 | Bava |
| 12,098,417 | B2 | 9/2024 | Engblom et al. |
| 12,098,985 | B2 | 9/2024 | Cox et al. |
| 12,110,541 | B2 | 10/2024 | Bava |
| 12,117,439 | B2 | 10/2024 | Delaney et al. |
| 12,128,403 | B2 | 10/2024 | Kim et al. |
| 12,129,516 | B2 | 10/2024 | Tentori et al. |
| 12,157,124 | B2 | 12/2024 | Cox et al. |
| 12,180,543 | B2 | 12/2024 | Uytingco et al. |
| 12,195,790 | B2 | 1/2025 | Sukovich et al. |
| 12,203,134 | B2 | 1/2025 | Nagendran et al. |
| 12,209,280 | B1 | 1/2025 | Mignardi et al. |
| 12,223,751 | B2 | 2/2025 | Li et al. |
| 12,228,544 | B2 | 2/2025 | Kim et al. |
| 12,234,505 | B2 | 2/2025 | Chee |
| 12,241,060 | B2 | 3/2025 | Kim et al. |
| 12,241,890 | B2 | 3/2025 | Delaney et al. |
| 12,249,085 | B2 | 3/2025 | Tentori et al. |
| 12,265,079 | B1 | 4/2025 | Bent |
| 12,270,077 | B2 | 4/2025 | Schnall-Levin et al. |
| 12,275,988 | B2 | 4/2025 | Galonska et al. |
| 12,281,357 | B1 | 4/2025 | Tentori et al. |
| 12,286,673 | B2 | 4/2025 | Bava |
| 12,287,264 | B2 | 4/2025 | Cox et al. |
| 12,297,486 | B2 | 5/2025 | Patterson et al. |
| 12,297,487 | B2 | 5/2025 | Chee |
| 12,297,488 | B2 | 5/2025 | Chee |
| 12,344,892 | B2 | 7/2025 | Schnall-Levin et al. |
| 12,365,935 | B2 | 7/2025 | Chew et al. |
| 12,365,942 | B2 | 7/2025 | Stoeckius |
| 12,371,688 | B2 | 7/2025 | Kim et al. |
| 12,378,607 | B2 | 8/2025 | Schnall-Levin et al. |
| 12,385,083 | B2 | 8/2025 | Shah |
| 12,391,979 | B2 | 8/2025 | Chee |
| 12,391,980 | B2 | 8/2025 | Chee |
| 12,399,123 | B1 | 8/2025 | Shah et al. |
| 12,404,544 | B2 | 9/2025 | Tentori et al. |
| 12,405,264 | B2 | 9/2025 | Stoeckius |
| 12,416,603 | B2 | 9/2025 | Tentori et al. |
| 12,435,363 | B1 | 10/2025 | Gallant et al. |
| 12,442,045 | B2 | 10/2025 | Williams |
| 12,497,654 | B2 | 12/2025 | Ramachandran Iyer et al. |
| 12,508,590 | B2 | 12/2025 | Kim et al. |
| D1,108,656 | S | 1/2026 | Alimsijah et al. |
| 12,529,094 | B2 | 1/2026 | Bent et al. |
| 12,545,949 | B2 | 2/2026 | Bent et al. |
| 12,553,805 | B2 | 2/2026 | Shahjamali |
| 12,553,898 | B1 | 2/2026 | Uytingco et al. |
| 12,566,113 | B2 | 3/2026 | Delaney et al. |
| 12,566,114 | B2 | 3/2026 | Cox et al. |
| 2002/0040275 | A1 | 4/2002 | Cravatt |
| 2002/0132246 | A1 | 9/2002 | Kallioniemi et al. |
| 2002/0164611 | A1 | 11/2002 | Bamdad |
| 2003/0017451 | A1 | 1/2003 | Wang et al. |
| 2003/0022207 | A1 | 1/2003 | Balasubramanian |
| 2003/0092624 | A1 | 5/2003 | Wang et al. |
| 2003/0148335 | A1 | 8/2003 | Shen et al. |
| 2003/0162216 | A1 | 8/2003 | Gold |
| 2003/0211489 | A1 | 11/2003 | Shen et al. |
| 2003/0224419 | A1 | 12/2003 | Corcoran |
| 2003/0232348 | A1 | 12/2003 | Jones et al. |
| 2003/0232382 | A1 | 12/2003 | Brennan |
| 2004/0033499 | A1 | 2/2004 | Ilsley et al. |
| 2004/0067492 | A1 | 4/2004 | Peng et al. |
| 2004/0071605 | A1 | 4/2004 | Coonan et al. |
| 2004/0082059 | A1 | 4/2004 | Webb et al. |
| 2004/0096853 | A1 | 5/2004 | Mayer |
| 2004/0106110 | A1 | 6/2004 | Balasubramanian |
| 2005/0037393 | A1 | 2/2005 | Gunderson et al. |
| 2005/0048580 | A1 | 3/2005 | Labaer |
| 2005/0100900 | A1 | 5/2005 | Kawashima et al. |
| 2005/0130120 | A1 | 6/2005 | Lambotte et al. |
| 2005/0130173 | A1 | 6/2005 | Leamon et al. |
| 2005/0130223 | A1 | 6/2005 | Varon |
| 2005/0136414 | A1 | 6/2005 | Gunderson et al. |
| 2005/0147537 | A1 | 7/2005 | Sangha |
| 2005/0170373 | A1 | 8/2005 | Monforte |
| 2005/0191656 | A1 | 9/2005 | Drmanac et al. |
| 2005/0191698 | A1 | 9/2005 | Chee et al. |
| 2005/0202433 | A1 | 9/2005 | Van Beuningen |
| 2005/0227271 | A1 | 10/2005 | Kwon |
| 2005/0260653 | A1 | 11/2005 | LaBaer |
| 2006/0041385 | A1 | 2/2006 | Bauer et al. |
| 2006/0073506 | A1 | 4/2006 | Christians et al. |
| 2006/0172278 | A1 | 8/2006 | Bonner et al. |
| 2006/0188901 | A1 | 8/2006 | Barnes et al. |
| 2006/0211001 | A1 | 9/2006 | Yu et al. |
| 2006/0216775 | A1 | 9/2006 | Burkart et al. |
| 2006/0240439 | A1 | 10/2006 | Smith et al. |
| 2006/0263789 | A1 | 11/2006 | Kincaid |
| 2006/0281109 | A1 | 12/2006 | Barr Ost et al. |
| 2007/0020640 | A1 | 1/2007 | McCloskey et al. |
| 2007/0054288 | A1 | 3/2007 | Su et al. |
| 2007/0099208 | A1 | 5/2007 | Drmanac et al. |
| 2007/0128624 | A1 | 6/2007 | Gormley et al. |
| 2007/0128656 | A1 | 6/2007 | Agrawal |
| 2007/0141718 | A1 | 6/2007 | Bui et al. |
| 2007/0166705 | A1 | 7/2007 | Milton et al. |
| 2007/0172873 | A1 | 7/2007 | Brenner et al. |
| 2007/0207482 | A1 | 9/2007 | Church et al. |
| 2007/0231824 | A1 | 10/2007 | Chee et al. |
| 2007/0254305 | A1 | 11/2007 | Paik et al. |
| 2007/0269805 | A1 | 11/2007 | Hogers |
| 2008/0009420 | A1 | 1/2008 | Schroth et al. |
| 2008/0108804 | A1 | 5/2008 | Hayashizaki et al. |
| 2008/0160580 | A1 | 7/2008 | Adessi et al. |
| 2008/0220434 | A1 | 9/2008 | Thomas |
| 2008/0261204 | A1 | 10/2008 | Lexow |
| 2008/0280773 | A1 | 11/2008 | Fedurco et al. |
| 2008/0286795 | A1 | 11/2008 | Kawashima et al. |
| 2009/0005252 | A1 | 1/2009 | Drmanac et al. |
| 2009/0006002 | A1 | 1/2009 | Honisch et al. |
| 2009/0018024 | A1 | 1/2009 | Church et al. |
| 2009/0026082 | A1 | 1/2009 | Rothberg et al. |
| 2009/0036323 | A1 | 2/2009 | van Eijk et al. |
| 2009/0082212 | A1 | 3/2009 | Williams |
| 2009/0099041 | A1 | 4/2009 | Church et al. |
| 2009/0105959 | A1 | 4/2009 | Braverman et al. |
| 2009/0117573 | A1 | 5/2009 | Fu et al. |
| 2009/0127589 | A1 | 5/2009 | Rothberg et al. |
| 2009/0155781 | A1 | 6/2009 | Drmanac et al. |
| 2009/0170713 | A1 | 7/2009 | van Eijk et al. |
| 2009/0181375 | A1 | 7/2009 | Peter et al. |
| 2009/0233802 | A1 | 9/2009 | Bignell et al. |
| 2009/0253581 | A1 | 10/2009 | van Eijk et al. |
| 2009/0264299 | A1 | 10/2009 | Drmanac et al. |
| 2009/0270273 | A1 | 10/2009 | Burns et al. |
| 2009/0291854 | A1 | 11/2009 | Weisinger-Mayr et al. |
| 2009/0312193 | A1 | 12/2009 | Kim et al. |
| 2010/0035249 | A1 | 2/2010 | Hayashizaki et al. |
| 2010/0047790 | A1 | 2/2010 | Southern et al. |
| 2010/0055733 | A1 | 3/2010 | Lutolf et al. |
| 2010/0105112 | A1 | 4/2010 | Heltze et al. |

(56) References Cited

U.S. PATENT DOCUMENTS

2010/0120097 A1 5/2010 Matz et al.
2010/0120098 A1 5/2010 Grunenwald et al.
2010/0137143 A1 6/2010 Rothberg et al.
2010/0145037 A1 6/2010 Brive et al.
2010/0151464 A1 6/2010 Stuelpnagel et al.
2010/0282617 A1 11/2010 Rothberg et al.
2011/0028685 A1 2/2011 Purkayastha et al.
2011/0059436 A1 3/2011 Hardin et al.
2011/0059865 A1 3/2011 Smith et al.
2011/0152111 A1 6/2011 Illumina
2011/0237449 A1 9/2011 McMaster et al.
2011/0245101 A1 10/2011 Chee et al.
2011/0245111 A1 10/2011 Chee
2011/0275077 A1 11/2011 James
2012/0065081 A1 3/2012 Chee
2012/0135871 A1 5/2012 van Eijk et al.
2012/0157322 A1 6/2012 Myllykangas
2012/0202698 A1 8/2012 van Eijk et al.
2012/0245053 A1 9/2012 Shirai et al.
2012/0258871 A1 10/2012 Kozlov et al.
2012/0270305 A1 10/2012 Reed et al.
2013/0079232 A1 3/2013 Kain et al.
2013/0252847 A1 9/2013 McKenna et al.
2013/0260372 A1 10/2013 Buermann et al.
2014/0066318 A1 3/2014 Frisen et al.
2014/0079923 A1 3/2014 George et al.
2014/0121118 A1 5/2014 Warner
2014/0155274 A1 6/2014 Xie et al.
2014/0155295 A1 6/2014 Hindson et al.
2014/0212881 A1 7/2014 Handique et al.
2014/0227705 A1 8/2014 Vogelstein et al.
2014/0270435 A1 9/2014 Dunn
2014/0274731 A1 9/2014 Raymond et al.
2014/0323330 A1 10/2014 Glezer et al.
2014/0378345 A1 12/2014 Hindson et al.
2014/0378350 A1 12/2014 Hindson et al.
2015/0072867 A1 3/2015 Soldatov
2015/0087027 A1 3/2015 Makarov et al.
2015/0148239 A1 5/2015 Jon
2015/0158027 A1 6/2015 Fleming et al.
2015/0253225 A1 9/2015 Ng et al.
2015/0292988 A1 10/2015 Bharadwaj et al.
2015/0344942 A1 12/2015 Frisen et al.
2015/0368704 A1 12/2015 Fan et al.
2015/0376609 A1 12/2015 Hindson et al.
2016/0003812 A1 1/2016 Porreca et al.
2016/0024576 A1 1/2016 Chee
2016/0090592 A1 3/2016 Banyai et al.
2016/0138091 A1 5/2016 Chee et al.
2016/0145677 A1 5/2016 Chee et al.
2016/0253584 A1 9/2016 Fodor et al.
2016/0265046 A1 9/2016 Zhang et al.
2016/0289669 A1 10/2016 Fan et al.
2016/0289740 A1 10/2016 Fu et al.
2016/0291007 A1 10/2016 Kozlov et al.
2016/0298180 A1 10/2016 Chee
2016/0303534 A1* 10/2016 Zhou .................... B01J 19/0046
2016/0333403 A1 11/2016 Chee
2016/0369334 A1 12/2016 Zhou et al.
2017/0016053 A1 1/2017 Beechem et al.
2017/0058339 A1 3/2017 Chee
2017/0058340 A1 3/2017 Chee
2017/0058345 A1 3/2017 Chee
2017/0088881 A1 3/2017 Chee
2017/0159109 A1 6/2017 Zheng et al.
2017/0166962 A1 6/2017 Van Eijk et al.
2017/0220733 A1 8/2017 Zhuang et al.
2017/0253918 A1 9/2017 Kohman
2017/0342405 A1 11/2017 Fu et al.
2017/0343545 A1 11/2017 Hadrup et al.
2018/0052081 A1 2/2018 Kohman
2018/0057873 A1 3/2018 Zhou et al.
2018/0088112 A1 3/2018 Fan et al.
2018/0105808 A1 4/2018 Mikkelsen et al.
2018/0112209 A1 4/2018 Eshoo
2018/0112261 A1 4/2018 Van Driel et al.
2018/0156784 A1 6/2018 Usmani et al.
2018/0179591 A1 6/2018 van Eijk
2018/0180601 A1 6/2018 Pedersen et al.
2018/0201980 A1 7/2018 Chee et al.
2018/0216162 A1 8/2018 Belhocine et al.
2018/0245142 A1 8/2018 So et al.
2018/0247017 A1 8/2018 van Eijk et al.
2018/0291439 A1 10/2018 van Eijk et al.
2018/0305681 A1 10/2018 Jovanovich et al.
2018/0334670 A1 11/2018 Bharadwaj et al.
2018/0347064 A1 12/2018 Rauenbusch et al.
2019/0017106 A1 1/2019 Frisen et al.
2019/0024153 A1 1/2019 Frisen et al.
2019/0024154 A1 1/2019 Frisen et al.
2019/0032121 A1 1/2019 Daugharthy et al.
2019/0064173 A1 2/2019 Bharadwaj et al.
2019/0161796 A1 5/2019 Hauling et al.
2019/0177777 A1 6/2019 Chee
2019/0177778 A1 6/2019 Chee
2019/0177789 A1 6/2019 Hindson et al.
2019/0177800 A1 6/2019 Boutet et al.
2019/0203275 A1 7/2019 Frisen et al.
2019/0233878 A1 8/2019 Delaney et al.
2019/0249226 A1 8/2019 Bent et al.
2019/0262831 A1 8/2019 West et al.
2019/0264268 A1 8/2019 Frisen et al.
2019/0271030 A1 9/2019 Chee
2019/0271031 A1 9/2019 Chee
2019/0300943 A1 10/2019 Chee et al.
2019/0300944 A1 10/2019 Chee et al.
2019/0300945 A1 10/2019 Chee et al.
2019/0309353 A1 10/2019 Chee
2019/0309354 A1 10/2019 Chee
2019/0309355 A1 10/2019 Chee
2019/0323071 A1 10/2019 Chee
2019/0323088 A1 10/2019 Boutet et al.
2019/0338353 A1 11/2019 Belgrader et al.
2019/0360034 A1 11/2019 Zhou et al.
2019/0367969 A1 12/2019 Belhocine et al.
2019/0367982 A1 12/2019 Belhocine et al.
2019/0367997 A1 12/2019 Bent et al.
2020/0002763 A1 1/2020 Belgrader et al.
2020/0047010 A1 2/2020 Lee et al.
2020/0048690 A1 2/2020 Chee
2020/0063191 A1 2/2020 Kennedy-Darling et al.
2020/0063195 A1 2/2020 Chee
2020/0063196 A1 2/2020 Chee
2020/0071751 A1 3/2020 Daugharthy et al.
2020/0109443 A1 4/2020 Chee
2020/0131570 A1 4/2020 Berti et al.
2020/0173985 A1 6/2020 Dong et al.
2020/0256867 A1 8/2020 Hennek et al.
2020/0277663 A1 9/2020 Iyer
2020/0277664 A1 9/2020 Frenz
2020/0299757 A1 9/2020 Chee et al.
2020/0325531 A1 10/2020 Chee
2020/0370095 A1 11/2020 Farmer et al.
2020/0399687 A1 12/2020 Frisen et al.
2020/0407781 A1 12/2020 Schnall-Levin
2021/0010068 A1 1/2021 Chee et al.
2021/0010070 A1 1/2021 Schnall-Levin et al.
2021/0095331 A1 4/2021 Fan et al.
2021/0123040 A1 4/2021 Macosko et al.
2021/0130881 A1 5/2021 Cox
2021/0140982 A1 5/2021 Uytingco et al.
2021/0150707 A1 5/2021 Weisenfeld et al.
2021/0155982 A1 5/2021 Yin et al.
2021/0158522 A1 5/2021 Weisenfeld et al.
2021/0172007 A1 6/2021 Chee et al.
2021/0189475 A1 6/2021 Tentori et al.
2021/0190770 A1 6/2021 Delaney et al.
2021/0198741 A1 7/2021 Williams
2021/0199660 A1 7/2021 Williams et al.
2021/0207202 A1 7/2021 Chee
2021/0214785 A1 7/2021 Stoeckius
2021/0222235 A1 7/2021 Chee
2021/0222241 A1 7/2021 Bharadwaj
2021/0222242 A1 7/2021 Ramachandran Iyer

(56) References Cited

U.S. PATENT DOCUMENTS

2021/0222253 A1 7/2021 Uytingco
2021/0223227 A1 7/2021 Stoeckius
2021/0230584 A1 7/2021 Mikkelsen et al.
2021/0230681 A1 7/2021 Patterson et al.
2021/0230692 A1 7/2021 Daugharthy et al.
2021/0237022 A1 8/2021 Bava
2021/0238581 A1 8/2021 Mikkelsen et al.
2021/0238664 A1 8/2021 Bava et al.
2021/0238675 A1 8/2021 Bava
2021/0238680 A1 8/2021 Bava
2021/0247316 A1 8/2021 Bava
2021/0255175 A1 8/2021 Chee et al.
2021/0262018 A1 8/2021 Bava et al.
2021/0262019 A1 8/2021 Alvarado Martinez et al.
2021/0269864 A1 9/2021 Chee
2021/0270822 A1 9/2021 Chee
2021/0277460 A1 9/2021 Bava
2021/0285036 A1 9/2021 Yin et al.
2021/0285046 A1 9/2021 Chell et al.
2021/0292748 A1 9/2021 Frisen et al.
2021/0292822 A1 9/2021 Frisen et al.
2021/0317510 A1 10/2021 Chee et al.
2021/0324457 A1 10/2021 Ramachandran Iyer et al.
2021/0332424 A1 10/2021 Schnall-Levin
2021/0332425 A1 10/2021 Pfeiffer et al.
2021/0348221 A1 11/2021 Chell et al.
2022/0002791 A1 1/2022 Frisen et al.
2022/0003755 A1 1/2022 Chee
2022/0010367 A1 1/2022 Ramachandran Iyer et al.
2022/0017951 A1 1/2022 Ramachandran Iyer et al.
2022/0025446 A1 1/2022 Shah
2022/0025447 A1 1/2022 Tentori et al.
2022/0033888 A1 2/2022 Schnall-Levin et al.
2022/0049293 A1 2/2022 Frenz et al.
2022/0049294 A1 2/2022 Uytingco et al.
2022/0064630 A1 3/2022 Bent et al.
2022/0081728 A1 3/2022 Williams
2022/0090058 A1 3/2022 Frisen et al.
2022/0090175 A1 3/2022 Uytingco et al.
2022/0090181 A1 3/2022 Gallant et al.
2022/0098576 A1 3/2022 Dadhwal
2022/0098661 A1 3/2022 Chew et al.
2022/0106632 A1 4/2022 Galonska et al.
2022/0106633 A1 4/2022 Engblom et al.
2022/0112486 A1 4/2022 Ramachandran Iyer et al.
2022/0112545 A1 4/2022 Chee
2022/0119869 A1 4/2022 Ramachandran Iyer et al.
2022/0127659 A1 4/2022 Frisen et al.
2022/0127666 A1 4/2022 Katiraee et al.
2022/0127672 A1 4/2022 Stoeckius
2022/0145361 A1 5/2022 Frenz et al.
2022/0154255 A1 5/2022 Chee et al.
2022/0170083 A1 6/2022 Khaled et al.
2022/0195422 A1 6/2022 Gallant et al.
2022/0195505 A1 6/2022 Frisen et al.
2022/0196644 A1 6/2022 Chee
2022/0213526 A1 7/2022 Frisen et al.
2022/0220544 A1 7/2022 Ach et al.
2022/0241780 A1 8/2022 Tentori et al.
2022/0267844 A1 8/2022 Ramachandran Iyer et al.
2022/0268673 A1 8/2022 Dyson-Holland et al.
2022/0282329 A1 9/2022 Chell et al.
2022/0290217 A1 9/2022 Frenz et al.
2022/0290219 A1 9/2022 Chee
2022/0298560 A1 9/2022 Frisen et al.
2022/0325325 A1 10/2022 Chee et al.
2022/0326251 A1 10/2022 Uytingco et al.
2022/0333171 A1 10/2022 Chee
2022/0333191 A1 10/2022 Mikkelsen et al.
2022/0333192 A1 10/2022 Uytingco
2022/0333195 A1 10/2022 Schnall-Levin et al.
2022/0334031 A1 10/2022 Delaney et al.
2022/0348905 A1 11/2022 Dadhwal
2022/0348992 A1 11/2022 Stoeckius et al.
2022/0356464 A1 11/2022 Kim et al.
2022/0364163 A1 11/2022 Stahl et al.
2022/0389491 A1 12/2022 Chee
2022/0389503 A1 12/2022 Mikkelsen et al.
2022/0389504 A1 12/2022 Chew et al.
2022/0403455 A1 12/2022 Ramachandran Iyer et al.
2022/0404245 A1 12/2022 Chell et al.
2023/0002812 A1 1/2023 Stoeckius et al.
2023/0014008 A1 1/2023 Shastry
2023/0017773 A1 1/2023 Kim et al.
2023/0031305 A1 2/2023 Neuta et al.
2023/0033960 A1 2/2023 Gallant et al.
2023/0034039 A1 2/2023 Shahjamali
2023/0034216 A1 2/2023 Bava
2023/0040363 A1 2/2023 Chee
2023/0042088 A1 2/2023 Chee
2023/0042817 A1 2/2023 Mignardi
2023/0047782 A1 2/2023 Tentori et al.
2023/0056549 A1 2/2023 Dadhwal
2023/0064372 A1 3/2023 Chell et al.
2023/0069046 A1 3/2023 Chew et al.
2023/0077364 A1 3/2023 Patterson et al.
2023/0080543 A1 3/2023 Katiraee et al.
2023/0081381 A1 3/2023 Chew et al.
2023/0100497 A1 3/2023 Frisen et al.
2023/0107023 A1 4/2023 Chee
2023/0111225 A1 4/2023 Chew et al.
2023/0113230 A1 4/2023 Kim et al.
2023/0126825 A1 4/2023 Nagendran et al.
2023/0129552 A1 4/2023 Ramachandran Iyer
2023/0135010 A1 5/2023 Tentori et al.
2023/0143569 A1 5/2023 Iyer et al.
2023/0145575 A1 5/2023 Gallant et al.
2023/0147726 A1 5/2023 Hadrup et al.
2023/0151412 A1 5/2023 Chee
2023/0159994 A1 5/2023 Chee
2023/0159995 A1 5/2023 Iyer et al.
2023/0160008 A1 5/2023 Chell et al.
2023/0175045 A1 6/2023 Katsori et al.
2023/0183684 A1 6/2023 Gallant et al.
2023/0183785 A1 6/2023 Frisen et al.
2023/0194469 A1 6/2023 Tentori et al.
2023/0194470 A1 6/2023 Kim et al.
2023/0203478 A1 6/2023 Kim et al.
2023/0212650 A1 7/2023 Chew et al.
2023/0212655 A1 7/2023 Chee
2023/0212656 A1 7/2023 Chow et al.
2023/0220368 A1 7/2023 Kim
2023/0220454 A1 7/2023 Bent et al.
2023/0220455 A1 7/2023 Galonska et al.
2023/0227811 A1 7/2023 Dadhwal
2023/0228762 A1 7/2023 Uytingco et al.
2023/0242973 A1 8/2023 Frisen et al.
2023/0242976 A1 8/2023 Tentori et al.
2023/0265488 A1 8/2023 Gohil et al.
2023/0265489 A1 8/2023 Uytingco et al.
2023/0265491 A1 8/2023 Tentori et al.
2023/0267625 A1 8/2023 Tentori et al.
2023/0279474 A1 9/2023 Katiraee
2023/0279477 A1 9/2023 Kvastad et al.
2023/0279481 A1 9/2023 Marrache et al.
2023/0287399 A1 9/2023 Gallant et al.
2023/0287475 A1 9/2023 Chell et al.
2023/0287481 A1 9/2023 Katsori et al.
2023/0295699 A1 9/2023 Sukovich et al.
2023/0295722 A1 9/2023 Bharadwaj
2023/0304072 A1 9/2023 Gohil et al.
2023/0304074 A1 9/2023 Chee et al.
2023/0304078 A1 9/2023 Frisen et al.
2023/0313279 A1 10/2023 Giacomello et al.
2023/0323340 A1 10/2023 Dadhwal
2023/0323434 A1 10/2023 Yin et al.
2023/0323436 A1 10/2023 Chee
2023/0323447 A1 10/2023 Schnall-Levin et al.
2023/0323453 A1 10/2023 Stoeckius
2023/0332138 A1 10/2023 Kim et al.
2023/0332211 A1 10/2023 Chee
2023/0332212 A1 10/2023 Chew et al.
2023/0332227 A1 10/2023 Ramachandran Iyer
2023/0332247 A1 10/2023 Singh et al.

(56) References Cited

U.S. PATENT DOCUMENTS

| | | | |
|---|---|---|---|
| 2023/0351619 | A1 | 11/2023 | Tentori et al. |
| 2023/0358733 | A1 | 11/2023 | Chee |
| 2023/0366008 | A1 | 11/2023 | Chew et al. |
| 2023/0383285 | A1 | 11/2023 | Kim et al. |
| 2023/0383344 | A1 | 11/2023 | Stoeckius |
| 2023/0392204 | A1 | 12/2023 | Chell et al. |
| 2023/0393071 | A1 | 12/2023 | Bava |
| 2023/0407404 | A1 | 12/2023 | Baumgartner et al. |
| 2023/0416807 | A1 | 12/2023 | Chee |
| 2023/0416808 | A1 | 12/2023 | Sukovich et al. |
| 2023/0416850 | A1 | 12/2023 | Singh et al. |
| 2024/0002931 | A1 | 1/2024 | Bava |
| 2024/0011081 | A1 | 1/2024 | Chee |
| 2024/0011090 | A1 | 1/2024 | Chew et al. |
| 2024/0018572 | A1 | 1/2024 | Mignardi |
| 2024/0018575 | A1 | 1/2024 | Gallant et al. |
| 2024/0018589 | A1 | 1/2024 | Schnall-Levin et al. |
| 2024/0026445 | A1 | 1/2024 | Ramachandran Iyer et al. |
| 2024/0033743 | A1 | 2/2024 | Tentori et al. |
| 2024/0035937 | A1 | 2/2024 | Cox et al. |
| 2024/0043908 | A1 | 2/2024 | Chew et al. |
| 2024/0043925 | A1 | 2/2024 | Bent et al. |
| 2024/0052343 | A1 | 2/2024 | Gallant et al. |
| 2024/0053351 | A1 | 2/2024 | Uytingco et al. |
| 2024/0060115 | A1 | 2/2024 | Chee et al. |
| 2024/0067953 | A1 | 2/2024 | Mikkelsen et al. |
| 2024/0068016 | A1 | 2/2024 | Frisen et al. |
| 2024/0068017 | A1 | 2/2024 | Lundeberg et al. |
| 2024/0076723 | A1 | 3/2024 | Mignardi |
| 2024/0080346 | A1 | 3/2024 | Engblom et al. |
| 2024/0084365 | A1 | 3/2024 | Frisen et al. |
| 2024/0084366 | A1 | 3/2024 | Chee |
| 2024/0084383 | A1 | 3/2024 | Ramachandran Iyer et al. |
| 2024/0093274 | A1 | 3/2024 | Frisen et al. |
| 2024/0093290 | A1 | 3/2024 | Stahl et al. |
| 2024/0110228 | A1 | 4/2024 | Uytingco et al. |
| 2024/0124933 | A1 | 4/2024 | Chell et al. |
| 2024/0125772 | A1 | 4/2024 | Delaney et al. |
| 2024/0141327 | A1 | 5/2024 | Kim et al. |
| 2024/0158838 | A1 | 5/2024 | Alvarado Martinez et al. |
| 2024/0175080 | A1 | 5/2024 | Galonska et al. |
| 2024/0182968 | A1 | 6/2024 | Bava |
| 2024/0191286 | A1 | 6/2024 | Boutet et al. |
| 2024/0200121 | A1 | 6/2024 | Boutet |
| 2024/0209425 | A1 | 6/2024 | Yin et al. |
| 2024/0218427 | A1 | 7/2024 | Sukovich et al. |
| 2024/0218432 | A1 | 7/2024 | Mielinis |
| 2024/0219701 | A1 | 7/2024 | Tentori et al. |
| 2024/0253036 | A1 | 8/2024 | Kim et al. |
| 2024/0263218 | A1 | 8/2024 | Katiraee et al. |
| 2024/0271190 | A1 | 8/2024 | Stoeckius et al. |
| 2024/0271195 | A1 | 8/2024 | Mikhaiel et al. |
| 2024/0279747 | A1 | 8/2024 | Williams |
| 2024/0287600 | A1 | 8/2024 | Iyer et al. |
| 2024/0294971 | A1 | 9/2024 | Galonska |
| 2024/0294974 | A1 | 9/2024 | Galonska et al. |
| 2024/0294975 | A1 | 9/2024 | Lin et al. |
| 2024/0301488 | A1 | 9/2024 | Stoeckius |
| 2024/0301489 | A1 | 9/2024 | Chew et al. |
| 2024/0360494 | A1 | 10/2024 | Costa et al. |
| 2024/0368711 | A1 | 11/2024 | Giacomello et al. |
| 2024/0377297 | A1 | 11/2024 | Cox et al. |
| 2024/0385088 | A1 | 11/2024 | Kim et al. |
| 2024/0392349 | A1 | 11/2024 | Frisen et al. |
| 2024/0392351 | A1 | 11/2024 | Chee |
| 2024/0392352 | A1 | 11/2024 | Stahl et al. |
| 2024/0392353 | A1 | 11/2024 | Engblom et al. |
| 2024/0401109 | A1 | 12/2024 | Kim et al. |
| 2024/0401117 | A1 | 12/2024 | Bava |
| 2024/0401118 | A1 | 12/2024 | Tentori et al. |
| 2024/0404301 | A1 | 12/2024 | Li et al. |
| 2024/0408593 | A1 | 12/2024 | Kim et al. |
| 2024/0416315 | A1 | 12/2024 | Bava |
| 2024/0417783 | A1 | 12/2024 | Chew et al. |
| 2024/0417784 | A1 | 12/2024 | Sukovich et al. |
| 2025/0002980 | A1 | 1/2025 | Tentori et al. |
| 2025/0002982 | A1 | 1/2025 | Stoeckius et al. |
| 2025/0003956 | A1 | 1/2025 | Delaney et al. |
| 2025/0019689 | A1 | 1/2025 | Galonska et al. |
| 2025/0019749 | A1 | 1/2025 | Katiraee et al. |
| 2025/0066762 | A1 | 2/2025 | Man et al. |
| 2025/0066770 | A1 | 2/2025 | Costa |
| 2025/0073719 | A1 | 3/2025 | Cox et al. |
| 2025/0075261 | A1 | 3/2025 | Kim |
| 2025/0101501 | A1 | 3/2025 | Chee |
| 2025/0101502 | A1 | 3/2025 | Chee |
| 2025/0101504 | A1 | 3/2025 | Nagendran et al. |
| 2025/0122564 | A1 | 4/2025 | Mignardi et al. |
| 2025/0122565 | A1 | 4/2025 | Schnall-Levin et al. |
| 2025/0129412 | A1 | 4/2025 | Uytingco et al. |
| 2025/0129421 | A1 | 4/2025 | Schnall-Levin et al. |
| 2025/0137043 | A1 | 5/2025 | Tentori |
| 2025/0145984 | A1 | 5/2025 | Ma et al. |
| 2025/0146057 | A1 | 5/2025 | Schnall-Levin et al. |
| 2025/0146058 | A1 | 5/2025 | Tentori |
| 2025/0146071 | A1 | 5/2025 | Schnall-Levin et al. |
| 2025/0146072 | A1 | 5/2025 | Schnall-Levin et al. |
| 2025/0154565 | A1 | 5/2025 | Chee |
| 2025/0154566 | A1 | 5/2025 | Chee |
| 2025/0154567 | A1 | 5/2025 | Chee |
| 2025/0154568 | A1 | 5/2025 | Frisen et al. |
| 2025/0154569 | A1 | 5/2025 | Stoeckius et al. |
| 2025/0154571 | A1 | 5/2025 | Ramachandran Iyer et al. |
| 2025/0154588 | A1 | 5/2025 | Ramachandran Iyer et al. |
| 2025/0155446 | A1 | 5/2025 | Uytingco et al. |
| 2025/0163501 | A1 | 5/2025 | Singh et al. |
| 2025/0163509 | A1 | 5/2025 | Daugharthy et al. |
| 2025/0171833 | A1 | 5/2025 | Frisen et al. |
| 2025/0171848 | A1 | 5/2025 | Chell et al. |
| 2025/0179475 | A1 | 6/2025 | Borgstrom et al. |
| 2025/0182305 | A1 | 6/2025 | Tentori et al. |
| 2025/0182503 | A1 | 6/2025 | Li et al. |
| 2025/0188526 | A1 | 6/2025 | Sukovich et al. |
| 2025/0189483 | A1 | 6/2025 | Kim et al. |
| 2025/0197847 | A1 | 6/2025 | Kim et al. |
| 2025/0197938 | A1 | 6/2025 | Bjorninen |
| 2025/0207125 | A1 | 6/2025 | Gupta et al. |
| 2025/0207182 | A1 | 6/2025 | Chee |
| 2025/0207183 | A1 | 6/2025 | Chee |
| 2025/0207195 | A1 | 6/2025 | Chell et al. |
| 2025/0208115 | A1 | 6/2025 | Bent |
| 2025/0215482 | A1 | 7/2025 | Mignardi et al. |
| 2025/0215484 | A1 | 7/2025 | Ramachandran Iyer et al. |
| 2025/0216300 | A1 | 7/2025 | Delaney et al. |
| 2025/0216303 | A1 | 7/2025 | Cox et al. |
| 2025/0223633 | A1 | 7/2025 | Frenz et al. |
| 2025/0230487 | A1 | 7/2025 | Chee et al. |
| 2025/0230498 | A1 | 7/2025 | Katiraee |
| 2025/0250621 | A1 | 8/2025 | Galonska et al. |
| 2025/0250632 | A1 | 8/2025 | Mignardi et al. |
| 2025/0257393 | A1 | 8/2025 | Katiraee et al. |
| 2025/0263791 | A1 | 8/2025 | Bava |
| 2025/0264411 | A1 | 8/2025 | Bava |
| 2025/0283154 | A1 | 9/2025 | Iyer et al. |
| 2025/0283157 | A1 | 9/2025 | Uytingco et al. |
| 2025/0297308 | A1 | 9/2025 | Tentori |
| 2025/0313890 | A1 | 10/2025 | Lundeberg et al. |
| 2025/0313892 | A1 | 10/2025 | Stoeckius |
| 2025/0340932 | A1 | 11/2025 | Chee |
| 2025/0340933 | A1 | 11/2025 | Giacomello et al. |
| 2025/0354931 | A1 | 11/2025 | Shah et al. |
| 2025/0369037 | A1 | 12/2025 | Gupta |
| 2025/0376676 | A1 | 12/2025 | Kim et al. |
| 2025/0376719 | A1 | 12/2025 | Shah |
| 2025/0382665 | A1 | 12/2025 | Frenz et al. |
| 2026/0002202 | A1 | 1/2026 | Schnall-Levin et al. |
| 2026/0009784 | A1 | 1/2026 | Stoeckius |
| 2026/0015653 | A1 | 1/2026 | Chew et al. |
| 2026/0022419 | A1 | 1/2026 | Bent et al. |
| 2026/0035740 | A1 | 2/2026 | Chee |

(56) References Cited

U.S. PATENT DOCUMENTS

2026/0049349 A1 2/2026 Gallant et al.
2026/0055443 A1 2/2026 Tentori et al.

FOREIGN PATENT DOCUMENTS

| | | |
|---|---|---|
| CN | 105142789 | 12/2015 |
| EP | 1910562 | 4/2008 |
| EP | 1923471 | 5/2008 |
| EP | 2002017 | 12/2008 |
| EP | 2130913 | 12/2009 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| JP | 2007-074967 | 3/2007 |
| JP | 2013-544498 | 12/2013 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 2000/063437 | 10/2000 |
| WO | WO 2000/075373 | 12/2000 |
| WO | WO 2002/059355 | 8/2002 |
| WO | WO 2002/077283 | 10/2002 |
| WO | WO 2003/002979 | 1/2003 |
| WO | WO 2003/010176 | 2/2003 |
| WO | WO 2005/007814 | 1/2005 |
| WO | WO 2005/026387 | 3/2005 |
| WO | WO 2005/065814 | 7/2005 |
| WO | WO 2006/064199 | 6/2006 |
| WO | WO 2006/081021 | 8/2006 |
| WO | WO 2007/010251 | 1/2007 |
| WO | WO 2007/073171 | 6/2007 |
| WO | WO 2007/076726 | 7/2007 |
| WO | WO 2007/145612 | 12/2007 |
| WO | WO 2008/075086 | 6/2008 |
| WO | WO 2009/032167 | 3/2009 |
| WO | WO 2009/036525 | 3/2009 |
| WO | WO 2009/152928 | 12/2009 |
| WO | WO 2010/088517 | 8/2010 |
| WO | WO 2010/126614 | 11/2010 |
| WO | WO 2011/002779 | 1/2011 |
| WO | WO 2011/068088 | 6/2011 |
| WO | WO 2011/094669 | 8/2011 |
| WO | WO 2011/127099 | 10/2011 |
| WO | WO 2012/140224 | 10/2012 |
| WO | WO 2012/142213 | 10/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/150082 | 10/2013 |
| WO | WO 2013/150083 | 10/2013 |
| WO | WO 2014/060483 | 4/2014 |
| WO | WO 2014/085725 | 6/2014 |
| WO | WO 2014/163886 | 10/2014 |
| WO | WO 2014/210223 | 12/2014 |
| WO | WO 2014/210225 | 12/2014 |
| WO | WO 2014/210233 | 12/2014 |
| WO | WO 2015/031691 | 3/2015 |
| WO | WO 2015/161173 | 10/2015 |
| WO | WO 2016/007839 | 1/2016 |
| WO | WO 2016/057552 | 4/2016 |
| WO | WO 2016/100196 | 6/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2017/019456 | 2/2017 |
| WO | WO 2017/027367 | 2/2017 |
| WO | WO 2017/027368 | 2/2017 |
| WO | WO-2017019456 A2 * | 2/2017 ........... C12Q 1/6816 |
| WO | WO 2017/075293 | 5/2017 |
| WO | WO 2017/096158 | 7/2017 |
| WO | WO 2017/144338 | 8/2017 |
| WO | WO 2017/147483 | 8/2017 |
| WO | WO 2017/192633 | 11/2017 |
| WO | WO 2017/222453 | 12/2017 |
| WO | WO 2018/022809 | 2/2018 |
| WO | WO 2018/045181 | 3/2018 |
| WO | WO 2018/045186 | 3/2018 |
| WO | WO 2018/057999 | 3/2018 |
| WO | WO 2018/064640 | 4/2018 |
| WO | WO 2018/075693 | 4/2018 |
| WO | WO 2018/091676 | 5/2018 |
| WO | WO 2018/107054 | 6/2018 |
| WO | WO 2018/136856 | 7/2018 |
| WO | WO 2018/148700 | 8/2018 |
| WO | WO 2018/175779 | 9/2018 |
| WO | WO 2018/217862 | 11/2018 |
| WO | WO 2019/028047 | 2/2019 |
| WO | WO 2019/068880 | 4/2019 |
| WO | WO 2019/075091 | 4/2019 |
| WO | WO 2019/113533 | 6/2019 |
| WO | WO 2019/213254 | 11/2019 |
| WO | WO 2019/213294 | 11/2019 |
| WO | WO 2020/028194 | 2/2020 |
| WO | WO 2020/041148 | 2/2020 |
| WO | WO 2020/047002 | 3/2020 |
| WO | WO 2020/047010 | 3/2020 |
| WO | WO 2020/076979 | 4/2020 |
| WO | WO 2020/099640 | 5/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/133842 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |

(56) References Cited

FOREIGN PATENT DOCUMENTS

| | | |
|---|---|---|
| WO | WO 2022/025965 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/137047 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |
| WO | WO 2026/024934 | 1/2026 |

OTHER PUBLICATIONS

Next-Generation Sequencing: From Basic Research to Diagnostics, Clinical Chemistry, 55(4), 641-658 (Year: 2009).*

Xia et al., “Spatial transcriptome profiling by MERFISH reveals subcellular RNA compartmentalization and cell cycle-dependent gene expression”, Proceedings of the National Academy of Sciences, Sep. 2019, 116(39): 19490-19499.

Sun et al., “Statistical Analysis of Spatial Expression Pattern for Spatially Resolved Transcriptomic Studies,” Nature Methods, Jan. 27, 2020, 17(2): 193-200.

Svensson et al., “SpatialDE: identification of spatially variable genes,” Nature Methods, May 2018, 15:343-346, 15 pages.

Takei et al., “Integrated Spatial Genomics Reveals Global Architecture Of Single Nuclei,” Nature, Jan. 27, 2021, 590(7845):344-350, 53 pages.

Burgess, “Spatial transcriptomics coming of age,” Nat Rev Genet., Jun. 2019, 20(6):317, 1 page.

10xGenomics.com, [online], “Visium Spatial Gene Expression Reagent Kits—User Guide,” Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

Asp et al., “A spatiotemporal organ-wide gene expression and cell atlas of the developing human heart,” Cell, Dec. 12, 2019, 179(7):1647-1660.

Kuhn et al., “A novel, high-performance random array platform for quantitative gene expression profiling,” Genome Res, 2004, 14:2347-2356.

Borm et al., “High throughput Human embryo spatial transcriptome mapping by surface transfer of tissue RNA,” Abstracts Selected Talks, Single Cell Genomics mtg, (SCG2019), 2019, 1 pages (Abstract Only).

Codeluppi et al., “Spatial organization of the somatosensory cortex revealed by osmFISH,” Nature Methods, Nov. 2018, 15:932-935.

Eng et al., “Transcriptome-scale super-resolved imaging in tissues by RNA seqFISH+,” Nature, Apr. 2019, 568(7751):235-239, 37 pages.

U.S. Appl. No. 60/416,118, filed Oct. 3, 2002, Fan et al.

U.S. Appl. No. 61/839,313, filed Jun. 25, 2013, Chee et al.

U.S. Appl. No. 61/839,320, filed Jun. 25, 2013, Chee et al.

[No Author Listed], “Chromium Next GEM Single Cell 3' Reagent Kits v3.1—User Guide,” 10x Genomics, Document No. CG000204, Nov. 2019, 58 pages.

[No Author Listed], “Chromium Next GEM Single Cell 3' Reagent Kits v3.1 (Dual Index)—User Guide,” 10x Genomics, Mar. 2021, Document No. CG000315, 61 pages.

[No Author Listed], “HuSNP Mapping Assay User’s Manual,” Affymetrix Part No. 90094 (Affymetrix, Santa Clara, Calif.), GeneChip, 2000, 104 pages.

[No Author Listed], “Microarray technologies have excellent possibilities in genomics-related rescarches,” Science Tools From Amersham Pharmacia Biotech, 1998, 3(4); 8 pages (with English Translation).

10xGenomics.com, [online], “Visium Spatial Gene Expression Reagent Kits—Tissue Optimization ~ User Guide,” Jul. 2020, retrieved on May 25, 2021, retrieved from URL<https://assets.ctfassets.net/an68im79xiti/5UJrNOCH17rEk0UXwd19It/e54d99fb08a8f1500aba503005a04a56/CG000238_VisiumSpatialTissueOptimizationUserGuide_RevD.pdf>, 42 pages.

10xGenomics.com, [online], “Visium Spatial Gene Expression Reagent Kits—Tissue Optimization,” Nov. 2019, retrieved on Jan. 25, 2022, retrieved from URL<https://assets.ctfassets.net/an68im79xiti/4q03w6959AJFxffSwSlee9/6a2ac61cf6388a72564eeb96bc294967/CG000238_VisiumSpatialTissueOptimizationUserGuide_Rev_A.pdf>, 46 pages.

10xGenomics.com, [online], “Visium Spatial Gene Expression Reagent Kits—Tissue Optimization,” Oct. 2020, retrieved on Dec. 28, 2021, retrieved from URL<https://assets.ctfassets.net/an68im79xiti/SUJrN0cH17rEk0UXwd19It/e54d99fb08a8f1500aba503005a04a56/CG000238_VisiumSpatialTissueOptimizationUserGuide_RevD.pdf>, 43 pages.

10xGenomics.com, [online], “Visium Spatial Gene Expression Reagent Kits—User Guide,” Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide RevD.pdf>, 69 pages.

10xGenomics.com, [online], “Visium Spatial Gene Expression Reagent Kits—User Guide,” Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.

(56) References Cited

OTHER PUBLICATIONS

Abaan et al., "The exomes of the NCI-60 panel: a genomic resource for cancer biology and systems pharmacology," Cancer Res., Jul. 2013, 73(14):4372-82.
Adessi et al., "Solid phase DNA amplification: characterisation of primer attachment and amplification mechanisms," Nucl. Acids Res., 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Archer et al., "Selective and flexible depletion of problematic sequences from RNA-seq libraries at the cDNA stage," BMC Genomics, May 2014, 15(1):401, 9 pages.
Armani et al., "2D-PCR; a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Beattie et al., "Advances in genosensor research," Clin Chem., May 1995, 41(5):700-6.
Bechara et al., "Cell-penetrating peptides: 20 years later, where do we stand?," FEBS Lett., Jun. 2013. 587(12):1693-702.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Beier et al., "Versatile derivatisation of solid support media for covalent bonding on DNA-microchips," Nucleic Acids Res., May 1999, 27(9):1970-7.
Berger et al., "Universal bases for hybridization, replication and chain termination," Nucleic Acid Res., Aug. 2000, 28(15):2911-2914.
Biol.wwu.edu [online], "Principles of Di-Base Sequencing and the Advantages of Color Space Analysis in the Solid System," 2008, retrieved on Mar. 11, 2022, retrieved from URL<https://biol.wwu.edu//young/470/stuff/abi-solid.pdf>, 4 pages.
Birney et al., "Identification and analysis of functional elements in 1% of the human genome by the Encode pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolognesi et al., "Multiplex Staining by Sequential Immunostaining and Antibody Removal on Routine Tissue Sections," J. Histochem. Cytochem., Aug. 2017, 65(8):431-444.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein, " Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Carter et al., "Stabilization of an optical microscope to 0.1 nm in three dimensions," Applied Optics, 2007, 46:421-427.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Cheung et al., "Chitosan: An Update on Potential Biomedical and Pharmaceutical Applications," Mar Drugs, Aug. 2015, 13(8):5156-86.
Chrisey et al., "Covalent attachment of synthetic DNA to self-assembled monolayer films," Nucleic Acids Res., Aug. 1996, 24(15):3031-9.
Cockroft et al., "A single-molecule nanopore device detects DNA polymerase activity with single-nucleotide resolution," J Am Chem Soc., Jan. 2008, 130(3):818-20.
Constantine et al., "Use of genechip high-density oligonucleotide arrays for gene expression monitoring," Life Sceience News, Amersham Life Science, 1998, pp. 11-14.
Crosetto et al., "Spatially resolved transcriptomics and beyond," Nature Review Genetics, 2015, 16(1):57-66.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Deamer et al., "Nanopores and nucleic acids: prospects for ultrarapid sequencing," Trends Biotechnol., Apr. 2000, 18(4):147-51.
Dean et al., "Comprehensive human genome amplification using multiple displacement amplification," Proc Natl. Acad. Sci. USA, 2002, 99(8):5261-66.

(56) References Cited

OTHER PUBLICATIONS

Dressman et al., "Transforming single DNA molecules into fluorescent magnetic particles for detection and enumeration of genetic variations," Proc. Natl. Acad. Sci, USA, 2003, 100(15):8817-8822.
Drmanac et al., "CoolMPS™M: Advanced massively parallel sequencing using antibodies specific to each natural nucleobase," BioRxiv, 2020, 19 pages.
Dtp.cancer. gov, [online], "A Catalog of in Vitro Cell Lines, Transplantable Animal and Human Tumors and Yeast," The Division of Cancer Treatment and Diagnosis (DCTD), National Cancer Institute, May 5, 2020, retrieved on Jun. 7, 2021, retrieved from URL<https://dtp.cancer.gov/organization/btb/docs/DCTDTumorRepositoryCatalog.pdf>, 77 pages.
Duncan et al., "Affinity chromatography of a sequence-specific DNA binding protein using Teflon-linked oligonucleotides," Anal. Biochem., 1988, 169(1):104-108.
Eagen, "Principles of Chromosome Architecture Revealed by Hi—C," Trends in Biochemical Sciences, Jun. 2018, 43(6):469-478.
Echeverria et al., "Functional Stimuli-Responsive Gels: Hydrogels and Microgels," Gels., Jun. 2018. 4(2):54, 37 pages.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Fahy et al., "Design and synthesis of polyacrylamide-based oligonucleotide supports for use in nucleic acid diagnostics." Nucleic Acids Res., Apr. 1993, 21(8):1819-26.
Fang et al., "Fluoride-cleavable biotinylation phosphoramidite for 5'-end-labeling and affinity purification of synthetic oligonucleotides," Nucleic Acids Res., Jan. 2003, 31(2):708-715.
Fire et al., "Rolling replication of short DNA circles," Proc. Natl. Acad. Sci., 1995, 92(10):4641-4645.
Fodor et al., "Light-directed, spatially addressable parallel chemical synthesis," Science, 1995, 251(4995):767-773.
Forcucci et al., "All-plastic miniature fluorescence microscope for point-of-care readout of bead-based bioassays.," J. Biomed Opt., 2015, 20(10):105010, 15 pages.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels, " PNAS, 2011. 108(22):9026-9031.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gans et al., "Inkjet Printing of Polymers: State of the Art and Future Developments," Advanced Materials, Feb. 2004, 16(3):203-213.
Gao et al., "Q&A: Expansion microscopy", BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gilles et al., "Single nucleotide polymorphic discrimination by an electronic dot blot assay on semiconductor microchips," Nat Biotechnol, Apr. 1999, 17(4):365-70.
Glass et al., "SIMPLE: a sequential immunoperoxidase labeling and erasing method," J. Histochem. Cytochem., Oct. 2009, 57(10):899-905.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Gracia Villacampa et al., "Genome-wide Spatial Expression Profiling in FFPE Tissues," bioRxiv, 2020, pp. 38 pages.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hein et al., "Click Chemistry, A Powerful Tool for Pharmaceutical Sciences," Pharm Res, 2008, 25(10): 2216-2230.
Hejatko et al., "In situ hybridization technique for mRNA detection in whole mount Arabidopsis samples," Nature Protocols, 2006, 1(4):1939-1946.
Hiatt et al., "Parallel, tag-directed assembly of locally derived short sequence reads," Nature Methods, 2010, 7(2):119-25.
Holmstrøm et al., "A highly sensitive and fast nonradioactive method for detection of polymerase chain reaction products," Anal Biochem, Mar. 1993, 209(2):278-83.
Hoyer et al., "Electrostatic spraying: a novel technique for preparation of polymer coatings on electrodes," Anal Chem, Nov. 1996, 68(21):3840-4.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Joos et al., "Covalent attachment of hybridizable oligonucleotides to glass supports," Anal Biochem., Apr. 1997, 247(1):96-101.
Juliano, "The delivery of therapeutic oligonucleotides," Nucleic Acids Res., Aug. 2016, 44(14):6518-6548.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Koch et al., "Photochemical immobilization of anthraquinone conjugated oligonucleotides and PCR amplicons on solid surfaces," Bioconjugate Chem., Jul. 2000, 11(4):474-483.
Kolb et al., "Click Chemistry: Diverse Chemical Function from a Few Good Reactions," Angew. Chem. Int. Ed., Jun. 2001, 40(11):2004-2021.
Korbel et al., "Paired-end mapping reveals extensive structural variation in the human genome," Science, 2007, 318(5849):420-426.
Korlach et al., "Selective aluminum passivation for targeted immobilization of single DNA polymerase molecules in zero-mode waveguide nanostructures," Proc. Natl. Acad. Sci. USA, 2008, 105:1176-1181.
Kozlov et al., "A highly scalable peptide-based assay system for proteomics," PLoS ONE, 2012, 7(6):e37441, 10 pages.

(56) References Cited

OTHER PUBLICATIONS

Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lamture et al., "Direct detection of nucleic acid hybridization on the surface of a charge coupled device," Nucleic Acid Res., Jun. 1994, 22(11):2121-5.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Lee et al., "Assembly of metallic nanoparticle arrays on glass via nanoimprinting and thin-film dewetting," Beilstein J Nanotechnol., May 2017, 8:1049-1055.
Lee et al., "Fluorescent in situ sequencing (FISSEQ) of RNA for gene expression profiling in intact cells and tissues," Nature Protocols, 2015, 10(3):442-458.
Lee et al., "Highly multiplexed subcellular RNA sequencing in situ", Science, 2014, 343(6177):1360-1363.
Leriche et al., "Cleavable linkers in chemical biology," Bioorganic & Medicinal Chemistry, 2012, 20:571-582.
Levene et al., "Zero-Mode Waveguides for Single-Molecule Analysis at High Concentrations," Science, 2003, 299:682-686.
Li et al., "DNA molecules and configurations in a solid-state nanopore microscope," Nat Mater,, Sep. 2003, 2(9):611-5.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "Surface and interface control on photochemically initiated immobilization," J Am Chem Soc., Nov. 2006, 128(43):14067-72.
Lizardi et al., "Mutation detection and single-molecule counting using isothermal rolling-circle amplification," Nat. Genet., 1998. 19(3):225-232.
Lovatt et al., "Transcriptome in vivo analysis (TIVA) of spatially defined single cells in live tissue," Nature Methods, 2013, 11(2):190-196.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundquist et al., "Parallel confocal detection of single molecules in real time," Opt. Lett., 2008, 33:1026-1028.
MacBeath et al., "Printing proteins as microarrays for high-throughput function determination," Science, Sep. 2000, 289(5485):1760-1763.
Macosko et al., "Highly Parallel Genome-wide Expression Profiling of Individual Cells Using Nanoliter Droplets." Cell, 2015, 161:1202-1214.
Marx, "Method of the Year: spatially resolved transcriptomics," Nature Methods, 2021, 18(1):9-14.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Mir et al., "Sequencing by cyclic ligation and cleavage (CycliC) directly on a microarray captured template, " Nucleic Acids Research, 37(1 ): e5-1, 2009.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mitra et al., "Fluorescent in situ sequencing on polymerase colonies," Anal Biochem, Sep. 2003, 320(1):55-65.
Mizusawa et al., "A bacteriophage lambda vector for cloning with BamHI and Sau3A," Gene, 1982. 20(3):317-322.
Moffitt et al., "RNA Imaging with Multiplexed Error-Robust Fluorescence In Situ Hybridization (MERFISH)," Methods Enzymol., 2016, 572:1-49.
Moshrefzadeh et al., "Nonuniform photobleaching of dyed polymers for optical waveguides," Applied Physics Letters, 1993, 62:16-18.
Nguyen et al., "Two-photon polymerization for biological applications," Materials Today, Jul. 2017, 20(6):314-322.
Nikiforov et al., "The use of 96-well polystyrene plates for DNA hybridization-based assays: an evaluation of different approaches to oligonucleotide immobilization," Anal Biochem, May 1995. 227(1):201-9.
Nowak et al., "Entering the Postgenome Era," Science, 1995, 270(5235):368-71.
PCT International Preliminary Report on Patentability in International Appln. No. PCT/US2019/048428, dated Mar. 2, 2021, 10 pages.
PCT International Search Report and Written Opinion in International Appln. No. PCT/US2019/048428, dated Jan. 10, 2020, 18 pages.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Pirici et al., "Antibody elution method for multiple immunohistochemistry on primary antibodies raised in the same species and of the same subtypem," J. Histochem. Cytochem., Jun. 2009, 57(6):567-75.
Polsky-Cynkin et al., "Use of DNA immobilized on plastic and agarose supports to detect DNA by sandwich hybridization," Clin. Chem., 1985, 31(9):1438-1443.
Raab et al., "Human tRNA genes function as chromatin insulators," EMBO J., Jan. 2012, 31(2):330-50.
Rajeswari et al., "Multiple pathogen biomarker detection using an encoded bead array in droplet Pcr," J. Microbial Methods, Aug. 2017, 139:22-28.
Ranki et al., "Sandwich hybridization as a convenient method for the detection of nucleic acids in crude samples," Gene, 1983, 21(1-2):77-85.
Raouane et al., "Lipid conjugated oligonucleotides: a useful strategy for delivery," Bioconjug Chem., Jun. 2012, 23(6):1091-104.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rideau et al., "Liposomes and polymersomes: a comparative review towards cell mimicking," Chem Soc Rev., Nov. 2018, 47(23):8572-8610.

(56) References Cited

OTHER PUBLICATIONS

Rodriques et al., "Slide-seq: A scalable technology for measuring genome-wide expression at high spatial resolution," Science, 2019, 363(6434):1463-1467.
Rogers et al., "Immobilization of oligonucleotides onto a glass support via disulfide bonds: A method for preparation of DNA microarrays," Anal Biochem., Jan. 1999, 266(1):23-30.
Rogers et al., "Use of a novel cross-linking method to modify adenovirus tropism," Gene Ther., Dec. 1997, 4(12):1387-92.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Running et al., "A procedure for productive coupling of synthetic oligonucleotides to polystyrene microtiter wells for hybridization capture," Biotechniques, Mar. 1990, 8(3):276-279.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020. 41 pages.
Schena et al., "Quantitative monitoring of gene expression patterns with a complementary DNA microarray," Science, Oct. 1995, 270(5235):467-470.
Shalon et al., "A Dna microarray system for analyzing complex DNA samples using two-color fluorescent probe hybridization," Genome Res., Jul. 1996, 6(7):639-45.
Sharma, "Self-Assembly of Colloidal Particles," Resonance, 2018, 23:263-275.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Söderberg et al., "Characterizing proteins and their interactions in cells and tissues using the in situ proximity ligation assay," Methods, Jul. 2008, 45(3):227-32.
Soni and Meller, "Progress toward ultrafast DNA sequencing using solid-state nanopores," Clin Chem., 2007, 53:1996-2001.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Strell et al., "Placing RNA in context and space—methods for spatially resolved transcriptomics," The FEBS Journal, 2019, 286(8):1468-1481.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Timofeev et al., "Regioselective immobilization of short oligonucleotides to acrylic copolymer gels," Nucleic Acids Res., Aug. 1996, 24(16):3142-8.
Trejo et al., "Extraction-free whole transcriptome gene expression analysis of FFPE sections and histology-directed subareas of tissue, " PLoS ONE, Feb. 2019, 14(2):e0212031, 22 pages.
Twyman et al., "Techniques Patents for SNP Genotyping," Pharmacogenomics, Jan. 2003, 4(1):67-79.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seg applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vickovic et al., "High-definition spatial transcriptomics for in situ tissue profiling," Nat Methods, Oct. 2019, 16(10):987-990.
Vogelstein et al., "Digital PCR," Proceedings of the National Academy of Sciences, Aug. 1999, 96(16):9236-9241.
Walker et al., "Strand displacement amplification—an isothermal, in vitro DNA amplification technique," Nucleic Acids Research, 1992, 20(7):1691-1696.
Wang et al., "Imaging plasma membranes without cellular internalization; multisite membrane anchoring reagents based on glycol chitosan derivatives," J Master Chem B., Aug. 2015, 3(30):6165-6173.
Wang et al., "Imaging-based pooled CRISPR screening reveals regulators of IncRNA localization," Proc Natl Acad Sci USA, May 2019, 116(22):10842-10851.
Wang et al., "Three-dimensional intact-tissue sequencing of single-cell transcriptional states," Science, Jul. 2018, 361(6400):eaat5691, 22 pages.
Wang et al., "High-fidelity mRNA amplification for gene profiling," Nature Biotechnology, Apr. 2000, 18(4):457-459.
Weinstein et al., "DNA microscopy: Optics-free spatio-genetic imaging by a stand-alone chemical reaction", bioRxiv, 41 pages, 2018.
Willner, "Stimuli-Controlled Hydrogels and Their Applications," Acc Chem Res., Apr. 2017, 50(4):657-658.
Worthington et al., "Cloning of random oligonucleotides to create single-insert plasmid libraries," Anal Biochem, 2001, 294(2):169-175.
Ye et al., "Triggered self-assembly of magnetic nanoparticles," Sci Rep., Mar. 2016, 6:23145, 9 pages.
Yershov et al., "DNA analysis and diagnostics on oligonucleotide microchips," Proc. Natl. Acad. Sci. USA, May 1996, 93(10):4913-4918.
Zhang et al., "Single-base mutational analysis of cancer and genetic diseases using membrane bound modified oligonucleotides," Nucleic Acids Res., Jul. 1991, 19(14):3929-33.
Zhu et al., "Reverse transcriptase template switching: a SMART approach for full-length cDNA library construction," Biotechniques, Apr. 2001, 30(4):892-897.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Asp et al., "Spatially Resolved Transcriptomes-Next Generation Tools for Tissue Exploration," Bioessays, Oct. 2020, 42(10):e1900221, 16 pages.
Bergenstråhle et al., "Seamless integration of image and molecular analysis for spatial transcriptomics workflows," BMC Genomics, Jul. 2020, 21(1):482, 7 pages.
Bolotin et al., "MIXCR: software for comprehensive adaptive immunity profiling," Nat Methods., May 2015, 12(5):380-1.
U.S. Appl. No. 16/353,937, filed Mar. 14, 2019, Frisen et al.
U.S. Appl. No. 17/707,189, filed Mar. 29, 2022, Chell et al.
Dalma-Weiszhausz et al., "The affymetrix GeneChip platform: an overview," Methods Enzymol., 2006, 410:3-28.
Miller et al., "Chapter 11—Solid and Suspension Microarrays for Microbial Diagnostics," Methods in Microbiology, 2015, 42:395-431.
Vickovic et al., "SM-Omics: An automated Platform for High-Throughput Spatial Multi-Omics," bioRxiv, Oct. 2020, 40 pages.
Ncbi.nlm.nih.gov, [online], "Molecular Inversion Probe Assay," available on or before Oct. 14, 2014, via Internet Archive: Wayback Machine URL<https://web.archive.org/web/20141014124037/https://

(56) References Cited

OTHER PUBLICATIONS www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Liu et al., "An integrated and sensitive detection platform for biosensing application based on Fe@Au magnetic nanoparticles as bead array carries," Biosens Bioelectron, Dec. 2010, 26(4): 1442-8.

Pray, "Eukaryotic Genome Complexity," Nature Education, 2008, 1(1):96, pp. 1-4.

Caliari et al., "A practical guide to hydrogels for cell culture," Nat Methods., Apr. 2016, 13(5):405-14.

Jonczyk et al., "Living cell microarrays: An overview of concepts," Microarrays, 2016, 5(11):1-29.

Lemire et al., "Alkaline hydrolysis to remove potentially infectious viral RNA contaminants from DNA," Virology Journal, 2016, 13:88, 12 pages.

Loessner et al., "Hydrogel microwell arrays allow the assessment of protease-associated enhancement of cancer cell aggregation and survival," Microarrays, 2013, 2:208-227.

Hribar et al., "Three dimensional direct cell patterning in collagen hydrogels with near-infrared femtosecond laser," Sci Reports, 2015, 5:17203, 7 pages.

Meyer et al., "Targeted high-throughput sequencing of tagged nucleic acid samples," Nucleic Acids Res., 2007, 35(15):e97.

Mishra et al., "Polymeric Hydrogels: A reivew of recent developments," Polymeric, Hydrojels as Smart Biomaterials, Springer, 2015, pp. 1-17.

Schulz et al., "Simultaneous Multiplexed Imaging of mRNA and Proteins with Subcellular Resolution in Breast Cancer Tissue Samples by Mass Cytometry," Cell Systems, Jan. 24, 2018, 6(1):25-36, 27 pages.

Hong et al., "Cell Microarray Technologies for High-Throughput Cell-Based Biosensors," Sensors (Basel), Jun. 5, 2017, 17(6):1293.

10x Genomics, "Assay Scheme and Configuration of Chromium™M Single Cell V(D)J Libraries," 10x Genomics, CG000109 Rev D, 2017, 10 pages.

* cited by examiner

Cell tagging / multiplexing
Spatial
Cell membrane anchor
Non-covalent interactions with cell membrane
Covalent conjugation to cell surface Cell tagging / multiplexing
Spatial
Cell membrane anchor
Delivery systems
Cell penetrating peptides

SEQUENCE LISTING

```
<160> NUMBER OF SEQ ID NOS: 6

<210> SEQ ID NO 1
<211> LENGTH: 16
<212> TYPE: PRT
<213> ORGANISM: Artificial sequence
<220> FEATURE:
<223> OTHER INFORMATION: Synthetic trademark of PURAMATRIX polypeptide
      sequence

<400> SEQUENCE: 1
```

-continued

```
Arg Ala Asp Ala Arg Ala Asp Ala Arg Ala Asp Ala Arg Ala Asp Ala
1               5                   10                  15


<210> SEQ ID NO 2
<211> LENGTH: 16
<212> TYPE: PRT
<213> ORGANISM: Artificial sequence
<220> FEATURE:
<223> OTHER INFORMATION: Synthetic EAK16 polypeptide sequence

<400> SEQUENCE: 2

Ala Glu Ala Glu Ala Lys Ala Lys Ala Glu Ala Glu Ala Lys Ala Lys
1               5                   10                  15


<210> SEQ ID NO 3
<211> LENGTH: 12
<212> TYPE: PRT
<213> ORGANISM: Artificial sequence
<220> FEATURE:
<223> OTHER INFORMATION: Synthetic KLD12 polypeptide sequence

<400> SEQUENCE: 3

Lys Leu Asp Leu Lys Leu Asp Leu Lys Leu Asp Leu
1               5                   10


<210> SEQ ID NO 4
<211> LENGTH: 20
<212> TYPE: DNA
<213> ORGANISM: Artificial sequence
<220> FEATURE:
<223> OTHER INFORMATION: Anchor Sequence 1

<400> SEQUENCE: 4

gtcagattga tagcctgtca                                                20


<210> SEQ ID NO 5
<211> LENGTH: 19
<212> TYPE: DNA
<213> ORGANISM: Artificial sequence
<220> FEATURE:
<223> OTHER INFORMATION: Anchor Sequence 2

<400> SEQUENCE: 5

tcagattgat agcctgtca                                                 19


<210> SEQ ID NO 6
<211> LENGTH: 18
<212> TYPE: DNA
<213> ORGANISM: Artificial sequence
<220> FEATURE:
<223> OTHER INFORMATION: Anchor Sequence 3

<400> SEQUENCE: 6

cagattgata gcctgtca                                                  18
```

RESOLVING SPATIAL ARRAYS

CROSS-REFERENCE TO RELATED APPLICATIONS

This application is a National Stage Application under 35 U.S.C. § 371 and claims the benefit of International Application No. PCT/US2019/048428, filed Aug. 27, 2019, which claims priority to U.S. Provisional Patent Application No. 62/724,489, filed Aug. 29, 2018, U.S. Provisional Patent Application No. 62/811,495, filed Feb. 27, 2019, U.S. Provisional Patent Application No. 62/723,950, filed Aug. 28, 2018, U.S. Provisional Patent Application No. 62/723,957, filed Aug. 28, 2018, U.S. Provisional Patent Application No. 62/723,960, filed Aug. 28, 2018, U.S. Provisional Patent Application No. 62/723,964, filed Aug. 28, 2018, U.S. Provisional Patent Application No. 62/723,970, filed Aug. 28, 2018, U.S. Provisional Patent Application No. 62/723,972, filed Aug. 28, 2018, U.S. Provisional Patent Application No. 62/724,483, filed Aug. 29, 2018, U.S. Provisional Patent Application No. 62/724,487, filed Aug. 29, 2018, U.S. Provisional Patent Application No. 62/724,561, filed Aug. 29, 2018, U.S. Provisional Patent Application No. 62/788,905, filed Jan. 6, 2019, U.S. Provisional Patent Application No. 62/788,867, filed Jan. 6, 2019, U.S. Provisional Patent Application No. 62/788,871, filed Jan. 6, 2019, U.S. Provisional Patent Application No. 62/788,897, filed Jan. 6, 2019, U.S. Provisional Patent Application No. 62/788,885, filed Jan. 6, 2019, U.S. Provisional Patent Application No. 62/779,342, filed Dec. 13, 2018, U.S. Provisional Patent Application No. 62/822,565, filed Mar. 22, 2019, U.S. Provisional Patent Application No. 62/819,496, filed Mar. 15, 2019, U.S. Provisional Patent Application No. 62/819,486, filed Mar. 15, 2019, U.S. Provisional Patent Application No. 62/819,467, filed Mar. 15, 2019, U.S. Provisional Patent Application No. 62/822,632, filed Mar. 22, 2019, U.S. Provisional Patent Application No. 62/822,618, filed Mar. 22, 2019, U.S. Provisional Patent Application No. 62/822,592, filed Mar. 22, 2019, U.S. Provisional Patent Application No. 62/819,468, filed Mar. 15, 2019, U.S. Provisional Patent Application No. 62/822,627, filed Mar. 22, 2019, U.S. Provisional Patent Application No. 62/819,448, filed Mar. 15, 2019, U.S. Provisional Patent Application No. 62/822,649, filed Mar. 22, 2019, U.S. Provisional Patent Application No. 62/819,456, filed Mar. 15, 2019, U.S. Provisional Patent Application No. 62/819,478, filed Mar. 15, 2019, U.S. Provisional Patent Application No. 62/819,449, filed Mar. 15, 2019, U.S. Provisional Patent Application No. 62/822,554, filed Mar. 22, 2019, U.S. Provisional Patent Application No. 62/822,575, filed Mar. 22, 2019, U.S. Provisional Patent Application No. 62/822,605, filed Mar. 22, 2019, U.S. Provisional Patent Application No. 62/812,219, filed Feb. 28, 2019, U.S. Provisional Patent Application No. 62/819,458, filed Mar. 15, 2019, U.S. Provisional Patent Application No. 62/839,223, filed Apr. 26, 2019, U.S. Provisional Patent Application No. 62/839,320, filed Apr. 26, 2019, U.S. Provisional Patent Application No. 62/839,346, filed Apr. 26, 2019, U.S. Provisional Patent Application No. 62/842,463, filed May 2, 2019, U.S. Provisional Patent Application No. 62/860,993, filed Jun. 13, 2019, U.S. Provisional Patent Application No. 62/839,526, filed Apr. 26, 2019 and U.S. Provisional Patent Application No. 62/858,331 filed on Jun. 7, 2019. The contents of each of these applications are incorporated herein by reference in their entireties.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the contact of an intact tissue or a portion of a tissue, or provide a lot of analyte data for single cells, but fail to provide information regarding the position of the single cell in a parent biological sample (e.g., tissue sample).

To assess spatial heterogeneity, spatially resolved measurements of analytes are performed. Methods for resolving such measurements at cellular and sub-cellular resolution can be challenging, in part due to the difficulty of correlating captured analytes with specific spatial locations in a biological sample.

SUMMARY

In an aspect, the disclosure features methods for determining a location of a feature in a spatial array of features, the methods including: (a) providing a spatial array having a plurality of features on a substrate, where a feature of the plurality of features includes a capture probe, and where the capture probe has a spatial barcode and a constant sequence; (b) hybridizing a first sequencing probe to the spatial barcode, where the first sequencing probe has a first label and a first nucleotide sequence; (c) obtaining a first image of the first label with the first sequencing probe hybridized to the spatial barcode; (d) determining, based on the first image, a first portion of a sequence of the spatial barcode; (e) hybridizing a second sequencing probe to the spatial barcode, where the second sequencing probe includes a second label and a second nucleotide sequence different from the first nucleotide sequence; (f) obtaining a second image of the second label with the second sequencing probe hybridized to the spatial barcode; (g) determining, based on the second image, a second portion of the sequence of the spatial barcode; and (h) associating the feature with a location in the spatial array based on a location of the first label in the first image.

Embodiments of the methods can include any one or more of the following features.

The methods can include repeating steps (e)-(g) with one or more additional sequencing probes, each additional sequencing probe having a label and a nucleotide sequence different from the first and second nucleotide sequences and nucleotide sequences of other additional sequencing probes, until the sequence of the spatial barcode is completely determined. One or more features of the plurality of features can include a plurality of capture probes.

The methods can include repeating steps (a)-(h) for multiple features in the spatial array, each of the multiple features having a capture probe including a spatial barcode and a constant sequence, to associate each of the multiple features with a location in the spatial array.

The methods can include, for multiple features in the spatial array each having a capture probe including a spatial barcode and a constant sequence, determining the complete sequence of the capture probe of each multiple feature, and associating each of the multiple features with a location in the spatial array. For each capture probe associated with one of the features and having a spatial barcode, the spatial barcode can be unique relative to spatial barcodes of capture probes associated with other features in the spatial array. The constant sequence can include a sequence for initiating a sequencing reaction.

The methods can include hybridizing a sequencing anchor to the constant sequence prior to hybridizing the first sequencing probe to the spatial barcode. The methods can include amplifying at least a portion of the capture probe before determining the first and second portions of the sequence of the spatial barcode. The methods can include amplifying the at least a portion of the capture probe using isothermal or non-isothermal amplification.

Determining the complete sequence of the spatial barcode can include sequentially hybridizing each of three or more sequencing probes to the spatial barcode. Determining the complete sequence of the spatial barcode can include sequentially hybridizing each of ten of more sequencing probes to portions of the spatial barcode. The spatial barcode can include N nucleic acids, and determining the complete sequence of the spatial barcode can include sequentially hybridizing N different sequencing probes to the spatial barcode. The spatial barcode can include N nucleic acids, and determining the complete sequence of the spatial barcode can include sequentially hybridizing fewer than N different sequencing probes to the spatial barcode.

The first and second sequencing probes can hybridize to a common portion of the spatial barcode. The common portion of the spatial barcode can include the entire spatial barcode. Each of the sequencing probes can hybridize to a common portion of the spatial barcode. The common portion of the spatial barcode can include the entire spatial barcode.

The methods can include, prior to hybridizing the first sequencing probe to the spatial barcode, hybridizing a sequencing anchor to at least a portion of the constant sequence, where the sequencing anchor includes a sequence that is complementary to at least a portion of the constant sequence. Hybridizing the first sequencing probe to the spatial barcode can include contacting the spatial barcode with a composition that includes the first sequencing probe and a first set of three auxiliary sequencing probes, where the first sequencing probe and each member of the first set of three auxiliary sequencing probes each have a known, different nucleic acid at a first common sequence position and a known, different label, and coupling the first sequencing probe to a free 5' end of the sequencing anchor.

Determining the first portion of the sequence of the spatial barcode can include identifying the nucleic acid at the first common sequence position of the first sequencing probe based on the first image of the first label, and identifying the first portion of the sequence of the spatial barcode as a nucleic acid complementary to the nucleic acid at the first common sequence position of the first sequencing probe. Hybridizing the second sequencing probe to the spatial barcode can include contacting the spatial barcode with a composition that includes the second sequencing probe and a second set of three auxiliary sequencing probes, where the second sequencing probe and each member of the second set of three auxiliary sequencing probes each has a known, different nucleic acid at a second common sequence position and a known, different label, and coupling the second sequencing probe to a free 5' end of the sequencing anchor or to a free 5' end of at least a portion of the first sequencing probe.

Determining the second portion of the sequence of the spatial barcode can include identifying the nucleic acid at the second common sequence position of the second sequencing probe based on the second image of the second label, and identifying the second portion of the sequence of the spatial barcode as a nucleic acid complementary to the nucleic acid at the second common sequence position of the second sequencing probe. The second common sequence position can be different from the first common sequence position. The methods can include removing all of the first sequencing probe from the spatial barcode, and coupling the second sequencing probe to the free 5' end of the sequencing anchor. The methods can include removing a portion of the first sequencing probe from the spatial barcode, and coupling the second sequencing probe to a free 5' end of a portion of the first sequencing probe that remains hybridized to the spatial barcode.

The methods can include coupling the first sequencing probe to the free 5' end of the sequencing anchor using a ligation reaction. The methods can include coupling the second sequencing probe to the free 5' end of the sequencing anchor or to the free 5' end of at least a portion of the first sequencing probe using a ligation reaction. The first sequencing probe can include a first nucleic acid sequence having a 3' end and a 5' end, and where a known nucleic acid is located at a first sequence position relative to the 3' end of the first nucleic acid sequence. Each of the nucleic acids in the first nucleic acid sequence other than the known nucleic acid can be a universal base. A length of the first nucleic acid sequence can be the same as a length of the spatial barcode.

The second sequencing probe can include a second nucleic acid sequence having a 3' end and a 5' end, and where a known nucleic acid can be located at a second sequence position relative to the 3' end of the second nucleic acid sequence. Each of the nucleic acids in the second nucleic acid sequence other than the known nucleic acid can be a universal base. A length of the second nucleic acid sequence can be the same as the length of the spatial barcode.

Each of the first and second sequencing probes can include a label coupled to the 5' end of the first and second nucleic acid sequences, respectively. The first sequencing probe can include a first nucleic acid sequence having a 3' end and a 5' end, and where known nucleic acids can be located at two sequence positions of the first nucleic acid sequence. The two sequence positions can be first and second sequence positions relative to the 3' end of the first nucleic acid sequence. Each of the nucleic acids in the first nucleic acid sequence other than the known nucleic acids can be a universal base. A length of the first nucleic acid sequence can be the same as a length of the spatial barcode.

The second sequencing probe can include a second nucleic acid sequence having a 3' end and a 5' end, and where known nucleic acids can be located at two sequence positions of the second nucleic acid sequence. The two sequence positions can be third and fourth positions relative to the 3' end of the second nucleic acid sequence. Each of the nucleic acids in the second nucleic acid sequence other than the known nucleic acids can be a universal base. A length of the second nucleic acid sequence can be the same as the length of the spatial barcode.

The label can be selected from the group consisting of an optical label, a radioactive label, a fluorescent label, an enzymatic label, a chemiluminescent label, a bioluminescent label, or a dye. The methods can include, prior to hybridizing the second sequencing probe to the spatial barcode, removing at least a portion of the first sequencing probe from the spatial barcode. Removing the at least a portion of the first sequencing probe from the spatial barcode can include cleaving the at least a portion of the first sequencing probe to generate a free 5' end capable of serving as substrate in a ligation reaction. The removed at least a portion of the first sequencing probe can include the first label. The methods can include cleaving the at least a portion of the first sequencing probe with a nuclease. The first sequencing probe can include a nuclease recognition site.

The methods can include removing the sequencing anchor after determining the second portion of the sequence of the spatial barcode, or after the sequence of the spatial barcode is completely determined.

The capture probe can include a capture domain. The capture probe can include, from a 5' end to a 3' end, the spatial barcode, the constant sequence, and the capture domain.

The spatial barcode can be a first spatial barcode, and the capture probe can include a second spatial barcode different from the first spatial barcode. The capture probe can include, from a 5' end to a 3' end, the second spatial barcode, the constant sequence, and the first spatial barcode. The capture probe can include a capture domain. The capture probe can include, from a 5' end to a 3' end, the second spatial barcode, the constant sequence, the first spatial barcode, and the capture domain.

The methods can include determining at least a portion of a sequence of the second spatial barcode. Determining the at least a portion of the sequence of the second spatial barcode can include: (i) hybridizing a third sequencing probe to the second spatial barcode, where the third sequencing probe includes a third label and a third nucleotide sequence; (j) obtaining a third image of the third label with the third sequencing probe hybridized to the second spatial barcode; and (k) determining, based on the third image, a first portion of a sequence of the second spatial barcode. The methods can include repeating steps (i)-(k) with one or more additional sequencing probes, each additional sequencing probe having a label and a nucleotide sequence different from the third nucleotide sequence and nucleotide sequences of other additional sequencing probes, until the sequence of the second spatial barcode is completely determined.

Hybridizing the third sequencing probe to the second spatial barcode can include contacting the spatial barcode with a composition including the third sequencing probe and a third set of three auxiliary sequencing probes, where the third sequencing probe and each member of the third set of three auxiliary sequencing probes each have a known, different nucleic acid at a first common sequence position and a known, different label, and coupling the third sequencing probe to a free 3' end of the sequencing anchor.

Determining the first portion of the sequence of the second spatial barcode can include identifying the nucleic acid at the first common sequence position of the third sequencing probe based on the third image of the third label, and identifying the first portion of the sequence of the second spatial barcode as a nucleic acid complementary to the nucleic acid at the first common sequence position of the third sequencing probe.

The third sequencing probe can include a nucleic acid sequence having a 5' end and a 3' end, where a known nucleic acid is located at first sequence position relative to the 5' end. The third sequencing probe can include universal bases at positions other than the first sequence position relative to the 5' end. The third sequencing probe can include a label coupled to the 3' end of the nucleic acid sequence.

The methods can also include any of the other aspects described herein, including aspects described in connection with different embodiments, in any combination except as expressly stated otherwise.

In another aspect, the disclosure features methods for associating an analyte of a biological sample with a spatial location in the biological sample, the methods including providing a spatial array having a plurality of features on a substrate, where a feature of the plurality of features includes a capture probe, and where the capture probe has a spatial barcode, a constant sequence, and a capture domain, determining a sequence of the spatial barcode and associating the feature with a location in the spatial array, capturing an analyte of a biological sample with the capture domain, and determining a location of the captured analyte in the biological sample based on the location of the feature in the spatial array, where determining the sequence of the spatial barcode and associating the feature with the location in the spatial array includes: (a) hybridizing a sequencing probe to the spatial barcode, where the sequencing probe has a label and a nucleotide sequence; (b) obtaining an image of the label with the sequencing probe hybridized to the spatial barcode; (c) determining, based on the image, a portion of a sequence of the spatial barcode; (d) repeating steps (a)-(c) until the sequence of the spatial barcode is completely determined; and (e) associating the feature with a location in the spatial array based on a location of the label in the image.

Embodiments of the methods can include any one or more of the following features.

The capture domain can hybridize to a nucleic acid sequence present on or associated with the analyte. Capturing the analyte of the biological sample with the capture domain can include contacting the spatial array with the biological sample and allowing the analyte to interact with the capture domain. Capturing the analyte of the biological sample with the capture domain can include releasing the capture probe from the spatial array and contacting the biological sample with the released capture probe.

The analyte can include DNA or RNA. The analyte can include a protein.

The methods can also include any of the other aspects described herein, including aspects described in connection with different embodiments, in any combination except as expressly stated otherwise.

In another aspect, the disclosure features methods for preparing a spatial array, the methods comprising: (a) providing a substrate having a plurality of oligonucleotides attached to a surface of the substrate, where an oligonucleotide of the plurality of oligonucleotides includes, from a 5' end to a 3' end, a spatial barcode, a constant sequence, and a capture domain; (b) determining a location of the spatial barcode in the array and a sequence of the spatial barcode; (c) attaching a feature having a plurality of capture probes to the substrate by coupling the feature to the oligonucleotide; and (d) associating the feature with a location in the spatial array based on the location of the spatial barcode in the array.

Embodiments of the methods can include any one or more of the following features.

Determining the location of the spatial barcode in the array and the sequence of the spatial barcode can include: (a) hybridizing a sequencing probe to the spatial barcode, where the sequencing probe includes a label and a nucleotide sequence; (b) obtaining an image of the label with the sequencing probe hybridized to the spatial barcode; (c) determining, based on the image, a portion of a sequence of the spatial barcode; (d) repeating steps (a)-(c) until the sequence of the spatial barcode is determined; and (e) determining a location of the spatial barcode based on a location of the label in the image.

The spatial barcode of the oligonucleotide can be a first spatial barcode, and one or more of the capture probes can include a second spatial barcode. The first and second spatial barcodes can be the same. The first and second spatial barcodes can be different. The constant sequence can include a sequence for initiating a sequencing reaction.

The methods can include hybridizing a sequencing anchor to at least a portion of the constant sequence prior to hybridizing the sequencing probe to the spatial barcode. The methods can include amplifying a portion of one of the plurality of capture probes. The methods can include amplifying the portion of one of the plurality of capture probes using isothermal or non-isothermal amplification.

A capture probe of the plurality of capture probes can include a universal molecular identifier (UMI). A capture probe of the plurality of capture probes can include a cleavage domain.

The capture probe can include a primer sequence, and the oligonucleotide can include a template sequence. The primer sequence can include a reverse transcriptase primer. The template sequence can include a sequence for a reverse transcription assay.

The spatial barcode can include N nucleic acids, and determining the sequence of the spatial barcode can include sequentially hybridizing N different sequencing probes to the spatial barcode. The spatial barcode can include N nucleic acids, and determining the sequence of the spatial barcode can include sequentially hybridizing fewer than N different sequencing probes to the spatial barcode.

Each of the sequencing probes can hybridize to a common portion of the spatial barcode. The common portion of the spatial barcode can include the entire spatial barcode.

Hybridizing the sequencing probe to the spatial barcode can include contacting the spatial barcode with a composition that includes the sequencing probe and a set of three auxiliary sequencing probes, where the sequencing probe and each member of the set of three auxiliary sequencing probes each has a known, different nucleic acid at a common sequence position and a known, different label, and coupling the sequencing probe to a free 5' end of the sequencing anchor or to a free 5' end of a portion of another sequencing probe.

Determining the portion of the sequence of the spatial barcode can include identifying the nucleic acid at the common sequence position based on the image of the label, and identifying the portion of the sequence of the spatial barcode as a nucleic acid complementary to the nucleic acid at the common sequence position of the sequencing probe.

The methods can include removing all of the sequencing probe from the spatial barcode prior to hybridizing another sequencing probe to the spatial barcode. The methods can include removing a portion of one sequencing probe from the spatial barcode, and coupling a successive sequencing probe to a free 5' end of a portion of the one sequencing probe that remains hybridized to the spatial barcode. The methods can include coupling the sequencing probe to the free 5' end of the sequencing anchor or to the free 5' end of the portion of another sequencing probe using a ligation reaction.

The sequencing probe can include a nucleic acid sequence having a 3' end and a 5' end, and a known nucleic acid can be located at a first sequence position relative to the 3' end of the first nucleic acid sequence. Each of the nucleic acids in the nucleic acid sequence other than the known nucleic acid can be a universal base. A length of the nucleic acid sequence can be the same as a length of the spatial barcode.

The label can be selected from the group consisting of an optical label, a radioactive label, a fluorescent label, an enzymatic label, a chemiluminescent label, a bioluminescent label, or a dye.

The methods can include removing the portion of the one sequencing probe from the spatial barcode by cleaving the one sequencing probe with a nuclease. The one sequencing probe can include a nuclease recognition site.

The methods can include capturing an analyte of a biological sample with a capture probe of the plurality of capture probes, and determining a location of the captured analyte in the biological sample based on the location of the feature in the spatial array. The capture probe can include a capture domain that can hybridize to a nucleic acid sequence present on or associated with the analyte.

Capturing the analyte of the biological sample with the capture probe can include contacting the spatial array with the biological sample and allowing the analyte to interact with the capture probe. Capturing the analyte of the biological sample with the capture probe can include releasing the capture probe from the spatial array and contacting the biological sample with the released capture probe.

The analyte can include DNA or RNA. The analyte can include a protein.

The methods can also include any of the other aspects described herein, including aspects described in connection with different embodiments, in any combination except as expressly stated otherwise.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

I. Introduction

Figure 1:
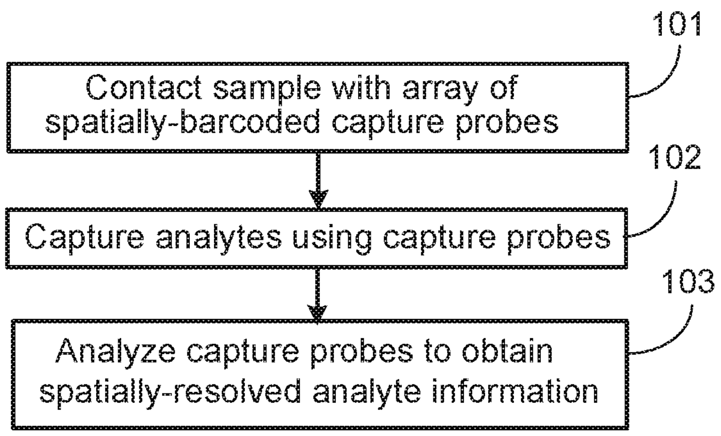
FIG. 1 shows an exemplary spatial analysis workflow.

This disclosure describes apparatus, systems, methods, and compositions for spatial analysis of biological samples. This section in particular describes certain general terminology, analytes, sample types, and preparative steps that are referred to in later sections of the disclosure.

(a) Spatial Analysis

Tissues and cells can be obtained from any source. For example, tissues and cells can be obtained from single-cell or multicellular organisms (e.g., a mammal). Tissues and cells obtained from a mammal, e.g., a human, often have varied analyte levels (e.g., gene and/or protein expression) which can result in differences in cell morphology and/or function. The position of a cell within a tissue can affect, e.g., the cell's fate, behavior, morphology, and signaling and cross-talk with other cells in the tissue. Information regarding the differences in analyte levels (gene and/or protein expression) within different cells in a tissue of a mammal can also help physicians select or administer a treatment that will be effective in the single-cell or multicellular organisms (e.g., a mammal) based on the detected differences in analyte levels within different cells in the tissue. Differences in analyte levels within different cells in a tissue of a mammal can also provide information on how tissues (e.g., healthy and diseased tissues) function and/or develop. Differences in analyte levels within different cells in a tissue of a mammal can also provide information of different mechanisms of disease pathogenesis in a tissue and mechanism of action of a therapeutic treatment within a tissue. Differences in analyte levels within different cells in a tissue of a mammal can also provide information on drug resistance mechanisms and the development of the same in a tissue of a mammal. Differences in the presence or absence of analytes within different cells in a tissue of a multicellular organism (e.g., a mammal) can provide information on drug resistance mechanisms and the development of the same in a tissue of a multicellular organism.

The spatial analysis methodologies provide for the detection of differences in an analyte level (e.g., gene and/or protein expression) within different cells in a tissue of a mammal or within a single cell from a mammal. For example, spatial analysis methodologies can be used to detect the differences in analyte levels (e.g., gene and/or protein expression) within different cells in histological slide samples, the data from which can be reassembled to generate a three-dimensional map of analyte levels (e.g., gene and/or protein expression) of a tissue sample obtained from a mammal, e.g., with a degree of spatial resolution (e.g., single-cell resolution).

Spatial heterogeneity in developing systems has typically been studied via RNA hybridization, immunohistochemistry, fluorescent reporters, or purification or induction of pre-defined subpopulations and subsequent genomic profiling (e.g., RNA-seq). Such approaches, however, rely on a relatively small set of pre-defined markers, therefore introducing selection bias that limits discovery. These prior approaches also rely on a priori knowledge. Spatial RNA assays traditionally relied on staining for a limited number of RNA species. In contrast, single-cell RNA-sequencing allows for deep profiling of cellular gene expression (including non-coding RNA), but the established methods separate cells from their native spatial context.

Current spatial analysis methodologies provide a vast amount of analyte level and/or expression data for a variety of multiple analytes within a sample at high spatial resolution, e.g., while retaining the native spatial context. Spatial analysis methods include, e.g., the use of a capture probe including a spatial barcode (e.g., a nucleic acid sequence that provides information as to the position of the capture probe within a cell or a tissue sample (e.g., mammalian cell or a mammalian tissue sample) and a capture domain that is capable of binding to an analyte (e.g., a protein and/or nucleic acid) produced by and/or present in a cell. As described herein, the spatial barcode can be a nucleic acid that has a unique sequence, a unique fluorophore or a unique combination of fluorophores, a unique amino acid sequence, a unique heavy metal or a unique combination of heavy metals, or any other unique detectable agent. The capture domain can be any agent that is capable of binding to an analyte produced by and/or present in a cell (e.g., a nucleic acid that is capable of hybridizing to a nucleic acid from a cell (e.g., an mRNA, genomic DNA, mitochondrial DNA, or miRNA), a substrate or binding partner of an analyte, or an antibody that binds specifically to an analyte). A capture probe can also include a nucleic acid sequence that is complementary to a sequence of a universal forward and/or universal reverse primer. A capture probe can also include a cleavage site (e.g., a cleavage recognition site of a restriction endonuclease), a photolabile bond, a thermosensitive bond, or a chemical-sensitive bond.

The binding of an analyte to a capture probe can be detected using a number of different methods, e.g., nucleic acid sequencing, fluorophore detection, nucleic acid amplification, detection of nucleic acid ligation, and/or detection of nucleic acid cleavage products. In some examples, the detection is used to associate a specific spatial barcode with a specific analyte produced by and/or present in a cell (e.g., a mammalian cell).

Capture probes can be, e.g., attached to a surface, e.g., a solid array, a bead, or a coverslip. In some examples, capture probes are not attached to a surface. In some examples, capture probes can be encapsulated within, embedded within, or layered on a surface of a permeable composition (e.g., any of the substrates described herein). For example, capture probes can be encapsulated or disposed within a permeable bead (e.g., a gel bead). In some examples, capture probes can be encapsulated within, embedded within, or layered on a surface of a substrate (e.g., any of the exemplary substrates described herein, such as a hydrogel or a porous membrane).

In some examples, a cell or a tissue sample including a cell are contacted with capture probes attached to a substrate (e.g., a surface of a substrate), and the cell or tissue sample is permeabilized to allow analytes to be released from the cell and bind to the capture probes attached to the substrate. In some examples, analytes released from a cell can be actively directed to the capture probes attached to a substrate using a variety of methods, e.g., electrophoresis, chemical gradient, pressure gradient, fluid flow, or magnetic field.

In other examples, a capture probe can be directed to interact with a cell or a tissue sample using a variety of methods, e.g., inclusion of a lipid anchoring agent in the capture probe, inclusion of an agent that binds specifically to, or forms a covalent bond with a membrane protein in the capture probe, fluid flow, pressure gradient, chemical gradient, or magnetic field.

Non-limiting aspects of spatial analysis methodologies are described in WO 2011/127099, WO 2014/210233, WO 2014/210225, WO 2016/162309, WO 2018/091676, WO 2012/140224, WO 2014/060483, U.S. Pat. Nos. 10,002,316, 9,727,810, U.S. Patent Application Publication No. 2017/0016053, Rodrigues et al., *Science* 363(6434):1463-1467, 2019; WO 2018/045186, Lee et al., *Nat. Protoc.* 10(3):442-458, 2015; WO 2016/007839, WO 2018/045181, WO 2014/163886, Trejo et al., *PLoS ONE* 14(2):e0212031, 2019, U.S. Patent Application Publication No. 2018/0245142, Chen et al., *Science* 348(6233):aaa6090, 2015, Gao et al., *BMC Biol.* 15:50, 2017, WO 2017/144338, WO 2018/107054, WO 2017/222453, WO 2019/068880, WO 2011/094669, U.S. Pat. Nos. 7,709,198, 8,604,182, 8,951,726, 9,783,841, 10,041,949, WO 2016/057552, WO 2017/147483, WO 2018/022809, WO 2016/166128, WO 2017/027367, WO 2017/027368, WO 2018/136856, WO 2019/075091, U.S. Pat. No. 10,059,990, WO 2018/057999, WO 2015/161173, and Gupta et al., *Nature Biotechnol.* 36:1197-1202, 2018, and can be used herein in any combination. Further non-limiting aspects of spatial analysis methodologies are described herein.

(b) General Terminology

Specific terminology is used throughout this disclosure to explain various aspects of the apparatus, systems, methods, and compositions that are described. This sub-section includes explanations of certain terms that appear in later sections of the disclosure. To the extent that the descriptions in this section are in apparent conflict with usage in other sections of this disclosure, the definitions in this section will control.

(i) Barcode

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide mononomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Subject

A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, or honey bee; an arachnid such as a spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum.*

(vi) Genome

A "genome" generally refers to genomic information from a subject, which can be, for example, at least a portion of, or the entirety of, the subject's gene-encoded hereditary information. A genome can include coding regions (e.g., that code for proteins) as well as non-coding regions. A genome can include the sequences of some or all of the subject's chromosomes. For example, the human genome ordinarily has a total of 46 chromosomes. The sequences of some or all of these can constitute the genome.

(vii) Adaptor, Adapter, and Tag

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

(viii) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(ix) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis).

Primers can vary in length. For example, primers can be about 6 bases to about 120 bases. For example, primers can include up to about 25 bases.

(x) Primer Extension

A "primer extension" refers to any method where two nucleic acid sequences (e.g., a constant region from each of two distinct capture probes) become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(xi) Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(xii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(xiii) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xiv) Antibody

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also include single domain antibodies (VHH domains and VNAR domains), scFvs, and Fab fragments.

(xv) Affinity Group

An "affinity group" is a molecule or molecular moiety which has a high affinity or preference for associating or binding with another specific or particular molecule or moiety. The association or binding with another specific or particular molecule or moiety can be via a non-covalent interaction, such as hydrogen bonding, ionic forces, and van der Waals interactions. An affinity group can, for example, be biotin, which has a high affinity or preference to associate or bind to the protein avidin or streptavidin. An affinity group, for example, can also refer to avidin or streptavidin which has an affinity to biotin. Other examples of an affinity group and specific or particular molecule or moiety to which it binds or associates with include, but are not limited to, antibodies or antibody fragments and their respective antigens, such as digoxigenin and anti-digoxigenin antibodies, lectin, and carbohydrates (e.g., a sugar, a monosaccharide, a disaccharide, or a polysaccharide), and receptors and receptor ligands.

Any pair of affinity group and its specific or particular molecule or moiety to which it binds or associates with can have their roles reversed, for example, such that between a first molecule and a second molecule, in a first instance the first molecule is characterized as an affinity group for the second molecule, and in a second instance the second molecule is characterized as an affinity group for the first molecule.

(xvi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a capture probe or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, capture probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18(5)), DIDS, Dil (DilC18(3)), DiO (DiOC18(3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66 W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters.

(xvii) Template Switching Oligonucleotide

A "template switching oligonucleotide" is an oligonucleotide that hybridizes to untemplated nucleotides added by a reverse transcriptase (e.g., enzyme with terminal transferase activity) during reverse transcription. In some embodiments, a template switching oligonucleotide hybridizes to untemplated poly(C) nucleotides added by a reverse transcriptase. In some embodiments, the template switching oligonucleotide adds a common 5' sequence to full-length cDNA that is used for cDNA amplification.

In some embodiments, the template switching oligonucleotide adds a common sequence onto the 5' end of the RNA being reverse transcribed. For example, a template switching oligonucleotide can hybridize to untemplated poly(C) nucleotides added onto the end of a cDNA molecule and provide a template for the reverse transcriptase to continue replication to the 5' end of the template switching oligonucleotide, thereby generating full-length cDNA ready for further amplification. In some embodiments, once a full-length cDNA molecule is generated, the template switching oligonucleotide can serve as a primer in a cDNA amplification reaction.

In some embodiments, a template switching oligonucleotide is added before, contemporaneously with, or after a reverse transcription, or other terminal transferase-based reaction. In some embodiments, a template switching oligonucleotide is included in the capture probe. In certain embodiments, methods of sample analysis using template switching oligonucleotides can involve the generation of nucleic acid products from analytes of the tissue sample, followed by further processing of the nucleic acid products with the template switching oligonucleotide.

Template switching oligonucleotides can include a hybridization region and a template region. The hybridization region can include any sequence capable of hybridizing to the target. In some embodiments, the hybridization region can, e.g., include a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In other embodiments, the hybridization region can include at least one base in addition to at least one G base. In other embodiments, the hybridization can include bases that are not a G base. In some embodiments, the template region includes at least 1 (e.g., at least 2, 3, 4, 5 or more) tag sequences and/or functional sequences. In some embodiments, the template region and hybridization region are separated by a spacer.

In some embodiments, the template regions include a barcode sequence. The barcode sequence can act as a spatial barcode and/or as a unique molecular identifier. Template switching oligonucleotides can include deoxyribonucleic acids; ribonucleic acids; modified nucleic acids including 2-aminopurine, 2,6-diaminopurine (2-amino-dA), inverted dT, 5-methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

In some embodiments, the length of a template switching oligonucleotide can be at least about 1, 2, 10, 20, 50, 75, 100, 150, 200, or 250 nucleotides or longer. In some embodiments, the length of a template switching oligonucleotide can be at most about 2, 10, 20, 50, 100, 150, 200, or 250 nucleotides or longer.

(xviii) Splint Oligonucleotide

A "splint oligonucleotide" is an oligonucleotide that, when hybridized to other polynucleotides, acts as a "splint" to position the polynucleotides next to one another so that they can be ligated together. In some embodiments, the splint oligonucleotide is DNA or RNA. The splint oligonucleotide can include a nucleotide sequence that is partially complimentary to nucleotide sequences from two or more different oligonucleotides. In some embodiments, the splint oligonucleotide assists in ligating a "donor" oligonucleotide and an "acceptor" oligonucleotide. In general, an RNA ligase, a DNA ligase, or another other variety of ligase is used to ligate two nucleotide sequences together In some embodiments, the splint oligonucleotide is between 10 and 50 oligonucleotides in length, e.g., between 10 and 45, 10 and 40, 10 and 35, 10 and 30, 10 and 25, or 10 and 20 oligonucleotides in length. In some embodiments, the splint oligonucleotide is between 15 and 50, 15 and 45, 15 and 40, 15 and 35, 15 and 30, 15 and 30, or 15 and 25 nucleotides in length.

(c) Analytes

The apparatus, systems, methods, and compositions described in this disclosure can be used to detect and analyze a wide variety of different analytes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte can be an organelle (e.g., nuclei or mitochondria).

Cell surface features corresponding to analytes can include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis.

Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids.

Examples of nucleic acid analytes also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

Additional examples of analytes include mRNA and cell surface features (e.g., using the labelling agents described herein), mRNA and intracellular proteins (e.g., transcription factors), mRNA and cell methylation status, mRNA and accessible chromatin (e.g., ATAC-seq, DNase-seq, and/or MNase-seq), mRNA and metabolites (e.g., using the labelling agents described herein), a barcoded labelling agent (e.g., the oligonucleotide tagged antibodies described herein) and a V(D) J sequence of an immune cell receptor (e.g., T-cell receptor), mRNA and a perturbation agent (e.g., a CRISPR crRNA/sgRNA, TALEN, zinc finger nuclease, and/or antisense oligonucleotide as described herein).

Analytes can include a nucleic acid molecule with a nucleic acid sequence encoding at least a portion of a V(D)J sequence of an immune cell receptor (e.g., a TCR or BCR). In some embodiments, the nucleic acid molecule is cDNA first generated from reverse transcription of the corresponding mRNA, using a poly(T) containing primer. The generated cDNA can then be barcoded using a capture probe, featuring a barcode sequence (and optionally, a UMI sequence) that hybridizes with at least a portion of the generated cDNA. In some embodiments, a template switching oligonucleotide hybridizes to a poly(C) tail added to a 3'end of the cDNA by a reverse transcriptase enzyme. The original mRNA template and template switching oligonucleotide can then be denatured from the cDNA and the barcoded capture probe can then hybridize with the cDNA and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described in PCT Patent Application PCT/US2017/057269, filed Oct. 18, 2017, and U.S. patent application Ser. No. 15/825,740, filed Nov. 29, 2017, both of which are incorporated herein by reference in their entireties. V(D)J analysis can also be completed with the use of one or more labelling agents that bind to particular surface features of immune cells and associated with barcode sequences. The one or more labelling agents can include an MHC or MHC multimer.

As described above, the analyte can include a nucleic acid capable of functioning as a component of a gene editing reaction, such as, for example, clustered regularly interspaced short palindromic repeats (CRISPR)-based gene editing. Accordingly, the capture probe can include a nucleic acid sequence that is complementary to the analyte (e.g., a sequence that can hybridize to the CRISPR RNA (crRNA), single guide RNA (sgRNA), or an adapter sequence engineered into a crRNA or sgRNA).

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

In general, the systems, apparatus, methods, and compositions can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate. Methods for performing multiplexed assays to analyze two or more different analytes will be discussed in a subsequent section of this disclosure.

(d) Biological Samples

(i) Types of Biological Samples

A "biological sample" is obtained from the subject for analysis using any of a variety of techniques including, but not limited to, biopsy, surgery, and laser capture microscopy (LCM), and generally includes cells and/or other biological material from the subject. In addition to the subjects described above, a biological sample can also be obtained from a prokaryote such as a bacterium, e.g., *Escherichia coli*, Staphylococci or *Mycoplasma pneumoniae*; an archaea; a virus such as Hepatitis C virus or human immunodeficiency virus; or a viroid. A biological sample can be obtained from non-mammalian organisms (e.g., a plants, an insect, an archnid, a nematode, a fungi, or an amphibian). A biological sample can also be obtained from a eukaryote, such as a patient derived organoid (PDO) or patient derived xenograft (PDX). Subjects from which biological samples can be obtained can be healthy or asymptomatic individuals, individuals that have or are suspected of having a disease (e.g., a patient with a disease such as cancer) or a predisposition to a disease, and/or individuals that are in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

Biological samples can also include fetal cells. For example, a procedure such as amniocentesis can be performed to obtain a fetal cell sample from maternal circulation. Sequencing of fetal cells can be used to identify any of a number of genetic disorders, including, e.g., aneuploidy such as Down's syndrome, Edwards syndrome, and Patau syndrome. Further, cell surface features of fetal cells can be used to identify any of a number of disorders or diseases.

Biological samples can also include immune cells. Sequence analysis of the immune repertoire of such cells, including genomic, proteomic, and cell surface features, can provide a wealth of information to facilitate an understanding the status and function of the immune system. By way of example, determining the status (e.g., negative or positive) of minimal residue disease (MRD) in a multiple myeloma (MM) patient following autologous stem cell transplantation is considered a predictor of MRD in the MM patient (see, e.g., U.S. Patent Application Publication No. 2018/0156784, the entire contents of which are incorporated herein by reference).

Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cells, thrombocytes/megakaryocytes, and dendritic cells.

As discussed above, a biological sample can include a single analyte of interest, or more than one analyte of interest. Methods for performing multiplexed assays to analyze two or more different analytes in a single biological sample will be discussed in a subsequent section of this disclosure.

(ii) Preparation of Biological Samples

A variety of steps can be performed to prepare a biological sample for analysis. Except where indicated otherwise, the preparative steps described below can generally be combined in any manner to appropriately prepare a particular sample for analysis.

(1) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 micrometers thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 micrometers. Thicker sections can also be used if desired or convenient, e.g., at least 70, 80, 90, or 100 micrometers or more. Typically, the thickness of a tissue section is between 1-100 micrometers, 1-50 micrometers, 1-30 micrometers, 1-25 micrometers, 1-20 micrometers, 1-15 micrometers, 1-10 micrometers, 2-8 micrometers, 3-7 micrometers, or 4-6 micrometers, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(2) Freezing

In some embodiments, the biological sample (e.g., a tissue section as described above) can be prepared by deep freezing at a temperature suitable to maintain or preserve the integrity (e.g., the physical characteristics) of the tissue structure. Such a temperature can be, e.g., less than −20° C., or less than −25° C., −30° C., −40° C., −50° C., −60° C., −70° C., −80° C. −90° C., −100° C., −110° C., −120° C., −130° C., −140° C., −150° C., −160° C., −170° C., −180° C., −190° C., or −200° C. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(3) Formalin Fixation and Paraffin Embedding

In some embodiments, the biological sample can be prepared using formalin-fixation and paraffin-embedding (FFPE), which are established methods. In some embodiments, cell suspensions and other non-tissue samples can be prepared using formalin-fixation and paraffin-embeddeding.

Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

(4) Fixation

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

(5) Embedding

As an alternative to paraffin embedding described above, a biological sample can be embedded in any of a variety of other embedding materials to provide structural substrate to the sample prior to sectioning and other handling steps. In general, the embedding material is removed prior to analysis of tissue sections obtained from the sample. Suitable embedding materials include, but are not limited to, waxes, resins (e.g., methacrylate resins), epoxies, and agar.

(6) Staining

To facilitate visualization, biological samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, propidium iodide, rhodamine, or safranine.

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(7) Hydrogel Embedding

In some embodiments, the biological sample can be embedded in a hydrogel matrix. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., *Science* 347(6221):543-548, 2015, the entire contents of which are incorporated herein by reference.

(8) Isometric Expansion

In some embodiments, a biological sample embedded in a hydrogel can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with capture probes, as will be discussed in greater detail in a subsequent section.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., *Nat. Methods* 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(9) Substrate Attachment

In some embodiments, the biological sample can be attached to a substrate. Examples of substrates suitable for this purpose are described in detail below. Attachment of the biological sample can be irreversible or reversible, depending upon the nature of the sample and subsequent steps in the analytical method.

In certain embodiments, the sample can be attached to the substrate reversibly by applying a suitable polymer coating to the substrate, and contacting the sample to the polymer coating. The sample can then be detached from the substrate using an organic solvent that at least partially dissolves the polymer coating. Hydrogels are examples of polymers that are suitable for this purpose.

More generally, in some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

(10) Disaggregation of Cells

In some embodiments, the biological sample corresponds to cells (e.g., derived from a cell culture or a tissue sample). In a cell sample with a plurality of cells, individual cells can be naturally unaggregated. For example, the cells can be derived from a suspension of cells and/or disassociated or disaggregated cells from a tissue or tissue section.

Alternatively, the cells in the sample may be aggregated, and may be disaggregated into individual cells using, for example, enzymatic or mechanical techniques. Examples of enzymes used in enzymatic disaggregation include, but are not limited to, dispase, collagenase, trypsin, and combinations thereof. Mechanical disaggregation can be performed, for example, using a tissue homogenizer.

(11) Suspended and Adherent Cells

In some embodiments, the biological sample can be derived from a cell culture grown in vitro. Samples derived from a cell culture can include one or more suspension cells which are anchorage-independent within the cell culture. Examples of such cells include, but are not limited to, cell lines derived from hematopoietic cells, and from the following cell lines: Colo205, CCRF-CEM, HL-60, K562, MOLT-4, RPMI-8226, SR, HOP-92, NCI-H322M, and MALME-3M.

Samples derived from a cell culture can include one or more adherent cells which grow on the surface of the vessel that contains the culture medium. Non-limiting examples of adherent cells include DU145 (prostate cancer) cells, H295R (adrenocortical cancer) cells, HeLa (cervical cancer) cells, KBM-7 (chronic myelogenous leukemia) cells, LNCaP (prostate cancer) cells, MCF-7 (breast cancer) cells, MDA-MB-468 (breast cancer) cells, PC3 (prostate cancer) cells, SaOS-2 (bone cancer) cells, SH-SY5Y (neuroblastoma, cloned from a myeloma) cells, T-47D (breast cancer) cells, THP-1 (acute myeloid leukemia) cells, U87 (glioblastoma) cells, National Cancer Institute's 60 cancer cell line panel (NCI60), vero (African green monkey Chlorocebus kidney epithelial cell line) cells, MC3T3 (embryonic calvarium) cells, GH3 (pituitary tumor) cells, PC12 (pheochromocytoma) cells, dog MDCK kidney epithelial cells, *Xenopus* A6 kidney epithelial cells, zebrafish AB9 cells, and Sf9 insect epithelial cells.

Additional examples of adherent cells are shown in Table 1 and catalogued, for example, in "A Catalog of in Vitro Cell Lines, Transplantable Animal and Human Tumors and Yeast," The Division of Cancer Treatment and Diagnosis (DCTD), National Cancer Institute (2013), and in Abaan et al., "The exomes of the NCI-60 panel: a genomic resource for cancer biology and systems pharmacology," *Cancer Research* 73(14):4372-82, 2013, the entire contents of each of which are incorporated by reference herein.

TABLE 1

Examples of adherent cells

| Cell Line | Species | Organ of Origin | Disease |
|---|---|---|---|
| BT549 | Human | Breast | Ductal Carcinoma |
| HS 578T | Human | Breast | Carcinoma |
| MCF7 | Human | Breast | Adenocarcinoma |
| MDA-MB-231 | Human | Breast | Adenocarcinoma |
| MDA-MB-468 | Human | Breast | Adenocarcinoma |
| T-47D | Human | Breast | Ductal Carcinoma |
| SF268 | Human | CNS | Anaplastic Astrocytoma |
| SF295 | Human | CNS | Glioblastoma-Multiforme |
| SF539 | Human | CNS | Glioblastoma |
| SNB-19 | Human | CNS | Glioblastoma |
| SNB-75 | Human | CNS | Astrocytoma |
| U251 | Human | CNS | Glioblastoma |
| Colo205 | Human | Colon | Dukes' type D, Colorectal adenocarcinoma |
| HCC 2998 | Human | Colon | Carcinoma |
| HCT-116 | Human | Colon | Carcinoma |
| HCT-15 | Human | Colon | Dukes' type C, Colorectal adenocarcinoma |
| HT29 | Human | Colon | Colorectal adenocarcinoma |
| KM12 | Human | Colon | Adenocarcinoma, Grade III |
| SW620 | Human | Colon | Adenocarcinoma |
| 786-O | Human | Kidney | renal cell adenocarcinoma |
| A498 | Human | Kidney | Adenocarcinoma |
| ACHN | Human | Kidney | renal cell adenocarcinoma |
| CAKI | Human | Kidney | clear cell carcinoma |
| RXF 393 | Human | Kidney | Poorly Differentiated Hypernephroma |
| SN12C | Human | Kidney | Carcinoma |
| TK-10 | Human | Kidney | Spindle Cell carcinoma |
| UO-31 | Human | Kidney | Carcinoma |
| A549 | Human | Lung | Adenocarcinoma |
| EKVX | Human | Lung | Adenocarcinoma |
| HOP-62 | Human | Lung | Adenocarcinoma |
| HOP-92 | Human | Lung | Large Cell, Undifferentiated |
| NCI-H226 | Human | Lung | squamous cell carcinoma; mesothelioma |
| NCI-H23 | Human | Lung | adenocarcinoma; non-small cell lung cancer |
| NCI-H460 | Human | Lung | carcinoma; large cell lung cancer |
| NCI-H522 | Human | Lung | adenocarcinoma; non-small cell lung cancer |

TABLE 1-continued

| Examples of adherent cells | | | |
|---|---|---|---|
| Cell Line | Species | Organ of Origin | Disease |
| LOX IMVI | Human | Melanoma | Malignant Amelanotic melanoma |
| M14 | Human | Melanoma | malignant melanoma |
| MALME-3M | Human | Melanoma | malignant melanoma |
| MDA-MB-435 | Human | Melanoma | Adenocarcinoma |
| SK-MEL-2 | Human | Melanoma | malignant melanoma |
| SK-MEL-28 | Human | Melanoma | malignant melanoma |
| SK-MEL-5 | Human | Melanoma | malignant melanoma |
| UACC-257 | Human | Melanoma | malignant melanoma |
| UACC-62 | Human | Melanoma | malignant melanoma |
| IGROV1 | Human | Ovary | Cystoadenocarcinoma |
| OVCAR-3 | Human | Ovary | Adenocarcinoma |
| OVCAR-4 | Human | Ovary | Adenocarcinoma |
| OVCAR-5 | Human | Ovary | Adenocarcinoma |
| OVCAR-8 | Human | Ovary | Adenocarcinoma |
| SK-OV-3 | Human | Ovary | Adenocarcinoma |
| NCI-ADR-RES | Human | Ovary | Adenocarcinoma |
| DU145 | Human | Prostate | Carcinoma |
| PC-3 | Human | Prostate | grade IV, adenocarcinoma |

In some embodiments, the adherent cells are cells that correspond to one or more of the following cell lines: BT549, HS 578T, MCF7, MDA-MB-231, MDA-MB-468, T-47D, SF268, SF295, SF539, SNB-19, SNB-75, U251, Colo205, HCC 2998, HCT-116, HCT-15, HT29, KM12, SW620, 786-O, A498, ACHN, CAKI, RXF 393, SN12C, TK-10, UO-31, A549, EKVX, HOP-62, HOP-92, NCI-H226, NCI-H23, NCI-H460, NCI-H522, LOX IMVI, M14, MALME-3M, MDA-MB-435, SK-, EL-2, SK-MEL-28, SK-MEL-5, UACC-257, UACC-62, IGROV1, OVCAR-3, OVCAR-4, OVCAR-5, OVCAR-8, SK-OV-3, NCI-ADR-RES, DU145, PC-3, DU145, H295R, HeLa, KBM-7, LNCaP, MCF-7, MDA-MB-468, PC3, SaOS-2, SH-SY5Y, T-47D, THP-1, U87, vero, MC3T3, GH3, PC12, dog MDCK kidney epithelial, *Xenopus* A6 kidney epithelial, zebrafish AB9, and Sf9 insect epithelial cell lines.

(12) Tissue Permeabilization

In some embodiments, a biological sample can be permeabilized to facilitate transfer of analytes out of the sample, and/or to facilitate transfer of species (such as capture probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., *Method Mol. Biol.* 588:63-66, 2010, the entire contents of which are incorporated herein by reference. Any suitable method for sample permeabilization can generally be used in connection with the samples described herein.

In some embodiments, where a diffusion-resistant medium is used to limit migration of analytes or other species during the analytical procedure, the diffusion-resistant medium can include at least one permeabilization reagent. For example, the diffusion-resistant medium can include wells (e.g., micro-, nano-, or picowells) containing a permeabilization buffer or reagents. In some embodiments, where the diffusion-resistant medium is a hydrogel, the hydrogel can include a permeabilization buffer. In some embodiments, the hydrogel is soaked in permeabilization buffer prior to contacting the hydrogel with a sample. In some embodiments, the hydrogel or other diffusion-resistant medium can contain dried reagents or monomers to deliver permeabilization reagents when the diffusion-resistant medium is applied to a biological sample. In some embodiments, the diffusion-resistant medium, (i.e. hydrogel) is covalently attached to a solid substrate (i.e. an acrylated glass slide). In some embodiments, the hydrogel can be modified to both contain capture probes and deliver permeabilization reagents. For example, a hydrogel film can be modified to include spatially-barcoded capture probes. The spatially-barcoded hydrogel film is then soaked in permeabilization buffer before contacting the spatially-barcoded hydrogel film to the sample. The spatially-barcoded hydrogel film thus delivers permeabilization reagents to a sample surface in contact with the spatially-barcoded hydrogel, enhancing analyte migration and capture. In some embodiments, the spatially-barcoded hydrogel is applied to a sample and placed in a permeabilization bulk solution. In some embodiments, the hydrogel film soaked in permeabilization reagents is sandwiched between a sample and a spatially-barcoded array. In some embodiments, target analytes are able to diffuse through the permeabilizing reagent soaked hydrogel and hybridize or bind the capture probes on the other side of the hydrogel. In some embodiments, the thickness of the hydrogel is proportional to the resolution loss. In some embodiments, wells (e.g., micro-, nano-, or picowells) can contain spatially-barcoded capture probes and permeabilization reagents and/or buffer. In some embodiments, spatially-barcoded capture probes and permeabilization reagents are held between spacers. In some embodiments, the sample is punch, cut, or transferred into the well, wherein a target analyte diffuses through the permeabilization reagent/buffer and to the spatially-barcoded capture probes. In some embodiments, resolution loss may be proportional to gap thickness (e.g. the amount of permeabilization buffer between the sample and the capture probes). In some embodiments, the diffusion-resistant medium (e.g. hydrogel) is between approximately 50-500 micrometers thick including 500, 450, 400, 350, 300, 250, 200, 150, 100, or 50 micrometers thick, or any thickness within 50 and 500 micrometers.

In some embodiments, permeabilization solution can be delivered to a sample through a porous membrane. In some embodiments, a porous membrane is used to limit diffusive analyte losses, while allowing permeabilization reagents to reach a sample. Membrane chemistry and pore size can be manipulated to minimize analyte loss. In some embodiments, the porous membrane may be made of glass, silicon, paper, hydrogel, polymer monoliths, or other material. In some embodiments, the material may be naturally porous. In some embodiments, the material may have pores or wells etched into solid material. In some embodiments, the permeabilization reagents are flowed through a microfluidic chamber or channel over the porous membrane. In some embodiments, the flow controls the sample's access to the permeabilization reagents. In some embodiments, a porous membrane is sandwiched between a spatially-barcoded array and the sample, wherein permeabilization solution is applied over the porous membrane. The permeabilization reagents diffuse through the pores of the membrane and into the tissue.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be peremeabilized by non-chemical permeabilization methods. Non-chemical permeabilization methods are known in the art. For example, non-chemical permeabilization methods that can be used include, but are not limited to, physical lysis techniques such as electroporation, mechanical permeabilitzation methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

(13) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by a polymerase. For example, one or more primer sequences with sequence complementarity to one or more RNAs of interest can be used to amplify the one or more RNAs of interest, thereby selectively enriching these RNAs. In some embodiments, an oligonucleotide with sequence complementarity to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using any of a variety of methods known to the field (e.g., streptavidin beads).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Subsequent application of the capture probes to the sample can result in improved capture of other types of RNA due to the reduction in non-specific RNA present in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics,* 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, Biotechniques, 53(6) 373-80, (2012), the entire contents of which are incorporated herein by reference).

(14) Other Reagents

Additional reagents can be added to a biological sample to perform various functions prior to analysis of the sample. In some embodiments, DNase and RNase inactivating agents or inhibitors such as proteinase K, and/or chelating agents such as EDTA, can be added to the sample.

In some embodiments, the sample can be treated with one or more enzymes. For example, one or more endonucleases to fragment DNA, DNA polymerase enzymes, and dNTPs used to amplify nucleic acids can be added. Other enzymes that can also be added to the sample include, but are not limited to, polymerase, transposase, ligase, and DNAse, and RNAse.

In some embodiments, reverse transcriptase enzymes can be added to the sample, including enzymes with terminal transferase activity, primers, and switch oligonucleotides. Template switching can be used to increase the length of a cDNA, e.g., by appending a predefined nucleic acid sequence to the cDNA.

(15) Pre-Processing for Capture Probe Interaction

In some embodiments, analytes in a biological sample can be pre-processed prior to interaction with a capture probe. For example, prior to interaction with capture probes, polymerization reactions catalyzed by a polymerase (e.g., DNA polymerase or reverse transcriptase) are performed in the biological sample. In some embodiments, a primer for the polymerization reaction includes a functional group that enhances hybridization with the capture probe. The capture probes can include appropriate capture domains to capture biological analytes of interest (e.g., poly(dT) sequence to capture poly(A) mRNA).

In some embodiments, biological analytes are pre-processed for library generation via next generation sequencing. For example, analytes can be pre-processed by addition of a modification (e.g., ligation of sequences that allow interaction with capture probes). In some embodiments, analytes (e.g., DNA or RNA) are fragmented using fragmentation techniques (e.g., using transposases and/or fragmentation buffers).

Fragmentation can be followed by a modification of the analyte. For example, a modification can be the addition through ligation of an adapter sequence that allows hybridization with the capture probe. In some embodiments, where the analyte of interest is RNA, poly(A) tailing is performed. Addition of a poly(A) tail to RNA that does not contain a poly(A) tail can facilitate hybridization with a capture probe that includes a capture domain with a functional amount of poly(dT) sequence.

In some embodiments, prior to interaction with capture probes, ligation reactions catalyzed by a ligase are performed in the biological sample. In some embodiments, ligation can be performed by chemical ligation. In some embodiments, the ligation can be performed using click chemistry as further below. In some embodiments, the capture domain includes a DNA sequence that has complementarity to a RNA molecule, where the RNA molecule has complementarity to a second DNA sequence, and where the RNA-DNA sequence complementarity is used to ligate the second DNA sequence to the DNA sequence in the capture domain. In these embodiments, direct detection of RNA molecules is possible.

In some embodiments, prior to interaction with capture probes, target-specific reactions are performed in the biological sample. Examples of target specific reactions include, but are not limited to, ligation of target specific adaptors, probes and/or other oligonucleotides, target specific amplification using primers specific to one or more analytes, and target-specific detection using in situ hybridization, DNA microscopy, and/or antibody detection. In some embodiments, a capture probe includes capture domains targeted to target-specific products (e.g., amplification or ligation).

II. General Spatial Array-Based Analytical Methodology

This section of the disclosure describes methods, apparatus, systems, and compositions for spatial array-based analysis of biological samples.

(a) Spatial Analysis Methods

Array-based spatial analysis methods involve the transfer of one or more analytes from a biological sample to an array of features on a substrate, each of which is associated with a unique spatial location on the array. Subsequent analysis of the transferred analytes includes determining the identity of the analytes and the spatial location of each analyte within the sample. The spatial location of each analyte within the sample is determined based on the feature to which each analyte is bound in the array, and the feature's relative spatial location within the array.

There are at least two general methods to associate a spatial barcode with one or more neighboring cells, such that the spatial barcode identifies the one or more cells, and/or contents of the one or more cells, as associated with a particular spatial location. One general method is to drive target analytes out of a cell and towards the spatially-barcoded array. FIG. 1 depicts an exemplary embodiment of this general method. In FIG. 1, the spatially-barcoded array populated with capture probes (as described further herein) is contacted with a sample 101, and sample is permeabilized, allowing the target analyte to migrate away from the sample and toward the array. The target analyte interacts with a capture probe on the spatially-barcoded array 102. Once the target analyte hybridizes/is bound to the capture probe, the sample is optionally removed from the array and the capture probes are analyzed in order to obtain spatially-resolved analyte information 103.

Figure 2:
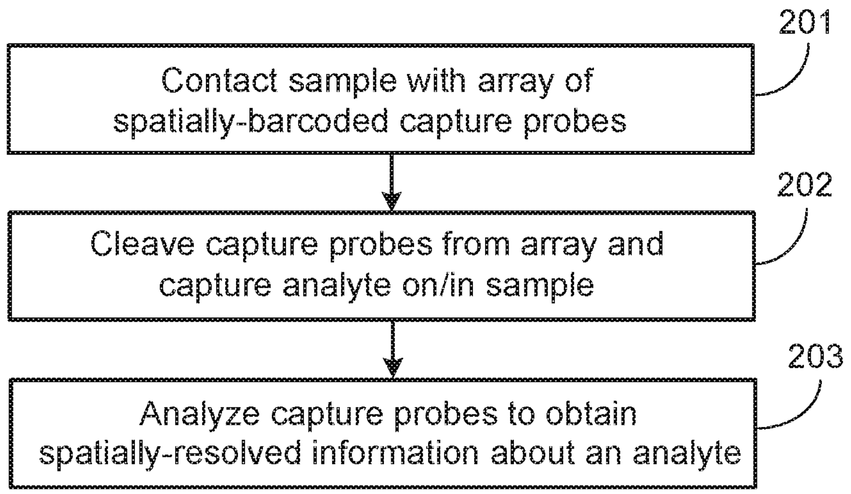
FIG. 2 shows an exemplary spatial analysis workflow.

Another general method is to cleave the spatially-barcoded capture probes from an array, and drive the spatially-barcoded capture probes towards and/or into or onto the sample. FIG. 2 depicts an exemplary embodiment of this general method, the spatially-barcoded array populated with capture probes (as described further herein) can be contacted with a sample 201. The spatially-barcoded capture probes are cleaved and then interact with cells within the provided sample 202. The interaction can be a covalent or non-covalent cell-surface interaction. The interaction can be an intracellular interaction facilitated by a delivery system or a cell penetration peptide. Once the spatially-barcoded capture probe is associated with a particular cell, the sample can be optionally removed for analysis. The sample can be optionally dissociated before analysis. Once the tagged cell is associated with the spatially-barcoded capture probe, the capture probes can be analyzed to obtain spatially-resolved information about the tagged cell 203.

Figure 3:
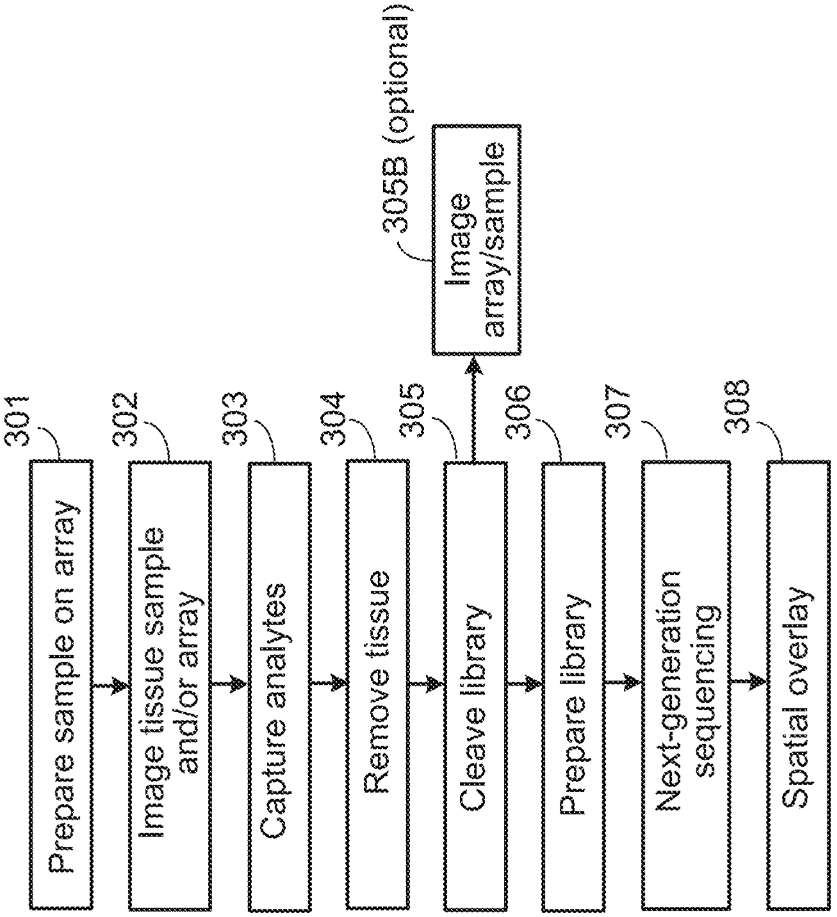
FIG. 3 shows an exemplary spatial analysis workflow.

FIG. 3 shows an exemplary workflow that includes preparing a sample on a spatially-barcoded array 301. Sample preparation may include placing the sample on a slide, fixing the sample, and/or staining the sample for imaging. The stained sample is then imaged on the array 302 using both brightfield (to image the sample hematoxylin and eosin stain) and fluorescence (to image features) modalities. In some embodiments, target analytes are then released from the sample and capture probes forming the spatially-barcoded array hybridize or bind the released target analytes 303. The sample is then removed from the array 304 and the capture probes cleaved from the array 305. The sample and array are then optionally imaged a second time in both modalities 305B while the analytes are reverse transcribed into cDNA, and an amplicon library is prepared 306 and sequenced 307. The two sets of images are then spatially-overlaid in order to correlate spatially-identified sample information 308. When the sample and array are not imaged a second time, 305B, a spot coordinate file is supplied by the manufacturer instead. The spot coordinate file replaces the second imaging step 305B. Further, amplicon library preparation 306 can be performed with a unique PCR adapter and sequenced 307.

Figure 4:
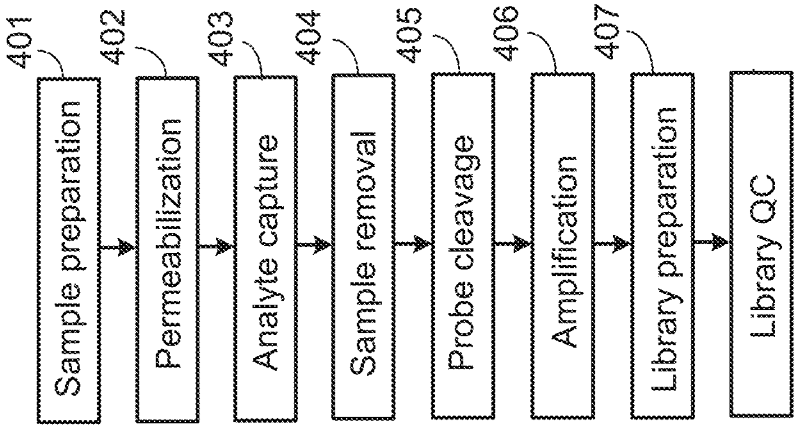
FIG. 4 shows an exemplary spatial analysis workflow.

FIG. 4 shows another exemplary workflow that utilizes a spatially-labelled array on a substrate, where capture probes labelled with spatial barcodes are clustered at areas called features. The spatially-labelled capture probes can include a cleavage domain, one or more functional sequences, a spatial barcode, a unique molecular identifier, and a capture domain. The spatially-labelled capture probes can also include a 5' end modification for reversible attachment to the substrate. The spatially-barcoded array is contacted with a sample 401, and the sample is permeabilized through application of permeabilization reagents 402. Permeabilization reagents may be administered by placing the array/sample assembly within a bulk solution. Alternatively, permeabilization reagents may be administered to the sample via a diffusion-resistant medium and/or a physical barrier such as a lid, wherein the sample is sandwiched between the diffusion-resistant medium and/or barrier and the array-containing substrate. The analytes are migrated toward the spatially-barcoded capture array using any number of techniques disclosed herein. For example, analyte migration can occur using a diffusion-resistant medium lid and passive migration. As another example, analyte migration can be active migration, using an electrophoretic transfer system, for example. Once the analytes are in close proximity to the spatially-barcoded capture probes, the capture probes can hybridize or otherwise bind a target analyte 403. The sample can be optionally removed from the array 404.

The capture probes can be optionally cleaved from the array 405, and the captured analytes can be spatially-tagged by performing a reverse transcriptase first strand cDNA reaction. A first strand cDNA reaction can be optionally performed using template switching oligonucleotides. For example, a template switching oligonucleotide can hybridize to a poly(C) tail added to a 3'end of the cDNA by a reverse transcriptase enzyme. The original mRNA template and template switching oligonucleotide can then be denatured from the cDNA and the barcoded capture probe can then hybridize with the cDNA and a complement of the cDNA can be generated. The first strand cDNA can then be purified and collected for downstream amplification steps. The first strand cDNA can be amplified using PCR 406, wherein the forward and reverse primers flank the spatial barcode and target analyte regions of interest, generating a library associated with a particular spatial barcode. In some embodiments, the cDNA comprises a sequencing by synthesis (SBS) primer sequence. The library amplicons are sequenced and analyzed to decode spatial information 407.

Figure 5:
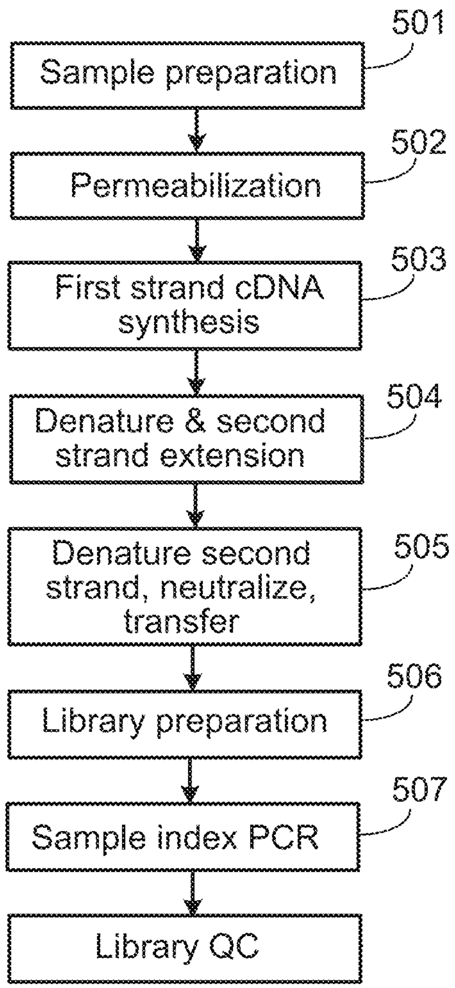
FIG. 5 shows an exemplary spatial analysis workflow.

FIG. 5 depicts an exemplary workflow where the sample is removed from the spatially-barcoded array and the spatially-barcoded capture probes are removed from the array for barcoded analyte amplification and library preparation. Another embodiment includes performing first strand synthesis using template switching oligonucleotides on the spatially-barcoded array without cleaving the capture probes. In this embodiment, sample preparation 501 and permeabilization 502 are performed as described elsewhere herein. Once the capture probes capture the target analyte(s), first strand cDNA created by template switching and reverse transcriptase 503 is then denatured and the second strand is then extended 504. The second strand cDNA is then denatured from the first strand cDNA, neutralized, and transferred to a tube 505. cDNA quantification and amplification can be performed using standard techniques discussed herein. The cDNA can then be subjected to library preparation 506 and indexing 507, including fragmentation, end-repair, and a-tailing, and indexing PCR steps.

In some non-limiting examples of the workflow above, the sample can be immersed in 100% chilled methanol and incubated for 30 minutes at −20° C. After 20 minutes, the sample can be removed and rinsed in ultrapure water. After rinsing the sample, fresh eosin solution is prepared, and the sample can be covered in isopropanol. After incubating the sample in isopropanol for 1 minute, the reagent can be removed by holding the slide at an angle, where the bottom edge of the slide can be in contact with a laboratory wipe and air dried. The sample can be uniformly covered in hematoxylin solution and incubated for 7 minutes at room temperature. After incubating the sample in hematoxylin for 7 minutes, the reagent can be removed by holding the slide at an angle, where the bottom edge of the slide can be in contact with a laboratory wipe. The slide containing the sample can be immersed in water and the excess liquid can be removed. After that, the sample can be covered with blueing buffer and can be incubated for 2 minutes at room temperature. The slide containing the sample can again be immersed in water, and uniformly covered with eosin solution and incubated for 1 minute at room temperature. The slide can be air-dried and incubated for 5 minutes at 37° C. The sample can be imaged using the methods disclosed herein.

The following are non-limiting, exemplary steps for sample permeabilization and cDNA generation. The sample can be exposed to a permeabilization enzyme and incubated for 6 minutes at 37° C. Other permeabilization methods are described herein. The permeabilization enzyme can be removed and the sample prepared for analyte capture by adding SSC buffer. The sample can then subjected to a pre-equilibration thermocycling protocol and the SSC buffer can be removed. A Master Mix, containing nuclease-free water, a reverse transcriptase reagent, a template switch oligo, a reducing agent, and a reverse transcriptase enzyme can be added, and the sample with the Master Mix can be subjected to a thermocycling protocol. The reagents can be removed from the sample and NaOH can be applied and incubated for 5 minutes at room temperature. The NaOH can be removed and elution buffer can be added and removed from the sample. A Second Strand Mix, including a second strand reagent, a second strand primer, and a second strand enzyme, can be added to the sample and the sample can be sealed and incubated. At the end of the incubation, the reagents can be removed and elution buffer can be added and removed from the sample, and NaOH can be added again to the sample and the sample can be incubated for 10 minutes at room temperature. Tris-HCl can be added and the reagents can be mixed.

The following steps are non-limiting, exemplary steps for cDNA amplification and quality control. A qPCR Mix, including nuclease-free water, qPCR Master Mix, and cDNA primers, can be prepared and the NaOH/Tris-HCl mix can be mixed with the qPCR Mix and the sample, and thermocycled according to a predetermined thermocycling protocol. After completing the thermocycling, a cDNA amplification mix can be prepared and combined with the sample and mixed. The sample can then be incubated and thermocycled. The sample can then be resuspended in SPRIselect Reagent and pipetted to ensure proper mixing. The sample can then be incubated at 5 minutes at room temperature, and cleared by placing the sample on a magnet (e.g., the magnet is in the high position). The supernatant can be removed and 80% ethanol can be added to the pellet, and incubated for 30 seconds. The ethanol can be removed and the pellet can be washed again. The sample can then be centrifuged and placed on a magnet (e.g., the magnet is on the low position). Any remaining ethanol can be removed and the sample can be air dried. The magnet can be removed and elution buffer can be added to the sample, mixed, and incubated for 2 minutes at room temperature. The sample can then be placed on the magnet (e.g., on high position) until the solution clears. A portion of the sample can be run on an Agilent Bioanalyzer High Sensitivity chip, where a region can be selected and the cDNA concentration can be measured to calculate the total cDNA yield. Alternatively, the quantification can be determined by Agilent Bioanalyzer or Agilent TapeStation.

The following steps are non-limiting, exemplary steps for spatial gene expression library construction. A Fragmentation Mix, including a fragmentation buffer and fragmentation enzyme, can be prepared on ice. Elution buffer and fragmentation mix can be added to each sample, mixed, and centrifuged. The sample mix can then be placed in a thermocycler and cycled according to a predetermined protocol. The SPRIselect Reagent can be added to the sample and incubated at 5 minutes at room temperature. The sample can be placed on a magnet (e.g., in the high position) until the solution clears, and the supernatant can be transferred to a new tube strip. SPRIselect Reagent can be added to the sample, mixed, and incubated for 5 minutes at room temperature. The sample can be placed on a magnet (e.g., in the high position) until the solution clears. The supernatant can be removed and 80% ethanol can be added to the pellet, the pellet can be incubated for 30 seconds, and the ethanol can be removed. The ethanol wash can be repeated and the sample placed on a magnet (e.g., in the low position) until the solution clears. The remaining ethanol can be removed and elution buffer can be added to the sample, mixed, and incubated for 2 minutes at room temperature. The sample can be placed on a magnet (e.g., in the high position) until the solution clears, and a portion of the sample can be moved to a new tube strip. An Adaptor Ligation Mix, including ligation buffer, DNA ligase, and adaptor oligos, can be prepared and centrifuged. The Adaptor Ligation Mix can be added to the sample, pipette-mixed, and centrifuged briefly. The sample can then be thermocycled according to a predetermined protocol. The SPRIsleect Reagent can be added to the sample, incubated for 5 minutes at room temperature, and placed on a magnet (e.g., in the high position) until the solution clears. The supernatant can be removed and the pellet can be washed with 80% ethanol, incubated for 30 seconds, and the ethanol can be removed. The ethanol wash can be repeated, and the sample can be centrifuged briefly before placing the sample on a magnet (e.g., in the low position). Any remaining ethanol can be removed and the sample can be air dried. Elution buffer can be added to the sample, the sample can be removed from the magnet, and the sample can be pipette-mixed, incubated for 2 minutes at room temperature, and placed on a magnet (e.g., in the low position) until the solution clears. A portion of the sample can be transferred to a new tube strip. A Sample Index PCR Mix, including amplification mix and SI primer, can be prepared and combined with the sample. The sample/Sample Index PCR Mix can be loaded into an individual Chromium i7 Sample Index well and a thermocycling protocol can be used. SPRIselect Reagent can be added to each sample, mixed, and incubated for 5 minutes at room temperature. The sample can be placed on a magnet (e.g., in the high position) until the solution clears, and the supernatant can be transferred to a new tube strip. The SPRIselect Reagent can be added to each sample, pipette-mixed, and incubated for 5 minutes at room temperature. The sample can then placed on a magnet (e.g., in the high position) until the solution clears. The supernatant can be removed, and the pellet can be washed with 80% ethanol, incubated for 30 seconds, and then the ethanol can be removed. The ethanol wash can be repeated, the sample centrifuged, and placed on a magnet (e.g., in the low position) to remove any remaining ethanol. The sample can be removed from the magnet and Elution Buffer can be added to the sample, pipette-mixed, and incubated at 2 minutes at room temperature. The sample can be placed on a magnet (e.g., in the low position) until the solution clears and a portion of the sample can be transferred to a new tube strip. The average fragment size can be determined using a Bioanalyzer trace or an Agilent TapeStation.

In some embodiments, performing correlative analysis of data produced by this workflow, and other workflows described herein, can yield over 95% correlation of genes expressed across two capture areas (e.g. 95% or greater, 96% or greater, 97% or greater, 98% or greater, or 99% or greater). When performing the described workflows using single cell RNA sequencing of nuclei, in some embodiments, correlative analysis of the data can yield over 90% (e.g. over 90%, 91%, 92%, 93%, 94%, 95%, 96%, 97%, 98%, or 99%) correlation of genes expressed across two capture areas.

(b) Capture Probes

A "capture probe" refers to any molecule capable of capturing (directly or indirectly) and/or labelling an analyte of interest in a biological sample. In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain.

Figure 6:
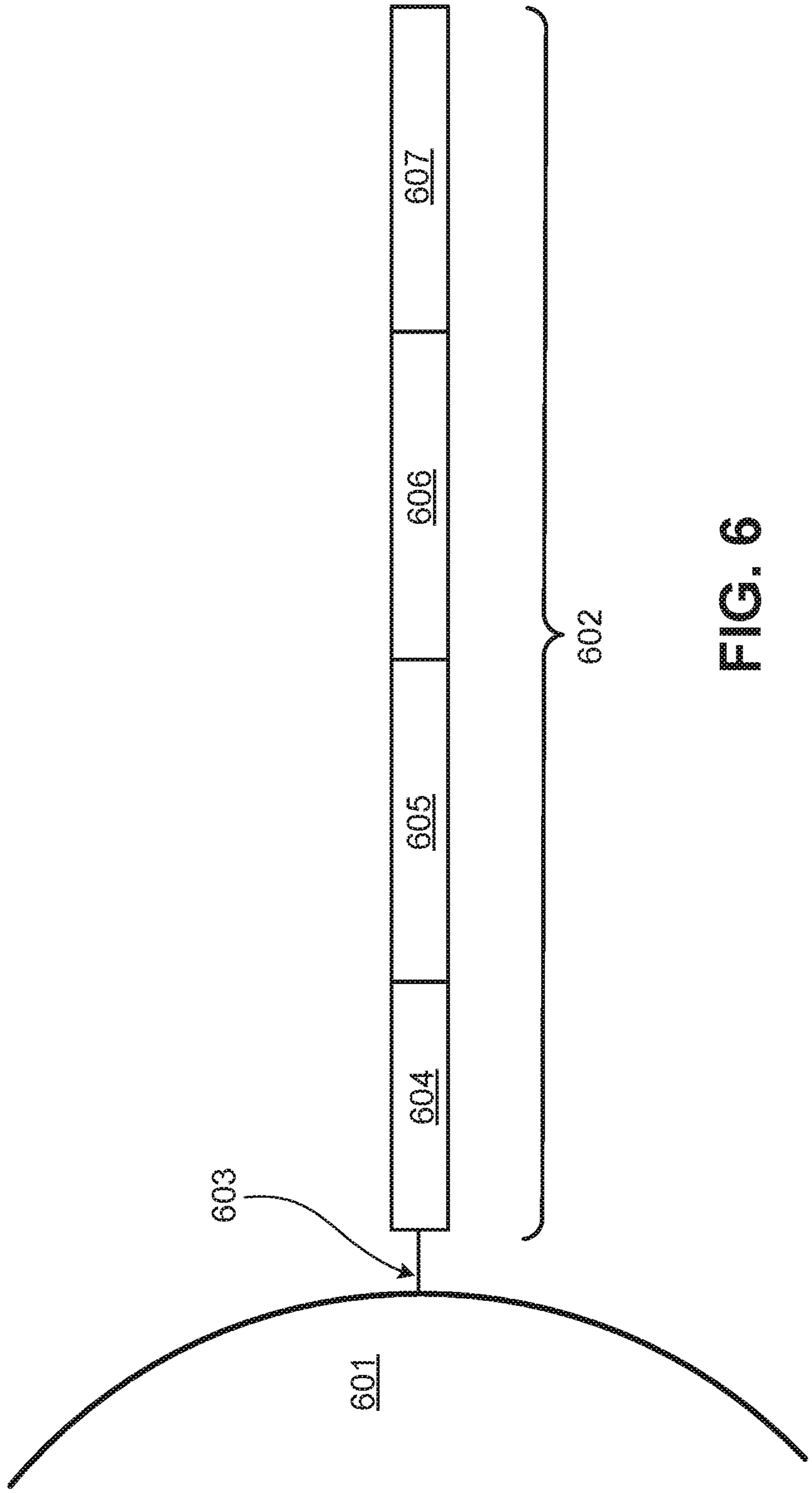
FIG. 6 is a schematic diagram showing an example of a barcoded capture probe, as described herein.

FIG. 6 is a schematic diagram showing an example of a capture probe, as described herein. As shown, the capture probe 602 is optionally coupled to a feature 601 by a cleavage domain 603, such as a disulfide linker. The capture probe can include functional sequences that are useful for subsequent processing, such as functional sequence 604, which can include a sequencer specific flow cell attachment sequence, e.g., a P5 sequence, as well as functional sequence 606, which can include sequencing primer sequences, e.g., a R1 primer binding site. In some embodiments, sequence 604 is a P7 sequence and sequence 606 is a R2 primer binding site. A spatial barcode 605 can be included within the capture probe for use in barcoding the target analyte. The functional sequences can generally be selected for compatibility with any of a variety of different sequencing systems, e.g., 454 Sequencing, Ion Torrent Proton or PGM, Illumina X10, PacBio, Nanopore, etc., and the requirements thereof. In some embodiments, functional sequences can be selected for compability with non-commercialized sequencing systems. Examples of such sequencing systems and techniques, for which suitable functional sequences can be used, include (but are not limited to) Roche 454 sequencing, Ion Torrent Proton or PGM sequencing, Illumina X10 sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 605, functional sequences 604 (e.g., flow cell attachment sequence) and 606 (e.g., sequencing primer sequences) can be common to all of the probes attached to a given feature. The spatial barcode can also include a capture domain 607 to facilitate capture of a target analyte.

Capture Domain

As discussed above, each capture probe includes at least one capture domain. The "capture domain" is an oligonucleotide, a polypeptide, a small molecule, or any combination thereof, that binds specifically to a desired analyte. In some embodiments, a capture domain can be used to capture or detect a desired analyte.

In some embodiments, the capture domain is a functional nucleic acid sequence configured to interact with one or more analytes, such as one or more different types of nucleic acids (e.g., RNA molecules and DNA molecules). In some embodiments, the functional nucleic acid sequence can include an N-mer sequence (e.g., a random N-mer sequence), which N-mer sequences are configured to interact with a plurality of DNA molecules. In some embodiments, the functional sequence can include a poly(T) sequence, which poly(T) sequences are configured to interact with messenger RNA (mRNA) molecules via the poly (A) tail of an mRNA transcript. In some embodiments, the functional nucleic acid sequence is the binding target of a protein (e.g., a transcription factor, a DNA binding protein, or a RNA binding protein), where the analyte of interest is a protein.

Capture probes can include ribonucleotides and/or deoxyribonucleotides as well as synthetic nucleotide residues that are capable of participating in Watson-Crick type or analogous base pair interactions. In some embodiments, the capture domain is capable of priming a reverse transcription reaction to generate cDNA that is complementary to the captured RNA molecules. In some embodiments, the capture domain of the capture probe can prime a DNA extension (polymerase) reaction to generate DNA that is complementary to the captured DNA molecules. In some embodiments, the capture domain can template a ligation reaction between the captured DNA molecules and a surface probe that is directly or indirectly immobilized on the substrate. In some embodiments, the capture domain can be ligated to one strand of the captured DNA molecules. For example, SplintR ligase along with RNA or DNA sequences (e.g., degenerate RNA) can be used to ligate a single-stranded DNA or RNA to the capture domain. In some embodiments, ligases with RNA-templated ligase activity, e.g., SplintR ligase, T4 RNA ligase 2 or KOD ligase, can be used to ligate a single-stranded DNA or RNA to the capture domain. In some embodiments, a capture domain includes a splint oligonucleotide. In some embodiments, a capture domain captures a splint oligonucleotide.

In some embodiments, the capture domain is located at the 3' end of the capture probe and includes a free 3' end that can be extended, e.g. by template dependent polymerization, to form an extended capture probe as described herein. In some embodiments, the capture domain includes a nucleotide sequence that is capable of hybridizing to nucleic acid, e.g. RNA or other analyte, present in the cells of the tissue sample contacted with the array. In some embodiments, the capture domain can be selected or designed to bind selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, i.e., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly(U) oligonucleotide or an oligonucleotide included of deoxythymidine analogues. In some embodiments, the capture domain includes at least 10, 11, 12, 13, 14, 15, 16, 17, 18, 19, or 20 nucleotides. In some embodiments, the capture domain includes at least 25, 30, or 35 nucleotides.

In some embodiments, random sequences, e.g., random hexamers or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" probe). This can, for example, be located 5' or 3' of the poly(T) sequence, e.g. at the 3' end of the capture domain. The poly(T)-random sequence probe can facilitate the capture of the mRNA poly(A) tail. In some embodiments, the capture domain can be an entirely random sequence. In some embodiments, degenerate capture domains can be used.

In some embodiments, a pool of two or more capture probes form a mixture, where the capture domain of one or more capture probes includes a poly(T) sequence and the capture domain of one or more capture probes includes random sequences. In some embodiments, a pool of two or more capture probes form a mixture where the capture domain of one or more capture probes includes poly(T)-like sequence and the capture domain of one or more capture probes includes random sequences. In some embodiments, a pool of two or more capture probes form a mixture where the capture domain of one or more capture probes includes a poly(T)-random sequences and the capture domain of one or more capture probes includes random sequences. In some embodiments, probes with degenerate capture domains can be added to any of the preceding combinations listed herein. In some embodiments, probes with degenerate capture domains can be substituted for one of the probes in each of the pairs described herein.

The capture domain can be based on a particular gene sequence or particular motif sequence or common/conserved sequence, that it is designed to capture (i.e., a sequence-specific capture domain). Thus, in some embodiments, the capture domain is capable of binding selectively to a desired sub-type or subset of nucleic acid, for example a particular type of RNA, such as mRNA, rRNA, tRNA, SRP RNA, tmRNA, snRNA, snoRNA, SmY RNA, scaRNA, gRNA, RNase P, RNase MRP, TERC, SL RNA, aRNA, cis-NAT, crRNA, lncRNA, miRNA, piRNA, siRNA, shRNA, tasiRNA, rasiRNA, 7SK, eRNA, ncRNA or other types of RNA. In a non-limiting example, the capture domain can be capable of binding selectively to a desired subset of ribonucleic acids, for example, microbiome RNA, such as 16S rRNA.

In some embodiments, a capture domain includes an "anchor" or "anchoring sequence", which is a sequence of nucleotides that is designed to ensure that the capture domain hybridizes to the intended biological analyte. In some embodiments, an anchor sequence includes a sequence of nucleotides, including a 1-mer, 2-mer, 3-mer or longer sequence. In some embodiments, the short sequence is random. For example, a capture domain including a poly(T) sequence can be designed to capture an mRNA. In such embodiments, an anchoring sequence can include a random 3-mer (e.g., GGG) that helps ensure that the poly(T) capture domain hybridizes to an mRNA. In some embodiments, an anchoring sequence can be VN, N, or NN. Alternatively, the sequence can be designed using a specific sequence of nucleotides. In some embodiments, the anchor sequence is at the 3' end of the capture domain. In some embodiments, the anchor sequence is at the 5' end of the capture domain.

In some embodiments, capture domains of capture probes are blocked prior to contacting the biological sample with the array, and blocking probes are used when the nucleic acid in the biological sample is modified prior to its capture on the array. In some embodiments, the blocking probe is used to block or modify the free 3' end of the capture domain. In some embodiments, blocking probes can be hybridized to the capture probes to mask the free 3' end of the capture domain, e.g., hairpin probes or partially double stranded probes. In some embodiments, the free 3' end of the capture domain can be blocked by chemical modification, e.g., addition of an azidomethyl group as a chemically reversible capping moiety such that the capture probes do not include a free 3' end. Blocking or modifying the capture probes, particularly at the free 3' end of the capture domain, prior to contacting the biological sample with the array, prevents modification of the capture probes, e.g., prevents the addition of a poly(A) tail to the free 3' end of the capture probes.

Non-limiting examples of 3' modifications include dideoxy C-3' (3'-ddC), 3' inverted dT, 3' C3 spacer, 3'Amino, and 3' phosphorylation. In some embodiments, the nucleic acid in the biological sample can be modified such that it can be captured by the capture domain. For example, an adaptor sequence (including a binding domain capable of binding to the capture domain of the capture probe) can be added to the end of the nucleic acid, e.g., fragmented genomic DNA. In some embodiments, this is achieved by ligation of the adaptor sequence or extension of the nucleic acid. In some embodiments, an enzyme is used to incorporate additional nucleotides at the end of the nucleic acid sequence, e.g., a poly(A) tail. In some embodiments, the capture probes can be reversibly masked or modified such that the capture domain of the capture probe does not include a free 3' end. In some embodiments, the 3' end is removed, modified, or made inaccessible so that the capture domain is not susceptible to the process used to modify the nucleic acid of the biological sample, e.g., ligation or extension.

In some embodiments, the capture domain of the capture probe is modified to allow the removal of any modifications of the capture probe that occur during modification of the nucleic acid molecules of the biological sample. In some embodiments, the capture probes can include an additional sequence downstream of the capture domain, i.e., 3' to the capture domain, namely a blocking domain.

In some embodiments, the capture domain of the capture probe can be a non-nucleic acid domain. Examples of suitable capture domains that are not exclusively nucleic-acid based include, but are not limited to, proteins, peptides, aptamers, antigens, antibodies, and molecular analogs that mimic the functionality of any of the capture domains described herein.

Cleavage Domain

Each capture probe can optionally include at least one cleavage domain. The cleavage domain represents the portion of the probe that is used to reversibly attach the probe to an array feature, as will be described further below. Further, one or more segments or regions of the capture probe can optionally be released from the array feature by cleavage of the cleavage domain. As an example spatial barcodes and/or universal molecular identifiers (UMIs) can be released by cleavage of the cleavage domain.

Figure 7:
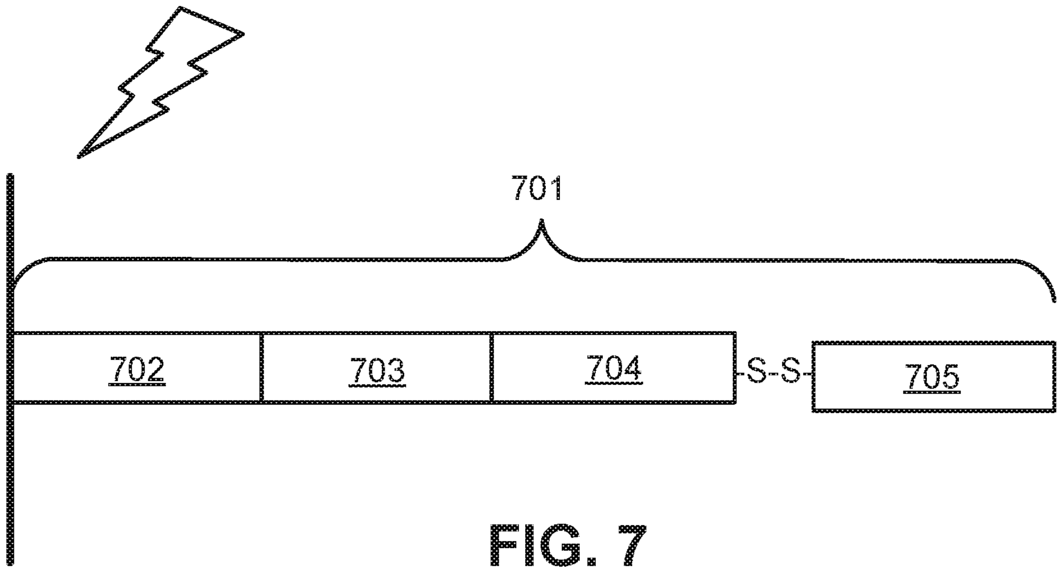
FIG. 7 is a schematic illustrating a cleavable capture probe, wherein the cleaved capture probe can enter into a non-permeabilized cell and bind to target analytes within the sample.

FIG. 7 is a schematic illustrating a cleavable capture probe, wherein the cleaved capture probe can enter into a non-permeabilized cell and bind to target analytes within the sample. The capture probe 701 contains a cleavage domain 702, a cell penetrating peptide 703, a reporter molecule 704, and a disulfide bond (—S—S—). 705 represents all other parts of a capture probe, for example a spatial barcode and a capture domain.

In some embodiments, the cleavage domain linking the capture probe to a feature is a disulfide bond. A reducing agent can be added to break the disulfide bonds, resulting in release of the capture probe from the feature. As another example, heating can also result in degradation of the cleavage domain and release of the attached capture probe from the array feature. In some embodiments, laser radiation is used to heat and degrade cleavage domains of capture probes at specific locations. In some embodiments, the cleavage domain is a photo-sensitive chemical bond (i.e., a chemical bond that dissociates when exposed to light such as ultraviolet light).

Other examples of cleavage domains include labile chemical bonds such as, but not limited to, ester linkages (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

In some embodiments, the cleavage domain includes a sequence that is recognized by one or more enzymes capable of cleaving a nucleic acid molecule, e.g., capable of breaking the phosphodiester linkage between two or more nucleotides. A bond can be cleavable via other nucleic acid molecule targeting enzymes, such as restriction enzymes (e.g., restriction endonucleases). For example, the cleavage domain can include a restriction endonuclease (restriction enzyme) recognition sequence. Restriction enzymes cut double-stranded or single stranded DNA at specific recognition nucleotide sequences known as restriction sites. In some embodiments, a rare-cutting restriction enzyme, i.e., enzymes with a long recognition site (at least 8 base pairs in length), is used to reduce the possibility of cleaving elsewhere in the capture probe.

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. Releasable capture probes can be available for reaction once released. Thus, for example, an activatable capture probe can be activated by releasing the capture probes from a feature.

In some embodiments, where the capture probe is attached indirectly to a substrate, e.g., via a surface probe, the cleavage domain includes one or more mismatch nucleotides, so that the complementary parts of the surface probe and the capture probe are not 100% complementary (for example, the number of mismatched base pairs can one, two, or three base pairs). Such a mismatch is recognized, e.g., by the MutY and T7 endonuclease I enzymes, which results in cleavage of the nucleic acid molecule at the position of the mismatch.

In some embodiments, where the capture probe is attached to a feature indirectly, e.g., via a surface probe, the cleavage domain includes a nickase recognition site or sequence. Nickases are endonucleases which cleave only a single strand of a DNA duplex. Thus, the cleavage domain can include a nickase recognition site close to the 5' end of the surface probe (and/or the 5' end of the capture probe) such that cleavage of the surface probe or capture probe destabilizes the duplex between the surface probe and capture probe thereby releasing the capture probe) from the feature.

Nickase enzymes can also be used in some embodiments where the capture probe is attached to the feature directly. For example, the substrate can be contacted with a nucleic acid molecule that hybridizes to the cleavage domain of the capture probe to provide or reconstitute a nickase recognition site, e.g., a cleavage helper probe. Thus, contact with a nickase enzyme will result in cleavage of the cleavage domain thereby releasing the capture probe from the feature. Such cleavage helper probes can also be used to provide or reconstitute cleavage recognition sites for other cleavage enzymes, e.g., restriction enzymes.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is incorporated herein by reference in its entirety. In general, any suitable nickase can be used to bind to a complementary nickase recognition site of a cleavage domain. Following use, the nickase enzyme can be removed from the assay or inactivated following release of the capture probes to prevent unwanted cleavage of the capture probes.

Examples of suitable capture domains that are not exclusively nucleic-acid based include, but are not limited to, proteins, peptides, aptamers, antigens, antibodies, and molecular analogs that mimic the functionality of any of the capture domains described herein.

In some embodiments, a cleavage domain is absent from the capture probe. Examples of substrates with attached capture probes lacking a cleavage domain are described for example in Macosko et al., (2015) Cell 161, 1202-1214, the entire contents of which are incorporated herein by reference.

In some embodiments, the region of the capture probe corresponding to the cleavage domain can be used for some other function. For example, an additional region for nucleic acid extension or amplification can be included where the cleavage domain would normally be positioned. In such embodiments, the region can supplement the functional domain or even exist as an additional functional domain. In some embodiments, the cleavage domain is present but its use is optional.

Functional Domain

Each capture probe can optionally include at least one functional domain. Each functional domain typically includes a functional nucleotide sequence for a downstream analytical step in the overall analysis procedure.

In some embodiments, the capture probe can include a functional domain for attachment to a sequencing flow cell, such as, for example, a P5 sequence for Illumina® sequencing. In some embodiments, the capture probe or derivative thereof can include another functional domain, such as, for example, a P7 sequence for attachment to a sequencing flow cell for Illumina® sequencing. The functional domains can be selected for compatibility with a variety of different sequencing systems, e.g., 454 Sequencing, Ion Torrent Proton or PGM, Illumina X10, etc., and the requirements thereof.

In some embodiments, the functional domain includes a primer. The primer can include an R1 primer sequence for Illumina® sequencing, and in some embodiments, an R2 primer sequence for Illumina® sequencing. Examples of such capture probes and uses thereof are described in U.S. Patent Publication Nos. 2014/0378345 and 2015/0376609, the entire contents of each of which are incorporated herein by reference.

Spatial Barcode

As discussed above, the capture probe can include one or more spatial barcodes (e.g., two or more, three or more, four or more, five or more) spatial barcodes. A "spatial barcode" is a contiguous nucleic acid segment or two or more non-contiguous nucleic acid segments that function as a label or identifier that conveys or is capable of conveying spatial information. In some embodiments, a capture probe includes a spatial barcode that possesses a spatial aspect, where the barcode is associated with a particular location within an array or a particular location on a substrate.

A spatial barcode can be part of an analyte, or independent from an analyte (i.e., part of the capture probe). A spatial barcode can be a tag attached to an analyte (e.g., a nucleic acid molecule) or a combination of a tag in addition to an endogenous characteristic of the analyte (e.g., size of the analyte or end sequence(s)). A spatial barcode can be unique. In some embodiments where the spatial barcode is unique, the spatial barcode functions both as a spatial barcode and as a unique molecular identifier (UMI), associated with one particular capture probe.

Spatial barcodes can have a variety of different formats. For example, spatial barcodes can include polynucleotide spatial barcodes; random nucleic acid and/or amino acid sequences; and synthetic nucleic acid and/or amino acid sequences. In some embodiments, a spatial barcode is attached to an analyte in a reversible or irreversible manner. In some embodiments, a spatial barcode is added to, for example, a fragment of a DNA or RNA sample before, during, and/or after sequencing of the sample. In some embodiments, a spatial barcode allows for identification and/or quantification of individual sequencing-reads. In some embodiments, a spatial barcode is a used as a fluorescent barcode for which fluorescently labeled oligonucleotide probes hybridize to the spatial barcode.

In some embodiments, the spatial barcode is a nucleic acid sequence that does not substantially hybridize to analyte nucleic acid molecules in a biological sample. In some embodiments, the spatial barcode has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The spatial barcode sequences can include from about 6 to about 20 or more nucleotides within the sequence of the capture probes. In some embodiments, the length of a spatial barcode sequence can be about 6, 7, 8, 9, 10, 11, 12, 13, 14, 15, 16, 17, 18, 19, 20 nucleotides or longer. In some embodiments, the length of a spatial barcode sequence can be at least about 6, 7, 8, 9, 10, 11, 12, 13, 14, 15, 16, 17, 18, 19, 20 nucleotides or longer. In some embodiments, the length of a spatial barcode sequence is at most about 6, 7, 8, 9, 10, 11, 12, 13, 14, 15, 16, 17, 18, 19, 20 nucleotides or shorter.

These nucleotides can be completely contiguous, i.e., in a single stretch of adjacent nucleotides, or they can be separated into two or more separate subsequences that are separated by 1 or more nucleotides. Separated spatial barcode subsequences can be from about 4 to about 16 nucleotides in length. In some embodiments, the spatial barcode subsequence can be about 4, 5, 6, 7, 8, 9, 10, 11, 12, 13, 14, 15, 16 nucleotides or longer. In some embodiments, the spatial barcode subsequence can be at least about 4, 5, 6, 7, 8, 9, 10, 11, 12, 13, 14, 15, 16 nucleotides or longer. In some embodiments, the spatial barcode subsequence can be at most about 4, 5, 6, 7, 8, 9, 10, 11, 12, 13, 14, 15, 16 nucleotides or shorter.

For multiple capture probes that are attached to a common array feature, the one or more spatial barcode sequences of the multiple capture probes can include sequences that are the same for all capture probes coupled to the feature, and/or sequences that are different across all capture probes coupled to the feature.

Figure 8:
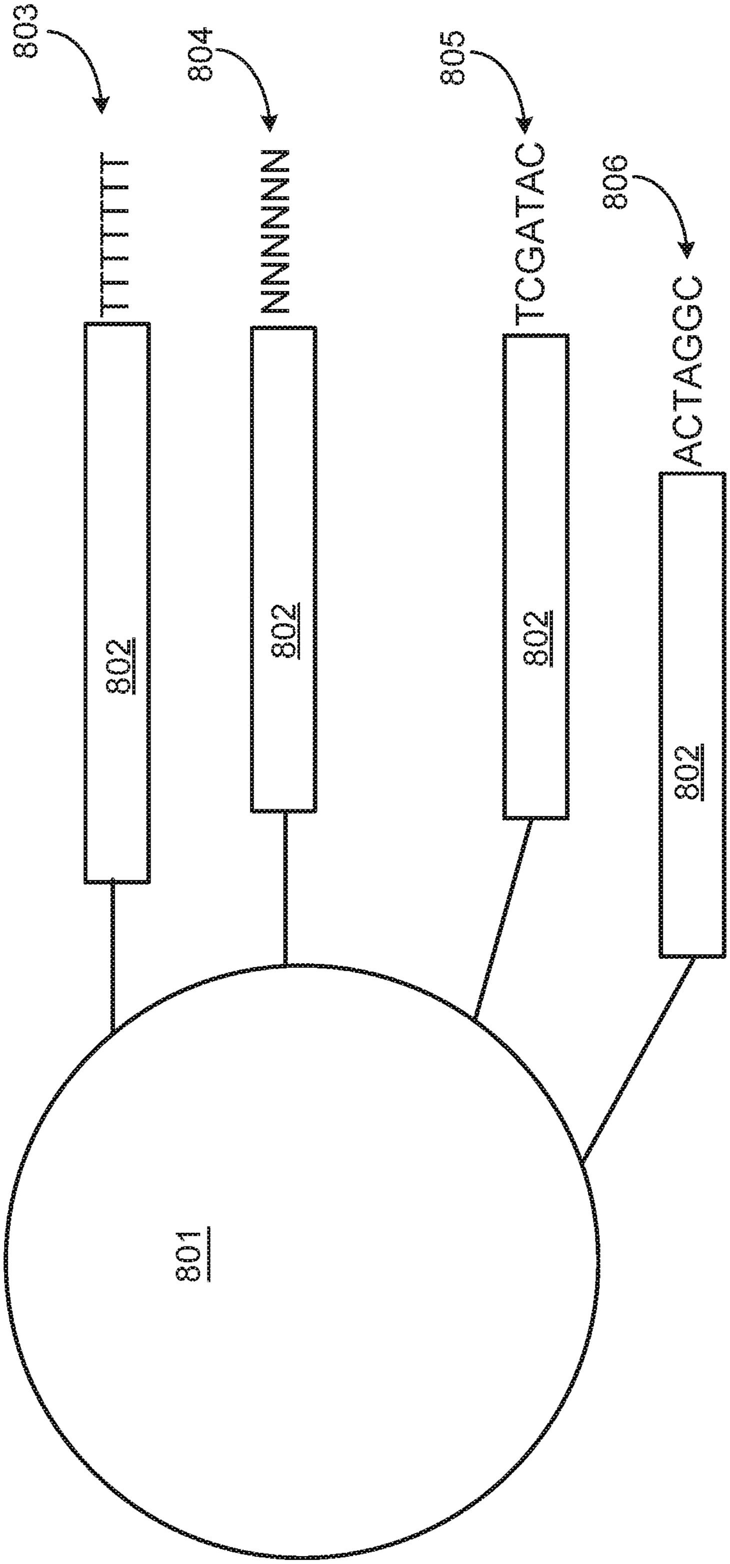
FIG. 8 is a schematic diagram of an exemplary multiplexed spatially-labelled feature.

FIG. 8 is a schematic diagram of an exemplary multiplexed spatially-labelled feature. In FIG. 8, the feature 801 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 802. One type of capture probe associated with the feature includes the spatial barcode 802 in combination with a poly(T) capture domain 803, designed to capture mRNA target analytes. A second type of capture probe associated with the feature includes the spatial barcode 802 in combination with a random N-mer capture domain 804 for gDNA analysis. A third type of capture probe associated with the feature includes the spatial barcode 802 in combination with a capture domain complementary to the capture domain on an analyte capture agent capture agent barcode domain 805. A fourth type of capture probe associated with the feature includes the spatial barcode 802 in combination with a capture probe that can specifically bind a nucleic acid molecule 806 that can function in a CRISPR assay (e.g., CRISPR/Cas9). While only four different capture probe-barcoded constructs are shown in FIG. 8, capture-probe barcoded constructs can be tailored for analyses of any given analyte associated with a nucleic acid and capable of binding with such a construct. For example, the schemes shown in FIG. 8 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor).

Capture probes attached to a single array feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

Unique Molecular Identifier

The capture probe can include one or more (e.g., two or more, three or more, four or more, five or more) Unique Molecular Identifiers (UMIs). A unique molecular identifier is a contiguous nucleic acid segment or two or more non-contiguous nucleic acid segments that function as a label or identifier for a particular analyte, or for a capture probe that binds a particular analyte (e.g., via the capture domain).

A UMI can be unique. A UMI can include one or more specific polynucleotides sequences, one or more random nucleic acid and/or amino acid sequences, and/or one or more synthetic nucleic acid and/or amino acid sequences.

In some embodiments, the UMI is a nucleic acid sequence that does not substantially hybridize to analyte nucleic acid molecules in a biological sample. In some embodiments, the UMI has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The UMI can include from about 6 to about 20 or more nucleotides within the sequence of the capture probes. In some embodiments, the length of a UMI sequence can be about 6, 7, 8, 9, 10, 11, 12, 13, 14, 15, 16, 17, 18, 19, 20 nucleotides or longer. In some embodiments, the length of a UMI sequence can be at least about 6, 7, 8, 9, 10, 11, 12, 13, 14, 15, 16, 17, 18, 19, 20 nucleotides or longer. In some embodiments, the length of a UMI sequence is at most about 6, 7, 8, 9, 10, 11, 12, 13, 14, 15, 16, 17, 18, 19, 20 nucleotides or shorter.

These nucleotides can be completely contiguous, i.e., in a single stretch of adjacent nucleotides, or they can be separated into two or more separate subsequences that are separated by 1 or more nucleotides. Separated UMI subsequences can be from about 4 to about 16 nucleotides in length. In some embodiments, the UMI subsequence can be about 4, 5, 6, 7, 8, 9, 10, 11, 12, 13, 14, 15, 16 nucleotides or longer. In some embodiments, the UMI subsequence can be at least about 4, 5, 6, 7, 8, 9, 10, 11, 12, 13, 14, 15, 16 nucleotides or longer. In some embodiments, the UMI subsequence can be at most about 4, 5, 6, 7, 8, 9, 10, 11, 12, 13, 14, 15, 16 nucleotides or shorter.

In some embodiments, a UMI is attached to an analyte in a reversible or irreversible manner. In some embodiments, a UMI is added to, for example, a fragment of a DNA or RNA sample before, during, and/or after sequencing of the analyte. In some embodiments, a UMI allows for identification and/or quantification of individual sequencing-reads. In some embodiments, a UMI is a used as a fluorescent barcode for which fluorescently labeled oligonucleotide probes hybridize to the UMI.

Other Aspects of Capture Probes

For capture probes that are attached to an array feature, an individual array feature can include one or more capture probes. In some embodiments, an individual array feature includes hundreds or thousands of capture probes. In some embodiments, the capture probes are associated with a particular individual feature, where the individual feature contains a capture probe including a spatial barcode unique to a defined region or location on the array.

In some embodiments, a particular feature can contain capture probes including more than one spatial barcode (e.g., one capture probe at a particular feature can include a spatial barcode that is different than the spatial barcode included in another capture probe at the same particular feature, while both capture probes include a second, common spatial barcode), where each spatial barcode corresponds to a particular defined region or location on the array. For example, multiple spatial barcode sequences associated with one particular feature on an array can provide a stronger address or attribution to a given location by providing duplicate or independent confirmation of the location. In some embodiments, the multiple spatial barcodes represent increasing specificity of the location of the particular array point. In a non-limiting example, a particular array point can be coded with two different spatial barcodes, where each spatial barcode identifies a particular defined region within the array, and an array point possessing both spatial barcodes identifies the sub-region where two defined regions overlap, e.g., such as the overlapping portion of a Venn diagram.

In another non-limiting example, a particular array point can be coded with three different spatial barcodes, where the first spatial barcode identifies a first region within the array, the second spatial barcode identifies a second region, where the second region is a subregion entirely within the first region, and the third spatial barcode identifies a third region, where the third region is a subregion entirely within the first and second subregions.

In some embodiments, capture probes attached to array features are released from the array features for sequencing. Alternatively, in some embodiments, capture probes remain attached to the array features, and the probes are sequenced while remaining attached to the array features (e.g., via in-situ sequencing). Further aspects of the sequencing of capture probes are described in subsequent sections of this disclosure.

In some embodiments, an array feature can include different types of capture probes attached to the feature. For example, the array feature can include a first type of capture probe with a capture domain designed to bind to one type of analyte, and a second type of capture probe with a capture domain designed to bind to a second type of analyte. In general, array features can include one or more (e.g., two or more, three or more, four or more, five or more, six or more, eight or more, ten or more, 12 or more, 15 or more, 20 or more, 30 or more, 50 or more) different types of capture probes attached to a single array feature.

In some embodiments, the capture probe is nucleic acid. In some embodiments, the capture probe is attached to the array feature via its 5' end. In some embodiments, the capture probe includes from the 5' to 3' end: one or more barcodes (e.g., a spatial barcode and/or a UMI) and one or more capture domains. In some embodiments, the capture probe includes from the 5' to 3' end: one barcode (e.g., a spatial barcode or a UMI) and one capture domain. In some embodiments, the capture probe includes from the 5' to 3' end: a cleavage domain, a functional domain, one or more barcodes (e.g., a spatial barcode and/or a UMI), and a capture domain. In some embodiments, the capture probe includes from the 5' to 3' end: a cleavage domain, a functional domain, one or more barcodes (e.g., a spatial barcode and/or a UMI), a second functional domain, and a capture domain. In some embodiments, the capture probe includes from the 5' to 3' end: a cleavage domain, a functional domain, a spatial barcode, a UMI, and a capture domain. In some embodiments, the capture probe does not include a spatial barcode. In some embodiments, the capture probe does not include a UMI. In some embodiments, the capture probe includes a sequence for initiating a sequencing reaction.

In some embodiments, the capture probe is immobilized on a feature via its 3' end. In some embodiments, the capture probe includes from the 3' to 5' end: one or more barcodes (e.g., a spatial barcode and/or a UMI) and one or more capture domains. In some embodiments, the capture probe includes from the 3' to 5' end: one barcode (e.g., a spatial barcode or a UMI) and one capture domain. In some embodiments, the capture probe includes from the 3' to 5' end: a cleavage domain, a functional domain, one or more barcodes (e.g., a spatial barcode and/or a UMI), and a capture domain. In some embodiments, the capture probe includes from the 3' to 5' end: a cleavage domain, a functional domain, a spatial barcode, a UMI, and a capture domain.

In some embodiments, a capture probe includes an in situ synthesized oligonucleotide. In some embodiments, the in situ synthesized oligonucleotide includes one or more constant sequences, one or more of which serves as a priming sequence (e.g., a primer for amplifying target nucleic acids). In some embodiments, a constant sequence is a cleavable sequence. In some embodiments, the in situ synthesized oligonucleotide includes a barcode sequence, e.g., a variable barcode sequence. In some embodiments, the in situ synthesized oligonucleotide is attached to a feature of an array.

In some embodiments, a capture probe is a product of two or more oligonucleotide sequences, e.g., two or more oligonucleotide sequences that are ligated together. In some embodiments, one of the oligonucleotide sequences is an in situ synthesized oligonucleotide.

In some embodiments, the capture probe includes a splint oligonucleotide. Two or more oligonucleotides can be ligated together using a splint oligonucleotide and any variety of ligases known in the art or described herein (e.g., SplintR ligase).

In some embodiments, one of the oligonucleotides includes: a constant sequence (e.g., a sequence complementary to a portion of a splint oligonucleotide), a degenerate sequence, and a capture domain (e.g., as described herein). In some embodiments, the capture probe is generated by having an enzyme add polynucleotides at the end of an oligonucleotide sequence. The capture probe can include a degenerate sequence, which can function as a unique molecular identifier.

A capture probe can include a degenerate sequence, which is a sequence in which some positions of a nucleotide sequence contain a number of possible bases. A degenerate sequence can be a degenerate nucleotide sequence including about or at least 5, 6, 7, 8, 9, 10, 11, 12, 13, 14, 15, 16, 17, 18, 19, 20, 25, 30, 35, 40, 45, or 50 nucleotides. In some embodiments, a nucleotide sequence contains 1, 2, 3, 4, 5, 6, 7, 8, 9, 0, 10, 15, 20, 25, or more degenerate positions within the nucleotide sequence. In some embodiments, the degenerate sequence is used as a UMI.

In some embodiments, a capture probe includes a restriction endonuclease recognition sequence or a sequence of nucleotides cleavable by specific enzyme activities. For example, uracil sequences can be cleaved by specific enzyme activity. As another example, other modified bases (e.g., modified by methylation) can be recognized and cleaved by specific endonucleases. The capture probes can be subjected to an enzymatic cleavage, which removes the blocking domain and any of the additional nucleotides that are added to the 3' end of the capture probe during the modification process. The removal of the blocking domain reveals and/or restores the free 3' end of the capture domain of the capture probe. In some embodiments, additional nucleotides can be removed to reveal and/or restore the 3' end of the capture domain of the capture probe.

In some embodiments, a blocking domain can be incorporated into the capture probe when it is synthesized, or after its synthesis. The terminal nucleotide of the capture domain is a reversible terminator nucleotide (e.g., 3'-O-blocked reversible terminator and 3'-unblocked reversible terminator), and can be included in the capture probe during or after probe synthesis.

Extended Capture Probes

An "extended capture probe" is a capture probe with an enlarged nucleic acid sequence. For example, where the capture probe includes nucleic acid, an "extended 3' end" indicates that further nucleotides were added to the most 3' nucleotide of the capture probe to extend the length of the capture probe, for example, by standard polymerization reactions utilized to extend nucleic acid molecules including templated polymerization catalyzed by a polymerase (e.g., a DNA polymerase or reverse transcriptase).

In some embodiments, extending the capture probe includes generating cDNA from the captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending the capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, the capture domain of the capture probe includes a primer for producing the complementary strand of the nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA, e.g. cDNA, molecule is generated. In some embodiments, a "full-length" DNA molecule refers to the whole of the captured nucleic acid molecule. However, if the nucleic acid, e.g. RNA, was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Epicentre Biotechnologies, Madison, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Epicentre Biotechnologies, Madison, WI), and SplintR (available from New England Biolabs, Ipswich, MA). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g. sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to an array feature specific for the affinity group. In some embodiments, the substrate can include an antibody or antibody fragment. In some embodiments, the array feature includes avidin or streptavidin and the affinity group includes biotin. In some embodiments, the array feature includes maltose and the affinity group includes maltose-binding protein. In some embodiments, the array feature includes maltose-binding protein and the affinity group includes maltose. In some embodiments, amplifying the extended capture probes can function to release the extended probes from the array feature, insofar as copies of the extended probes are not attached to the array feature.

In some embodiments, the extended capture probe or complement or amplicon thereof is released from an array feature. The step of releasing the extended capture probe or complement or amplicon thereof from an array feature can be achieved in a number of ways. In some embodiments, an extended capture probe or a complement thereof is released from the feature by nucleic acid cleavage and/or by denaturation (e.g. by heating to denature a double-stranded molecule).

In some embodiments, the extended capture probe or complement or amplicon thereof is released from the array feature by physical means. For example, methods for inducing physical release include denaturing double stranded nucleic acid molecules. Another method for releasing the extended capture probes is to use a solution that interferes with the hydrogen bonds of the double stranded molecules. In some embodiments, the extended capture probe is released by applying heated water such as water or buffer of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the array feature. In some embodiments, a formamide solution can be used to destabilize the interaction between nucleic acid molecules to release the extended capture probe from the array feature.

Analyte Capture Agents

This disclosure also provides methods and materials for using analyte capture agents for spatial profiling of biological analytes (e.g., mRNA, genomic DNA, accessible chromatin, and cell surface or intracellular proteins and/or metabolites). As used herein, an "analyte capture agent" (also referred to previously at times as a "cell labelling" agent") refers to an agent that interacts with an analyte (e.g., an analyte in a sample) and with a capture probe (e.g., a capture probe attached to a substrate) to identify the analyte. In some embodiments, the analyte capture agent includes an analyte binding moiety and a capture agent barcode domain.

Figure 9:
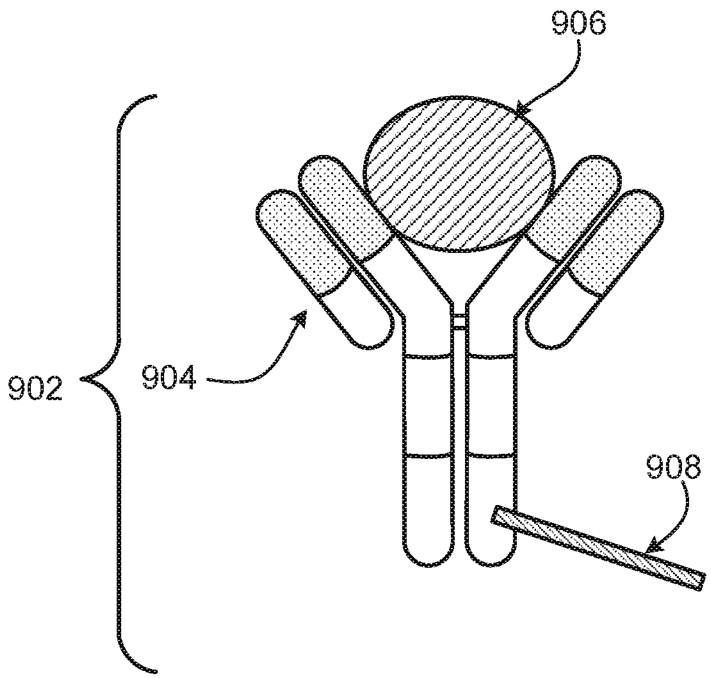
FIG. 9 is a schematic diagram of an exemplary analyte capture agent.

FIG. 9 is a schematic diagram of an exemplary analyte capture agent 902 comprised of an analyte binding moiety 904 and a capture agent barcode domain 908. An analyte binding moiety 904 is a molecule capable of binding to an analyte 906 and interacting with a spatially-barcoded capture probe. The analyte binding moiety can bind to the analyte 906 with high affinity and/or with high specificity. The analyte capture agent can include a capture agent barcode domain 908, a nucleotide sequence (e.g., an oligonucleotide), which can hybridize to at least a portion or an entirety of a capture domain of a capture probe. The analyte binding moiety 904 can include a polypeptide and/or an aptamer (e.g., an oligonucleotide or peptide molecule that binds to a specific target analyte). The analyte binding moiety 904 can include an antibody or antibody fragment (e.g., an antigen-binding fragment).

As used herein, the term "analyte binding moiety" refers to a molecule or moiety capable of binding to a macromolecular constituent (e.g., an analyte, e.g., a biological analyte). In some embodiments of any of the spatial profiling methods described herein, the analyte binding moiety of the analyte capture agent that binds to a biological analyte can include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The analyte binding moiety can bind to the macromolecular constituent (e.g., analyte) with high affinity and/or with high specificity. The analyte binding moiety can include a nucleotide sequence (e.g., an oligonucleotide), which can correspond to at least a portion or an entirety of the analyte binding moiety. The analyte binding moiety can include a polypeptide and/or an aptamer (e.g., a polypeptide and/or an aptamer that binds to a specific target molecule, e.g., an analyte). The analyte binding moiety can include an antibody or antibody fragment (e.g., an antigen-binding fragment) that binds to a specific analyte (e.g., a polypeptide).

In some embodiments, analyte capture agents are capable of binding to analytes present inside a cell. In some embodiments, analyte capture agents are capable of binding to cell surface analytes that can include, without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified. In such embodiments, analyte capture agents can be specific for cell surface analytes based on a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some embodiments, the analyte capture agent includes a capture agent barcode domain that is conjugated or otherwise attached to the analyte binding moiety. In some embodiments, the capture agent barcode domain is covalently-linked to the analyte binding moiety. In some embodiments, a capture agent barcode domain is a nucleic acid sequence. In some embodiments, a capture agent barcode domain includes an analyte binding moiety barcode and an analyte capture sequence.

As used herein, the term "analyte binding moiety barcode" refers to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein. For example, an analyte capture agent that is specific to one type of analyte can have coupled thereto a first capture agent barcode domain (e.g., that includes a first analyte binding moiety barcode), while an analyte capture agent that is specific to a different analyte can have a different capture agent barcode domain (e.g., that includes a second barcode analyte binding moiety barcode) coupled thereto. In some aspects, such a capture agent barcode domain can include an analyte binding moiety barcode that permits identification of the analyte binding moiety to which the capture agent barcode domain is coupled. The selection of the capture agent barcode domain can allow significant diversity in terms of sequence, while also being readily attachable to most analyte binding moieties (e.g., antibodies) as well as being readily detected, (e.g., using sequencing or array technologies). In some embodiments, the analyte capture agents can include analyte binding moieties with capture agent barcode domains attached to them. For example, an analyte capture agent can include a first analyte binding moiety (e.g., an antibody that binds to an analyte, e.g., a first cell surface feature) having associated with it a capture agent barcode domain that includes a first analyte binding moiety barcode.

In some embodiments, the capture agent barcode domain of an analyte capture agent includes an analyte capture sequence. As used herein, the term "analyte capture sequence" refers to region or moiety of configured to hybridize to, bind to, couple to, or otherwise interact with a capture domain of a capture probe. In some embodiments, an analyte capture sequence includes a nucleic acid sequence that is complementary to or substantially complementary to the capture domain of a capture probe such that the analyte capture sequence hybridizes to the capture domain of the capture probe. In some embodiments, an analyte capture sequence comprises a poly(A) nucleic acid sequence that hybridizes to a capture domain that comprises a poly(T) nucleic acid sequence. In some embodiments, an analyte capture sequence comprises a poly(T) nucleic acid sequence that hybridizes to a capture domain that comprises a poly(A) nucleic acid sequence. In some embodiments, an analyte capture sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the analyte capture region.

In some embodiments of any of the spatial analysis methods described herein that employ an analyte capture agent, the capture agent barcode domain can be directly coupled to the analyte binding moiety, or they can be attached to a bead, molecular lattice, e.g., a linear, globular, cross-slinked, or other polymer, or other framework that is attached or otherwise associated with the analyte binding moiety, which allows attachment of multiple capture agent barcode domains to a single analyte binding moiety. Attachment (coupling) of the capture agent barcode domains to the analyte binding moieties can be achieved through any of a variety of direct or indirect, covalent or non-covalent associations or attachments. For example, in the case of a capture agent barcode domain coupled to an analyte binding moiety that includes an antibody or antigen-binding fragment, such capture agent barcode domains can be covalently attached to a portion of the antibody or antigen-binding fragment using chemical conjugation techniques (e.g., Lightning-Link® antibody labelling kits available from Innova Biosciences). In some embodiments, a capture agent barcode domain can be coupled to an antibody or antigen-binding fragment using non-covalent attachment mechanisms (e.g., using biotinylated antibodies and oligonucleotides or beads that include one or more biotinylated linker, coupled to oligonucleotides with an avidin or streptavidin linker.) Antibody and oligonucleotide biotinylation techniques can be used, and are described for example in Fang et al., Nucleic Acids Res. (2003), 31(2): 708-715, the entire contents of which are incorporated by reference herein. Likewise, protein and peptide biotinylation techniques have been developed and can be used, and are described for example in U.S. Pat. No. 6,265,552, the entire contents of which are incorporated by reference herein. Furthermore, click reaction chemistry such as a methyltetrazine-PEG5-NHS ester reaction, a TCO-PEG4-NHS ester reaction, or the like, can be used to couple capture agent barcode domains to analyte binding moieties. The reactive moiety on the analyte binding moiety can also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., NH2). The reactive moiety on the analyte binding moiety can be a chemical compound or group that binds to the reactive moiety on the analyte binding moiety. Exemplary strategies to conjugate the analyte binding moiety to the capture agent barcode domain include the use of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation. In the cases where the analyte binding moiety is an antibody, the antibody can be modified prior to or contemporaneously with conjugation of the oligonucleotide. For example, the antibody can be glycosylated with a substrate-permissive mutant of β-1,4-galactosyltransferase, GalT (Y289L) and azide-bearing uridine diphosphate-N-acetylgalactosamine analog uridine diphosphate-GalNAz. The modified antibody can be conjugated to an oligonucleotide with a dibenzocyclooctyne-PEG4-NHS group. In some embodiments, certain steps (e.g., COOH activation (e.g., EDC) and homobifunctional cross linkers) can be avoided to prevent the analyte binding moieties from conjugating to themselves. In some embodiments of any of the spatial profiling methods described herein, the analyte capture agent (e.g., analyte binding moiety coupled to an oligonucleotide) can be delivered into the cell, e.g., by transfection (e.g., using transfectamine, cationic polymers, calcium phosphate or electroporation), by transduction (e.g., using a bacteriophage or recombinant viral vector), by mechanical delivery (e.g., magnetic beads), by lipid (e.g., 1,2-Dioleoyl-sn-glycero-3-phosphocholine (DOPC)), or by transporter proteins. An analyte capture agent can be delivered into a cell using exosomes. For example, a first cell can be generated that releases exosomes comprising an analyte capture agent. An analyte capture agent can be attached to an exosome membrane. An analyte capture agent can be contained within the cytosol of an exosome. Released exosomes can be harvested and provided to a second cell, thereby delivering the analyte capture agent into the second cell. An analyte capture agent can be releasable from an exosome membrane before, during, or after delivery into a cell. In some embodiments, the cell is permeabilized to allow the analyte capture agent to couple with intracellular cellular constituents (such as, without limitation, intracellular proteins, metabolites and nuclear membrane proteins). Following intracellular delivery, analyte capture agents can be used to analyze intracellular constituents as described herein.

In some embodiments of any of the spatial profiling methods described herein, the capture agent barcode domain coupled to an analyte capture agent can include modifications that render it non-extendable by a polymerase. In some embodiments, when binding to a capture domain of a capture probe or nucleic acid in a sample for a primer extension reaction, the capture agent barcode domain can serve as a template, not a primer. When the capture agent barcode domain also includes a barcode (e.g., an analyte binding moiety barcode), such a design can increase the efficiency of molecular barcoding by increasing the affinity between the capture agent barcode domain and unbarcoded sample nucleic acids, and eliminate the potential formation of adaptor artifacts. In some embodiments, the capture agent barcode domain can include a random N-mer sequence that is capped with modifications that render it non-extendable by a polymerase. In some cases, the composition of the random N-mer sequence can be designed to maximize the binding efficiency to free, unbarcoded ssDNA molecules. The design can include a random sequence composition with a higher GC content, a partial random sequence with fixed G or C at specific positions, the use of guanosines, the use of locked nucleic acids, or any combination thereof.

A modification for blocking primer extension by a polymerase can be a carbon spacer group of different lengths or a dideoxynucleotide. In some embodiments, the modification can be an abasic site that has an apurine or apyrimidine structure, a base analog, or an analogue of a phosphate backbone, such as a backbone of N-(2-aminoethyl)-glycine linked by amide bonds, tetrahydrofuran, or 1', 2'-Dideoxyribose. The modification can also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer), biotin, di-deoxynucleotide triphosphate, ethylene glycol, amine, or phosphate.

In some embodiments of any of the spatial profiling methods described herein, the capture agent barcode domain coupled to the analyte binding moiety includes a cleavable domain. For example, after the analyte capture agent binds to an analyte (e.g., a cell surface analyte), the capture agent barcode domain can be cleaved and collected for downstream analysis according to the methods as described herein. In some embodiments, the cleavable domain of the capture agent barcode domain includes a U-excising element that allows the species to release from the bead. In some embodiments, the U-excising element can include a single-stranded DNA (ssDNA) sequence that contains at least one uracil. The species can be attached to a bead via the ssDNA sequence. The species can be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment can be included in downstream processing to eliminate the phosphate group, e.g., prior to ligation of additional sequencing handle elements, e.g., Illumina full P5 sequence, partial P5 sequence, full sequence, and/or partial R1 sequence.

In some embodiments, an analyte binding moiety of an analyte capture agent includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte capture agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte capture agents are the same. In some embodiments in which the plurality of analytes includes a single species of analyte, the analyte binding moieties of the plurality of analyte capture agents are the different (e.g., members of the plurality of analyte capture agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte capture agent comprising an analyte binding moiety that binds to the cell surface protein and an analyte binding moiety barcode that identifies that analyte binding moiety, and the cell can be subjected to spatial analysis (e.g., any of the variety of spatial analysis methods described herein). For example, the analyte capture agent bound to the cell surface protein can be bound to a capture probe (e.g., a capture probe on an array), which capture probe includes a capture domain that interacts with an analyte capture sequence present on the capture agent barcode domain of the analyte capture agent. All or part of the capture agent barcode domain (including the analyte binding moiety barcode) can be copied with a polymerase using a 3' end of the capture domain as a priming site, generating an extended capture probe that includes the all or part of the capture probe (including a spatial barcode present on the capture probe) and a copy of the analyte binding moiety barcode. In some embodiments, the spatial array with the extended capture probe(s) can be contacted with a sample, where the analyte capture agent(s) associated with the spatial array capture the target analyte(s). The analyte capture agent(s) containing the extended capture probe(s), which includes the spatial barcode(s) of the capture probe(s) and the analyte binding moiety barcode(s), can then be denatured from the capture probe(s) of the spatial array. This allows the spatial array to be reused. The sample can be dissociated into non-aggregated cells (e.g. single cells) and analyzed by the single cell/droplet methods described herein. The extended capture probe can be sequenced to obtain a nucleic acid sequence, in which the spatial barcode of the capture probe is associated with the analyte binding moiety barcode of the analyte capture agent. The nucleic acid sequence of the extended capture probe can thus be associated with the analyte (e.g., cell surface protein), and in turn, with the one or more physical properties of the cell (e.g., a shape or cell type). In some embodiments, the nucleic acid sequence of the extended capture probe can be associated with an intracellular analyte of a nearby cell, where the intracellular analyte was released using any of the cell permeabilization or analyte migration techniques described herein.

In some embodiments of any of the spatial profiling methods described herein, the capture agent barcode domains released from the analyte capture agents can then be subjected to sequence analysis to identify which analyte capture agents were bound to analytes. Based upon the capture agent barcode domains that are associated with a feature (e.g., a feature at a particular location) on a spatial array and the presence of the analyte binding moiety barcode sequence, an analyte profile can be created for a biological sample. Profiles of individual cells or populations of cells can be compared to profiles from other cells, e.g., 'normal' cells, to identify variations in analytes, which can provide diagnostically relevant information. In some embodiments, these profiles can be useful in the diagnosis of a variety of disorders that are characterized by variations in cell surface receptors, such as cancer and other disorders.

Figure 10:
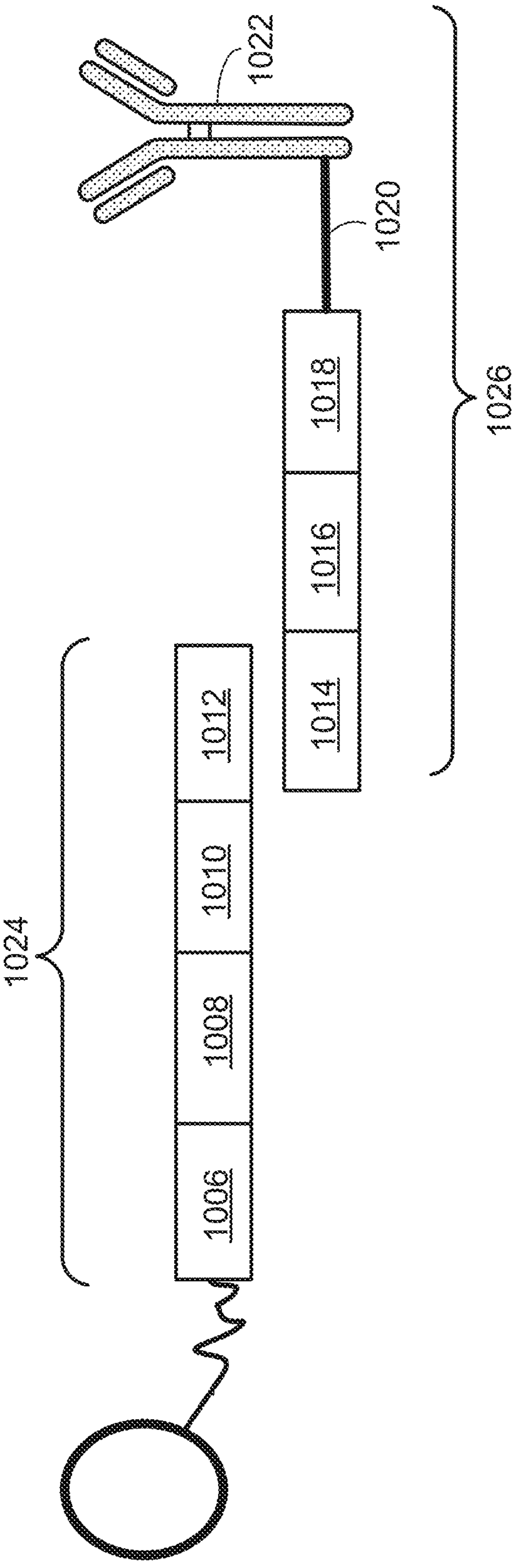
FIG. 10 is a schematic diagram depicting an exemplary interaction between a feature-immobilized capture probe 1024 and an analyte capture agent 1026.

FIG. 10 is a schematic diagram depicting an exemplary interaction between a feature-immobilized capture probe 1024 and an analyte capture agent 1026. The feature-immobilized capture probe 1024 can include a spatial barcode 1008 as well as one or more functional sequences 1006 and 1010, as described elsewhere herein. The capture probe can also include a capture domain 1012 that is capable of binding to an analyte capture agent 1026. The analyte capture agent 1026 can include a functional sequence 1018, capture agent barcode domain 1016, and an analyte capture sequence 1014 that is capable of binding to the capture domain 1012 of the capture probe 1024. The analyte capture agent can also include a linker 1020 that allows the capture agent barcode domain 1016 to couple to the analyte binding moiety 1022.

In some embodiments of any of the spatial profiling methods described herein, the methods are used to identify immune cell profiles. Immune cells express various adaptive immunological receptors relating to immune function, such as T cell receptors (TCRs) and B cell receptors (BCRs). T cell receptors and B cell receptors play a part in the immune response by specifically recognizing and binding to antigens and aiding in their destruction.

The T cell receptor, or TCR, is a molecule found on the surface of T cells that is generally responsible for recognizing fragments of antigen as peptides bound to major histocompatibility complex (WIC) molecules. The TCR is generally a heterodimer of two chains, each of which is a member of the immunoglobulin superfamily, possessing an N-terminal variable (V) domain, and a C terminal constant domain. In humans, in 95% of T cells, the TCR consists of an alpha (α) and beta (β) chain, whereas in 5% of T cells, the TCR consists of gamma and delta (γ/δ) chains. This ratio can change during ontogeny and in diseased states as well as in different species. When the TCR engages with antigenic peptide and WIC (peptide/WIC or pMHC), the T lymphocyte is activated through signal transduction.

Each of the two chains of a TCR contains multiple copies of gene segments—a variable 'V' gene segment, a diversity 'D' gene segment, and a joining 1' gene segment. The TCR alpha chain (TCRa) is generated by recombination of V and J segments, while the beta chain (TCRb) is generated by recombination of V, D, and J segments. Similarly, generation of the TCR gamma chain involves recombination of V and J gene segments, while generation of the TCR delta chain occurs by recombination of V, D, and J gene segments. The intersection of these specific regions (V and J for the alpha or gamma chain, or V, D and J for the beta or delta chain) corresponds to the CDR3 region that is important for antigen-MHC recognition. Complementarity determining regions (e.g., CDR1, CDR2, and CDR3), or hypervariable regions, are sequences in the variable domains of antigen receptors (e.g., T cell receptor and immunoglobulin) that can complement an antigen. Most of the diversity of CDRs is found in CDR3, with the diversity being generated by somatic recombination events during the development of T lymphocytes. A unique nucleotide sequence that arises during the gene arrangement process can be referred to as a clonotype.

The B cell receptor, or BCR, is a molecule found on the surface of B cells. The antigen binding portion of a BCR is composed of a membrane-bound antibody that, like most antibodies (e.g., immunoglobulins), has a unique and randomly determined antigen-binding site. The antigen binding portion of a BCR includes membrane-bound immunoglobulin molecule of one isotype (e.g., IgD, IgM, IgA, IgG, or IgE). When a B cell is activated by its first encounter with a cognate antigen, the cell proliferates and differentiates to generate a population of antibody-secreting plasma B cells and memory B cells. The various immunoglobulin isotypes differ in their biological features, structure, target specificity and distribution. A variety of molecular mechanisms exist to generate initial diversity, including genetic recombination at multiple sites.

The BCR is composed of two genes IgH and IgK (or IgL) coding for antibody heavy and light chains. Immunoglobulins are formed by recombination among gene segments, sequence diversification at the junctions of these segments, and point mutations throughout the gene. Each heavy chain gene contains multiple copies of three different gene segments—a variable 'V' gene segment, a diversity 'D' gene segment, and a joining 1' gene segment. Each light chain gene contains multiple copies of two different gene segments for the variable region of the protein—a variable 'V' gene segment and a joining T gene segment.

The recombination can generate a molecule with one of each of the V, D, and J segments. Furthermore, several bases can be deleted and others added (called N and P nucleotides) at each of the two junctions, thereby generating further diversity. After B cell activation, a process of affinity maturation through somatic hypermutation occurs. In this process, progeny cells of the activated B cells accumulate distinct somatic mutations throughout the gene with higher mutation concentration in the CDR regions leading to the generation of antibodies with higher affinity to the antigens.

In addition to somatic hypermutation, activated B cells undergo the process of isotype switching. Antibodies with the same variable segments can have different forms (isotypes) depending on the constant segment. Whereas all naïve B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. A unique nucleotide sequence that arises during the gene arrangement process can similarly be referred to as a clonotype.

Certain methods described herein are utilized to analyze the various sequences of TCRs and BCRs from immune cells, for example, various clonotypes. In some embodiments, the methods are used to analyze the sequence of a TCR alpha chain, a TCR beta chain, a TCR delta chain, a TCR gamma chain, or any fragment thereof (e.g., variable regions including V(D)J or VJ regions, constant regions, transmembrane regions, fragments thereof, combinations thereof, and combinations of fragments thereof). In some embodiments, the methods described herein can be used to analyze the sequence of a B cell receptor heavy chain, B cell receptor light chain, or any fragment thereof (e.g., variable regions including V(D)J or VJ regions, constant regions, transmembrane regions, fragments thereof, combinations thereof, and combinations of fragments thereof).

Where immune cells are to be analyzed, primer sequences useful in any of the various operations for attaching barcode sequences and/or amplification reactions can include gene specific sequences which target genes or regions of genes of immune cell proteins, for example immune receptors. Such gene sequences include, but are not limited to, sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), and T cell receptor delta constant genes (TRDC genes).

In some embodiments, the analyte binding moiety is based on the Major Histocompatibility Complex (MHC) class I or class II. In some embodiments, the analyte binding moiety is an MHC multimer including, without limitation, MEW dextramers, MHC tetramers, and MEW pentamers (see, for example, U.S. Patent Application Publication Nos. US 2018/0180601 and US 2017/0343545, the entire contents of each of which are incorporated herein by reference. MHCs (e.g., a soluble MHC monomer molecule), including full or partial MHC-peptides, can be used as analyte binding moieties of analyte capture agents that are coupled to capture agent barcode domains that include an analyte binding moiety barcode that identifies its associated MHC (and, thus, for example, the MEW's TCR binding partner). In some embodiments, MHCs are used to analyze one or more cell-surface features of a T-cell, such as a TCR. In some cases, multiple MHCs are associated together in a larger complex (MEW multi-mer) to improve binding affinity of MHCs to TCRs via multiple ligand binding synergies.

Figure 11A:
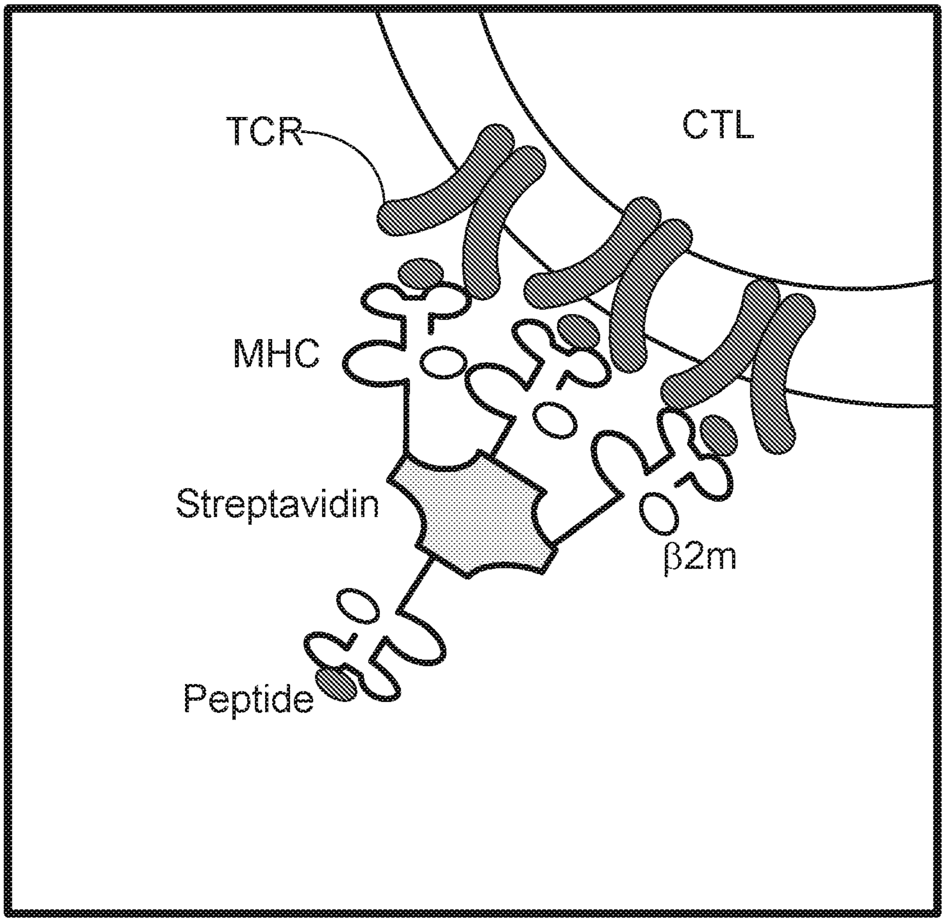
FIGS. 11A, 11B, and 11C are schematics illustrating how streptavidin cell tags can be utilized in an array-based system to produce a spatially-barcoded cells or cellular contents.
Figure 11B:
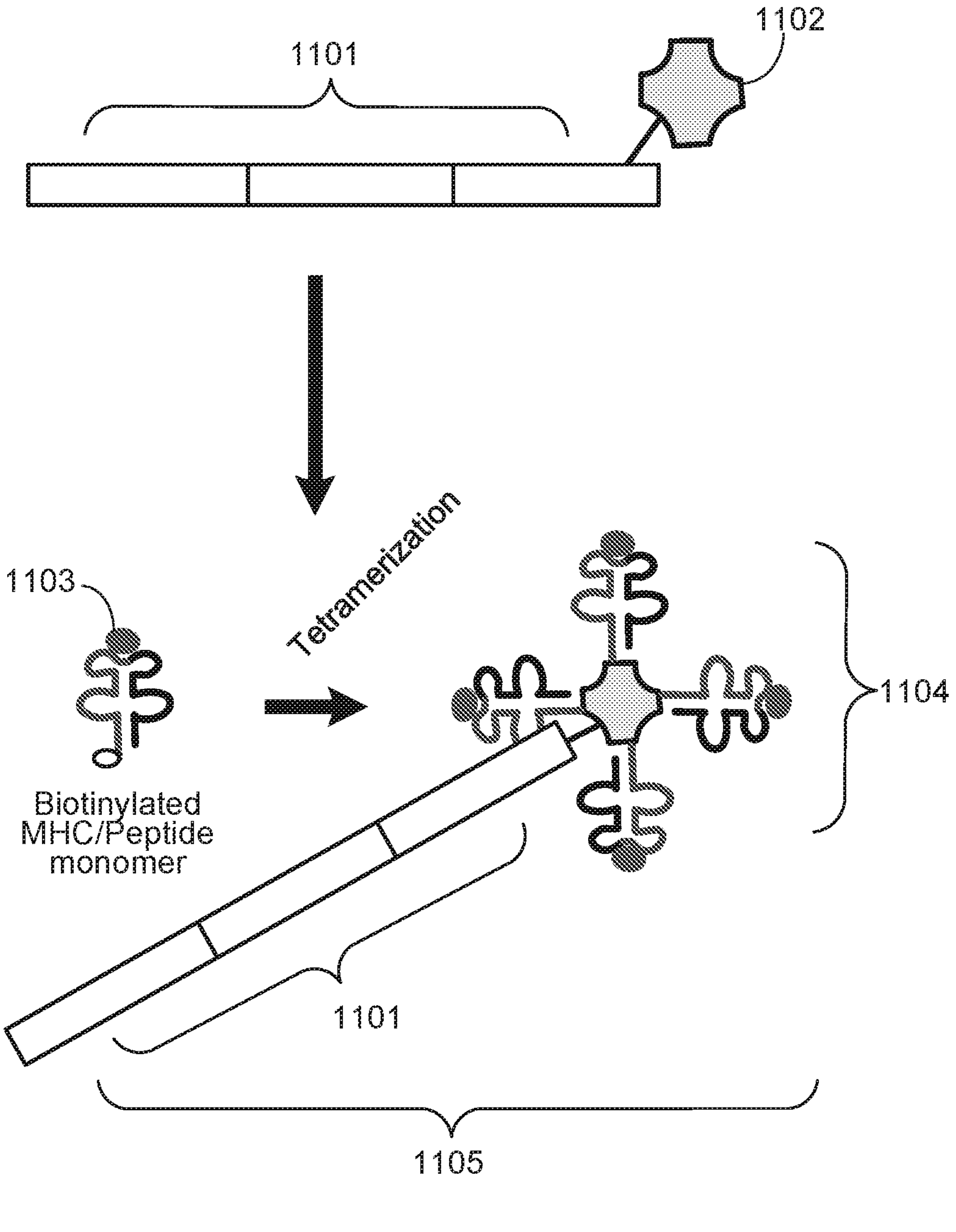
Figure 11C:
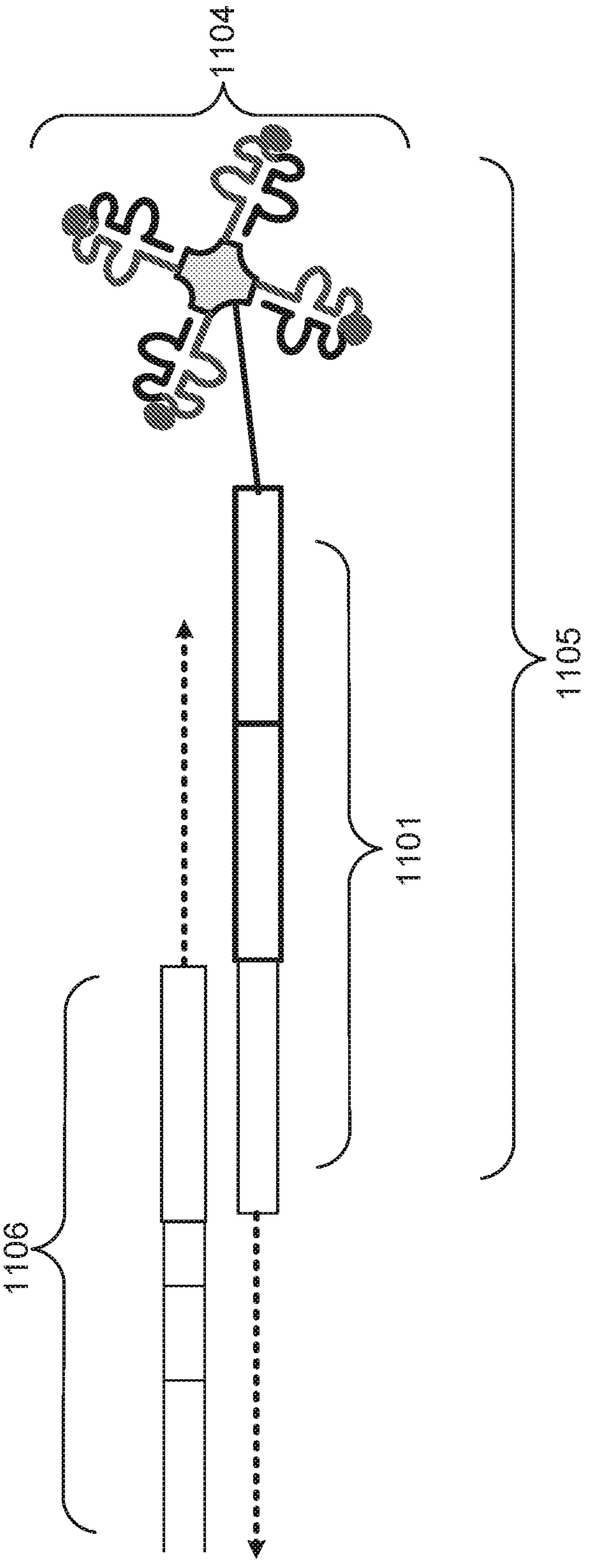

FIGS. 11A, 11B, and 11C are schematics illustrating how streptavidin cell tags can be utilized in an array-based system to produce a spatially-barcoded cell or cellular contents. For example, as shown in FIG. 11, peptide-bound major histocompatibility complex (pMHCs) can be individually associated with biotin and bound to a streptavidin moiety such that the streptavidin moiety comprises multiple pMHC moieties. Each of these moieties can bind to a TCR such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 11B, a capture agent barcode domain 1101 can be modified with streptavidin 1102 and contacted with multiple molecules of biotinylated MHC 1103 (such as a pMHC) such that the biotinylated MHC

1103 molecules are coupled with the streptavidin conjugated capture agent barcode domain 1101. The result is a barcoded MEW multimer complex 1105. As shown in FIG. 11B, the capture agent barcode domain sequence 1101 can identify the MHC as its associated label and also includes optional functional sequences such as sequences for hybridization with other oligonucleotides. As shown in FIG. 11C, one example oligonucleotide is capture probe 1106 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1")), a flow cell attachment sequence (e.g., P5 or P7 or partial sequences thereof)), etc. In some cases, capture probe 1106 may at first be associated with a feature (e.g., a gel bead) and released from the feature. In other embodiments, capture probe 1106 can hybridize with a capture agent barcode domain 1101 of the WIC-oligonucleotide complex 1105. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 1106 or capture agent barcode domain 1101. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 1106 spatial barcode sequence may be used to identify a feature and the sequence derived from spatial barcode sequence on the capture agent barcode domain 1101 may be used to identify the particular peptide WIC complex 1104 bound on the surface of the cell (e.g., when using MHC-peptide libraries for screening immune cells or immune cell populations).

(c) Substrate

For the spatial array-based analytical methods described in this section, the substrate functions as a support for direct or indirect attachment of capture probes to features of the array. In addition, in some embodiments, a substrate (e.g., the same substrate or a different substrate) can be used to provide support to a biological sample, particularly, for example, a thin tissue section. Accordingly, a "substrate" is a support that is insoluble in aqueous liquid and which allows for positioning of biological samples, analytes, features, and/or capture probes on the substrate.

A wide variety of different substrates can be used for the foregoing purposes. In general, a substrate can be any suitable support material. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate.

The substrate can also correspond to a flow cell. Flow cells can be formed of any of the foregoing materials, and can include channels that permit reagents, solvents, features, and molecules to pass through the cell.

Among the examples of substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In some embodiments, a substrate is coated with a surface treatment such as poly(L)-lysine. Additionally or alternatively, the substrate can be treated by silanation, e.g. with epoxy-silane, amino-silane, and/or by a treatment with polyacrylamide.

The substrate can generally have any suitable form or format. For example, the substrate can be flat, curved, e.g. convexly or concavely curved towards the area where the interaction between a biological sample, e.g. tissue sample, and the substrate takes place. In some embodiments, the substrate is a flat, e.g., planar, chip or slide. The substrate can contain one or more patterned surfaces within the substrate (e.g., channels, wells, projections, ridges, divots, etc.).

A substrate can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or cross-table). In some embodiments, where a substrate structure is flat, the substrate structure can be any appropriate type of support having a flat surface (e.g., a chip or a slide such as a microscope slide).

Substrates can optionally include various structures such as, but not limited to, projections, ridges, and channels. A substrate can be micropatterned to limit lateral diffusion (e.g., to prevent overlap of spatial barcodes). A substrate modified with such structures can be modified to allow association of analytes, features (e.g., beads), or probes at individual sites. For example, the sites where a substrate is modified with various structures can be contiguous or non-contiguous with other sites.

In some embodiments, the surface of a substrate can be modified so that discrete sites are formed that can only have or accommodate a single feature. In some embodiments, the surface of a substrate can be modified so that features adhere to random sites.

In some embodiments, the surface of a substrate is modified to contain one or more wells, using techniques such as (but not limited to) stamping techniques, microetching techniques, and molding techniques. In some embodiments in which a substrate includes one or more wells, the substrate can be a concavity slide or cavity slide. For example, wells can be formed by one or more shallow depressions on the surface of the substrate. In some embodiments, where a substrate includes one or more wells, the wells can be formed by attaching a cassette (e.g., a cassette containing one or more chambers) to a surface of the substrate structure.

In some embodiments, the structures of a substrate (e.g., wells) can each bear a different capture probe. Different capture probes attached to each structure can be identified according to the locations of the structures in or on the surface of the substrate. Exemplary substrates include arrays in which separate structures are located on the substrate including, for example, those having wells that accommodate features.

In some embodiments, a substrate includes one or more markings on a surface of the substrate, e.g., to provide guidance for correlating spatial information with the characterization of the analyte of interest. For example, a substrate can be marked with a grid of lines (e.g., to allow the size of objects seen under magnification to be easily estimated and/or to provide reference areas for counting objects). In some embodiments, fiducial markers can be included on the substrate. Such markings can be made using techniques including, but not limited to, printing, sand-blasting, and depositing on the surface.

In some embodiments where the substrate is modified to contain one or more structures, including but not limited to wells, projections, ridges, or markings, the structures can include physically altered sites. For example, a substrate modified with various structures can include physical properties, including, but not limited to, physical configurations, magnetic or compressive forces, chemically functionalized sites, chemically altered sites, and/or electrostatically altered sites.

In some embodiments where the substrate is modified to contain various structures, including but not limited to wells, projections, ridges, or markings, the structures are applied in a pattern. Alternatively, the structures can be randomly distributed.

In some embodiments, a substrate is treated in order to minimize or reduce non-specific analyte hybridization within or between features. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Application Publication Nos. U.S. 2017/0253918 and U.S. 2018/0052081, can be used. The entire contents of each of the foregoing documents are incorporated herein by reference.

Treatment can include adding a functional group that is reactive or capable of being activated such that it becomes reactive after receiving a stimulus (e.g., photoreactive). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

The substrate (e.g., a bead or a feature on an array) can include tens to hundreds of thousands or millions of individual oligonucleotide molecules (e.g., at least about 10,000, 50,000, 100,000, 500,000, 1,000,000, 10,000,000, 100,000,000, 1,000,000,000, or 10,000,000,000 oligonucleotide molecules).

In some embodiments, the surface of the substrate is coated with a cell-permissive coating to allow adherence of live cells. A "cell-permissive coating" is a coating that allows or helps cells to maintain cell viability (e.g., remain viable) on the substrate. For example, a cell-permissive coating can enhance cell attachment, cell growth, and/or cell differentiation, e.g., a cell-permissive coating can provide nutrients to the live cells. A cell-permissive coating can include a biological material and/or a synthetic material. Non-limiting examples of a cell-permissive coating include coatings that feature one or more extracellular matrix (ECM) components (e.g., proteoglycans and fibrous proteins such as collagen, elastin, fibronectin and laminin), poly-lysine, poly (L)-ornithine, and/or a biocompatible silicone (e.g., CYTOSOFT®). For example, a cell-permissive coating that includes one or more extracellular matrix components can include collagen Type I, collagen Type II, collagen Type IV, elastin, fibronectin, laminin, and/or vitronectin. In some embodiments, the cell-permissive coating includes a solubilized basement membrane preparation extracted from the Engelbreth-Holm-Swarm (EHS) mouse sarcoma (e.g., MATRIGEL®). In some embodiments, the cell-permissive coating includes collagen. A cell-permissive coating can be used to culture adherent cells on a spatially-barcoded array, or to maintain cell viability of a tissue sample or section while in contact with a spatially-barcoded array.

Where the substrate includes a gel (e.g., a hydrogel or gel matrix), oligonucleotides within the gel can attach to the substrate. The terms "hydrogel" and "hydrogel matrix" are used interchangeably herein to refer to a macromolecular polymer gel including a network. Within the network, some polymer chains can optionally be cross-linked, although cross-linking does not always occur.

In some embodiments, a hydrogel can include hydrogel subunits. A "hydrogel subunit" is a hydrophilic monomer, a molecular precursor, or a polymer that can be polymerized (e.g., cross-linked) to form a three-dimensional (3D) hydrogel network. The hydrogel subunits can include any convenient hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, cross-linkers and/or initiators are added to hydrogel subunits. Examples of cross-linkers include, without limitation, bis-acrylamide and diazirine. Examples of initiators include, without limitation, azobisisobutyronitrile (AIBN), riboflavin, and L-arginine. Inclusion of cross-linkers and/or initiators can lead to increased covalent bonding between interacting biological macromolecules in later polymerization steps.

In some embodiments, hydrogels can have a colloidal structure, such as agarose, or a polymer mesh structure, such as gelatin.

In some embodiments, some hydrogel subunits are polymerized (e.g., undergo "formation") covalently or physically cross-linked, to form a hydrogel network. For example, hydrogel subunits can be polymerized by any method including, but not limited to, thermal crosslinking, chemical crosslinking, physical crosslinking, ionic crosslinking, photo-crosslinking, irradiative crosslinking (e.g., x-ray, electron beam), and combinations thereof. Techniques such as lithographic photopolymerization can also be used to form hydrogels.

Polymerization methods for hydrogel subunits can be selected to form hydrogels with different properties (e.g., pore size, swelling properties, biodegradability, conduction, transparency, and/or permeability of the hydrogel). For example, a hydrogel can include pores of sufficient size to allow the passage of macromolecules, (e.g., nucleic acids, proteins, chromatin, metabolites, gRNA, antibodies, carbohydrates, peptides, metabolites, and/or small molecules) into the sample (e.g., tissue section). It is known that pore size generally decreases with increasing concentration of hydrogel subunits and generally increases with an increasing ratio of hydrogel subunits to crosslinker. Therefore, a fixative/hydrogel composition can be prepared that includes a concentration of hydrogel subunits that allows the passage of such biological macromolecules.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after features (e.g., beads) are attached to the substrate. For example, when a capture probe is attached (e.g., directly or indirectly) to a substrate, hydrogel formation can be performed on the substrate already containing the capture probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological marcomolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., capture probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

A "conditionally removable coating" is a coating that can be removed from the surface of a substrate upon application of a releasing agent. In some embodiments, a conditionally removable coating includes a hydrogel as described herein, e.g., a hydrogel including a polypeptide-based material. Non-limiting examples of a hydrogel featuring a polypeptide-based material include a synthetic peptide-based material featuring a combination of spider silk and a transmembrane segment of human muscle L-type calcium channel (e.g., PEPGEL®), an amphiphilic 16 residue peptide containing a repeating arginine-alanine-aspartate-alanine sequence (RADARADARADARADA) (e.g., PURAMATRIX®), EAK16 (AEAEAKAKAEAEAKAK), KLD12 (KLDLKLDLKLDL), and PGMATRIX™.

In some embodiments, the hydrogel in the conditionally removable coating is a stimulus-responsive hydrogel. A stimulus-responsive hydrogel can undergo a gel-to-solution and/or gel-to-solid transition upon application of one or more external triggers (e.g., a releasing agent). See, e.g., Willner, *Acc. Chem. Res.* 50:657-658, 2017, which is incorporated herein by reference in its entirety. Non-limiting examples of a stimulus-responsive hydrogel include a thermoresponsive hydrogel, a pH-responsive hydrogel, a light-responsive hydrogel, a redox-responsive hydrogel, an analyte-responsive hydrogel, or a combination thereof. In some embodiments, a stimulus-responsive hydrogel can be a multi-stimuli-responsive hydrogel.

A "releasing agent" or "external trigger" is an agent that allows for the removal of a conditionally removable coating from a substrate when the releasing agent is applied to the conditionally removable coating. An external trigger or releasing agent can include physical triggers such as thermal, magnetic, ultrasonic, electrochemical, and/or light stimuli as well as chemical triggers such as pH, redox reactions, supramolecular complexes, and/or biocatalytically driven reactions. See e.g., Echeverria, et al., Gels (2018), 4, 54; doi:10.3390/gels4020054, which is incorporated herein by reference in its entirety. The type of "releasing agent" or "external trigger" can depend on the type of conditionally removable coating. For example, a conditionally removable coating featuring a redox-responsive hydrogel can be removed upon application of a releasing agent that includes a reducing agent such as dithiothreitol (DTT). As another example, a pH-responsive hydrogel can be removed upon the application of a releasing agent that changes the pH.

(d) Arrays

In many of the methods described herein, features (as described further below) are collectively positioned on a substrate. An "array" is a specific arrangement of a plurality of features that is either irregular or forms a regular pattern. Individual features in the array differ from one another based on their relative spatial locations. In general, at least two of the plurality of features in the array include a distinct capture probe (e.g., any of the examples of capture probes described herein).

Arrays can be used to measure large numbers of analytes simultaneously. In some embodiments, oligonucleotides are used, at least in part, to create an array. For example, one or more copies of a single species of oligonucleotide (e.g., capture probe) can correspond to or be directly or indirectly attached to a given feature in the array. In some embodiments, a given feature in the array includes two or more species of oligonucleotides (e.g., capture probes). In some embodiments, the two or more species of oligonucleotides (e.g., capture probes) attached directly or indirectly to a given feature on the array include a common (e.g., identical) spatial barcode.

A "feature" is an entity that acts as a support or repository for various molecular entities used in sample analysis. Examples of features include, but are not limited to, a bead, a spot of any two- or three-dimensional geometry (e.g., an ink jet spot, a masked spot, a square on a grid), a well, and a hydrogel pad. In some embodiments, features are directly or indirectly attached or fixed to a substrate. In some embodiments, the features are not directly or indirectly attached or fixed to a substrate, but instead, for example, are disposed within an enclosed or partially enclosed three dimensional space (e.g., wells or divots).

In addition to those above, a wide variety of other features can be used to form the arrays described herein. For example, in some embodiments, features that are formed from polymers and/or biopolymers that are jet printed, screen printed, or electrostatically deposited on a substrate can be used to form arrays. Jet printing of biopolymers is described, for example, in PCT Patent Application Publication No. WO 2014/085725. Jet printing of polymers is described, for example, in de Gans et al., *Adv Mater.* 16(3): 203-213 (2004). Methods for electrostatic deposition of polymers and biopolymers are described, for example, in Hoyer et al., *Anal. Chem.* 68(21): 3840-3844 (1996). The entire contents of each of the foregoing references are incorporated herein by reference.

As another example, in some embodiments, features are formed by metallic micro- or nanoparticles. Suitable methods for depositing such particles to form arrays are described, for example, in Lee et al., *Beilstein J. Nanotechnol.* 8: 1049-1055 (2017), the entire contents of which are incorporated herein by reference.

As a further example, in some embodiments, features are formed by magnetic particles that are assembled on a substrate. Examples of such particles and methods for assembling arrays are described in Ye et al., *Scientific Reports* 6: 23145 (2016), the entire contents of which are incorporated herein by reference.

As another example, in some embodiments, features correspond to regions of a substrate in which one or more optical labels have been incorporated, and/or which have been altered by a process such as permanent photobleaching. Suitable substrates to implement features in this manner include a wide variety of polymers, for example. Methods for forming such features are described, for example, in Moshrefzadeh et al., *Appl. Phys. Lett.* 62: 16 (1993), the entire contents of which are incorporated herein by reference.

As yet another example, in some embodiments, features can correspond to colloidal particles assembled (e.g., via self-assembly) to form an array. Suitable colloidal particles are described for example in Sharma, *Resonance* 23(3): 263-275 (2018), the entire contents of which are incorporated herein by reference.

As a further example, in some embodiments, features can be formed via spot-array photopolymerization of a monomer solution on a substrate. In particular, two-photon and three-photon polymerization can be used to fabricate features of relatively small (e.g., sub-micron) dimensions. Suitable methods for preparing features on a substrate in this manner are described for example in Nguyen et al., *Materials Today* 20(6): 314-322 (2017), the entire contents of which are incorporated herein by reference.

In some embodiments, features are directly or indirectly attached or fixed to a substrate that is liquid permeable. In some embodiments, features are directly or indirectly attached or fixed to a substrate that is biocompatible. In some embodiments, features are directly or indirectly attached or fixed to a substrate that is a hydrogel.

Figure 12:
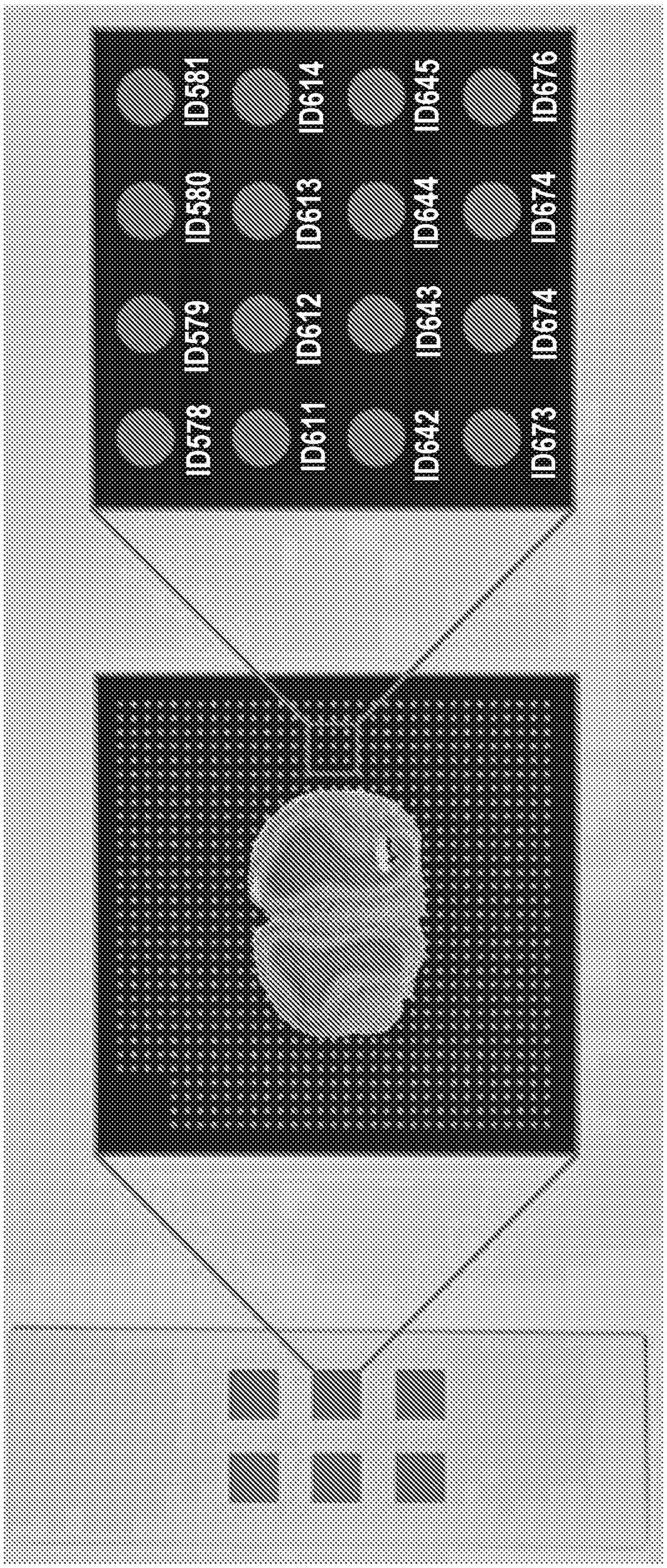
FIG. 12 is a schematic showing the arrangement of barcoded features within an array.

FIG. 12 depicts an exemplary arrangement of barcoded features within an array. From left to right, FIG. 12 shows (L) a slide including six spatially-barcoded arrays, (C) an enlarged schematic of one of the six spatially-barcoded arrays, showing a grid of barcoded features in relation to a biological sample, and (R) an enlarged schematic of one section of an array, showing the specific identification of multiple features within the array (labelled as ID578, ID579, ID560, etc.).

As used herein, the term "bead array" refers to an array that includes a plurality of beads as the features in the array. In some embodiments, the beads are attached to a substrate. For example, the beads can optionally attach to a substrate such as a microscope slide and in proximity to a biological sample (e.g., a tissue section that includes cells). The beads can also be suspended in a solution and deposited on a surface (e.g., a membrane, a tissue section, or a substrate (e.g., a microscope slide)).

Examples of arrays of beads on or within a substrate include beads located in wells such as the BeadChip array (available from Illumina Inc., San Diego, CA), arrays used in sequencing platforms from 454 LifeSciences (a subsidiary of Roche, Basel, Switzerland), and array used in sequencing platforms from Ion Torrent (a subsidiary of Life Technologies, Carlsbad, CA). Examples of bead arrays are described in, e.g., U.S. Pat. Nos. 6,266,459; 6,355,431; 6,770,441; 6,859,570; 6,210,891; 6,258,568; and 6,274,320; U.S. Pat. Application Publication Nos. 2009/0026082; 2009/0127589; 2010/0137143; and 2010/0282617; and PCT Patent Application Publication Nos. WO 00/063437 and WO 2016/162309, the entire contents of each of which is incorporated herein by reference.

In some embodiments, the bead array includes a plurality of beads. For example, the bead array can include at least 10,000 beads (e.g., at least 100,000 beads, at least 1,000,000 beads, at least 5,000,000 beads, at least 10,000,000 beads). In some embodiments, the plurality of beads includes a single type of beads (e.g., substantially uniform in size, shape, and other physical properties, such as translucence). In some embodiments, the plurality of beads includes two or more types of different beads.

In some embodiments, a bead array is formed when beads are embedded in a hydrogel layer where the hydrogel polymerizes and secures the relative bead positions. The bead-arrays can be pre-equilibrated and combined with reaction buffers and enzymes (e.g., reverse-transcription mix). In some embodiments, the bead arrays are frozen.

A "flexible array" includes a plurality of spatially-barcoded features attached to, or embedded in, a flexible substrate (e.g., a membrane or tape) placed onto a biological sample. In some embodiments, a flexible array includes a plurality of spatially-barcoded features embedded within a hydrogel matrix. To form such an array, features of a microarray are copied into a hydrogel, and the size of the hydrogel is reduced by removing water. These steps can be performed multiple times. For example, in some embodiments, a method for preparing a high-density spatially barcoded array can include copying a plurality of features from a microarray into a first hydrogel, where the first hydrogel is in contact with the microarray; reducing the size of the first hydrogel including the copied features by removing water, forming a first shrunken hydrogel including the copied features; copying the features in the first shrunken hydrogel into a second hydrogel, where the second hydrogel is in contact with the first hydrogel; and reducing the size of the second hydrogel including the copied features by removing water, forming a second shrunken hydrogel including the copied features, thus generating a high-density spatially barcoded array. The result is a high-density flexible array including spatially-barcoded features.

In some embodiments, spatially-barcoded beads can be loaded onto a substrate (e.g., a hydrogel) to produce a high-density self-assembled bead array.

Flexible arrays can be pre-equilibrated, combined with reaction buffers and enzymes at functional concentrations (e.g., a reverse-transcription mix). In some embodiments, the flexible bead-arrays can be stored for extended periods (e.g., days) or frozen until ready for use. In some embodiments, permeabilization of biological samples (e.g., a tissue section) can be performed with the addition of enzymes/detergents prior to contact with the flexible array. The flexible array can be placed directly on the sample, or placed in indirect contact with the biological sample (e.g., with an intervening layer or substance between the biological sample and the flexible bead-array). In some embodiments, once a flexible array is applied to the sample, reverse transcription and targeted capture of analytes can be performed on solid microspheres, or circular beads of a first size and circular beads of a second size.

A "microcapillary array" is an arrayed series of features that are partitioned by microcapillaries. A "microcapillary channel" is an individual partition created by the microcapillaries. For example, microcapillary channels can be fluidically isolated from other microcapillary channels, such that fluid or other contents in one microcapillary channel in the array are separated from fluid or other contents in a neighboring microcapillary channel in the array. The density and order of the microcapillaries can be any suitable density or order of discrete sites.

In some embodiments, microcapillary arrays are treated to generate conditions that facilitate loading. An example is the use of a corona wand (BD-20AC, Electro Technic Products) to generate a hydrophilic surface. In some embodiments, a feature (e.g., a bead with capture probe attached) is loaded onto a microcapillary array such that the exact position of the feature within the array is known. For example, a capture probe containing a spatial barcode can be placed into a microcapillary channel so that the spatial barcode can enable identification of the location from which the barcode sequence of the barcoded nucleic acid molecule was derived.

In some embodiments, when random distribution is used to distribute features, empirical testing can be performed to generate loading/distribution conditions that facilitate a single feature per microcapillary. In some embodiments, it can be desirable to achieve distribution conditions that facilitate only a single feature (e.g., bead) per microcapillary channel. In some embodiments, it can be desirable to achieve distribution conditions that facilitate more than one feature (e.g., bead) per microcapillary channel, by flowing the features through the microcapillary channel.

In some embodiments, the microcapillary array is placed in contact with a sample (e.g., on top or below) so that microcapillaries containing a feature (e.g., a bead, which can include a capture probe) are in contact with the biological sample. In some embodiments, a biological sample is placed onto an exposed side of a microcapillary array and mechanical compression is applied, moving the biological sample into the microcapillary channel to create a fluidically isolated reaction chamber containing the biological sample.

In some embodiments, a biological sample is partitioned by contacting a microcapillary array to the biological sample, thereby creating microcapillary channels including a bead and a portion of the biological sample. In some embodiments, a portion of a biological sample contained in a microcapillary channel is one or more cells. In some embodiments, a feature is introduced into a microcapillary array by flow after one or more cells are added to a microcapillary channel.

In some embodiments, reagents are added to the microcapillary array. The added reagents can include enzymatic reagents, and reagent mixtures for performing amplification of a nucleic acid. In some embodiments, the reagents include a reverse transcriptase, a ligase, one or more nucleotides, and any combinations thereof. One or more microcapillary channels can be sealed after reagents are added to the microcapillary channels, e.g. using silicone oil, mineral oil, a non-porous material, or lid.

In some embodiments, a reagent solution is removed from each microcapillary channel following an incubation for an amount of time and at a certain temperature or range of temperatures, e.g., following a hybridization or an amplification reaction. Reagent solutions can be processed individually for sequencing, or pooled for sequencing analysis.

In some embodiments, some or all features in an array include a capture probe. In some embodiments, an array can include a capture probe attached directly or indirectly to the substrate.

The capture probe includes a capture domain (e.g., a nucleotide sequence) that can specifically bind (e.g., hybridize) to a target analyte (e.g., mRNA, DNA, or protein) within a sample. In some embodiments, the binding of the capture probe to the target (e.g., hybridization) can be detected and quantified by detection of a visual signal, e.g. a fluorophore, a heavy metal (e.g., silver ion), or chemiluminescent label, which has been incorporated into the target. In some embodiments, the intensity of the visual signal correlates with the relative abundance of each analyte in the biological sample. Since an array can contain thousands or millions of capture probes (or more), an array of features with capture probes can interrogate many analytes in parallel.

In some embodiments, a substrate includes one or more capture probes that are designed to capture analytes from one or more organisms. In a non-limiting example, a substrate can contain one or more capture probes designed to capture mRNA from one organism (e.g., a human) and one or more capture probes designed to capture DNA from a second organism (e.g., a bacterium).

The capture probes can be attached to a substrate or feature using a variety of techniques. In some embodiments, the capture probe is directly attached to a feature that is fixed on an array. In some embodiments, the capture probes are immobilized to a substrate by chemical immobilization. For example, a chemical immobilization can take place between functional groups on the substrate and corresponding functional elements on the capture probes. Exemplary corresponding functional elements in the capture probes can either be an inherent chemical group of the capture probe, e.g. a hydroxyl group, or a functional element can be introduced on to the capture probe. An example of a functional group on the substrate is an amine group. In some embodiments, the capture probe to be immobilized includes a functional amine group or is chemically modified in order to include a functional amine group. Means and methods for such a chemical modification are well known in the art.

In some embodiments, the capture probe is a nucleic acid. In some embodiments, the capture probe is immobilized on the feature or the substrate via its 5' end. In some embodiments, the capture probe is immobilized on a feature or a substrate via its 5' end and includes from the 5' to 3' end: one or more barcodes (e.g., a spatial barcode and/or a UMI) and one or more capture domains. In some embodiments, the capture probe is immobilized on a feature via its 5' end and includes from the 5' to 3' end: one barcode (e.g., a spatial barcode or a UMI) and one capture domain. In some embodiments, the capture probe is immobilized on a feature or a substrate via its 5' end and includes from the 5' to 3' end: a cleavage domain, a functional domain, one or more barcodes (e.g., a spatial barcode and/or a UMI), and a capture domain.

In some embodiments, the capture probe is immobilized on a feature or a substrate via its 5' end and includes from the 5' to 3' end: a cleavage domain, a functional domain, one or more barcodes (e.g., a spatial barcode and/or a UMI), a second functional domain, and a capture domain. In some embodiments, the capture probe is immobilized on a feature or a substrate via its 5' end and includes from the 5' to 3' end: a cleavage domain, a functional domain, a spatial barcode, a UMI, and a capture domain. In some embodiments, the capture probe is immobilized on a feature or a substrate via its 5' end and does not include a spatial barcode. In some embodiments, the capture probe is immobilized on a feature or a substrate via its 5' end and does not include a UMI. In some embodiments, the capture probe includes a sequence for initiating a sequencing reaction.

In some embodiments, the capture probe is immobilized on a feature or a substrate via its 3' end. In some embodiments, the capture probe is immobilized on a feature or a substrate via its 3' end and includes from the 3' to 5' end: one or more barcodes (e.g., a spatial barcode and/or a UMI) and one or more capture domains. In some embodiments, the capture probe is immobilized on a feature or a substrate via its 3' end and includes from the 3' to 5' end: one barcode (e.g., a spatial barcode or a UMI) and one capture domain. In some embodiments, the capture probe is immobilized on a feature or a substrate via its 3' end and includes from the 3' to 5' end: a cleavage domain, a functional domain, one or more barcodes (e.g., a spatial barcode and/or a UMI), and a capture domain. In some embodiments, the capture probe is immobilized on a feature or a substrate via its 3' end and includes from the 3' to 5' end: a cleavage domain, a functional domain, a spatial barcode, a UMI, and a capture domain.

The localization of the functional group within the capture probe to be immobilized can be used to control and shape the binding behavior and/or orientation of the capture probe, e.g. the functional group can be placed at the 5' or 3' end of the capture probe or within the sequence of the capture probe. In some embodiments, a capture probe can further include a substrate (e.g., a support attached to the capture probe, a support attached to the feature, or a support attached to the substrate). A typical substrate for a capture probe to be immobilized includes moieties which are capable of binding to such capture probes, e.g., to amine-functionalized nucleic acids. Examples of such substrates are carboxy, aldehyde, or epoxy supports.

In some embodiments, the substrates on which capture probes can be immobilized can be chemically activated, e.g. by the activation of functional groups, available on the substrate. The term "activated substrate" relates to a material in which interacting or reactive chemical functional groups are established or enabled by chemical modification procedures. For example, a substrate including carboxyl groups can be activated before use. Furthermore, certain substrates contain functional groups that can react with specific moieties already present in the capture probes.

In some embodiments, a covalent linkage is used to directly couple a capture probe to a substrate. In some embodiments a capture probe is indirectly coupled to a substrate through a linker separating the "first" nucleotide of the capture probe from the substrate, i.e., a chemical linker. In some embodiments, a capture probe does not bind directly to the array, but interacts indirectly, for example by binding to a molecule which itself binds directly or indirectly to the array. In some embodiments, the capture probe is indirectly attached to a substrate (e.g., via a solution including a polymer).

In some embodiments where the capture probe is immobilized on the feature of the array indirectly, e.g. via hybridization to a surface probe capable of binding the capture probe, the capture probe can further include an upstream sequence (5' to the sequence that hybridizes to the nucleic acid, e.g. RNA of the tissue sample) that is capable of hybridizing to 5' end of the surface probe. Alone, the capture domain of the capture probe can be seen as a capture domain oligonucleotide, which can be used in the synthesis of the capture probe in embodiments where the capture probe is immobilized on the array indirectly.

In some embodiments, a substrate is comprised of an inert material or matrix (e.g., glass slides) that has been functionalization by, for example, treatment with a material comprising reactive groups which enable immobilization of capture probes. See, for example, WO 2017/019456, the entire contents of which are herein incorporated by reference. Non-limiting examples include polyacrylamide hydrogels supported on an inert substrate (e.g., glass slide; see WO 2005/065814 and U.S. Patent Application No. 2008/0280773, the entire contents of which are incorporated herein by reference).

In some embodiments, functionalized biomolecules (e.g., capture probes) are immobilized on a functionalized substrate using covalent methods. Methods for covalent attachment include, for example, condensation of amines and activated carboxylic esters (e.g., N-hydroxysuccinimide esters); condensation of amine and aldehydes under reductive amination conditions; and cycloaddition reactions such as the Diels-Alder [4+2] reaction, 1,3-dipolar cycloaddition reactions, and [2+2] cycloaddition reactions. Methods for covalent attachment also include, for example, click chemistry reactions, including [3+2] cycloaddition reactions (e.g., Huisgen 1,3-dipolar cycloaddition reaction and copper(I)-catalyzed azide-alkyne cycloaddition (CuAAC)); thiol-ene reactions; the Diels-Alder reaction and inverse electron demand Diels-Alder reaction; [4+1] cycloaddition of isonitriles and tetrazines; and nucleophilic ring-opening of small carbocycles (e.g., epoxide opening with amino oligonucleotides). Methods for covalent attachment also include, for example, maleimides and thiols; and para-nitrophenyl ester-functionalized oligonucleotides and polylysine-functionalized substrate. Methods for covalent attachment also include, for example, disulfide reactions; radical reactions (see, e.g., U.S. Pat. No. 5,919,626, the entire contents of which are herein incorporated by reference); and hydrazide-functionalized substrate (e.g., wherein the hydrazide functional group is directly or indirectly attached to the substrate) and aldehyde-functionalized oligonucleotides (see, e.g., Yershov et al. (1996) Proc. Natl. Acad. Sci. USA 93, 4913-4918, the entire contents of which are herein incorporated by reference).

In some embodiments, functionalized biomolecules (e.g., capture probes) are immobilized on a functionalized substrate using photochemical covalent methods. Methods for photochemical covalent attachment include, for example, immobilization of antraquinone-conjugated oligonucleotides (see, e.g., Koch et al. (2000) Bioconjugate Chem. 11, 474-483, the entire contents of which are herein incorporated by reference).

In some embodiments, functionalized biomolecules (e.g., capture probes are immobilized on a functionalized substrate using non-covalent methods. Methods for non-covalent attachment include, for example, biotin-functionalized oligonucleotides and streptavidin-treated substrates (see, e.g., Holmstrom et al. (1993) Analytical Biochemistry 209, 278-283 and Gilles et al. (1999) Nature Biotechnology 17, 365-370, the entire contents of which are herein incorporated by reference).

In some embodiments, an oligonucleotide (e.g., a capture probe) can be attached to a substrate or feature according to the methods set forth in U.S. Pat. Nos. 6,737,236, 7,259,258, 7,375,234, 7,427,678, 5,610,287, 5,807,522, 5,837,860, and 5,472,881; U.S. Patent Application Publication Nos. 2008/0280773 and 2011/0059865; Shalon et al. (1996) Genome Research, 639-645; Rogers et al. (1999) Analytical Biochemistry 266, 23-30; Stimpson et al. (1995) Proc. Natl. Acad. Sci. USA 92, 6379-6383; Beattie et al. (1995) Clin. Chem. 45, 700-706; Lamture et al. (1994) Nucleic Acids Research 22, 2121-2125; Beier et al. (1999) Nucleic Acids Research 27, 1970-1977; Joos et al. (1997) Analytical Biochemistry 247, 96-101; Nikiforov et al. (1995) Analytical Biochemistry 227, 201-209; Timofeev et al. (1996) Nucleic Acids Research 24, 3142-3148; Chrisey et al. (1996) Nucleic Acids Research 24, 3031-3039; Guo et al. (1994) Nucleic Acids Research 22, 5456-5465; Running and Urdea (1990) BioTechniques 8, 276-279; Fahy et al. (1993) Nucleic Acids Research 21, 1819-1826; Zhang et al. (1991) 19, 3929-3933; and Rogers et al. (1997) Gene Therapy 4, 1387-1392. The entire contents of each of the foregoing documents are incorporated herein by reference.

Arrays can be prepared by a variety of methods. In some embodiments, arrays are prepared through the synthesis (e.g., in-situ synthesis) of oligonucleotides on the array, or by jet printing or lithography. For example, light-directed synthesis of high-density DNA oligonucleotides can be achieved by photolithography or solid-phase DNA synthesis. To implement photolithographic synthesis, synthetic linkers modified with photochemical protecting groups can be attached to a substrate and the photochemical protecting groups can be modified using a photolithographic mask (applied to specific areas of the substrate) and light, thereby producing an array having localized photo-deprotection. Many of these methods are known in the art, and are described e.g., in Miller et al., "Basic concepts of microarrays and potential applications in clinical microbiology." Clinical microbiology reviews 22.4 (2009): 611-633; US201314111482A; U.S. Pat. No. 9,593,365B2; US2019203275; and WO2018091676, which are incorporated herein by reference in the entirety.

In some embodiments, the arrays are "spotted" or "printed" with oligonucleotides and these oligonucleotides (e.g., capture probes) are then attached to the substrate. The oligonucleotides can be applied by either noncontact or contact printing. A noncontact printer can use the same method as computer printers (e.g., bubble jet or inkjet) to expel small droplets of probe solution onto the substrate. The specialized inkjet-like printer can expel nanoliter to picoliter volume droplets of oligonucleotide solution, instead of ink, onto the substrate. In contact printing, each print pin directly applies the oligonucleotide solution onto a specific location on the surface. The oligonucleotides can be attached to the substrate surface by the electrostatic interaction of the negative charge of the phosphate backbone of the DNA with a positively charged coating of the substrate surface or by UV-cross-linked covalent bonds between the thymidine bases in the DNA and amine groups on the treated substrate surface. In some embodiments, the substrate is a glass slide. In some embodiments, the oligonucleotides (e.g., capture probes) are attached to the substrate by a covalent bond to a chemical matrix, e.g. epoxy-silane, amino-silane, lysine, polyacrylamide, etc.

The arrays can also be prepared by in situ-synthesis. In some embodiments, these arrays can be prepared using photolithography. The method typically relies on UV masking and light-directed combinatorial chemical synthesis on a substrate to selectively synthesize probes directly on the surface of the array, one nucleotide at a time per spot, for many spots simultaneously. In some embodiments, a substrate contains covalent linker molecules that have a protecting group on the free end that can be removed by light. UV light is directed through a photolithographic mask to deprotect and activate selected sites with hydroxyl groups that initiate coupling with incoming protected nucleotides that attach to the activated sites. The mask is designed in such a way that the exposure sites can be selected, and thus specify the coordinates on the array where each nucleotide can be attached. The process can be repeated, a new mask is applied activating different sets of sites and coupling different bases, allowing arbitrary oligonucleotides to be constructed at each site. This process can be used to synthesize hundreds of thousands of different oligonucleotides. In some embodiments, maskless array synthesizer technology can be used. It uses an array of programmable micromirrors to create digital masks that reflect the desired pattern of UV light to deprotect the features.

In some embodiments, the inkjet spotting process can also be used for in-situ oligonucleotide synthesis. The different nucleotide precursors plus catalyst can be printed on the substrate, and are then combined with coupling and deprotection steps. This method relies on printing picoliter volumes of nucleotides on the array surface in repeated rounds of base-by-base printing that extends the length of the oligonucleotide probes on the array.

Arrays can also be prepared by active hybridization via electric fields to control nucleic acid transport. Negatively charged nucleic acids can be transported to specific sites, or features, when a positive current is applied to one or more test sites on the array. The surface of the array can contain a binding molecule, e.g., streptavidin, which allows for the formation of bonds (e.g., streptavidin-biotin bonds) once electronically addressed biotinylated probes reach their targeted location. The positive current is then removed from the active features, and new test sites can be activated by the targeted application of a positive current. The process are repeated until all sites on the array are covered.

An array for spatial analysis can be generated by various methods as described herein. In some embodiments, the array has a plurality of capture probes comprising spatial barcodes. These spatial barcodes and their relationship to the locations on the array can be determined. In some cases, such information is readily available, because the oligonucleotides are spotted, printed, or synthesized on the array with a pre-determined pattern. In some cases, the spatial barcode can be decoded by methods described herein, e.g., by in-situ sequencing, by various labels associated with the spatial barcodes etc. In some embodiments, an array can be used as a template to generate a daughter array. Thus, the spatial barcode can be transferred to the daughter array with a known pattern.

In some embodiments, an array comprising barcoded probes can be generated through ligation of a plurality of oligonucleotides. In some instances, an oligonucleotide of the plurality contains a portion of a barcode, and the complete barcode is generated upon ligation of the plurality of oligonucleotides. For example, a first oligonucleotide containing a first portion of a barcode can be attached to a substrate (e.g., using any of the methods of attaching an oligonucleotide to a substrate described herein), and a second oligonucleotide containing a second portion of the barcode can then be ligated onto the first oligonucleotide to generate a complete barcode. Different combinations of the first, second and any additional portions of a barcode can be used to increase the diversity of the barcodes. In instances where the second oligonucleotide is also attached to the substrate prior to ligation, the first and/or the second oligonucleotide can be attached to the substrate via a surface linker which contains a cleavage site. Upon ligation, the ligated oligonucleotide is linearized by cleaving at the cleavage site.

To increase the diversity of the barcodes, a plurality of second oligonucleotides comprising two or more different barcode sequences can be ligated onto a plurality of first oligonucleotides that comprise the same barcode sequence, thereby generating two or more different species of barcodes. To achieve selective ligation, a first oligonucleotide attached to a substrate containing a first portion of a barcode can initially be protected with a protective group (e.g., a photocleavable protective group), and the protective group can be removed prior to ligation between the first and second oligonucleotide. In instances where the barcoded probes on an array are generated through ligation of two or more oligonucleotides, a concentration gradient of the oligonucleotides can be applied to a substrate such that different combinations of the oligonucleotides are incorporated into a barcoded probe depending on its location on the substrate.

Barcoded probes on an array can also be generated by adding single nucleotides to existing oligonucleotides on an array, for example, using polymerases that function in a template-independent manner. Single nucleotides can be added to existing oligonucleotides in a concentration gradient, thereby generating probes with varying length, depending on the location of the probes on the array.

Arrays can also be prepared by modifying existing arrays, for example, by modifying the oligonucleotides attached to the arrays. For instance, probes can be generated on an array that comprises oligonucleotides that are attached to the array at the 3' end and have a free 5' end. The oligonucleotides can be in situ synthesized oligonucleotides, and can include a barcode. The length of the oligonucleotides can be less than 50 nucleotides (nts) (e.g., less than 45, 40, 35, 30, 25, 20, 15, or 10 nts). To generate probes using these oligonucleotides, a primer complementary to a portion of an oligonucleotide (e.g., a constant sequence shared by the oligonucleotides) can be used to hybridize with the oligonucleotide and extend (using the oligonucleotide as a template) to form a duplex and to create a 3' overhang. The 3' overhang thus allows additional nucleotides or oligonucleotides to be added on to the duplex. A capture probe can be generated by, for instance, adding one or more oligonucleotides to the end of the 3' overhang (e.g., via splint oligonucleotide mediated ligation), where the added oligonucleotides can include the sequence or a portion of the sequence of a capture domain.

In instances where the oligonucleotides on an existing array include a recognition sequence that can hybridize with a splint oligonucleotide, probes can also be generated by directly ligating additional oligonucleotides onto the existing oligonucleotides via the splint oligonucleotide. The recognition sequence can at the free 5' end or the free 3' end of an oligonucleotide on the existing array. Recognition sequences useful for the methods of the present disclosure may not contain restriction enzyme recognition sites or secondary structures (e.g., hairpins), and may include high contents of Guanine and Cytosine nucleotides and thus have high stability.

Bead arrays can be generated by attaching beads (e.g., barcoded beads) to a substrate in a regular pattern, or an irregular arrangement. Beads can be attached to selective regions on a substrate by, e.g., selectively activating regions on the substrate to allow for attachment of the beads. Activating selective regions on the substrate can include activating a coating (e.g., a photocleavable coating) or a polymer that is applied on the substrate. Beads can be attached iteratively, e.g., a subset of the beads can be attached at one time, and the same process can be repeated to attach the remaining beads. Alternatively, beads can be attached to the substrate all in one step.

Barcoded beads, or beads comprising a plurality of barcoded probes, can be generated by first preparing a plurality of barcoded probes on a substrate, depositing a plurality of beads on the substrate, and generating probes attached to the beads using the probes on the substrate as a template.

Large scale commercial manufacturing methods allow for millions of oligonucleotides to be attached to an array. Commercially available arrays include those from Roche NimbleGen, Inc., (Wisconsin) and Affymetrix (ThermoFisher Scientific).

In some embodiments, arrays can be prepared according to the methods set forth in WO 2012/140224, WO 2014/060483, WO 2016/162309, WO 2017/019456, WO 2018/091676, and WO 2012/140224, and U.S. Patent Application No. 2018/0245142. The entire contents of the foregoing documents are herein incorporated by reference.

In some embodiments, a feature on the array includes a bead. In some embodiments, two or more beads are dispersed onto a substrate to create an array, where each bead is a feature on the array. Beads can optionally be dispersed into wells on a substrate, e.g., such that only a single bead is accommodated per well.

A "bead" is a particle. A bead can be porous, non-porous, solid, semi-solid, and/or a combination thereof. In some embodiments, a bead can be dissolvable, disruptable, and/or degradable, whereas in certain embodiments, a bead is not degradable.

A bead can generally be of any suitable shape. Examples of bead shapes include, but are not limited to, spherical, non-spherical, oval, oblong, amorphous, circular, cylindrical, and variations thereof. A cross section (e.g., a first cross-section) can correspond to a diameter or maximum cross-sectional dimension of the bead. In some embodiments, the bead can be approximately spherical. In such embodiments, the first cross-section can correspond to the diameter of the bead. In some embodiments, the bead can be approximately cylindrical. In such embodiments, the first cross-section can correspond to a diameter, length, or width along the approximately cylindrical bead.

Beads can be of uniform size or heterogeneous size. "Polydispersity" generally refers to heterogeneity of sizes of molecules or particles. The polydispersity index (PDI) of a bead can be calculated using the equation PDI=Mw/Mn, where Mw is the weight-average molar mass and Mn is the number-average molar mass. In certain embodiments, beads can be provided as a population or plurality of beads having a relatively monodisperse size distribution. Where it can be desirable to provide relatively consistent amounts of reagents, maintaining relatively consistent bead characteristics, such as size, can contribute to the overall consistency.

In some embodiments, the beads provided herein can have size distributions that have a coefficient of variation in their cross-sectional dimensions of less than 50%, less than 40%, less than 30%, less than 20%, less than 15%, less than 10%, less than 5%, or lower. In some embodiments, a plurality of beads provided herein has a polydispersity index of less than 50%, less than 45%, less than 40%, less than 35%, less than 30%, less than 25%, less than 20%, less than 15%, less than 10%, less than 5%, or lower.

In some embodiments, the bead can have a diameter or maximum dimension no larger than 100 μm (e.g., no larger than 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm.)

In some embodiments, a plurality of beads has an average diameter no larger than 100 μm. In some embodiments, a plurality of beads has an average diameter or maximum dimension no larger than 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm.

In some embodiments, the volume of the bead can be at least about 1 $μm^3$, e.g., at least 1 $μm^3$, 2 $μm^3$, 3 $μm^3$, 4 $μm^3$, 5 $μm^3$, 6 $μm^3$, 7 $μm^3$, 8 $μm^3$, 9 $μm^3$, 10 $μm^3$, 12 $μm^3$, 14 $μm^3$, 16 $μm^3$, 18 $μm^3$, 20 $μm^3$, 25 $μm^3$, 30 $μm^3$, 35 $μm^3$, 40 $μm^3$, 45 $μm^3$, 50 $μm^3$, 55 $μm^3$, 60 $μm^3$, 65 $μm^3$, 70 $μm^3$, 75 $μm^3$, 80 $μm^3$, 85 $μm^3$, 90 $μm^3$, 95 $μm^3$, 100 $μm^3$, 125 $μm^3$, 150 $μm^3$, 175 $μm^3$, 200 $μm^3$, 250 $μm^3$, 300 $μm^3$, 350 $μm^3$, 400 $μm^3$, 450 $μm^3$, $μm^3$, 500 $μm^3$, 550 $μm^3$, 600 $μm^3$, 650 $μm^3$, 700 $μm^3$, 750 $μm^3$, 800 $μm^3$, 850 $μm^3$, 900 $μm^3$, 950 $μm^3$, 1000 $μm^3$, 1200 $μm^3$, 1400 $μm^3$, 1600 $μm^3$, 1800 $μm^3$, 2000 $μm^3$, 2200 $μm^3$, 2400 $μm^3$, 2600 $μm^3$, 2800 $μm^3$, 3000 $μm^3$, or greater.

In some embodiments, the bead can have a volume of between about 1 $μm^3$ and 100 $μm^3$, such as between about 1 $μm^3$ and 10 $μm^3$, between about 10 $μm^3$ and 50 $μm^3$, or between about 50 $μm^3$ and 100 $μm^3$. In some embodiments, the bead can include a volume of between about 100 $μm^3$ and 1000 $μm^3$, such as between about 100 $μm^3$ and 500 $μm^3$ or between about 500 $μm^3$ and 1000 $μm^3$. In some embodiments, the bead can include a volume between about 1000 $μm^3$ and 3000 $μm^3$, such as between about 1000 $μm^3$ and 2000 $μm^3$ or between about 2000 $μm^3$ and 3000 $μm^3$. In some embodiments, the bead can include a volume between about 1 $μm^3$ and 3000 $μm^3$, such as between about 1 $μm^3$ and 2000 $μm^3$, between about 1 $μm^3$ and 1000 $μm^3$, between about 1 $μm^3$ and 500 $μm^3$, or between about 1 $μm^3$ and 250 $μm^3$.

The bead can include one or more cross-sections that can be the same or different. In some embodiments, the bead can have a first cross-section that is different from a second cross-section. The bead can have a first cross-section that is at least about 0.0001 micrometer, 0.001 micrometer, 0.01 micrometer, 0.1 micrometer, or 1 micrometer. In some embodiments, the bead can include a cross-section (e.g., a first cross-section) of at least about 1 micrometer (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 100 μm, 120 μm, 140 μm, 160 μm, 180 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), or greater. In some embodiments, the bead can include a cross-section (e.g., a first cross-section) of between about 1 μm and 500 μm, such as between about 1 μm and 100 μm, between about 100 μm and 200 μm, between about 200 μm and 300 μm, between about 300 μm and 400 μm, or between about 400 μm and 500 μm. For example, the bead can include a cross-section (e.g., a first cross-section) of between about 1 μm and 100 μm. In some embodiments, the bead can have a second cross-section that is at least about 1 μm. For example, the bead can include a second cross-section of at least about 1 micrometer (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 100 μm, 120 μm, 140 μm, 160 μm, 180 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), or greater. In some embodiments, the bead can include a second cross-section of between about 1 μm and 500 μm, such as between about 1 μm and 100 μm, between about 100 μm and 200 μm, between about 200 μm and 300 μm, between about 300 μm and 400 μm, or between about 400 μm and 500 μm. For example, the bead can include a second cross-section of between about 1 μm and 100 μm.

In some embodiments, beads can be of a nanometer scale (e.g., beads can have a diameter or maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). A plurality of beads can have an average diameter or average maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). In some embodiments, a bead has a diameter or size that is about the size of a single cell (e.g., a single cell under evaluation).

In some embodiments, the bead can be a gel bead. A "gel" is a semi-rigid material permeable to liquids and gases. Exemplary gels include, but are not limited to, those having a colloidal structure, such as agarose; polymer mesh structures, such as gelatin; hydrogels; and cross-linked polymer structures, such as polyacrylamide, SFA (see, for example, U.S. Patent Application Publication No. 2011/0059865, which is incorporated herein by reference in its entirety) and PAZAM (see, for example, U.S. Patent Application Publication No. 2014/0079923, which is incorporated herein by reference in its entirety).

A gel can be formulated into various shapes and dimensions depending on the context of intended use. In some embodiments, a gel is prepared and formulated as a gel bead (e.g., a gel bead including capture probes attached or associated with the gel bead). A gel bead can be a hydrogel bead. A hydrogel bead can be formed from molecular precursors, such as a polymeric or monomeric species.

In some embodiments, a hydrogel bead can include a polymer matrix (e.g., a matrix formed by polymerization or cross-linking). A polymer matrix can include one or more polymers (e.g., polymers having different functional groups or repeat units). Cross-linking can be via covalent, ionic, and/or inductive interactions, and/or physical entanglement.

A semi-solid bead can be a liposomal bead.

Solid beads can include metals including, without limitation, iron oxide, gold, and silver. In some embodiments, the bead can be a silica bead. In some embodiments, the bead can be rigid. In some embodiments, the bead can be flexible and/or compressible.

The bead can be a macromolecule. The bead can be formed of nucleic acid molecules bound together. The bead can be formed via covalent or non-covalent assembly of molecules (e.g., macromolecules), such as monomers or polymers. Polymers or monomers can be natural or synthetic. Polymers or monomers can be or include, for example, nucleic acid molecules (e.g., DNA or RNA).

A bead can be rigid, or flexible and/or compressible. A bead can include a coating including one or more polymers. Such a coating can be disruptable or dissolvable. In some embodiments, a bead includes a spectral or optical label (e.g., dye) attached directly or indirectly (e.g., through a linker) to the bead. For example, a bead can be prepared as a colored preparation (e.g., a bead exhibiting a distinct color within the visible spectrum) that can change color (e.g., colorimetric beads) upon application of a desired stimulus (e.g., heat and/or chemical reaction) to form differently colored beads (e.g., opaque and/or clear beads).

A bead can include natural and/or synthetic materials. For example, a bead can include a natural polymer, a synthetic polymer or both natural and synthetic polymers. Examples of natural polymers include, without limitation, proteins, sugars such as deoxyribonucleic acid, rubber, cellulose, starch (e.g., amylose, amylopectin), enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include, without limitation, acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., copolymers) thereof. Beads can also be formed from materials other than polymers, including for example, lipids, micelles, ceramics, glass-ceramics, material composites, metals, and/or other inorganic materials.

In some embodiments, a bead is a degradable bead. A degradable bead can include one or more species (e.g., disulfide linkers, primers, other oligonucleotides, etc.) with a labile bond such that, when the bead/species is exposed to the appropriate stimuli, the labile bond is broken and the bead degrades. The labile bond can be a chemical bond (e.g., covalent bond, ionic bond) or can be another type of physical interaction (e.g., van der Waals interactions, dipole-dipole interactions, etc.). In some embodiments, a cross-linker used to generate a bead can include a labile bond. Upon exposure to the appropriate conditions, the labile bond can be broken and the bead degraded. For example, upon exposure of a polyacrylamide gel bead including cystamine crosslinkers to a reducing agent, the disulfide bonds of the cystamine can be broken and the bead degraded.

Degradation can refer to the disassociation of a bound or entrained species (e.g., disulfide linkers, primers, other oligonucleotides, etc.) from a bead, both with and without structurally degrading the physical bead itself. For example, entrained species can be released from beads through osmotic pressure differences due to, for example, changing chemical environments. By way of example, alteration of bead pore sizes due to osmotic pressure differences can generally occur without structural degradation of the bead itself. In some embodiments, an increase in pore size due to osmotic swelling of a bead can permit the release of entrained species within the bead. In some embodiments, osmotic shrinking of a bead can cause a bead to better retain an entrained species due to pore size contraction.

Any suitable agent that can degrade beads can be used. In some embodiments, changes in temperature or pH can be used to degrade thermo-sensitive or pH-sensitive bonds within beads. In some embodiments, chemical degrading agents can be used to degrade chemical bonds within beads by oxidation, reduction or other chemical changes. For example, a chemical degrading agent can be a reducing agent, such as DTT, where DTT can degrade the disulfide bonds formed between a crosslinker and gel precursors, thus degrading the bead. In some embodiments, a reducing agent can be added to degrade the bead, which can cause the bead to release its contents. Examples of reducing agents can include, without limitation, dithiothreitol (DTT), (3-mercaptoethanol, (2S)-2-amino-1,4-dimercaptobutane (dithiobutylamine or DTBA), tris(2-carboxyethyl) phosphine (TCEP), or combinations thereof.

Any of a variety of chemical agents can be used to trigger the degradation of beads. Examples of chemical agents include, but are not limited to, pH-mediated changes to the integrity of a component within the bead, degradation of a component of a bead via cleavage of cross-linked bonds, and depolymerization of a component of a bead.

In some embodiments, a bead can be formed from materials that include degradable chemical crosslinkers, such as N,N'-bis-(acryloyl)cystamine (BAC) or cystamine. Degradation of such degradable crosslinkers can be accomplished through any variety of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof.

In some embodiments, exposure to an aqueous solution, such as water, can trigger hydrolytic degradation, and thus degradation of the bead. Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In some embodiments, heat can increase the internal pressure of the bead components such that the bead ruptures or explodes. Heat can also act upon heat-sensitive polymers used as materials to construct beads.

Where degradable beads are used, it can be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads include reducible cross-linking groups, such as disulfide groups, it will be desirable to avoid contacting such beads with reducing agents, e.g., DTT or other disulfide cleaving reagents. In such embodiments, treatment of the beads described herein will, in some embodiments be provided free of reducing agents, such as DTT. Because reducing agents are often provided in commercial enzyme preparations, it can be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that can be used to treat the beads described herein. The terms "reducing agent free" or "DTT free" preparations refer to a preparation having less than about 1/10th, less than about 1/50th, or less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or less than about 0.0001 mM DTT. In some embodiments, the amount of DTT can be undetectable.

A degradable bead can be useful to more quickly release an attached capture probe (e.g., a nucleic acid molecule, a spatial barcode sequence, and/or a primer) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a capture probe having one or more spatial barcodes can be attached, via a disulfide bond, to a polyacrylamide bead including cystamine. Upon exposure of the spatially barcoded bead to a reducing agent, the bead degrades and the capture probe having the one or more spatial barcode sequences is released upon breakage of both the disulfide linkage between the capture probe and the bead and the disulfide linkages of the cystamine in the bead.

The addition of multiple types of labile bonds to a bead can result in the generation of a bead capable of responding to varied stimuli. Each type of labile bond can be sensitive to an associated stimulus (e.g., chemical stimulus, light, temperature, pH, enzymes, etc.) such that release of reagents attached to a bead via each labile bond can be controlled by the application of the appropriate stimulus. Some non-limiting examples of labile bonds that can be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond can be cleavable via other nucleic acid molecule targeting enzymes, such as restriction enzymes (e.g., restriction endonucleases). Such functionality can be useful in controlled release of reagents from a bead. In some embodiments, another reagent including a labile bond can be linked to a bead after gel bead formation via, for example, an activated functional group of the bead as described above. In some embodiments, a gel bead including a labile bond is reversible. In some embodiments, a gel bead with a reversible labile bond is used to capture one or more regions of interest of a biological sample. For example, without limitation, a bead including a thermolabile bond can be heated by a light source (e.g., a laser) that causes a change in the gel bead that facilitates capture of a biological sample in contact with the gel bead. Capture probes having one or more spatial barcodes that are releasably, cleavably, or reversibly attached to the beads described herein include capture probes that are released or releasable through cleavage of a linkage between the capture probe and the bead, or that are released through degradation of the underlying bead itself, allowing the capture probes having the one or more spatial barcodes to be accessed or become accessible by other reagents, or both.

Beads can have different physical properties. Physical properties of beads can be used to characterize the beads. Non-limiting examples of physical properties of beads that can differ include size, shape, circularity, density, symmetry, and hardness. For example, beads can be of different sizes. Different sizes of beads can be obtained by using microfluidic channel networks configured to provide specific sized beads (e.g., based on channel sizes, flow rates, etc.). In some embodiments, beads have different hardness values that can be obtained by varying the concentration of polymer used to generate the beads. In some embodiments, a spatial barcode attached to a bead can be made optically detectable using a physical property of the capture probe. For example, a nucleic acid origami, such as a deoxyribonucleic acid (DNA) origami, can be used to generate an optically detectable spatial barcode. To do so, a nucleic acid molecule, or a plurality of nucleic acid molecules, can be folded to create two- and/or three-dimensional geometric shapes. The different geometric shapes can be optically detected.

In some embodiments, special types of nanoparticles with more than one distinct physical property can be used to make the beads physically distinguishable. For example, Janus particles with both hydrophilic and hydrophobic surfaces can be used to provide unique physical properties.

In some embodiments, a bead is able to identify multiple analytes (e.g., nucleic acids, proteins, chromatin, metabolites, drugs, gRNA, and lipids) from a single cell. In some embodiments, a bead is able to identify a single analyte from a single cell (e.g., mRNA).

A bead can have a tunable pore size. The pore size can be chosen to, for instance, retain denatured nucleic acids. The pore size can be chosen to maintain diffusive permeability to exogenous chemicals such as sodium hydroxide (NaOH) and/or endogenous chemicals such as inhibitors. A bead can be formed of a biocompatible and/or biochemically compatible material, and/or a material that maintains or enhances cell viability. A bead can be formed from a material that can be depolymerized thermally, chemically, enzymatically, and/or optically.

In some embodiments, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. Swelling of the beads can be accomplished, for instance, by placing the beads in a thermodynamically favorable solvent, subjecting the beads to a higher or lower temperature, subjecting the beads to a higher or lower ion concentration, and/or subjecting the beads to an electric field.

The swelling of the beads can be accomplished by various swelling methods. In some embodiments, swelling is reversible (e.g., by subjecting beads to conditions that promote de-swelling). In some embodiments, the de-swelling of the beads is accomplished, for instance, by transferring the beads in a thermodynamically unfavorable solvent, subjecting the beads to lower or higher temperatures, subjecting the beads to a lower or higher ion concentration, and/or adding or removing an electric field. The de-swelling of the beads can be accomplished by various de-swelling methods. In some embodiments, de-swelling is reversible (e.g., subject beads to conditions that promote swelling). In some embodiments, the de-swelling of beads can include transferring the beads to cause pores in the bead to shrink. The shrinking can then hinder reagents within the beads from diffusing out of the interiors of the beads. The hindrance created can be due to steric interactions between the reagents and the interiors of the beads. The transfer can be accomplished microfluidically. For instance, the transfer can be achieved by moving the beads from one co-flowing solvent stream to a different co-flowing solvent stream. The swellability and/or pore size of the beads can be adjusted by changing the polymer composition of the bead.

A bead can include a polymer that is responsive to temperature so that when the bead is heated or cooled, the characteristics or dimensions of the bead can change. For example, a polymer can include poly(N-isopropylacrylamide). A gel bead can include poly(N-isopropylacrylamide) and when heated the gel bead can decrease in one or more dimensions (e.g., a cross-sectional diameter, multiple cross-sectional diameters). A temperature sufficient for changing one or more characteristics of the gel bead can be, for example, at least about 0 degrees Celsius (° C.), 1° C., 2° C., 3° C., 4° C., 5° C., 10° C., or higher. For example, the temperature can be about 4° C. In some embodiments, a temperature sufficient for changing one or more characteristics of the gel bead can be, for example, at least about 25° C., 30° C., 35° C., 37° C., 40° C., 45° C., 50° C., or higher. For example, the temperature can be about 37° C.

Functionalization of beads for attachment of capture probes can be achieved through a wide range of different approaches, including, without limitation, activation of chemical groups within a polymer, incorporation of active or activatable functional groups in the polymer structure, or attachment at the pre-polymer or monomer stage in bead production. The bead can be functionalized to bind to targeted analytes, such as nucleic acids, proteins, carbohydrates, lipids, metabolites, peptides, or other analytes.

In some embodiments, a bead can contain molecular precursors (e.g., monomers or polymers), which can form a polymer network via polymerization of the molecular precursors. In some embodiments, a precursor can be an already polymerized species capable of undergoing further polymerization via, for example, a chemical cross-linkage. In some embodiments, a precursor can include one or more of an acrylamide or a methacrylamide monomer, oligomer, or polymer. In some embodiments, the bead can include prepolymers, which are oligomers capable of further polymerization. For example, polyurethane beads can be prepared using prepolymers. In some embodiments, a bead can contain individual polymers that can be further polymerized together (e.g., to form a co-polymer). In some embodiments, a bead can be generated via polymerization of different precursors, such that they include mixed polymers, co-polymers, and/or block co-polymers. In some embodiments, a bead can include covalent or ionic bonds between polymeric precursors (e.g., monomers, oligomers, and linear polymers), nucleic acid molecules (e.g., oligonucleotides), primers, and other entities. In some embodiments, covalent bonds can be carbon-carbon bonds or thioether bonds.

Cross-linking of polymers can be permanent or reversible, depending upon the particular cross-linker used. Reversible cross-linking can allow the polymer to linearize or dissociate under appropriate conditions. In some embodiments, reversible cross-linking can also allow for reversible attachment of a material bound to the surface of a bead. In some embodiments, a cross-linker can form a disulfide linkage. In some embodiments, a chemical cross-linker forming a disulfide linkage can be cystamine or a modified cystamine.

For example, where the polymer precursor material includes a linear polymer material, such as a linear polyacrylamide, PEG, or other linear polymeric material, the activation agent can include a cross-linking agent, or a chemical that activates a cross-linking agent within formed droplets. Likewise, for polymer precursors that include polymerizable monomers, the activation agent can include a polymerization initiator. For example, in certain embodiments, where the polymer precursor includes a mixture of acrylamide monomer with a N,N'-bis-(acryloyl)cystamine (BAC) comonomer, an agent such as tetraethylmethylenediamine (TEMED) can be provided, which can initiate the copolymerization of the acrylamide and BAC into a cross-linked polymer network, or other conditions sufficient to polymerize or gel the precursors. The conditions sufficient to polymerize or gel the precursors can include exposure to heating, cooling, electromagnetic radiation, and/or light.

Following polymerization or gelling, a polymer or gel can be formed. The polymer or gel can be diffusively permeable to chemical or biochemical reagents. The polymer or gel can be diffusively impermeable to macromolecular constituents. The polymer or gel can include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel can include any other polymer or gel.

In some embodiments, disulfide linkages can be formed between molecular precursor units (e.g., monomers, oligomers, or linear polymers) or precursors incorporated into a bead and nucleic acid molecules (e.g., oligonucleotides, capture probes). Cystamine (including modified cystamines), for example, is an organic agent including a disulfide bond that can be used as a crosslinker agent between individual monomeric or polymeric precursors of a bead. Polyacrylamide can be polymerized in the presence of cystamine or a species including cystamine (e.g., a modified cystamine) to generate polyacrylamide gel beads including disulfide linkages (e.g., chemically degradable beads including chemically-reducible cross-linkers). The disulfide linkages can permit the bead to be degraded (or dissolved) upon exposure of the bead to a reducing agent.

In some embodiments, chitosan, a linear polysaccharide polymer, can be cross-linked with glutaraldehyde via hydrophilic chains to form a bead. Crosslinking of chitosan polymers can be achieved by chemical reactions that are initiated by heat, pressure, change in pH, and/or radiation.

In some embodiments, a bead can include an acrydite moiety, which in certain aspects can be used to attach one or more capture probes to the bead. In some embodiments, an acrydite moiety can refer to an acrydite analogue generated from the reaction of acrydite with one or more species (e.g., disulfide linkers, primers, other oligonucleotides, etc.), such as, without limitation, the reaction of acrydite with other monomers and cross-linkers during a polymerization reaction. Acrydite moieties can be modified to form chemical bonds with a species to be attached, such as a capture probe. Acrydite moieties can be modified with thiol groups capable of forming a disulfide bond or can be modified with groups already including a disulfide bond. The thiol or disulfide (via disulfide exchange) can be used as an anchor point for a species to be attached or another part of the acrydite moiety can be used for attachment. In some embodiments, attachment can be reversible, such that when the disulfide bond is broken (e.g., in the presence of a reducing agent), the attached species is released from the bead. In some embodiments, an acrydite moiety can include a reactive hydroxyl group that can be used for attachment of species.

In some embodiments, precursors (e.g., monomers or cross-linkers) that are polymerized to form a bead can include acrydite moieties, such that when a bead is generated, the bead also includes acrydite moieties. The acrydite moieties can be attached to a nucleic acid molecule (e.g., an oligonucleotide), which can include a priming sequence (e.g., a primer for amplifying target nucleic acids, random primer, primer sequence for messenger RNA) and/or one or more capture probes. The one or more capture probes can include sequences that are the same for all capture probes coupled to a given bead and/or sequences that are different across all capture probes coupled to the given bead. The capture probe can be incorporated into the bead. In some embodiments, the capture probe can be incorporated or attached to the bead such that the capture probe retains a free 3' end. In some embodiments, the capture probe can be incorporated or attached to the bead such that the capture probe retains a free 5' end. In some embodiments, beads can be functionalized such that each bead contains a plurality of different capture probes. For example, a bead can include a plurality of capture probes e.g., Capture Probe 1, Capture Probe 2, and Capture Probe 3, and each of Capture Probes 1, Capture Probes 2, and Capture Probes 3 contain a distinct capture domain (e.g., capture domain of Capture Probe 1 includes a poly(dT) capture domain, capture domain of Capture Probe 2 includes a gene-specific capture domain, and capture domain of Capture Probe 3 includes a CRISPR-specific capture domain). By functionalizing beads to contain a plurality of different capture domains per bead, the level of multiplex capability for analyte detection can be improved.

In some embodiments, precursors (e.g., monomers or cross-linkers) that are polymerized to form a bead can include a functional group that is reactive or capable of being activated such that when it becomes reactive it can be polymerized with other precursors to generate beads including the activated or activatable functional group. The functional group can then be used to attach additional species (e.g., disulfide linkers, primers, other oligonucleotides, etc.) to the beads. For example, some precursors including a carboxylic acid (COOH) group can co-polymerize with other precursors to form a bead that also includes a COOH functional group. In some embodiments, acrylic acid (a species including free COOH groups), acrylamide, and bis(acryloyl)cystamine can be co-polymerized together to generate a bead including free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species including an amine functional group where the carboxylic acid groups are activated to be reactive with an amine functional group) as a functional group on a moiety to be linked to the bead.

Beads including disulfide linkages in their polymeric network can be functionalized with additional species (e.g., disulfide linkers, primers, other oligonucleotides, etc.) via reduction of some of the disulfide linkages to free thiols. The disulfide linkages can be reduced via, for example, the action of a reducing agent (e.g., DTT, TCEP, etc.) to generate free thiol groups, without dissolution of the bead. Free thiols of the beads can then react with free thiols of a species or a species including another disulfide bond (e.g., via thiol-disulfide exchange) such that the species can be linked to the beads (e.g., via a generated disulfide bond). In some embodiments, free thiols of the beads can react with any other suitable group. For example, free thiols of the beads can react with species including an acrydite moiety. The free thiol groups of the beads can react with the acrydite via Michael addition chemistry, such that the species including the acrydite is linked to the bead. In some embodiments, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control can be exerted, for example, by controlling the concentration of a reducing agent used to generate free thiol groups and/or concentration of reagents used to form disulfide bonds in bead polymerization. In some embodiments, a low concentration of reducing agent (e.g., molecules of reducing agent:gel bead ratios) of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, or less than or equal to about 1:10,000) can be used for reduction. Controlling the number of disulfide linkages that are reduced to free thiols can be useful in ensuring bead structural integrity during functionalization. In some embodiments, optically-active agents, such as fluorescent dyes can be coupled to beads via free thiol groups of the beads and used to quantify the number of free thiols present in a bead and/or track a bead.

In some embodiments, addition of moieties to a bead after bead formation can be advantageous. For example, addition of a capture probe after bead formation can avoid loss of the species (e.g., disulfide linkers, primers, other oligonucleotides, etc.) during chain transfer termination that can occur during polymerization. In some embodiments, smaller precursors (e.g., monomers or cross linkers that do not include side chain groups and linked moieties) can be used for polymerization and can be minimally hindered from growing chain ends due to viscous effects. In some embodiments, functionalization after bead synthesis can minimize exposure of species (e.g., oligonucleotides) to be loaded with potentially damaging agents (e.g., free radicals) and/or chemical environments. In some embodiments, the generated hydrogel can possess an upper critical solution temperature (UCST) that can permit temperature driven swelling and collapse of a bead. Such functionality can aid in oligonucleotide (e.g., a primer) infiltration into the bead during subsequent functionalization of the bead with the oligonucleotide. Post-production functionalization can also be useful in controlling loading ratios of species in beads, such that, for example, the variability in loading ratio is minimized. Species loading can also be performed in a batch process such that a plurality of beads can be functionalized with the species in a single batch.

Reagents can be encapsulated in beads during bead generation (e.g., during polymerization of precursors). Such reagents can or cannot participate in polymerization. Such reagents can be entered into polymerization reaction mixtures such that generated beads include the reagents upon bead formation. In some embodiments, such reagents can be added to the beads after formation. Such reagents can include, for example, capture probes (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such reagents can include one or more enzymes described herein, including without limitation, polymerase, reverse transcriptase, restriction enzymes (e.g., endonuclease), transposase, ligase, proteinase K, DNAse, etc. Such reagents can also or alternatively include one or more reagents such as lysis agents, inhibitors, inactivating agents, chelating agents, stimulus agents. Trapping of such reagents can be controlled by the polymer network density generated during polymerization of precursors, control of ionic charge within the bead (e.g., via ionic species linked to polymerized species), or by the release of other species. Encapsulated reagents can be released from a bead upon bead degradation and/or by application of a stimulus capable of releasing the reagents from the bead.

In some embodiments, the beads can also include (e.g., encapsulate or have attached thereto) a plurality of capture probes that include spatial barcodes, and the optical properties of the spatial barcodes can be used for optical detection of the beads. For example, the absorbance of light by the spatial barcodes can be used to distinguish the beads from one another. In some embodiments, a detectable label can directly or indirectly attach to a spatial barcode and provide optical detection of the bead. In some embodiments, each bead in a group of one or more beads has a unique detectable label, and detection of the unique detectable label determines the location of the spatial barcode sequence associated with the bead.

Optical properties giving rise to optical detection of beads can be due to optical properties of the bead surface (e.g., a detectable label attached to the bead or the size of the bead), or optical properties from the bulk region of the bead (e.g., a detectable label incorporated during bead formation or an optical property of the bead itself). In some embodiments, a detectable label can be associated with a bead or one or more moieties coupled to the bead.

In some embodiments, the beads include a plurality of detectable labels. For example, a fluorescent dye can be attached to the surface of the beads and/or can be incorporated into the beads. Different intensities of the different fluorescent dyes can be used to increase the number of optical combinations that can be used to differentiate between beads. For example, if N is the number of fluorescent dyes (e.g., between 2 and 10 fluorescent dyes, such as 4 fluorescent dyes) and M is the possible intensities for the dyes (e.g., between 2 and 50 intensities, such as 20 intensities), then $M^N$ are the possible distinct optical combinations. In one example, 4 fluorescent dyes with 20 possible intensities can be used to generate 160,000 distinct optical combinations.

One or more optical properties of the beads or biological contents, such as cells or nuclei, can be used to distinguish the individual beads or biological contents from other beads or biological contents. In some embodiments, the beads are made optically detectable by including a detectable label having optical properties to distinguish the beads from one another.

In some embodiments, optical properties of the beads can be used for optical detection of the beads. For example, without limitation, optical properties can include absorbance, birefringence, color, fluorescence, luminosity, photosensitivity, reflectivity, refractive index, scattering, or transmittance. For example, beads can have different birefringence values based on degree of polymerization, chain length, or monomer chemistry.

In some embodiments, nanobeads, such as quantum dots or Janus beads, can be used as optical labels or components thereof. For example, a quantum dot can be attached to a spatial barcode of a bead.

Optical labels of beads can provide enhanced spectral resolution to distinguish between beads with unique spatial barcodes (e.g., beads including unique spatial barcode sequences). In some embodiments, a first bead includes a first optical label and spatial barcodes each having a first spatial barcode sequence. A second bead includes a second optical label and spatial barcodes each having a second spatial barcode sequence. The first optical label and second optical label can be different (e.g., provided by two different fluorescent dyes or the same fluorescent dye at two different intensities). The first and second spatial barcode sequences can be different nucleic acid sequences. In some embodiments, the beads can be imaged to identify the first and second optical labels, and the first and second optical barcodes can then be used to associate the first and second optical labels with the first and second spatial barcode sequences, respectively.

Optical labels can be included while generating the beads. For example, optical labels can be included in the polymer structure of a gel bead, or attached at the pre-polymer or monomer stage in bead production. In some embodiments, the beads include moieties that attach to one or more optical labels (e.g., at a surface of a bead and/or within a bead). In some embodiments, optical labels can be loaded into the beads with one or more reagents. For example, reagents and optical labels can be loaded into the beads by diffusion of the reagents (e.g., a solution of reagents including the optical barcodes). In some embodiments, optical labels can be included while preparing spatial barcodes. For example, spatial barcodes can be prepared by synthesizing molecules including barcode sequences (e.g., using a split pool or combinatorial approach). Optical labels can be attached to spatial barcodes prior to attaching the spatial barcodes to a bead. In some embodiments, optical labels can be included after attaching spatial barcodes to a bead. For example, optical labels can be attached to spatial barcodes coupled to the bead. In some embodiments, spatial barcodes or sequences thereof can be releasably or cleavably attached to the bead. Optical labels can be releasably or non-releasably attached to the bead. In some embodiments, a first bead (e.g., a bead including a plurality of spatial barcodes) can be coupled to a second bead including one or more optical labels. For example, the first bead can be covalently coupled to the second bead via a chemical bond. In some embodiments, the first bead can be non-covalently associated with the second bead.

The first and/or second bead can include a plurality of spatial barcodes. The plurality of spatial barcodes coupled to a given bead can include the same barcode sequences. Where both the first and second beads include spatial barcodes, the first and second beads can include spatial barcodes including the same barcode sequences or different barcode sequences.

Bead arrays containing captured analytes can be processed in bulk or partitioned into droplet emulsions for preparing sequencing libraries. In some embodiments, next generation sequencing reads are clustered and correlated to the spatial position of the spatial barcode on the bead array. For example, the information can be computationally superimposed over a high-resolution image of the tissue section to identify the location(s), where the analytes were detected.

In some embodiments, de-cross linking can be performed to account for de-crosslinking chemistries that may be incompatible with certain barcoding/library prep biochemistry (e.g., presence of proteases). For example, a two-step process is possible. In the first step, beads can be provided in droplets such that DNA binds to the beads after the conventional de-crosslinking chemistry is performed. In the second step, the emulsion is broken and beads collected and then re-encapsulated after washing for further processing.

In some embodiments, beads can be affixed or attached to a substrate using photochemical methods. For example, a bead can be functionalized with perfluorophenylazide silane (PFPA silane), contacted with a substrate, and then exposed to irradiation (see, e.g., Liu et al. (2006) Journal of the American Chemical Society 128, 14067-14072). For example, immobilization of antraquinone-functionalized substrates (see, e.g., Koch et al. (2000) Bioconjugate Chem. 11, 474-483, the entire contents of which are herein incorporated by reference).

The arrays can also be prepared by bead self-assembly. Each bead can be covered with hundreds of thousands of copies of a specific oligonucleotide. In some embodiments, each bead can be covered with about 1,000 to about 1,000,000 oligonucleotides. In some embodiments, each bead can be covered with about 1,000,000 to about 10,000,000 oligonucleotides. In some embodiments, each bead can covered with about 2,000,000 to about 3,000,000, about 3,000,000 to about 4,000,000, about 4,000,000 to about 5,000,000, about 5,000,000 to about 6,000,000, about 6,000,000 to about 7,000,000, about 7,000,000 to about 8,000,000, about 8,000,000 to about 9,000,000, or about 9,000,000 to about 10,000,000 oligonucleotides. In some embodiments, each bead can be covered with about 10,000,000 to about 100,000,000 oligonucleotides. In some embodiments, each bead can be covered with about 100,000,000 to about 1,000,000,000 oligonucleotides. In some embodiments, each bead can be covered with about 1,000,000,000 to about 10,000,000,000 oligonucleotides. The beads can be irregularly distributed across etched substrates during the array production process. During this process, the beads can be self-assembled into arrays (e.g., on a fiber-optic bundle substrate or a silica slide substrate). In some embodiments, the beads irregularly arrive at their final location on the array. Thus, the bead location may need to be mapped or the oligonucleotides may need to be synthesized based on a predetermined pattern.

Beads can be affixed or attached to a substrate covalently, non-covalently, with adhesive, or a combination thereof. The attached beads can be, for example, layered in a monolayer, a bilayer, a trilayer, or as a cluster. As defined herein, a "monolayer" generally refers to an arrayed series of probes, beads, spots, dots, features, micro-locations, or islands that are affixed or attached to a substrate, such that the beads are arranged as one layer of single beads. In some embodiments, the beads are closely packed.

As defined herein, the phrase "substantial monolayer" or "substantially form(s) a monolayer" generally refers to (the formation of) an arrayed series of probes, beads, microspheres, spots, dots, features, micro-locations, or islands that are affixed or attached to a substrate, such that about 50% to about 99% (e.g., about 50% to about 98%) of the beads are arranged as one layer of single beads. This arrangement can be determined using a variety of methods, including microscopic imaging.

In some embodiments, the monolayer of beads is a located in a predefined area on the substrate. For example, the predefined area can be partitioned with physical barriers, a photomask, divots in the substrate, or wells in the substrate.

As used herein, the term "reactive element" generally refers to a molecule or molecular moiety that can react with another molecule or molecular moiety to form a covalent bond. Reactive elements include, for example, amines, aldehydes, alkynes, azides, thiols, haloacetyls, pyridyl disulfides, hydrazides, carboxylic acids, alkoxyamines, sulfhydryls, maleimides, Michael acceptors, hydroxyls, and active esters. Some reactive elements, for example, carboxylic acids, can be treated with one or more activating agents (e.g., acylating agents, isourea-forming agents) to increase susceptibility of the reactive element to nucleophilic attack. Non-limiting examples of activating agents include N-hydroxysuccinimide, N-hydroxysulfosuccinimide, 1-ethyl-3-(3-dimethylaminopropyl)carbodiimide, dicyclohexylcarbodiimide, diisopropylcarbodiiimide, 1-hydroxybenzotriazole, (benzotriazol-1-yloxy)tripyrrolidinophosphonium hexfluorophosphate, (benzotriazol-1-yl)-N,N,N',N'-tetramethyluronium hexafluorophosphate, 4-(N,N-dimethylamino)pyridine, and carbonyldiimidazole.

In some embodiments, the reactive element is bound directly to a bead. For example, hydrogel beads can be treated with an acrylic acid monomer to form acrylic acid-functionalized hydrogel beads. In some cases, the reactive element is bound indirectly to the bead via one or more linkers. As used herein, a "linker" generally refers to a multifunctional (e.g., bifunctional, trifunctional) reagent used for conjugating two or more chemical moieties. A linker can be a cleavable linker that can undergo induced dissociation. For example, the dissociation can be induced by a solvent (e.g., hydrolysis and solvolysis); by irradiation (e.g., photolysis); by an enzyme (e.g., enzymolysis); or by treatment with a solution of specific pH (e.g., pH 4, 5, 6, 7, or 8).

In some embodiments, the reactive element is bound directly to a substrate. For example, a glass slide can be coated with (3-aminopropyl)triethoxysilane. In some embodiments, the reactive element is bound indirectly to a substrate via one or more linkers.

Methods for Covalently Bonding Beads to a Substrate

Provided herein are methods for the covalent bonding of beads (e.g., optically labeled beads, hydrogel beads, microsphere beads) to a substrate.

In some embodiments, the beads are coupled to a substrate via a covalent bond between a first reactive element and a second reactive element. In some embodiments, the covalently-bound beads substantially form a monolayer of beads (e.g., hydrogel beads, microsphere beads) on the substrate.

In some embodiments, the beads are functionalized with a first reactive element, which is directly bound to the beads. In some embodiments, the beads are functionalized with a first reactive element, which is indirectly bound to the beads via a linker. In some embodiments, the linker is a benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments, the substrate is functionalized with a second reactive element, which is directly bound to the substrate. In some embodiments, the substrate is functionalized with a second reactive element, which is indirectly bound to the beads via a linker. In some embodiments, the linker is a benzophenone. For example, the linker can be benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments, the substrate is a glass slide. In some embodiments, the substrate is a pre-functionalized glass slide.

In some embodiments, about 99% of the covalently-bound beads form a monolayer of beads on the substrate. In some embodiments, about 50% to about 98% form a monolayer of beads on the substrate. For example, about 50% to about 95%, about 50% to about 90%, about 50% to about 85%, about 50% to about 80%, about 50% to about 75%, about 50% to about 70%, about 50% to about 65%, about 50% to about 60%, or about 50% to about 55% of the covalently-bound beads form a monolayer of beads on the substrate. In some embodiments, about 55% to about 98%, about 60% to about 98%, about 65% to about 98%, about 70% to about 98%, about 75% to about 98%, about 80% to about 98%, about 85% to about 98%, about 90% to about 95%, or about 95% to about 98% of the covalently-bound beads form a monolayer of beads on the substrate. In some embodiments, about 55% to about 95%, about 60% to about 90%, about 65% to about 95%, about 70% to about 95%, about 75% to about 90%, about 75% to about 95%, about 80% to about 90%, about 80% to about 95%, about 85% to about 90%, or about 85% to about 95% of the covalently-bound beads for a monolayer of beads on the substrate.

In some embodiments, at least one of the first reactive element and the second reactive element is selected from the group consisting of:

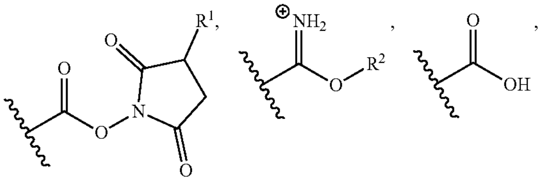

-continued

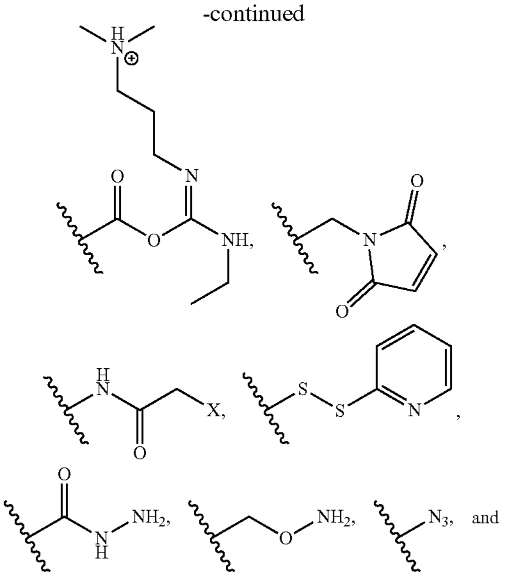

and

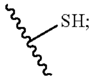

wherein $R^1$ is selected from H, $C_1$-$C_6$ alkyl, or —$SO_3$;

$R^2$ is $C_1$-$C_6$ alkyl; and

X is a halo moiety.

In some embodiments, at least one of the first reactive element or the second reactive element comprises

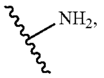

or

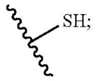

wherein the  indicates the point of attachment of the first reactive element or the second reactive element to the bead (e.g., hydrogel bead or microsphere bead) or to the substrate.

In some embodiments, at least one of the first reactive element or the second reactive element is selected from the group consisting of:

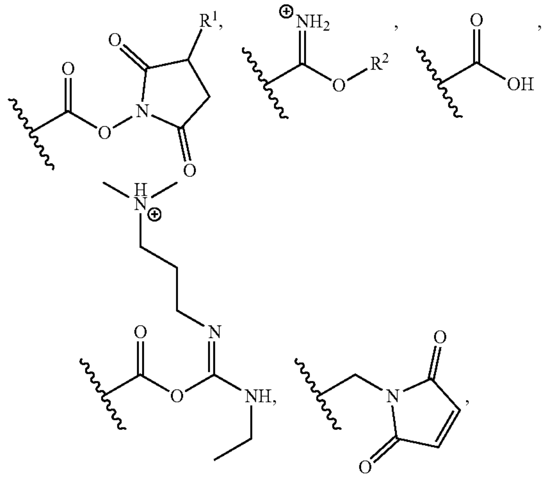

-continued

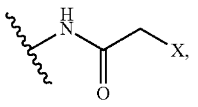 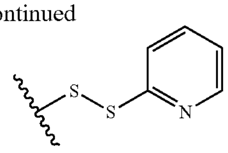

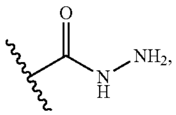 and 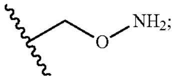

wherein $R^1$ is selected from H, $C_1$-$C_6$ alkyl, or —$SO_3$;

$R^2$ is $C_1$-$C_6$ alkyl; and

X is a halo moiety.

In some embodiments, at least one of the first reactive element or the second reactive element comprises

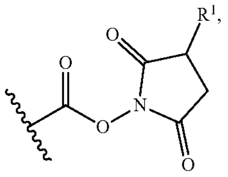

wherein $R^1$ is selected from H, $C_1$-$C_6$ alkyl, or —$SO_3$. In some embodiments, $R^1$ is H. In some embodiments, $R^1$ is $C_1$-$C_6$ alkyl. In some embodiments, $R^1$ is —$SO_3$.

In some embodiments, at least one of the first reactive element or the second reactive element comprises

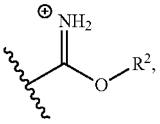

wherein $R^2$ is $C_1$-$C_6$ alkyl. In some embodiments, $R^2$ is methyl.

In some embodiments, at least one of the first reactive element or the second reactive element comprises

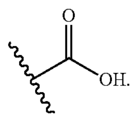 [SMILES: *C(=O)O]

Is some embodiments,

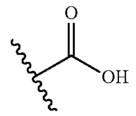 [SMILES: *C(=O)O]

can be reacted with an activating agent to form an active ester. In some embodiments, the active ester is

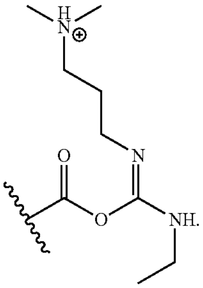

In some embodiments, the activating agent is an acylating agent (e.g., N-hydroxysuccinimide and N-hydroxysulfosuccinimide). In some embodiments, the activating agent is an O-acylisourea-forming agent (e.g., 1-ethyl-3-(3-dimethylaminopropyl)carbodiimide (EDC), dicyclohexylcarbodiimide, and diisopropylcarbodiiimide). In some embodiments, the activating agent is a combination of at least one acylating agent and at least one O-isourea-forming agents (e.g., N-hydroxysuccinimide (NHS), 1-ethyl-3-(3-dimethylaminopropyl)carbodiimide (EDC), N-hydroxysulfosuccinimide (sulfo-NHS), and a combination thereof).

In some embodiments, at least one of the first reactive element or the second reactive element comprises

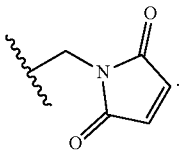 [SMILES: *CN1C(=O)C=CC1=O]

In some embodiments, at least one of the first reactive element or the second reactive element comprises

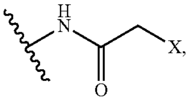

wherein X is a halo moiety. For example, X is chloro, bromo, or iodo.

In some embodiments, at least one of the first reactive element or the second reactive element comprises

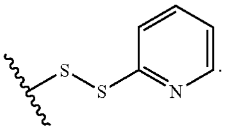 [SMILES: *SSc1ccccn1]

In some embodiments, at least one of the first reactive element or the second reactive element comprises

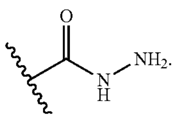 [SMILES: *C(=O)NN]

In some embodiments, at least one of the first reactive element or the second reactive element comprises

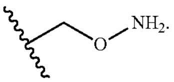 [SMILES: *CON]

In some embodiments, at least one of the first reactive element or the second reactive element is selected from the group consisting of:

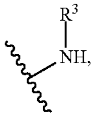 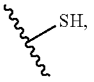 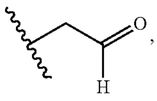, and

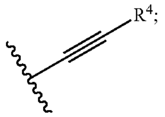

wherein $R^3$ is H or $C_1$-$C_6$ alkyl; and $R^4$ is H or trimethylsilyl.

In some embodiments, at least one of the first reactive element or the second reactive element comprises

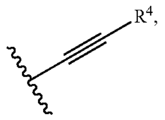

wherein $R^4$ is H or trimethylsilyl. In some embodiments, $R^4$ is H.

In some embodiments, at least one of the first reactive element or the second reactive element is selected from the group consisting of:

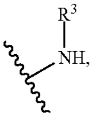 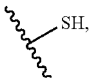 and 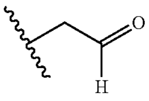

wherein $R^3$ is H or $C_1$-$C_6$ alkyl. In some embodiments, $R^3$ is H. In some embodiments, $R^3$ is $C_1$-$C_6$ alkyl.

In some embodiments, at least one of the first reactive element or the second reactive element comprises

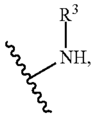

wherein $R^3$ is H or $C_1$-$C_6$ alkyl. In some embodiments, $R^3$ is H. In some embodiments, $R^3$ is $C_1$-$C_6$ alkyl.

In some embodiments, at least one of the first reactive elements or the second reactive elements comprises

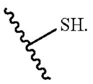

In some embodiments, at least one of the first reactive elements or the second reactive elements comprises

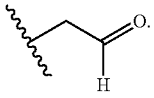 [SMILES: *CC=O]

In some embodiments, one of the first reactive elements or the second reactive elements is selected from the group consisting of:

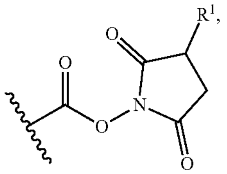 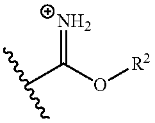, 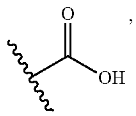,

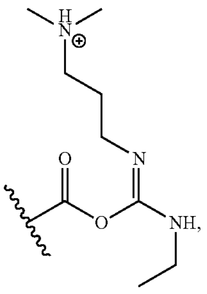 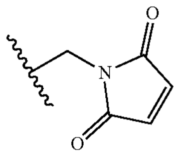,

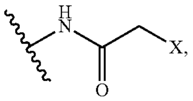 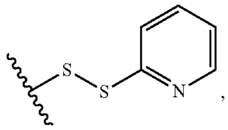,

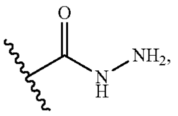 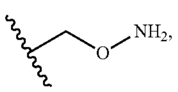 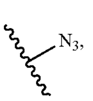 and

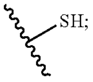

wherein $R^1$ is selected from H, $C_1$-$C_6$ alkyl, or $—SO_3$;

$R^2$ is $C_1$-$C_6$ alkyl;

X is a halo moiety;

and the other of the first reactive element or the second reactive element is selected from the group consisting of:

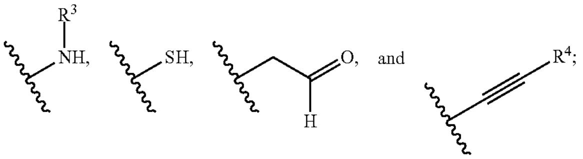

and wherein $R^3$ is H or $C_1$-$C_6$ alkyl; and $R^4$ is H or trimethylsilyl.

In some embodiments, one of the first reactive elements or the second reactive elements is selected from the group consisting of

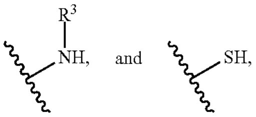

and wherein $R^3$ is H or $C_1$-$C_6$ alkyl;

and the other of the first reactive element or the second reactive element is

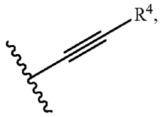

wherein $R^4$ is H or trimethylsilyl. In some embodiments, $R^3$ is H. In some embodiments, $R^3$ is $C_1$-$C_6$ alkyl. In some embodiments, $R^4$ is H. In some embodiments, $R^4$ is trimethylsilyl.

In some embodiments, one of the first reactive element or the second reactive element is selected from the group consisting of:

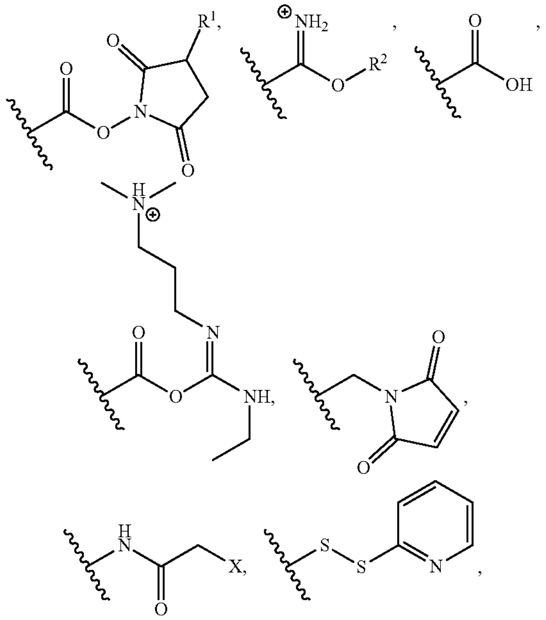

-continued

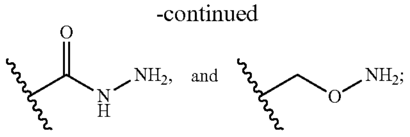

and wherein $R^1$ is selected from H, $C_1$-$C_6$ alkyl, or —$SO_3$;

$R^2$ is $C_1$-$C_6$ alkyl;

X is a halo moiety;

and the other of the first reactive element or the second reactive element is selected from the group consisting of:

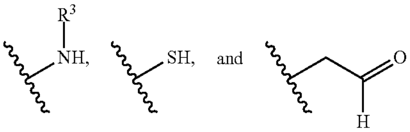

and wherein $R^3$ is H or $C_1$-$C_6$ alkyl. In some embodiments, $R^1$ is H. In some embodiments, $R^1$ is $C_1$-$C_6$ alkyl. In some embodiments, $R^1$ is —$SO_3$. In some embodiments, $R^2$ is methyl. In some embodiments, X is iodo. In some embodiments, $R^3$ is H. In some embodiments, $R^3$ is $C_1$-$C_6$ alkyl.

In some embodiments, one of the first reactive elements or the second reactive elements is selected from the group consisting of:

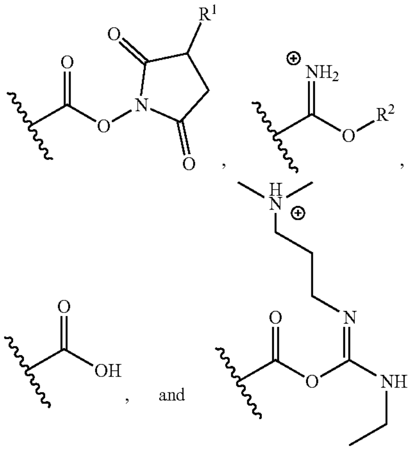

and wherein $R^1$ is selected from H, $C_1$-$C_6$ alkyl, or —$SO_3$;

$R^2$ is $C_1$-$C_6$ alkyl;

and the other of the first reactive elements or the second reactive elements comprises

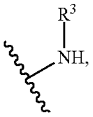

wherein $R^3$ is H or $C_1$-$C_6$ alkyl. In some embodiments, $R^1$ is H. In some embodiments, $R^1$ is $C_1$-$C_6$ alkyl. In some embodiments, $R^1$ is —$SO_3$. In some embodiments, $R^2$ is methyl. In some embodiments, $R^3$ is H. In some embodiments, $R^3$ is $C_1$-$C_6$ alkyl.

In some embodiments, one of the first reactive element or the second reactive element is selected from the group consisting of:

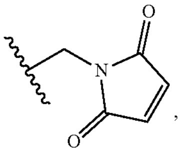 , 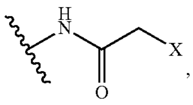 , and

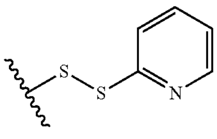

wherein X is a halo moiety;

and the other of the first reactive element or the second reactive element comprises

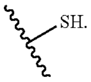

In some embodiments, X is bromo. In some embodiments, X is iodo.

In some embodiments, one of the first reactive element or the second reactive element is selected from the group consisting of

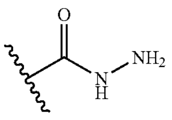 and 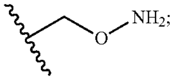

and the other of the first reactive element or the second reactive element comprises

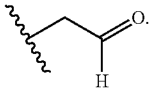 [SMILES: *CC=O]

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —$OCH_3$).

The term "alkylene" refers to a divalent alkyl (e.g., —$CH_2$-).

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system); and wherein 0, 1, 2, 3, or 4 atoms of each ring may be substituted by a substituent. Examples of aryl groups include phenyl, naphthyl, tetrahydronaphthyl, and the like.

Methods for Non-Covalently Bonding Beads to a Substrate

Provided herein are methods for the non-covalent bonding of beads (e.g., optically-labeled beads, hydrogel beads, or microsphere beads) to a substrate.

In some embodiments, beads are coupled to a substrate via a non-covalent bond between a first affinity group and a second affinity group. In some embodiments, the non-covalently-bound beads substantially form a monolayer of beads (e.g., hydrogel beads, microsphere beads) on the substrate.

In some embodiments, the beads are functionalized with a first affinity group, which is directly bound to the beads. In some embodiments, the beads are functionalized with a first affinity group, which is indirectly bound to the beads via a linker. In some embodiments, the linker is a benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments, the substrate is functionalized with a second affinity group, which is directly bound to the substrate. In some embodiments, the substrate is functionalized with a second affinity group, which is indirectly bound to the beads via a linker. In some embodiments, the linker is a benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments the first affinity group or the second affinity group is biotin, and the other of the first affinity group or the second affinity group is streptavidin.

In some embodiments, about 99% of the non-covalently-bound beads form a monolayer of beads on the substrate. In some embodiments, about 50% to about 98% form a monolayer of beads on the substrate. For example, about 50% to about 95%, about 50% to about 90%, about 50% to about 85%, about 50% to about 80%, about 50% to about 75%, about 50% to about 70%, about 50% to about 65%, about 50% to about 60%, or about 50% to about 55% of the non-covalently-bound beads form a monolayer of beads on the substrate. In some embodiments, about 55% to about 98%, about 60% to about 98%, about 65% to about 98%, about 70% to about 98%, about 75% to about 98%, about 80% to about 98%, about 85% to about 98%, about 90% to about 95%, or about 95% to about 98% of the non-covalently-bound beads form a monolayer of beads on the substrate. In some embodiments, about 55% to about 95%, about 60% to about 90%, about 65% to about 95%, about 70% to about 95%, about 75% to about 90%, about 75% to about 95%, about 80% to about 90%, about 80% to about 95%, about 85% to about 90%, or about 85% to about 95% of the non-covalently-bound beads for a monolayer of beads on the substrate.

In some embodiments, the monolayer of beads is a formed in a predefined area on the substrate. In some embodiments, the predefined area is partitioned with physical barriers. For example, divots or wells in the substrate. In some embodiments, the predefined area is partitioned using a photomask. For example, the substrate is coated with a photo-activated solution, dried, then irradiated under a photomask. In some embodiments, the photo-activated solution is UV-activated.

As used herein, an "adhesive" generally refers to a substance used for sticking objects or materials together. Adhesives include, for example, glues, pastes, liquid tapes, epoxy, bioadhesives, gels, and mucilage. In some embodiments, an adhesive is liquid tape. In some embodiments, the adhesive is glue.

In some embodiments, beads are adhered to a substrate using an adhesive (e.g., liquid tape, glue, paste). In some embodiments, the adhered beads substantially form a monolayer of beads on the substrate (e.g., a glass slide). In some embodiments, the beads are hydrogel beads. In some embodiments, the beads are microsphere beads. In some embodiments, the beads are coated with the adhesive, and then the beads are contacted with the substrate. In some embodiments, the substrate is coated with the adhesive, and then the substrate is contacted with the beads. In some embodiments, both the substrate is coated with the adhesive and the beads are coated with the adhesive, and then the beads and substrate are contacted with one another.

In some embodiments, about 99% of the adhered beads form a monolayer of beads on the substrate. In some embodiments, about 50% to about 98% form a monolayer of beads on the substrate. For example, about 50% to about 95%, about 50% to about 90%, about 50% to about 85%, about 50% to about 80%, about 50% to about 75%, about 50% to about 70%, about 50% to about 65%, about 50% to about 60%, or about 50% to about 55% of the adhered beads form a monolayer of beads on the substrate. In some embodiments, about 55% to about 98%, about 60% to about 98%, about 65% to about 98%, about 70% to about 98%, about 75% to about 98%, about 80% to about 98%, about 85% to about 98%, about 90% to about 95%, or about 95% to about 98% of the adhered beads form a monolayer of beads on the substrate. In some embodiments, about 55% to about 95%, about 60% to about 90%, about 65% to about 95%, about 70% to about 95%, about 75% to about 90%, about 75% to about 95%, about 80% to about 90%, about 80% to about 95%, about 85% to about 90%, or about 85% to about 95% of the adhered beads for a monolayer of beads on the substrate.

In some embodiments, beads can be deposited onto a biological sample such that the deposited beads form a monolayer of beads on the biological sample (e.g., over or under the biological sample). In some embodiments, beads deposited on the substrate can self-assemble into a monolayer of beads that saturate the intended surface area of the biological sample under investigation. In this approach, bead arrays can be designed, formulated, and prepared to evaluate a plurality of analytes from a biological sample of any size or dimension. In some embodiments, the concentration or density of beads (e.g., gel beads) applied to the biological sample is such that the area as a whole, or one or more regions of interest in the biological sample, is saturated with a monolayer of beads. In some embodiments, the beads are contacted with the biological sample by pouring, pipetting, spraying, and the like, onto the biological sample. Any suitable form of bead deposition can be used.

In some embodiments, the biological sample can be confined to a specific region or area of the array. For example, a biological sample can be affixed to a glass slide and a chamber, gasket, or cage positioned over the biological sample to act as a containment region or frame within which the beads are deposited. As will be apparent, the density or concentration of beads needed to saturate an area or biological sample can be readily determined by one of ordinary skill in the art (e.g., through microscopic visualization of the beads on the biological sample). In some embodiments, the bead array contains microfluidic channels to direct reagents to the spots or beads of the array.

Feature Geometric Attributes

Features on an array can have a variety of sizes. In some embodiments, a feature of an array can have a diameter or maximum dimension between 1 μm to 100 For example, between 1 μm to 10 μm, 1 μm to 20 μm, 1 μm to 30 μm, 1 μm to 40 μm, 1 μm to 50 μm, to 1 μm to 60 μm, 1 μm to 70 μm, 1 μm to 80 μm, 1 μm to 90 μm, 90 μm to 100 μm, 80 μm to 100 μm, 70 μm to 100 μm, 60 μm to 100 μm, 50 μm to 100 μm, 40 μm to 100 μm, 30 μm to 100 μm, 20 μm to 100 or 10 μm to 100 μm. In some embodiments, the feature has a diameter or maximum dimension between 30 μm to 100 μm, 40 μm to 90 μm, 50 μm to 80 μm, 60 μm to 70 μm, or any range within the disclosed sub-ranges. In some embodiments, the feature has a diameter or maximum dimension no larger than 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 14 μm, 13 μm, 12 μm, 11 μm, 9 μm, 8 μm, 7 μm, 6 μm, 5 μm, 4 μm, 3 μm, 2 μm, or 1 μm. In some embodiments, the feature has a diameter or maximum dimension of approximately 65 μm.

In some embodiments, the size and/or shape of a plurality of features of an array are approximately uniform. In some embodiments, the size and/or shape of a plurality of features of an array is not uniform. For example, in some embodiments, features in an array can have an average cross-sectional dimension, and a distribution of cross-sectional dimensions among the features can have a full-width and half-maximum value of 0% or more (e.g., 5% or more, 10% or more, 20% or more, 30% or more, 40% or more, 50% or more, 70% or more, or 100% or more) of the average cross-sectional dimension for the distribution.

In certain embodiments, features in an array can have an average cross-sectional dimension of between about 1 μm and about 10 μm. This range in average feature cross-sectional dimension corresponds to the approximate diameter of a single mammalian cell. Thus, an array of such features can be used to detect analytes at, or below, mammalian single-cell resolution.

In some embodiments, a plurality of features has a mean diameter or mean maximum dimension of about 0.1 μm to about 100 μm (e.g., about 0.1 μm to about 5 μm, about 1 μm to about 10 about 1 μm to about 20 about 1 μm to about 30 about 1 μm to about 40 about 1 μm to about 50 about 1 μm to about 60 about 1 μm to about 70 about 1 μm to about 80 about 1 μm to about 90 about 90 μm to about 100 about 80 μm to about 100 about 70 μm to about 100 about 60 μm to about 100 about 50 μm to about 100 about 40 μm to about 100 about 30 μm to about 100 about 20 μm to about 100 or about 10 μm to about 100 μm). In some embodiments, the plurality of features has a mean diameter or mean maximum dimension between 30 μm to 100 40 μm to 90 50 μm to 80 60 μm to 70 or any range within the disclosed sub-ranges. In some embodiments, the plurality of features has a mean diameter or a mean maximum dimension no larger than 95 μm, 90 μm, 85 μm, 80 μm, 75 μm, 70 μm, 65 μm, 60 μm, 55 μm, 50 μm, 45 μm, 35 μm, 30 μm, 25 μm, 20 μm, 15 μm, 14 μm, 13 μm, 12 μm, 11 μm, 10 μm, 9 μm, 8 μm, 6 μm, 5 μm, 4 μm, 3 μm, 2 or 1 In some embodiments, the plurality of features has a mean average diameter or a mean maximum dimension of approximately 65

In some embodiments, where the feature is a bead, the bead can have a diameter or maximum dimension no larger than 100 μm (e.g., no larger than 95 μm, 90 μm, 85 μm, 80 μm, 70 μm, 65 μm, 60 μm, 55 μm, 50 μm, 45 μm, 40 μm, 35 μm, 30 μm, 25 μm, 20 μm, 15 μm, 13 μm, 12 μm, 11 μm, 10 μm, 9 μm, 8 μm, 7 μm, 6 μm, 5 μm, 4 μm, 3 μm, 2 μm, or 1 μm).

In some embodiments, a plurality of beads has an average diameter no larger than 100 μm. In some embodiments, a plurality of beads has an average diameter or maximum dimension no larger than 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm.

In some embodiments, the volume of the bead can be at least about 1 $\mu m^3$, e.g., at least 1 $\mu m^3$, 2 $\mu m^3$, 3 $\mu m^3$, 4 $\mu m^3$, 5 $\mu m^3$, 6 $\mu m^3$, 7 $\mu m^3$, 8 $\mu m^3$, 9 $\mu m^3$, 10 $\mu m^3$, 12 $\mu m^3$, 14 $\mu m^3$, 16 $\mu m^3$, 18 $\mu m^3$, 20 $\mu m^3$, 25 $\mu m^3$, 30 $\mu m^3$, 35 $\mu m^3$, 40 $\mu m^3$, 45 $\mu m^3$, 50 $\mu m^3$, 55 $\mu m^3$, 60 $\mu m^3$, 65 $\mu m^3$, 70 $\mu m^3$, 75 $\mu m^3$, 80 $\mu m^3$, 85 $\mu m^3$, 90 $\mu m^3$, 95 $\mu m^3$, 100 $\mu m^3$, 125 $\mu m^3$, 150 $\mu m^3$, 175 $\mu m^3$, 200 $\mu m^3$, 250 $\mu m^3$, 300 $\mu m^3$, 350 $\mu m^3$, 400 $\mu m^3$, 450 $\mu m^3$, $\mu m^3$, 500 $\mu m^3$, 550 $\mu m^3$, 600 $\mu m^3$, 650 $\mu m^3$, 700 $\mu m^3$, 750 $\mu m^3$, 800 $\mu m^3$, 850 $\mu m^3$, 900 $\mu m^3$, 950 $\mu m^3$, 1000 $\mu m^3$, 1200 $\mu m^3$, 1400 $\mu m^3$, 1600 $\mu m^3$, 1800 $\mu m^3$, 2000 $\mu m^3$, 2200 $\mu m^3$, 2400 $\mu m^3$, 2600 $\mu m^3$, 2800 $\mu m^3$, 3000 $\mu m^3$, or greater.

In some embodiments, the bead can have a volume of between about 1 $\mu m^3$ and 100 $\mu m^3$, such as between about 1 $\mu m^3$ and 10 $\mu m^3$, between about 10 $\mu m^3$ and 50 $\mu m^3$, or between about 50 $\mu m^3$ and 100 $\mu m^3$. In some embodiments, the bead can include a volume of between about 100 $\mu m^3$ and 1000 $\mu m^3$, such as between about 100 $\mu m^3$ and 500 $\mu m^3$ or between about 500 $\mu m^3$ and 1000 $\mu m^3$. In some embodiments, the bead can include a volume between about 1000 $\mu m^3$ and 3000 $\mu m^3$, such as between about 1000 $\mu m^3$ and 2000 $\mu m^3$ or between about 2000 $\mu m^3$ and 3000 $\mu m^3$. In some embodiments, the bead can include a volume between about 1 $\mu m^3$ and 3000 $\mu m^3$, such as between about 1 $\mu m^3$ and 2000 $\mu m^3$, between about 1 $\mu m^3$ and 1000 $\mu m^3$, between about 1 $\mu m^3$ and 500 $\mu m^3$, or between about 1 $\mu m^3$ and 250 $\mu m^3$.

The bead can include one or more cross-sections that can be the same or different. In some embodiments, the bead can have a first cross-section that is different from a second cross-section. The bead can have a first cross-section that is at least about 0.0001 micrometer, 0.001 micrometer, 0.01 micrometer, 0.1 micrometer, or 1 micrometer. In some embodiments, the bead can include a cross-section (e.g., a first cross-section) of at least about 1 micrometer (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 100 μm, 120 μm, 140 μm, 160 μm, 180 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), or greater. In some embodiments, the bead can include a cross-section (e.g., a first cross-section) of between about 1 μm and 500 μm, such as between about 1 μm and 100 μm, between about 100 μm and 200 μm, between about 200 μm and 300 μm, between about 300 μm and 400 μm, or between about 400 μm and 500 μm. For example, the bead can include a cross-section (e.g., a first cross-section) of between about 1 μm and 100 μm. In some embodiments, the bead can have a second cross-section that is at least about 1 μm. For example, the bead can include a second cross-section of at least about 1 micrometer (μm), 2 μm, 3 μm, 4 μm, 5 μm, 6 μm, 7 μm, 8 μm, 9 μm, 10 μm, 11 μm, 12 μm, 13 μm, 15 μm, 16 μm, 17 μm, 18 μm, 19 μm, 20 μm, 25 μm, 30 μm, 35 μm, 40 μm, 45 μm, 55 μm, 60 μm, 65 μm, 70 μm, 75 μm, 80 μm, 85 μm, 90 μm, 100 μm, 120 μm, 140 μm, 160 μm, 180 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), or greater. In some embodiments, the bead can include a second cross-section of between about 1 μm and 500 μm, such as between about 1 μm and 100 μm, between about 100 μm and 200 μm, between about 200 μm and 300 μm, between about 300 μm and 400 μm, or between about 400 μm and 500 μm. For example, the bead can include a second cross-section of between about 1 μm and 100 μm.

In some embodiments, beads can be of a nanometer scale (e.g., beads can have a diameter or maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). A plurality of beads can have an average diameter or average maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). In some embodiments, a bead has a diameter or size that is about the size of a single cell (e.g., a single cell under evaluation).

Beads can be of uniform size or heterogeneous size. "Polydispersity" generally refers to heterogeneity of sizes of molecules or particles. The polydispersity (PDI) can be calculated using the equation PDI=Mw/Mn, where Mw is the weight-average molar mass and Mn is the number-average molar mass. In certain embodiments, beads can be provided as a population or plurality of beads having a relatively monodisperse size distribution. Where it can be desirable to provide relatively consistent amounts of reagents, maintaining relatively consistent bead characteristics, such as size, can contribute to the overall consistency.

In some embodiments, the beads provided herein can have size distributions that have a coefficient of variation in their cross-sectional dimensions of less than 50%, less than 40%, less than 30%, less than 20%, less than 15%, less than 10%, less than 5%, or lower. In some embodiments, a plurality of beads provided herein has a polydispersity index of less than 50%, less than 45%, less than 40%, less than 35%, less than 30%, less than 25%, less than 20%, less than 15%, less than 10%, less than 5%, or lower.

Array Geometric Attributes

In some embodiments, an array includes a plurality of features. For example, an array includes between 4,000 and 10,000 features, or any range within 4,000 to 6000 features. For example, an array includes between 4,000 to 4,400 features, 4,000 to 4,800 features, 4,000 to 5,200 features, 4,000 to 5,600 features, 5,600 to 6,000 features, 5,200 to 6,000 features, 4,800 to 6,000 features, or 4,400 to 6,000 features. In some embodiments, the array includes between 4,100 and 5,900 features, between 4,200 and 5,800 features, between 4,300 and 5,700 features, between 4,400 and 5,600 features, between 4,500 and 5,500 features, between 4,600 and 5,400 features, between 4,700 and 5,300 features, between 4,800 and 5,200 features, between 4,900 and 5,100 features, or any range within the disclosed sub-ranges. For example, the array can include about 4,000 features, about 4,200 features, about 4,400 features, about 4,800 features, about 5,000 features, about 5,200 features, about 5,400 features, about 5,600 features, or about 6,000 features. In some embodiments, the array comprises at least 4,000 features. In some embodiments, the array includes approximately 5,000 features.

In some embodiments, features within an array have an irregular arrangement or relationship to one another, such that no discernable pattern or regularity is evident in the geometrical spacing relationships among the features. For example, features within an array may be positioned randomly with respect to one another. Alternatively, features within an array may be positioned irregularly, but the spacings may be selected deterministically to ensure that the resulting arrangement of features is irregular.

In some embodiments, features within an array are positioned regularly with respect to one another to form a pattern. A wide variety of different patterns of features can be implemented in arrays. Examples of such patterns include, but are not limited to, square arrays of features, rectangular arrays of features, hexagonal arrays of features (including hexagonal close-packed arrays), radial arrays of features, spiral arrays of features, triangular arrays of features, and more generally, any array in which adjacent features in the array are reached from one another by regular increments in linear and/or angular coordinate dimensions.

In some embodiments, features within an array are positioned with a degree of regularity with respect to one another such that the array of features is neither perfectly regular nor perfectly irregular (i.e., the array is "partially regular"). For example, in some embodiments, adjacent features in an array can be separated by a displacement in one or more linear and/or angular coordinate dimensions that is 10% or more (e.g., 20% or more, 30% or more, 40% or more, 50% or more, 60% or more, 70% or more, 80% or more, 90% or more, 100% or more, 110% or more, 120% or more, 130% or more, 140% or more, 150% or more, 160% or more, 170% or more, 180% or more, 190% or more, 200% or more) of an average displacement or a nominal displacement between adjacent features in the array. In certain embodiments, the distribution of displacements (linear and/or angular) between adjacent features in an array has a full-width at half-maxium of between 0% and 200% (e.g., between 0% and 100%, between 0% and 75%, between 0% and 50%, between 0% and 25%, between 0% and 15%, between 0% and 10%) of an average displacement or nominal displacement between adjacent features in the array.

In some embodiments, arrays of features can have a variable geometry. For example, a first subset of features in an array can be arranged according to a first geometrical pattern, and a second subset of features in the array can be arranged according to a second geometrical pattern that is different from the first pattern. Any of the patterns described above can correspond to the first and/or second geometrical patterns, for example.

In general, arrays of different feature densities can be prepared by adjusting the spacing between adjacent features in the array. In some embodiments, the geometric center-to-center spacing between adjacent features in an array is between 100 nm and 100 μm. For example, the center-to-center spacing can be between 20 μm to 40 μm, 20 μm to 60 μm, 20 μm to 80 μm, 80 μm to 100 μm, 60 μm to 100 μm, or 40 μm to 100 μm. In some embodiments, the center-to-center spacing between adjacent array features is between 30 μm and 100 μm, 40 μm and 90 μm, 50 μm and 80 μm, 60 μm and 70 μm, 80 μm and 120 μm, or any range within the disclosed sub-ranges. In some embodiments, the center-to-center spacing between adjacent array features of a feature of an array is approximately 65 μm.

In some embodiments, an array of features can have a spatially varying resolution. In general, an array with a spatially varying resolution is an array in which the center-to-center spacing (along linear, angular, or both linear and angular coordinate dimensions) between adjacent features in the array varies. Such arrays can be useful in a variety of applications. For example, in some embodiments, depending upon the spatial resolution at which the sample is to be investigated, the sample can be selectively associated with the portion of the array that corresponds approximately to the desired spatial resolution of the measurement.

Arrays of spatially varying resolution can be implemented in a variety of ways. In some embodiments, for example, the center-to-center spacing between adjacent features in the array varies continuously along one or more linear and/or angular coordinate directions. Thus, for a rectangular array, the spacing between successive rows of features, between successive columns of features, or between both successive rows and successive columns of features, can vary continuously.

In certain embodiments, arrays of spatially varying resolution can include discrete domains with populations of features. Within each domain, adjacent features can have regular center-to-center spacings. Thus, for example, an array can include a first domain within which adjacent features are spaced from one another along linear and/or angular coordinate dimensions by a first set of uniform coordinate displacements, and a second domain within which adjacent features are spaced from one another along linear and/or angular coordinate dimensions by a second set of uniform coordinate displacements. The first and second sets of displacements differ in at least one coordinate displacement, such that adjacent features in the two domains are spaced differently, and the resolution of the array in the first domain is therefore different from the resolution of the array in the second domain.

In some embodiments, the center-to-center spacing of array features can be sufficiently small such that array features are effectively positioned continuously or nearly continuously along one or more array dimensions, with little or no displacement between array features along those dimensions. For example, in a feature array where the features correspond to regions of a substrate (i.e., oligonucleotides are directly bound to the substrate), the displacement between adjacent oligonucleotides can be very small—effectively, the molecular width of a single oligonucleotide. In such embodiments, each oligonucleotide can include a distinct spatial barcode such that the spatial location of each oligonucleotide in the array can be determined during sample analysis. Arrays of this type can have very high spatial resolution, but may only include a single oligonucleotide corresponding to each distinct spatial location in a sample. In general, the size of the array (which corresponds to the maximum dimension of the smallest boundary that encloses all features in the array along one coordinate direction) can be selected as desired, based on criteria such as the size of the sample, the feature sizes, and the density of capture probes within each feature. For example, in some embodiments, the array can be a rectangular or square array for which the maximum array dimension along each coordinate direction is 10 mm or less (e.g., 9 mm or less, 8 mm or less, 7 mm or less, 6 mm or less, 5 mm or less, 4 mm or less, 3 mm or less). Thus, for example, a square array of features can have dimensions of 8 mm by 8 mm, 7 mm by 7 mm, 5 mm by 5 mm, or be smaller than 5 mm by 5 mm.

(e) Analyte Capture

In this section, general aspects of methods and systems for capturing analytes are described. Individual method steps and system features can be present in combination in many different embodiments; the specific combinations described herein do not in any way limit other combinations of steps and features.

Generally, analytes can be captured when contacting a biological sample with, e.g., a substrate comprising capture probes (e.g., substrate with capture probes embedded, spotted, printed on the substrate or a substrate with features (e.g., beads, wells) comprising capture probes).

As used herein, "contact," "contacted," and/or "contacting," a biological sample with a substrate comprising features refers to any contact (e.g., direct or indirect) such that capture probes can interact (e.g., capture) with analytes from the biological sample. For example, the substrate may be near or adjacent to the biological sample without direct physical contact, yet capable of capturing analytes from the biological sample. In some embodiments the biological sample is in direct physical contact with the substrate. In some embodiments, the biological sample is in indirect physical contact with the substrate. For example, a liquid layer may be between the biological sample and the substrate. In some embodiments, the analytes diffuse through the liquid layer. In some embodiments the capture probes diffuse through the liquid layer. In some embodiments reagents may be delivered via the liquid layer between the biological sample and the substrate. In some embodiments, indirect physical contact may be the presence of a second substrate (e.g., a hydrogel, a film, a porous membrane) between the biological sample and the first substrate comprising features with capture probes. In some embodiments, reagents may be delivered by the second substrate to the biological sample.

Diffusion-Resistant Media/Lids

To increase efficiency by encouraging analyte diffusion toward the spatially-labelled capture probes, a diffusion-resistant medium can be used. In general, molecular diffusion of biological analytes occurs in all directions, including toward the capture probes (i.e. toward the spatially-barcoded array), and away from the capture probes (i.e. into the bulk solution). Increasing diffusion toward the spatially-barcoded array reduces analyte diffusion away from the spatially-barcoded array and increases the capturing efficiency of the capture probes.

In some embodiments, a biological sample is placed on the top of a spatially-barcoded substrate and a diffusion-resistant medium is placed on top of the biological sample. For example, the diffusion-resistant medium can be placed onto an array that has been placed in contact with a biological sample. In some embodiments, the diffusion-resistant medium and spatially-labelled array are the same component. For example, the diffusion-resistant medium can contain spatially-labelled capture probes within or on the diffusion-resistant medium (e.g., coverslip, slide, hydrogel, or membrane). In some embodiments, a sample is placed on a substrate and a diffusion-resistant medium is placed on top of the biological sample. Additionally, a spatially-barcoded capture probe array can be placed in close proximity over the diffusion-resistant medium. For example, a diffusion-resistant medium may be sandwiched between a spatially-labelled array and a sample on a substrate. In some embodiments, the diffusion-resistant medium is disposed or spotted onto the sample. In other embodiments, the diffusion-resistant medium is placed in close proximity to the sample.

In general, the diffusion-resistant medium can be any material known to limit diffusivity of biological analytes. For example, the diffusion-resistant medium can be a solid lid (e.g., coverslip or glass slide). In some embodiments, the diffusion-resistant medium may be made of glass, silicon, paper, hydrogel polymer monoliths, or other material. In some embodiments, the glass side can be an acrylated glass slide. In some embodiments, the diffusion-resistant medium is a porous membrane. In some embodiments, the material may be naturally porous. In some embodiments, the material may have pores or wells etched into solid material. In some embodiments, the pore size can be manipulated to minimize loss of target analytes. In some embodiments, the membrane chemistry can be manipulated to minimize loss of target analytes. In some embodiments, the diffusion-resistant medium (i.e. hydrogel) is covalently attached to a substrate (i.e. glass slide). In some embodiments, the diffusion-resistant medium can be any material known to limit diffusivity of poly(A) transcripts. In some embodiments, the diffusion-resistant medium can be any material known to limit the diffusivity of proteins. In some embodiments, the diffusion-resistant medium can be any material know to limit the diffusivity of macromolecular constituents.

In some embodiments, a diffusion-resistant medium includes one or more diffusion-resistant media. For example, one or more diffusion-resistant media can be combined in a variety of ways prior to placing the media in contact with a biological sample including, without limitation, coating, layering, or spotting. As another example, a hydrogel can be placed onto a biological sample followed by placement of a lid (e.g., glass slide) on top of the hydrogel. In some embodiments, a force (e.g., hydrodynamic pressure, ultrasonic vibration, solute contrasts, microwave radiation, vascular circulation, or other electrical, mechanical, magnetic, centrifugal, and/or thermal forces) is applied to control diffusion and enhance analyte capture. In some embodiments, one or more forces and one or more diffusion-resistant media are used to control diffusion and enhance capture. For example, a centrifugal force and a glass slide can used contemporaneously. Any of a variety of combinations of a force and a diffusion-resistant medium can be used to control or mitigate diffusion and enhance analyte capture.

In some embodiments, the diffusion-resistant medium, along with the spatially-barcoded array and sample, is submerged in a bulk solution. In some embodiments, the bulk solution includes permeabilization reagents. In some embodiments, the diffusion-resistant medium includes at least one permeabilization reagent. In some embodiments, the diffusion-resistant medium (i.e. hydrogel) is soaked in permeabilization reagents before contacting the diffusion-resistant medium to the sample. In some embodiments, the diffusion-resistant medium can include wells (e.g., micro-, nano-, or picowells) containing a permeabilization buffer or reagents. In some embodiments, the diffusion-resistant medium can include permeabilization reagents. In some embodiments, the diffusion-resistant medium can contain dried reagents or monomers to deliver permeabilization reagents when the diffusion-resistant medium is applied to a biological sample. In some embodiments, the diffusion-resistant medium is added to the spatially-barcoded array and sample assembly before the assembly is submerged in a bulk solution. In some embodiments, the diffusion-resistant medium is added to the spatially-barcoded array and sample assembly after the sample has been exposed to permeabilization reagents. In some embodiments, the permeabilization reagents are flowed through a microfluidic chamber or channel over the diffusion-resistant medium. In some embodiments, the flow controls the sample's access to the permeabilization reagents. In some embodiments, the target analytes diffuse out of the sample and toward a bulk solution and get embedded in a spatially-labelled capture probe-embedded diffusion-resistant medium. In some embodiments, a free solution is sandwiched between the biological sample and a diffusion-resistant medium.

Figure 13:
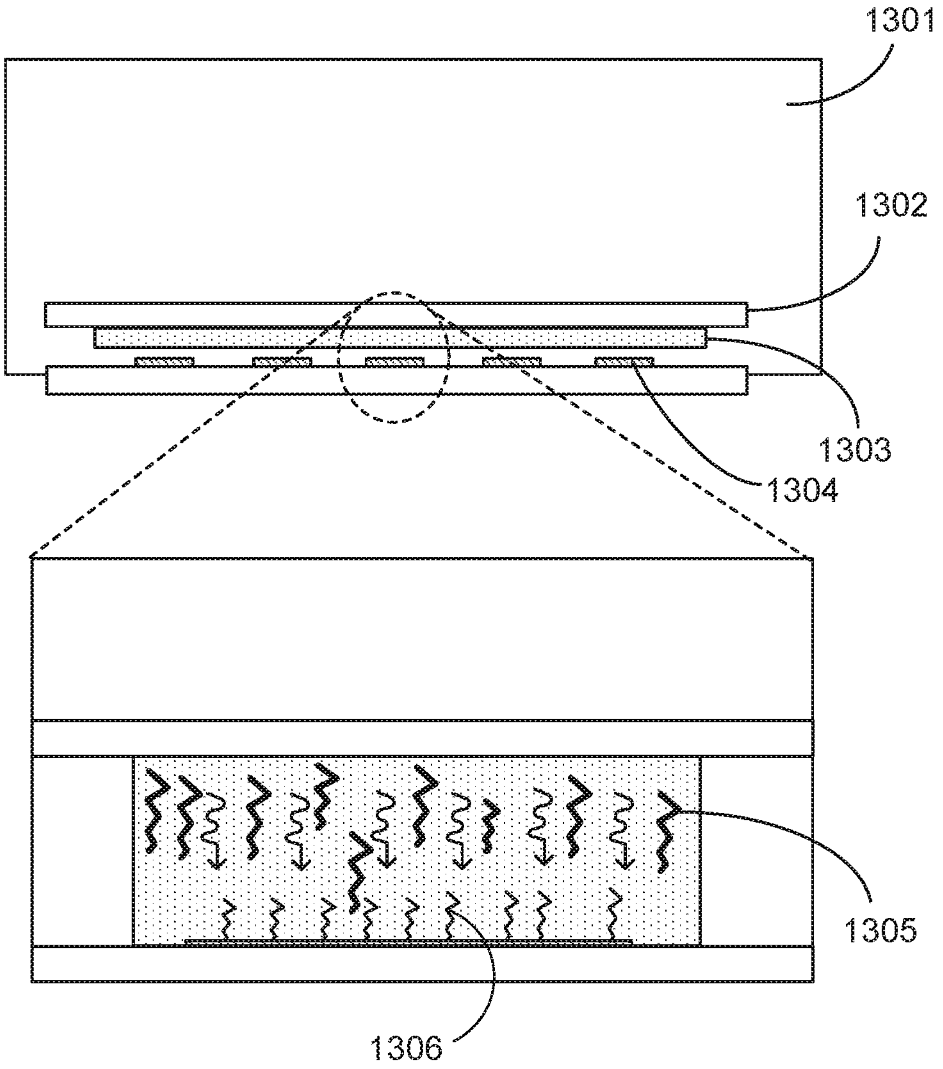
FIG. 13 is a schematic illustrating a side view of a diffusion-resistant medium, e.g., a lid.

FIG. 13 is an illustration of an exemplary use of a diffusion-resistant medium. A diffusion-resistant medium 1302 can be contacted with a sample 1303. In FIG. 13, a glass slide 1304 is populated with spatially-barcoded capture probes 1306, and the sample 1303, 1305 is contacted with the array 1304, 1306. A diffusion-resistant medium 1302 can be applied to the sample 1303, wherein the sample 1303 is sandwiched between a diffusion-resistant medium 1302 and a capture probe coated slide 1304. When a permeabilization solution 1301 is applied to the sample, using the diffusion-resistant medium/lid 1302 directs migration of the analytes 1305 toward the capture probes 1306 by reducing diffusion of the analytes out into the medium. Alternatively, the lid may contain permeabilization reagents.

Conditions for Capture

Capture probes on the substrate (or on a feature on the substrate) interact with released analytes through a capture domain, described elsewhere, to capture analytes. In some embodiments, certain steps are performed to enhance the transfer or capture of analytes by the capture probes of the array. Examples of such modifications include, but are not limited to, adjusting conditions for contacting the substrate with a biological sample (e.g., time, temperature, orientation, pH levels, pre-treating of biological samples, etc.), using force to transport analytes (e.g., electrophoretic, centrifugal, mechanical, etc.), performing amplification reactions to increase the amount of biological analytes (e.g., PCR amplification, in situ amplification, clonal amplification), and/or using labeled probes for detecting of amplicons and barcodes.

In some embodiments, capture of analytes is facilitated by treating the biological sample with permeabilization reagents. If a biological sample is not permeabilized sufficiently, the amount of analyte captured on the substrate can be too low to enable adequate analysis. Conversely, if the biological sample is too permeable, the analyte can diffuse away from its origin in the biological sample, such that the relative spatial relationship of the analytes within the biological sample is lost. Hence, a balance between permeabilizing the biological sample enough to obtain good signal intensity while still maintaining the spatial resolution of the analyte distribution in the biological sample is desired. Methods of preparing biological samples to facilitation are known in the art and can be modified depending on the biological sample and how the biological sample is prepared (e.g., fresh frozen, FFPE, etc.).

Passive Capture Methods

In some embodiments, analytes can be migrated from a sample to a substrate. Methods for facilitating migration can be passive (e.g., diffusion) and/or active (e.g., electrophoretic migration of nucleic acids). Non-limiting examples of passive migration can include simple diffusion and osmotic pressure created by the rehydration of dehydrated objects.

Passive migration by diffusion uses concentration gradients. Diffusion is movement of untethered objects toward equilibrium. Therefore, when there is a region of high object concentration and a region of low object concentration, the object (capture probe, the analyte, etc.) moves to an area of lower concentration. In some embodiments, untethered analytes move down a concentration gradient.

In some embodiments, different reagents may be added to the biological sample, such that the biological sample is rehydrated while improving capture of analytes. In some embodiments, the biological sample can be rehydrated with permeabilization reagents. In some embodiments, the biological sample can be rehydrated with a staining solution (e.g., hematoxylin and eosin stain).

Active Capture Methods

In some examples of any of the methods described herein, an analyte in a cell or a biological sample can be transported (e.g., passively or actively) to a capture probe (e.g., a capture probe affixed to a solid surface).

For example, analytes in a cell or a biological sample can be transported to a capture probe (e.g., an immobilized capture probe) using an electric field (e.g., using electrophoresis), a pressure gradient, fluid flow, a chemical concentration gradient, a temperature gradient, and/or a magnetic field. For example, analytes can be transported through, e.g., a gel (e.g., hydrogel matrix), a fluid, or a permeabilized cell, to a capture probe (e.g., an immobilized capture probe).

In some examples, an electrophoretic field can be applied to analytes to facilitate migration of the analytes towards a capture probe. In some examples, a sample contacts a substrate and capture probes fixed on a substrate (e.g., a slide, cover slip, or bead), and an electric current is applied to promote the directional migration of charged analytes towards the capture probes fixed on the substrate. An electrophoresis assembly, where a cell or a biological sample is in contact with a cathode and capture probes (e.g., capture probes fixed on a substrate), and where the capture probes (e.g., capture probes fixed on a substrate) is in contact with the cell or biological sample and an anode, can be used to apply the current.

Electrophoretic transfer of analytes can be performed while retaining the relative spatial alignment of the analytes in the sample. As such, an analyte captured by the capture probes (e.g., capture probes fixed on a substrate) retains the spatial information of the cell or the biological sample. Applying an electrophoretic field to analytes can also result in an increase in temperature (e.g., heat). In some embodiments, the increased temperature (e.g., heat) can facilitate the migration of the analytes towards a capture probe.

In some examples, a spatially-addressable microelectrode array is used for spatially-constrained capture of at least one charged analyte of interest by a capture probe. The microelectrode array can be configured to include a high density of discrete sites having a small area for applying an electric field to promote the migration of charged analyte(s) of interest. For example, electrophoretic capture can be performed on a region of interest using a spatially-addressable microelectrode array.

A high density of discrete sites on a microelectrode array can be used for small device. The surface can include any suitable density of discrete sites (e.g., a density suitable for processing the sample on the conductive substrate in a given amount of time). In an embodiment, the surface has a density of discrete sites greater than or equal to about 500 sites per 1 $mm^2$. In some embodiments, the surface has a density of discrete sites of about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 20,000, about 40,000, about 60,000, about 80,000, about 100,000, or about 500,000 sites per 1 $mm^2$. In some embodiments, the surface has a density of discrete sites of at least about 200, at least about 300, at least about 400, at least about 500, at least about 600, at least about 700, at least about 800, at least about 900, at least about 1,000, at least about 2,000, at least about 3,000, at least about 4,000, at least about 5,000, at least about 6,000, at least about 7,000, at least about 8,000, at least about 9,000, at least about 10,000, at least about 20,000, at least about 40,000, at least about 60,000, at least about 80,000, at least about 100,000, or at least about 500,000 sites per 1 $mm^2$.

Figure 14A:
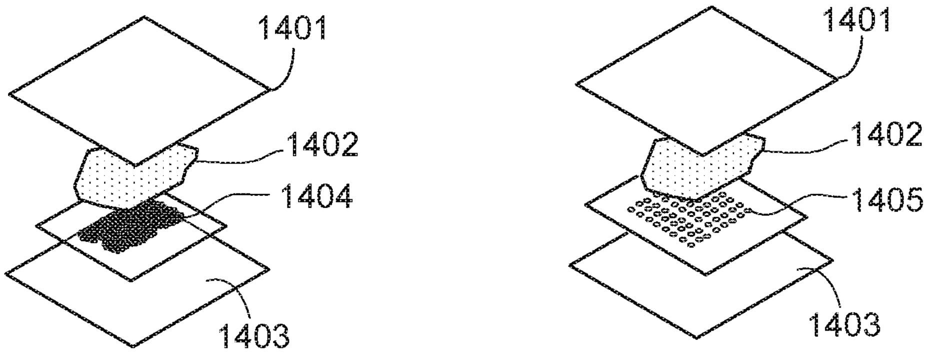
FIGS. 14A and 14B are schematics illustrating expanded FIG. 14A and side views FIG. 14B of an electrophoretic transfer system configured to direct transcript analytes toward a spatially-barcoded capture probe array.
Figure 14B:
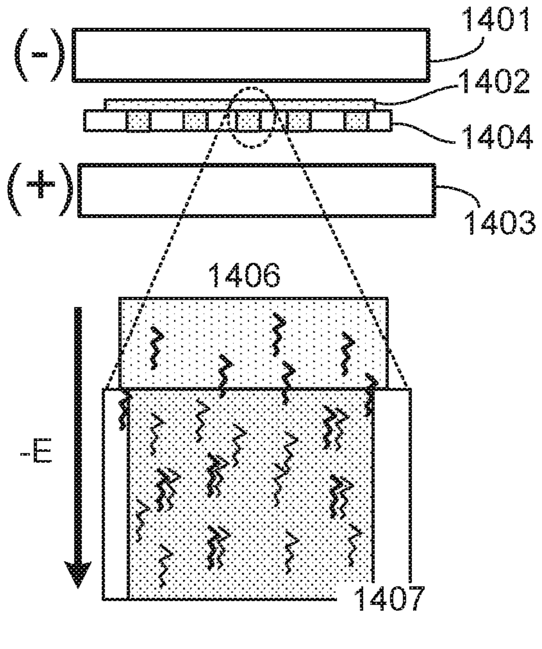

Schematics illustrating an electrophoretic transfer system configured to direct transcript analytes toward a spatially-barcoded capture probe array are shown in FIG. 14A and FIG. 14B. In this exemplary configuration of an electrophoretic system, a sample 1402 is sandwiched between the cathode 1401 and the spatially-barcoded capture probe array 1404, 1405, and the spatially-barcoded capture probe array 1404, 1405 is sandwiched between the sample 1402 and the anode 1403, such that the sample 1402, 1406 is in contact with the spatially-barcoded capture probes 1407. When an electric field is applied to the electrophoretic transfer system, negatively charged mRNA analytes 1406 will be pulled toward the positively charged anode 1403 and into the spatially-barcoded array 1404, 1405 containing the spatially-barcoded capture probes 1407. The spatially-barcoded capture probes 1407 then interact with/hybridize with/immobilize the mRNA target analytes 1406, making the analyte capture more efficient. The electrophoretic system set-up may change depending on the target analyte. For example, proteins may be positive, negative, neutral, or polar depending on the protein as well as other factors (e.g. isoelectric point, solubility, etc.). The skilled practitioner has the knowledge and experience to arrange the electrophoretic transfer system to facilitate capture of a particular target analyte.

Figure 15:
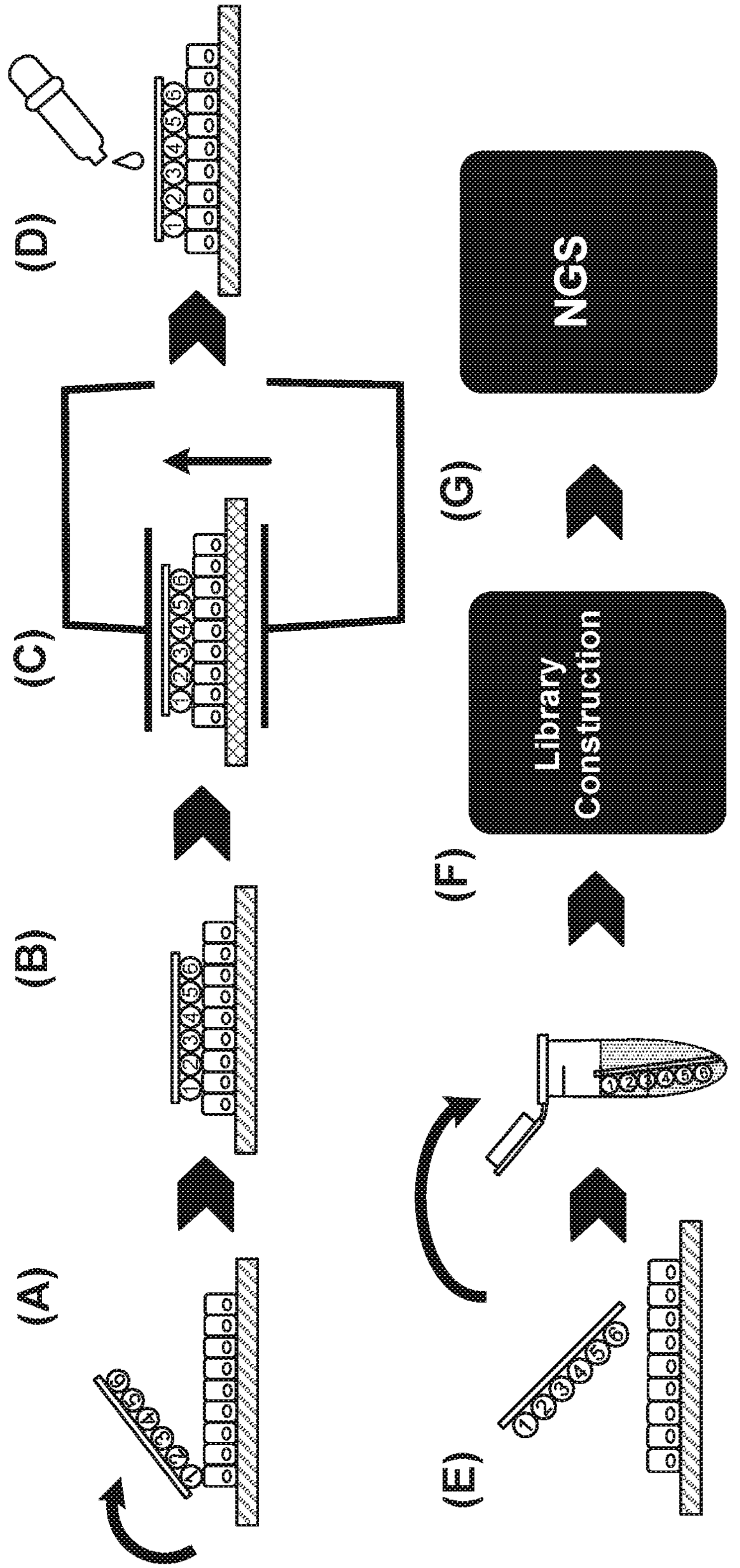
FIG. 15 is a schematic illustrating an exemplary workflow protocol utilizing an electrophoretic transfer system.

FIG. 15 is an illustration showing an exemplary workflow protocol utilizing an electrophoretic transfer system. In the example, Panel A depicts a flexible spatially-barcoded feature array being contacted with a sample. The sample can be a flexible array, wherein the array is immobilized on a hydrogel, membrane, or other flexible substrate. Panel B depicts contact of the array with the sample and imaging of the array-sample assembly. The image of the sample/array assembly can be used to verify sample placement, choose a region of interest, or any other reason for imaging a sample on an array as described herein. Panel C depicts application of an electric field using an electrophoretic transfer system to aid in efficient capture of a target analyte. Here, negatively charged mRNA target analytes migrate toward the positively charged anode. Panel D depicts application of reverse transcription reagents and first strand cDNA synthesis of the captured target analytes. Panel E depicts array removal and preparation for library construction (Panel F) and next-generation sequencing (Panel G).

Region of Interest

A biological sample can have regions that show morphological feature(s) that may indicate the presence of disease or the development of a disease phenotype. For example, morphological features at a specific site within a tumor biopsy sample can indicate the aggressiveness, therapeutic resistance, metastatic potential, migration, stage, diagnosis, and/or prognosis of cancer in a subject. A change in the morphological features at a specific site within a tumor biopsy sample often correlate with a change in the level or expression of an analyte in a cell within the specific site, which can, in turn, be used to provide information regarding the aggressiveness, therapeutic resistance, metastatic potential, migration, stage, diagnosis, and/or prognosis of cancer in a subject. A region or area within a biological sample that is selected for specific analysis (e.g., a region in a biological sample that has morphological features of interest) is often described as "a region of interest."

A region of interest in a biological sample can be used to analyze a specific area of interest within a biological sample, and thereby, focus experimentation and data gathering to a specific region of a biological sample (rather than an entire biological sample). This results in increased time efficiency of the analysis of a biological sample.

A region of interest can be identified in a biological sample using a variety of different techniques, e.g., expansion microscopy, bright field microscopy, dark field microscopy, phase contrast microscopy, electron microscopy, fluorescence microscopy, reflection microscopy, interference microscopy, confocal microscopy, and visual identification (e.g., by eye), and combinations thereof. For example, the staining and imaging of a biological sample can be performed to identify a region of interest. In some examples, the region of interest can correspond to a specific structure of cytoarchitecture. In some embodiments, a biological sample can be stained prior to visualization to provide contrast between the different regions of the biological sample. The type of stain can be chosen depending on the type of biological sample and the region of the cells to be stained. In some embodiments, more than one stain can be used to visualize different aspects of the biological sample, e.g., different regions of the sample, specific cell structures (e.g. organelles), or different cell types. In other embodiments, the biological sample can be visualized or imaged without staining the biological sample.

In some embodiments, imaging can be performed using one or more fiducial markers, i.e., objects placed in the field of view of an imaging system which appear in the image produced. Fiducial markers are typically used as a point of reference or measurement scale. Fiducial markers can include, but are not limited to, detectable labels such as fluorescent, radioactive, chemiluminescent, and colorimetric labels. The use of fiducial markers to stabilize and orient biological samples is described, for example, in Carter et al., *Applied Optics* 46:421-427, 2007), the entire contents of which are incorporated herein by reference. In some embodiments, a fiducial marker can be a physical particle (e.g., a nanoparticle, a microsphere, a nanosphere, a bead, or any of the other exemplary physical particles described herein or known in the art).

In some embodiments, a fiducial marker can be present on a substrate to provide orientation of the biological sample. In some embodiments, a microsphere can be coupled to a substrate to aid in orientation of the biological sample. In some examples, a microsphere coupled to a substrate can produce an optical signal (e.g., fluorescence). In another example, a microsphere can be attached to a portion (e.g., corner) of an array in a specific pattern or design (e.g., hexagonal design) to aid in orientation of a biological sample on an array of features on the substrate. In some embodiments, a quantum dot can be coupled to the substrate to aid in the orientation of the biological sample. In some examples, a quantum dot coupled to a substrate can produce an optical signal.

In some embodiments, a fiducial marker can be an immobilized molecule with which a detectable signal molecule can interact to generate a signal. For example, a marker nucleic acid can be linked or coupled to a chemical moiety capable of fluorescing when subjected to light of a specific wavelength (or range of wavelengths). Such a marker nucleic acid molecule can be contacted with an array before, contemporaneously with, or after the tissue sample is stained to visualize or image the tissue section. Although not required, it can be advantageous to use a marker that can be detected using the same conditions (e.g., imaging conditions) used to detect a labelled cDNA.

In some embodiments, fiducial markers are included to facilitate the orientation of a tissue sample or an image thereof in relation to an immobilized capture probes on a substrate. Any number of methods for marking an array can be used such that a marker is detectable only when a tissue section is imaged. For instance, a molecule, e.g. a fluorescent molecule that generates a signal, can be immobilized directly or indirectly on the surface of a substrate. Markers can be provided on a substrate in a pattern (e.g., an edge, one or more rows, one or more lines, etc.).

In some embodiments, a fiducial marker can be randomly placed in the field of view. For example, an oligonucleotide containing a fluorophore can be randomly printed, stamped, synthesized, or attached to a substrate (e.g., a glass slide) at a random position on the substrate. A tissue section can be contacted with the substrate such that the oligonucleotide containing the fluorophore contacts, or is in proximity to, a cell from the tissue section or a component of the cell (e.g., an mRNA or DNA molecule). An image of the substrate and the tissue section can be obtained, and the position of the fluorophore within the tissue section image can be determined (e.g., by reviewing an optical image of the tissue section overlaid with the fluorophore detection). In some embodiments, fiducial markers can be precisely placed in the field of view (e.g., at known locations on a substrate). In this instance, a fiducial marker can be stamped, attached, or synthesized on the substrate and contacted with a biological sample. Typically, an image of the sample and the fiducial marker is taken, and the position of the fiducial marker on the substrate can be confirmed by viewing the image.

In some embodiments, a fiducial marker can be an immobilized molecule (e.g., a physical particle) attached to the substrate. For example, a fiducial marker can be a nanoparticle, e.g., a nanorod, a nanowire, a nanocube, a nanopyramid, or a spherical nanoparticle. In some examples, the nanoparticle can be made of a heavy metal (e.g., gold). In some embodiments, the nanoparticle can be made from diamond. In some embodiments, the fiducial marker can be visible by eye.

As noted herein, any of the fiducial markers described herein (e.g., microspheres, beads, or any of the other physical particles described herein) can be located at a portion (e.g., corner) of an array in a specific pattern or design (e.g., hexagonal design) to aid in orientation of a biological sample on an array of features on the substrate. In some embodiments, the fiducial markers located at a portion (e.g., corner) of an array (e.g., an array on a substrate) can be pattern or designed in at least 1, at least 2, at least 3, or at least 4 unique patterns. In some examples, the fiducial markers located at the corners of the array (e.g., an array on a substrate) can have four unique patterns of fiducial markers.

In some examples, fiducial markers can surround the array. In some embodiments the fiducial markers allow for detection of, e.g., mirroring. In some embodiments, the fiducial markers may completely surround the array. In some embodiments, the fiducial markers may not completely surround the array. In some embodiments, the fiducial markers identify the corners of the array. In some embodiments, one or more fiducial markers identify the center of the array. In some embodiments, the fiducial markers comprise patterned spots, wherein the diameter of one or more patterned spot fiducial markers is approximately 100 micrometers. The diameter of the fiducial markers can be any useful diameter including, but not limited to, 50 micrometers to 500 micrometers in diameter. The fiducial markers may be arranged in such a way that the center of one fiducial marker is between 100 micrometers and 200 micrometers from the center of one or more other fiducial markers surrounding the array. In some embodiments, the array with the surrounding fiducial markers is approximately 8 mm by 8 mm. In some embodiments, the array without the surrounding fiducial markers is smaller than 8 mm by 50 mm.

In some embodiments, an array can be enclosed within a frame. Put another way, the perimeter of an array can have fiducial markers such that the array is enclosed, or substantially enclosed. In some embodiments, the perimeter of an array can be fiducial markers (e.g., any fiducial marker described herein). In some embodiments, the perimeter of an array can be uniform. For example, the fiducial markings can connect, or substantially connect, consecutive corners of an array in such a fashion that the non-corner portion of the array perimeter is the same on all sides (e.g., four sides) of the array. In some embodiments, the fiducial markers attached to the non-corner portions of the perimeter can be pattered or designed to aid in the orientation of the biological sample on the array. In some embodiments, the particles attached to the non-corner portions of the perimeter can be patterned or designed in at least 1, at least 2, at least 3, or at least 4 patterns. In some embodiments, the patterns can have at least 2, at least 3, or at least 4 unique patterns of fiducial markings on the non-corner portion of the array perimeter.

In some embodiments, an array can include at least two fiducial markers (e.g., at least 3, at least 4, at least 5, at least 6, at least 7, at least 8, at least 9, at least 10, at least 12, at least 15, at least 20, at least 30, at least 40, at least 50, at least 60, at least 70, at least 80, at least 90, at least 100 fiducial markers or more (e.g., several hundred, several thousand, or tens of thousands of fiducial markers)) in distinct positions on the surface of a substrate. Fiducial markers can be provided on a substrate in a pattern (e.g., an edge, one or more rows, one or more lines, etc.).

In some embodiments, staining and imaging a biological sample prior to contacting the biological sample with a spatial array is performed to select samples for spatial analysis. In some embodiments, the staining includes applying a fiducial marker as described above, including fluorescent, radioactive, chemiluminescent, or colorimetric detectable markers. In some embodiments, the staining and imaging of biological samples allows the user to identify the specific sample (or region of interest) the user wishes to assess.

In some embodiments, a lookup table (LUT) can be used to associate one property with another property of a feature. These properties include, e.g., locations, barcodes (e.g., nucleic acid barcode molecules), spatial barcodes, optical labels, molecular tags, and other properties.

In some embodiments, a lookup table can associate a nucleic acid barcode molecule with a feature. In some embodiments, an optical label of a feature can permit associating the feature with a biological particle (e.g., cell or nuclei). The association of a feature with a biological particle can further permit associating a nucleic acid sequence of a nucleic acid molecule of the biological particle to one or more physical properties of the biological particle (e.g., a type of a cell or a location of the cell). For example, based on the relationship between the barcode and the optical label, the optical label can be used to determine the location of a feature, thus associating the location of the feature with the barcode sequence of the feature. Subsequent analysis (e.g., sequencing) can associate the barcode sequence and the analyte from the sample. Accordingly, based on the relationship between the location and the barcode sequence, the location of the biological analyte can be determined (e.g., in a specific type of cell or in a cell at a specific location of the biological sample).

In some embodiments, a feature can have a plurality of nucleic acid barcode molecules attached thereto. The plurality of nucleic acid barcode molecules can include barcode sequences. The plurality of nucleic acid molecules attached to a given feature can have the same barcode sequences, or two or more different barcode sequences. Different barcode sequences can be used to provide improved spatial location accuracy.

In some embodiments, a substrate is treated in order to minimize or reduce non-specific analyte hybridization within or between features. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Application Publication Nos. U.S. 2017/0253918 and U.S. 2018/0052081, can be used. The entire contents of each of the foregoing documents are incorporated herein by reference.

Treatment can include adding a functional group that is reactive or capable of being activated such that it becomes reactive after receiving a stimulus (e.g., photoreactive). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

In some examples, an array (e.g., any of the exemplary arrays described herein) can be contacted with only a portion of a biological sample (e.g., a cell, a feature, or a region of interest). In some examples, a biological sample is contacted with only a portion of an array (e.g., any of the exemplary arrays described herein). In some examples, a portion of the array can be deactivated such that it does not interact with the analytes in the biological sample (e.g., optical deactivation, chemical deactivation, heat deactivation, or blocking of the capture probes in the array (e.g., using blocking probes)). In some examples, a region of interest can be removed from a biological sample and then the region of interest can be contacted to the array (e.g., any of the arrays described herein). A region of interest can be removed from a biological sample using microsurgery, laser capture microdissection, chunking, a microtome, dicing, trypsinization, labelling, and/or fluorescence-assisted cell sorting.

(f) Partitioning

As discussed above, in some embodiments, the sample can optionally be separated into single cells, cell groups, or other fragments/pieces that are smaller than the original, unfragmented sample. Each of these smaller portions of the sample can be analyzed to obtain spatially-resolved analyte information for the sample.

For samples that have been separated into smaller fragments—and particularly, for samples that have been disaggregated, dissociated, or otherwise separated into individual cells—one method for analyzing the fragments involves partitioning the fragments into individual partitions (e.g., fluid droplets), and then analyzing the contents of the partitions. In general, each partition maintains separation of its own contents from the contents of other partitions. The partition can be a droplet in an emulsion, for example.

In addition to analytes, a partition can include additional components, and in particular, one or more beads. A partition can include a single gel bead, a single cell bead, or both a single cell bead and single gel bead.

A partition can also include one or more reagents. Unique identifiers, such as barcodes, can be injected into the droplets previous to, subsequent to, or concurrently with droplet generation, such as via a microcapsule (e.g., bead). Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids.

The partitions can be flowable within fluid streams. The partitions can include, for example, micro-vesicles that have an outer barrier surrounding an inner fluid center or core. In some cases, the partitions can include a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions can be provided in a water-in-oil emulsion or oil-in-water emulsion. A variety of different vessels are described in, for example, U.S. Patent Application Publication No. 2014/0155295, the entire contents of which are incorporated herein by reference. Emulsion systems for creating stable droplets in non-aqueous or oil continuous phases are described, for example, in U.S. Patent Application Publication No. 2010/0105112, the entire contents of which are incorporated herein by reference.

For droplets in an emulsion, allocating individual particles to discrete partitions can be accomplished, for example, by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters can be adjusted to control the occupancy of the resulting partitions (e.g., number of analytes per partition, number of beads per partition, etc.). For example, partition occupancy can be controlled by providing the aqueous stream at a certain concentration and/or flow rate of analytes.

To generate single analyte partitions, the relative flow rates of the immiscible fluids can be selected such that, on average, the partitions can contain less than one analyte per partition to ensure that those partitions that are occupied are primarily singly occupied. In some cases, partitions among a plurality of partitions can contain at most one analyte. In some embodiments, the various parameters (e.g., fluid properties, particle properties, microfluidic architectures, etc.) can be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

The channel segments described herein can be coupled to any of a variety of different fluid sources or receiving components, including reservoirs, tubing, manifolds, or fluidic components of other systems. As will be appreciated, the microfluidic channel structure can have a variety of geometries. For example, a microfluidic channel structure can have one or more than one channel junction. As another example, a microfluidic channel structure can have 2, 3, 4, or 5 channel segments each carrying particles that meet at a channel junction. Fluid can be directed to flow along one or more channels or reservoirs via one or more fluid flow units. A fluid flow unit can include compressors (e.g., providing positive pressure), pumps (e.g., providing negative pressure), actuators, and the like to control flow of the fluid. Fluid can also or otherwise be controlled via applied pressure differentials, centrifugal force, electrokinetic pumping, vacuum, capillary, and/or gravity flow.

A partition can include one or more unique identifiers, such as barcodes. Barcodes can be previously, subsequently, or concurrently delivered to the partitions that hold the compartmentalized or partitioned biological particle. For example, barcodes can be injected into droplets previous to, subsequent to, or concurrently with droplet generation. The delivery of the barcodes to a particular partition allows for the later attribution of the characteristics of the individual biological particle to the particular partition. Barcodes can be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can include a bead.

In some embodiments, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus can disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

In some embodiments, one more barcodes (e.g., spatial barcodes, UMIs, or a combination thereof) can be introduced into a partition as part of the analyte. As described previously, barcodes can be bound to the analyte directly, or can form part of a capture probe or analyte capture agent that is hybridized to, conjugated to, or otherwise associated with an analyte, such that when the analyte is introduced into the partition, the barcode(s) are introduced as well. As described above, FIG. 16 shows an example of a microfluidical channel structure for partitioning individual analytes (e.g., cells) into discrete partitions.

Figure 16:
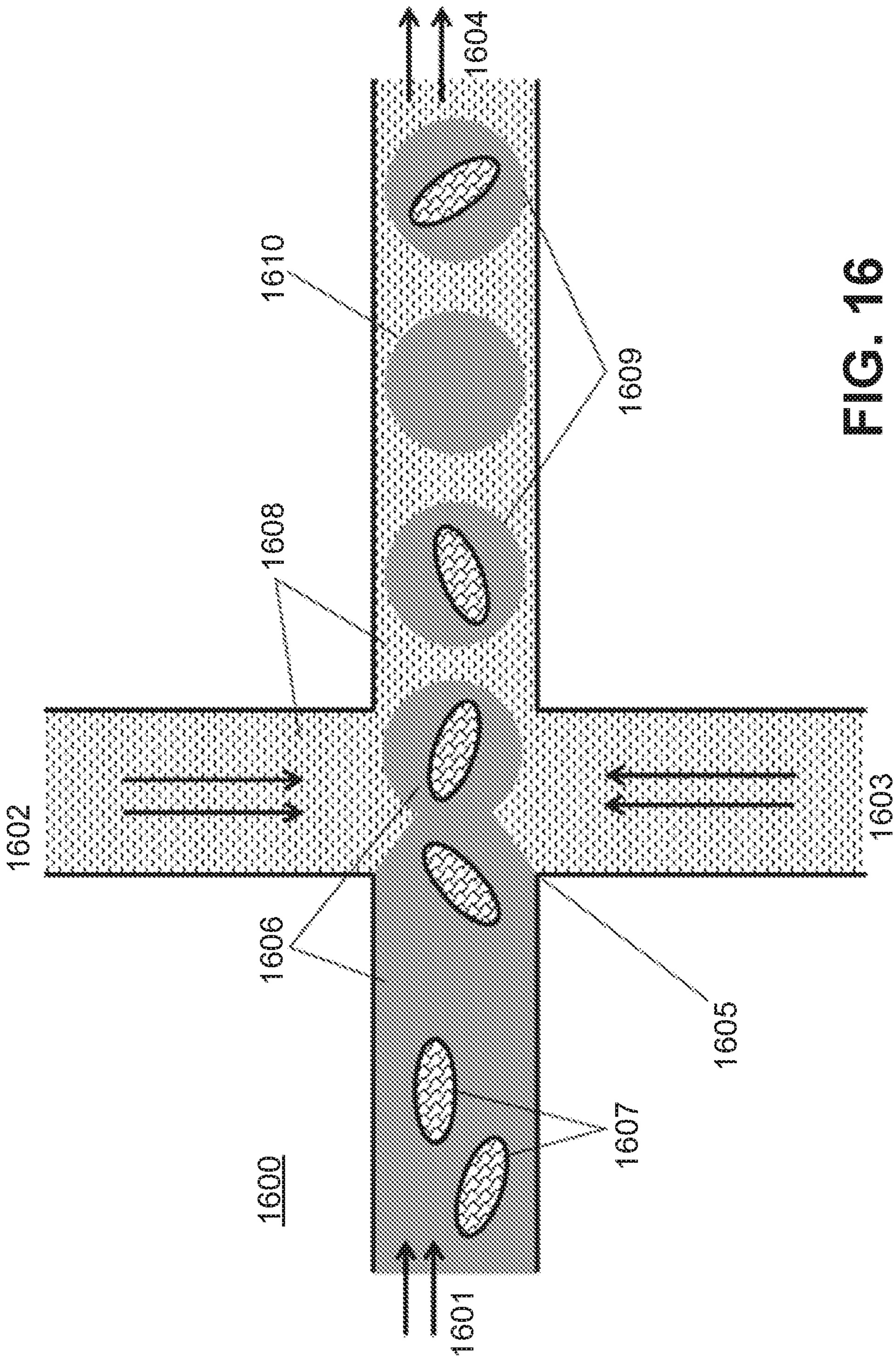
FIG. 16 shows an example of a microfluidic channel structure 1600 for partitioning dissociated sample (e.g. biological particles or individual cells from a sample).

FIG. 16 shows an example of a microfluidic channel structure for partitioning individual analytes (e.g., cells) into discrete partitions. The channel structure can include channel segments 1601, 1602, 1603, and 1604 communicating at a channel junction 1605. In operation, a first aqueous fluid 1606 that includes suspended biological particles (or cells) 1607 may be transported along channel segment 1601 into junction 1605, while a second fluid 1608 that is immiscible with the aqueous fluid 1606 is delivered to the junction 1605 from each of channel segments 1602 and 1603 to create discrete droplets 1609, 1610 of the first aqueous fluid 1606 flowing into channel segment 1604, and flowing away from junction 1605. The channel segment 1604 may be fluidically coupled to an outlet reservoir where the discrete droplets can be stored and/or harvested. A discrete droplet generated may include an individual biological particle 1607 (such as droplets 1609). A discrete droplet generated may include more than one individual biological particle 1607. A discrete droplet may contain no biological particle 1607 (such as droplet 1610). Each discrete partition may maintain separation of its own contents (e.g., individual biological particle 1607) from the contents of other partitions.

Figure 17A:
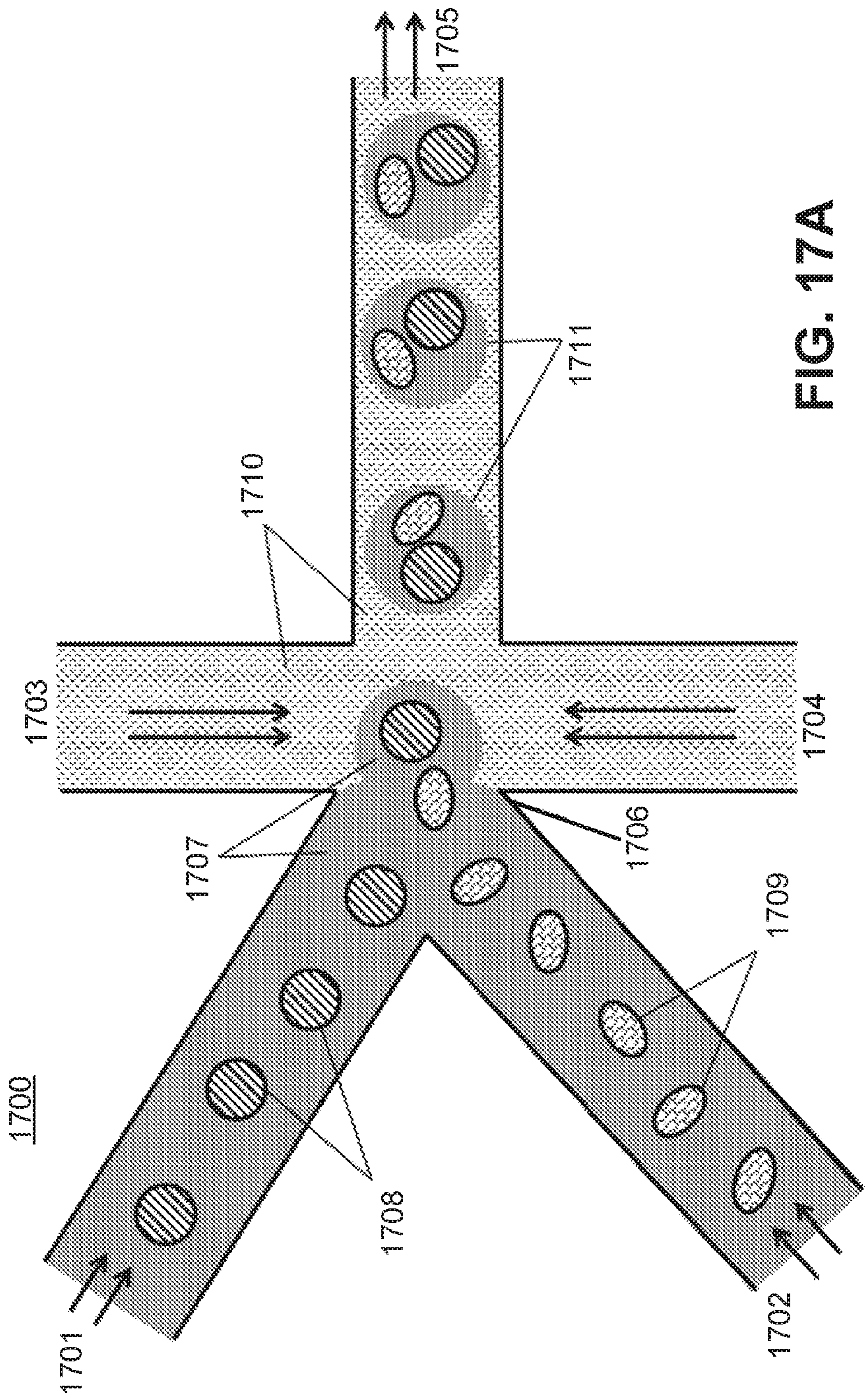
FIG. 17A shows an example of a microfluidic channel structure 1700 for delivering spatial barcode carrying beads to droplets.

FIG. 17A shows another example of a microfluidic channel structure 1700 for delivering beads to droplets. The channel structure includes channel segments 1701, 1702, 1703, 1704 and 1705 communicating at a channel junction 1706. During operation, the channel segment 1701 can transport an aqueous fluid 1707 that includes a plurality of beads 1708 along the channel segment 1701 into junction 1706. The plurality of beads 1708 can be sourced from a suspension of beads. For example, the channel segment 1701 can be connected to a reservoir that includes an aqueous suspension of beads 1708. The channel segment 1702 can transport the aqueous fluid 1707 that includes a plurality of particles 1709 (e.g., cells) along the channel segment 1702 into junction 1706. In some embodiments, the aqueous fluid 1707 in either the first channel segment 1701 or the second channel segment 1702, or in both segments, can include one or more reagents, as further described below.

A second fluid 1710 that is immiscible with the aqueous fluid 1707 (e.g., oil) can be delivered to the junction 1706 from each of channel segments 1703 and 1704. Upon meeting of the aqueous fluid 1707 from each of channel segments 1701 and 1702 and the second fluid 1710 from each of channel segments 1703 and 1704 at the channel junction 1706, the aqueous fluid 1707 can be partitioned as discrete droplets 1711 in the second fluid 1710 and flow away from the junction 1706 along channel segment 1705. The channel segment 1705 can deliver the discrete droplets to an outlet reservoir fluidly coupled to the channel segment 1705, where they can be harvested.

As an alternative, the channel segments 1701 and 1702 can meet at another junction upstream of the junction 1706. At such junction, beads and biological particles can form a mixture that is directed along another channel to the junction 1706 to yield droplets 1711. The mixture can provide the beads and biological particles in an alternating fashion, such that, for example, a droplet includes a single bead and a single biological particle.

The second fluid 1710 can include an oil, such as a fluorinated oil, that includes a fluorosurfactant for stabilizing the resulting droplets, for example, inhibiting subsequent coalescence of the resulting droplets 1711.

The partitions described herein can include small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less. In the foregoing discussion, droplets with beads were formed at the junction of different fluid streams. In some embodiments, droplets can be formed by gravity-based partitioning methods.

Figure 17B:
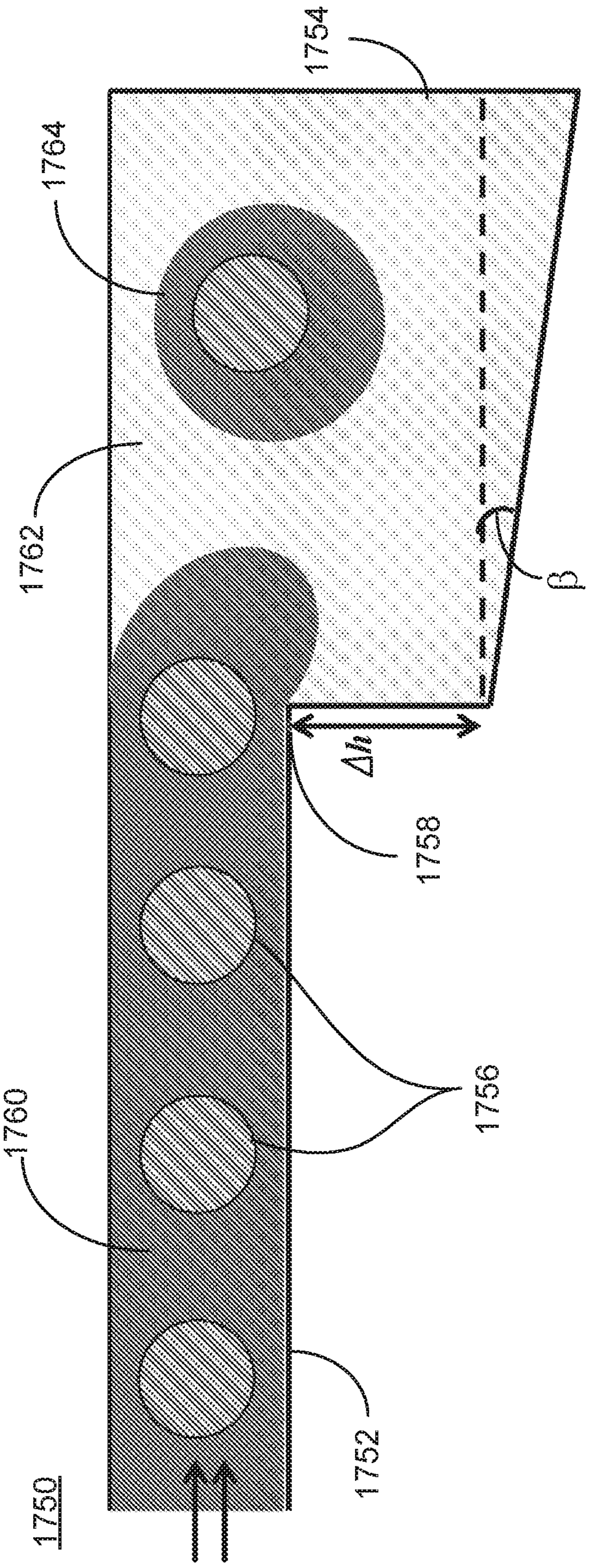
FIG. 17B shows a cross-section view of another example of a microfluidic channel structure 1750 with a geometric feature for controlled partitioning.

FIG. 17B shows a cross-section view of another example of a microfluidic channel structure 1750 with a geometric feature for controlled partitioning. A channel structure 1750 can include a channel segment 1752 communicating at a channel junction 1758 (or intersection) with a reservoir 1754. In some instances, the channel structure 1750 and one or more of its components can correspond to the channel structure 1700 and one or more of its components.

An aqueous fluid 1760 comprising a plurality of particles 1756 may be transported along the channel segment 1752 into the junction 1758 to meet a second fluid 1762 (e.g., oil, etc.) that is immiscible with the aqueous fluid 1760 in the reservoir 1754 to create droplets 1764 of the aqueous fluid 1760 flowing into the reservoir 1754. At the junction 1758 where the aqueous fluid 1760 and the second fluid 1762 meet, droplets can form based on factors such as the hydrodynamic forces at the junction 1758, relative flow rates of the two fluids 1760, 1762, fluid properties, and certain geometric parameters (e.g., Δh, etc.) of the channel structure 1750. A plurality of droplets can be collected in the reservoir 1754 by continuously injecting the aqueous fluid 1760 from the channel segment 1752 at the junction 1758.

A discrete droplet generated may comprise one or more particles of the plurality of particles 1756. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 1760 can have a substantially uniform concentration or frequency of particles 1756. As described elsewhere herein, the particles 1756 (e.g., beads) can be introduced into the channel segment 1752 from a separate channel (not shown in FIG. 17). The frequency of particles 1756 in the channel segment 1752 may be controlled by controlling the frequency in which the particles 1756 are introduced into the channel segment 1752 and/or the relative flow rates of the fluids in the channel segment 1752 and the separate channel. In some instances, the particles 1756 can be introduced into the channel segment 1752 from a plurality of different channels, and the frequency controlled accordingly. In some instances, different particles may be introduced via separate channels. For example, a first separate channel can introduce beads and a second separate channel can introduce biological particles into the channel segment 1752. The first separate channel introducing the beads may be upstream or downstream of the second separate channel introducing the biological particles.

In some instances, the second fluid 1762 may not be subjected to and/or directed to any flow in or out of the reservoir 1754. For example, the second fluid 1762 may be substantially stationary in the reservoir 1754. In some instances, the second fluid 1762 may be subjected to flow within the reservoir 1754, but not in or out of the reservoir 1754, such as via application of pressure to the reservoir 1754 and/or as affected by the incoming flow of the aqueous fluid 1760 at the junction 1758. Alternatively, the second fluid 1762 may be subjected and/or directed to flow in or out of the reservoir 1754. For example, the reservoir 1754 can be a channel directing the second fluid 1762 from upstream to downstream, transporting the generated droplets.

The channel structure 1750 at or near the junction 1758 may have certain geometric features that at least partly determine the sizes and/or shapes of the droplets formed by the channel structure 1750. The channel segment 1752 can have a first cross-section height, h1, and the reservoir 1754 can have a second cross-section height, h2. The first cross-section height, h1, and the second cross-section height, h2, may be different, such that at the junction 1758, there is a height difference of Δh. The second cross-section height, h2, may be greater than the first cross-section height, h1. In some instances, the reservoir may thereafter gradually increase in cross-section height, for example, the more distant it is from the junction 1758. In some instances, the cross-section height of the reservoir may increase in accordance with expansion angle, β, at or near the junction 1758. The height difference, Δh, and/or expansion angle, β, can allow the tongue (portion of the aqueous fluid 1760 leaving channel segment 1752 at junction 1758 and entering the reservoir 1754 before droplet formation) to increase in depth and facilitate decrease in curvature of the intermediately formed droplet. For example, droplet size may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, β, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 1760 entering the junction 1758 can be between about 0.04 microliters (μL)/minute (min) and about 40 μL/min. In some instances, the flow rate of the aqueous fluid 1760 entering the junction 1758 can be between about 0.01 microliters (μL)/minute (min) and about 100 μL/min. Alternatively, the flow rate of the aqueous fluid 1760 entering the junction 1758 can be less than about 0.01 μL/min. alternatively, the flow rate of the aqueous fluid 1760 entering the junction 1758 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 1760 entering the junction 1758. The second fluid 1762 may be stationary, or substantially stationary, in the reservoir 1754. Alternatively, the second fluid 1762 may be flowing, such as at the above flow rates described for the aqueous fluid 1760.

While FIG. 17B illustrates the height difference, Δh, being abrupt at the junction 1758 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 1758, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIG. 17B illustrates the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

A variety of different beads can be incorporated into partitions as described above. In some embodiments, for example, non-barcoded beads can be incorporated into the partitions. For example, where the biological particle (e.g., a cell) that is incorporated into the partitions carries one or more barcodes (e.g., spatial barcode(s), UMI(s), and combinations thereof), the bead can be a non-barcoded bead.

In some embodiments, a barcode carrying bead can be incorporated into partitions. For example, a nucleic acid molecule, such as an oligonucleotide, can be coupled to a bead by a releasable linkage, such as, for example, a disulfide linker. The same bead can be coupled (e.g., via releasable linkage) to one or more other nucleic acid molecules. The nucleic acid molecule can be or include a barcode. As noted elsewhere herein, the structure of the barcode can include a number of sequence elements.

The nucleic acid molecule can include a functional domain that can be used in subsequent processing. For example, the functional domain can include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule can include a barcode sequence for use in barcoding the sample (e.g., DNA, RNA, protein, etc.). In some cases, the barcode sequence can be bead-specific such that the barcode sequence is common to all nucleic acid molecules coupled to the same bead. Alternatively or in addition, the barcode sequence can be partition-specific such that the barcode sequence is common to all nucleic acid molecules coupled to one or more beads that are partitioned into the same partition. The nucleic acid molecule can include a specific priming sequence, such as an mRNA specific priming sequence (e.g., poly(T) sequence), a targeted priming sequence, and/or a random priming sequence. The nucleic acid molecule can include an anchoring sequence to ensure that the specific priming sequence hybridizes at the sequence end (e.g., of the mRNA). For example, the anchoring sequence can include a random short sequence of nucleotides, such as a 1-mer, 2-mer, 3-mer or longer sequence, which can ensure that a poly(T) segment is more likely to hybridize at the sequence end of the poly(A) tail of the mRNA.

The nucleic acid molecule can include a unique molecular identifying sequence (e.g., unique molecular identifier (UMI)). In some embodiments, the unique molecular identifying sequence can include from about 5 to about 8 nucleotides. Alternatively, the unique molecular identifying sequence can include less than about 5 or more than about 8 nucleotides. The unique molecular identifying sequence can be a unique sequence that varies across individual nucleic acid molecules coupled to a single bead.

In some embodiments, the unique molecular identifying sequence can be a random sequence (e.g., such as a random N-mer sequence). For example, the UMI can provide a unique identifier of the starting mRNA molecule that was captured, in order to allow quantitation of the number of original expressed RNA.

In general, an individual bead can be coupled to any number of individual nucleic acid molecules, for example, from one to tens to hundreds of thousands or even millions of individual nucleic acid molecules. The respective barcodes for the individual nucleic acid molecules can include both common sequence segments or relatively common sequence segments and variable or unique sequence segments between different individual nucleic acid molecules coupled to the same bead.

Figure 17C:
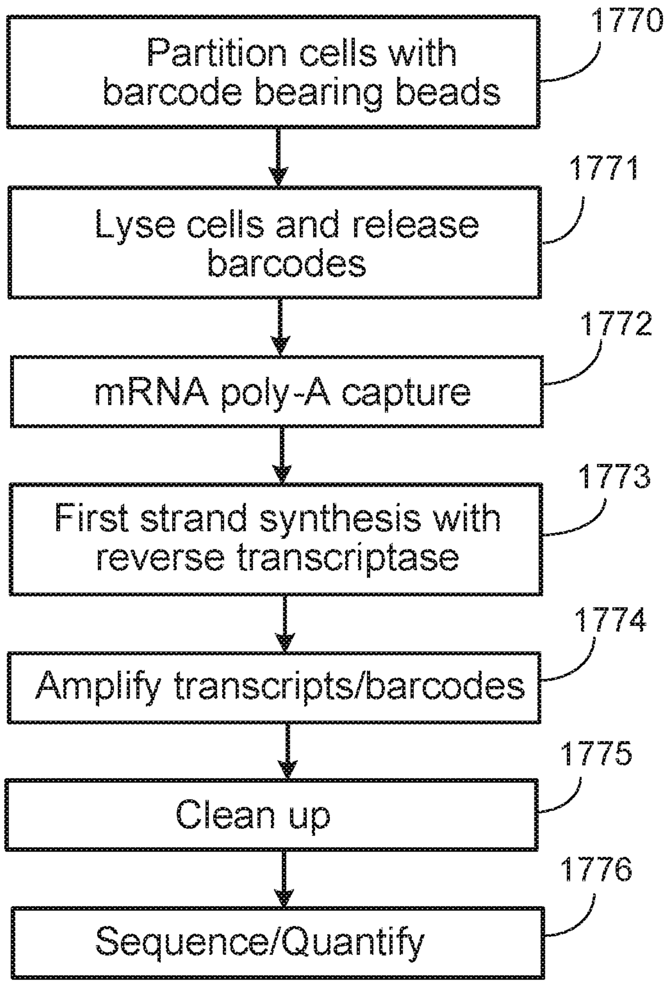
FIG. 17C shows a workflow schematic.

FIG. 17C depicts a workflow wherein cells are partitioned into droplets along with barcode-bearing beads 1770. See FIG. 17A. The droplet forms an isolated reaction chamber wherein the cells can be lysed 1771 and target analytes within the cells can then be captured 1772 and amplified 1773, 1774 according to previously described methods. After sequence library preparation clean-up 1775, the material is sequenced and/or quantified 1776 according to methods described herein.

It should be noted that while the example workflow in FIG. 17C includes steps specifically for the analysis of mRNA, analogous workflows can be implemented for a wide variety of other analytes, including any of the analytes described previously.

By way of example, in the context of analyzing sample RNA as shown in FIG. 17C, the poly(T) segment of one of the released nucleic acid molecules (e.g., from the bead) can hybridize to the poly(A) tail of a mRNA molecule. Reverse transcription can result in a cDNA transcript of the mRNA, which transcript includes each of the sequence segments of the nucleic acid molecule. If the nucleic acid molecule includes an anchoring sequence, it will more likely hybridize to and prime reverse transcription at the sequence end of the poly(A) tail of the mRNA.

Within any given partition, all of the cDNA transcripts of the individual mRNA molecules can include a common barcode sequence segment. However, the transcripts made from the different mRNA molecules within a given partition can vary at the unique molecular identifying sequence segment (e.g., UMI segment). Beneficially, even following any subsequent amplification of the contents of a given partition, the number of different UMIs can be indicative of the quantity of mRNA originating from a given partition. As noted above, the transcripts can be amplified, cleaned up and sequenced to identify the sequence of the cDNA transcript of the mRNA, as well as to sequence the barcode segment and the UMI segment. While a poly(T) primer sequence is described, other targeted or random priming sequences can also be used in priming the reverse transcription reaction. Likewise, although described as releasing the barcoded oligonucleotides into the partition, in some cases, the nucleic acid molecules bound to the bead can be used to hybridize and capture the mRNA on the solid phase of the bead, for example, in order to facilitate the separation of the RNA from other cell contents.

In some embodiments, precursors that include a functional group that is reactive or capable of being activated such that it becomes reactive can be polymerized with other precursors to generate gel beads that include the activated or activatable functional group. The functional group can then be used to attach additional species (e.g., disulfide linkers, primers, other oligonucleotides, etc.) to the gel beads. For example, some precursors featuring a carboxylic acid (COOH) group can co-polymerize with other precursors to form a bead that also includes a COOH functional group. In some cases, acrylic acid (a species comprising free COOH groups), acrylamide, and bis(acryloyl)cystamine can be co-polymerized together to generate a bead with free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

In some embodiments, a degradable bead can be introduced into a partition, such that the bead degrades within the partition and any associated species (e.g., oligonucleotides) are released within the droplet when the appropriate stimulus is applied. The free species (e.g., oligonucleotides, nucleic acid molecules) can interact with other reagents contained in the partition. For example, a polyacrylamide bead featuring cystamine and linked, via a disulfide bond, to a barcode sequence, can be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet with a bead-bound barcode sequence in basic solution can also result in bead degradation and release of the attached barcode sequence into the aqueous, inner environment of the droplet.

Any suitable number of species (e.g., primer, barcoded oligonucleotide) can be associated with a bead such that, upon release from the bead, the species (e.g., primer, e.g., barcoded oligonucleotide) are present in the partition at a pre-defined concentration. Such pre-defined concentration can be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

A degradable bead can include one or more species with a labile bond such that, when the bead/species is exposed to the appropriate stimulus, the bond is broken and the bead degrades. The labile bond can be a chemical bond (e.g., covalent bond, ionic bond) or can be another type of physical interaction (e.g., van der Waals interactions, dipole-dipole interactions, etc.) In some embodiments, a crosslinker used to generate a bead can include a labile bond. Upon exposure to the appropriate conditions, the labile bond can be broken and the bead degraded. For example, upon exposure of a polyacrylamide gel bead that includes cystamine crosslinkers to a reducing agent, the disulfide bonds of the cystamine can be broken and the bead degraded.

A degradable bead can be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a barcode sequence can be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above description, while referred to as degradation of a bead, in many embodiments, degradation can refer to the disassociation of a bound or entrained species from a bead, both with and without structurally degrading the physical bead itself. For example, entrained species can be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In some embodiments, osmotic shrinking of a bead can cause a bead to better retain an entrained species due to pore size contraction. Numerous chemical triggers can be used to trigger the degradation of beads within partitions. Examples of these chemical changes can include, but are not limited to pH-mediated changes to the integrity of a component within the bead, degradation of a component of a bead via cleavage of cross-linked bonds, and depolymerization of a component of a bead.

In some embodiments, a bead can be formed from materials that include degradable chemical cross-linkers, such as BAC or cystamine. Degradation of such degradable cross-linkers can be accomplished through a number of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof. A reducing agent can degrade the disulfide bonds formed between gel precursors forming the bead, and thus, degrade the bead.

In certain embodiments, a change in pH of a solution, such as an increase in pH, can trigger degradation of a bead. In other embodiments, exposure to an aqueous solution, such as water, can trigger hydrolytic degradation, and thus degradation of the bead. In some cases, any combination of stimuli can trigger degradation of a bead. For example, a change in pH can enable a chemical agent (e.g., DTT) to become an effective reducing agent.

Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In other cases, heat can increase the internal pressure of the bead components such that the bead ruptures or explodes. Heat can also act upon heat-sensitive polymers used as materials to construct beads.

In addition to beads and analytes, partitions that are formed can include a variety of different reagents and species. For example, when lysis reagents are present within the partitions, the lysis reagents can facilitate the release of analytes within the partition. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St. Louis, MO), as well as other commercially available lysis enzymes. Other lysis agents can additionally or alternatively be co-partitioned to cause the release analytes into the partitions. For example, in some cases, surfactant-based lysis solutions can be used to lyse cells, although these can be less desirable for emulsion based systems where the surfactants can interfere with stable emulsions. In some embodiments, lysis solutions can include non-ionic surfactants such as, for example, TritonX-100 and Tween 20. In some embodiments, lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of analytes that can be in addition to or in place of droplet partitioning, where any pore size of the encapsulate is sufficiently small to retain nucleic acid fragments of a given size, following cellular disruption.

Examples of other species that can be co-partitioned with analytes in the partitions include, but are not limited to, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. Additional reagents can also be co-partitioned, including endonucleases to fragment DNA, DNA polymerase enzymes and dNTPs used to amplify nucleic acid fragments and to attach the barcode molecular tags to the amplified fragments.

Additional reagents can also include reverse transcriptase enzymes, including enzymes with terminal transferase activity, primers and oligonucleotides, and switch oligonucleotides (also referred to herein as “switch oligos” or “template switching oligonucleotides”) which can be used for template switching. In some embodiments, template switching can be used to increase the length of a cDNA. Template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., poly(C), to the cDNA in a template independent manner. Switch oligos can include sequences complementary to the additional nucleotides, e.g., poly(G). The additional nucleotides (e.g., poly(C)) on the cDNA can hybridize to the additional nucleotides (e.g., poly(G)) on the switch oligo, whereby the switch oligo can be used by the reverse transcriptase as template to further extend the cDNA. Template switching oligonucleotides can include a hybridization region and a template region. The hybridization region can include any sequence capable of hybridizing to the target. In some cases, the hybridization region includes a series of G bases to complement the overhanging C bases at the 3' end of a cDNA molecule. The series of G bases can include 1 G base, 2 G bases, 3 G bases, 4 G bases, 5 G bases or more than 5 G bases. The template sequence can include any sequence to be incorporated into the cDNA. In some cases, the template region includes at least 1 (e.g., at least 2, 3, 4, 5 or more) tag sequences and/or functional sequences. Switch oligos can include deoxyribonucleic acids; ribonucleic acids; bridged nucleic acids, modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), and combinations of the foregoing.

In some embodiments, beads that are partitioned with the analyte can include different types of oligonucleotides bound to the bead, where the different types of oligonucleotides bind to different types of analytes. For example, a bead can include one or more first oligonucleotides (which can be capture probes, for example) that can bind or hybridize to a first type of analyte, such as mRNA for example, and one or more second oligonucleotides (which can be capture probes, for example) that can bind or hybridize to a second type of analyte, such as gDNA for example. Partitions can also include lysis agents that aid in releasing nucleic acids from the co-partitioned cell, and can also include an agent (e.g., a reducing agent) that can degrade the bead and/or break covalent linkages between the oligonucleotides and the bead, releasing the oligonucleotides into the partition. The released barcoded oligonucleotides (which can also be barcoded) can hybridize with mRNA released from the cell and also with gDNA released from the cell.

Barcoded constructs thus formed from hybridization can include a first type of construct that includes a sequence corresponding to an original barcode sequence from the bead and a sequence corresponding to a transcript from the cell, and a second type of construct that includes a sequence corresponding to the original barcode sequence from the bead and a sequence corresponding to genomic DNA from the cell. The barcoded constructs can then be released/removed from the partition and, in some embodiments, further processed to add any additional sequences. The resulting constructs can then be sequenced, the sequencing data processed, and the results used to spatially characterize the mRNA and the gDNA from the cell.

In another example, a partition includes a bead that includes a first type of oligonucleotide (e.g., a first capture probe) with a first barcode sequence, a poly(T) priming sequence that can hybridize with the poly(A) tail of an mRNA transcript, and a UMI barcode sequence that can uniquely identify a given transcript. The bead also includes a second type of oligonucleotide (e.g., a second capture probe) with a second barcode sequence, a targeted priming sequence that is capable of specifically hybridizing with a third barcoded oligonucleotide (e.g., an analyte capture agent) coupled to an antibody that is bound to the surface of the partitioned cell. The third barcoded oligonucleotide includes a UMI barcode sequence that uniquely identifies the antibody (and thus, the particular cell surface feature to which it is bound).

In this example, the first and second barcoded oligonucleotides include the same spatial barcode sequence (e.g., the first and second barcode sequences are the same), which permits downstream association of barcoded nucleic acids with the partition. In some embodiments, however, the first and second barcode sequences are different.

The partition also includes lysis agents that aid in releasing nucleic acids from the cell and can also include an agent (e.g., a reducing agent) that can degrade the bead and/or break a covalent linkage between the barcoded oligonucleotides and the bead, releasing them into the partition. The first type of released barcoded oligonucleotide can hybridize with mRNA released from the cell and the second type of released barcoded oligonucleotide can hybridize with the third type of barcoded oligonucleotide, forming barcoded constructs.

The first type of barcoded construct includes a spatial barcode sequence corresponding to the first barcode sequence from the bead and a sequence corresponding to the UMI barcode sequence from the first type of oligonucleotide, which identifies cell transcripts. The second type of barcoded construct includes a spatial barcode sequence corresponding to the second barcode sequence from the second type of oligonucleotide, and a UMI barcode sequence corresponding to the third type of oligonucleotide (e.g., the analyte capture agent) and used to identify the cell surface feature. The barcoded constructs can then be released/removed from the partition and, in some embodiments, further processed to add any additional sequences. The resulting constructs are then sequenced, sequencing data processed, and the results used to characterize the mRNA and cell surface feature of the cell.

The foregoing discussion involves two specific examples of beads with oligonucleotides for analyzing two different analytes within a partition. More generally, beads that are partitioned can have any of the structures described previously, and can include any of the described combinations of oligonucleotides for analysis of two or more (e.g., three or more, four or more, five or more, six or more, eight or more, ten or more, 12 or more, 15 or more, 20 or more, 25 or more, 30 or more, 40 or more, 50 or more) different types of analytes within a partition. Examples of beads with combinations of different types of oligonucleotides (e.g., capture probes) for concurrently analyzing different combinations of analytes within partitions include, but are not limited to: (a) genomic DNA and cell surface features (e.g., using the analyte capture agents described herein); (b) mRNA and a lineage tracing construct; (c) mRNA and cell methylation status; (d) mRNA and accessible chromatin (e.g., ATAC-seq, DNase-seq, and/or MNase-seq); (e) mRNA and cell surface or intracellular proteins and/or metabolites; (f) a barcoded analyte capture agent (e.g., the MHC multimers described herein) and a V(D)J sequence of an immune cell receptor (e.g., T-cell receptor); and (g) mRNA and a perturbation agent (e.g., a CRISPR crRNA/sgRNA, TALEN, zinc finger nuclease, and/or antisense oligonucleotide as described herein).

Additionally, in some embodiments, the unaggregated cell or disaggregated cells introduced and processed within partitions or droplets as described herein, can be removed from the partition, contacted with a spatial array, and spatially barcoded according to methods described herein. For example, single cells of an unaggregated cell sample can be partitioned into partitions or droplets as described herein. The partitions or droplets can include reagents to permeabilize a cell, barcode targeted cellular analyte(s) with a cellular barcode, and amplify the barcoded analytes. The partitions or droplets can be contacted with any of the spatial arrays described herein. In some embodiments, the partition can be dissolved, such that the contents of the partition are placed in contact with the capture probes of the spatial array. The capture probes of the spatial array can then capture target analytes from the ruptured partitions or the droplets, and processed by the spatial workflows described herein.

(g) Analysis of Captured Analytes

Removal of Sample from Array

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, analysis of an analyte bound to capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture prove bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; and (d) analyzing the captured biological analyte, thereby spatially detecting the biological analyte of interest; where the biological sample is not removed from the substrate.

In some embodiments, the method further includes selecting a region of interest in the biological sample to subject to spatial transcriptomic analysis. In some embodiments, one or more of the one or more capture probes include a capture domain. In some embodiments, one or more of the one or more capture probe pluralities comprise a unique molecular identifier (UMI). In some embodiments, one or more of the one or more capture probe pluralities comprise a cleavage domain. In some embodiments, the cleavage domain comprises a sequence recognized and cleaved by a uracil-DNA glycosylase, apurinic/apyrimidinic (AP) endonuclease (APE1), U uracil-specific excision reagent (USER), and/or an endonuclease VIII. In some embodiments, one or more capture probes do not comprise a cleavage domain and is not cleaved from the array. A set of experiments performed determined methods that did not remove the biological sample from the substrate yielded higher quality sequencing data, higher median genes per cell, and higher median UMI counts per cell compared to a similar methods where the biological sample was removed from the substrate (data not shown).

In some embodiments, a capture probe can be extended. For example, extending a capture probe can includes generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA, e.g. cDNA, molecule is generated. In some embodiments, a "full-length" DNA molecule refers to the whole of the captured nucleic acid molecule. However, if the nucleic acid, e.g. RNA, was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Epicentre Biotechnologies, Madison, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Epicentre Biotechnologies, Madison, WI), and SplintR (available from New England Biolabs, Ipswich, MA). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g. sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g. by heating to denature a double-stranded molecule).

In some embodiments, the extended capture probe or complement or amplicon thereof is released from the surface of the substrate (e.g., array) by physical means. For example, where the extended capture probe is indirectly immobilized on the array substrate, e.g. via hybridization to a surface probe, it can be sufficient to disrupt the interaction between the extended capture probe and the surface probe. Methods for disrupting the interaction between nucleic acid molecules include denaturing double stranded nucleic acid molecules art. A straightforward method for releasing the DNA molecules (i.e., of stripping the array of the extended probes) is to use a solution that interferes with the hydrogen bonds of the double stranded molecules. In some embodiments, the extended capture probe is released by applying heated water such as water or buffer of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

Capture probes can optionally include a "cleavage domain," where one or more segments or regions of the capture probe (e.g., spatial barcodes and/or UMIs) can be releasably, cleavably, or reversibly attached to a feature, or some other substrate, so that spatial barcodes and/or UMIs can be released or be releasable through cleavage of a linkage between the capture probe and the feature, or released through degradation of the underlying support, allowing the spatial barcode(s) and/or UMI(s) of the cleaved capture probe to be accessed or be accessible by other reagents, or both.

In some embodiments, the capture probe is linked, via a disulfide bond, to a feature. In some embodiments, the capture probe is linked to a feature via a propylene group (e.g., Spacer C3). A reducing agent can be added to break the various disulfide bonds, resulting in release of the capture probe including the spatial barcode sequence. In another example, heating can also result in degradation and release of the attached capture probe. In some embodiments, the heating is done by laser (e.g., laser ablation) and features at specific locations can be degraded. In addition to thermally cleavable bonds, disulfide bonds, photo-sensitive bonds, and UV sensitive bonds, other non-limiting examples of labile bonds that can be coupled to a capture probe (i.e., spatial barcode) include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

In some embodiments, the cleavage domain includes a sequence that is recognized by one or more enzymes capable of cleaving a nucleic acid molecule, e.g., capable of breaking the phosphodiester linkage between two or more nucleotides. A bond can be cleavable via other nucleic acid molecule targeting enzymes, such as restriction enzymes (e.g., restriction endonucleases). For example, the cleavage domain can include a restriction endonuclease (restriction enzyme) recognition sequence. Restriction enzymes cut double-stranded or single stranded DNA at specific recognition nucleotide sequences known as restriction sites. In some embodiments, a rare-cutting restriction enzyme, i.e., enzymes with a long recognition site (at least 8 base pairs in length), is used to reduce the possibility of cleaving elsewhere in the capture probe.

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. In some embodiments, the cleavage domain can be a single U. In some embodiments, the cleavage domain can be an abasic site that can be cleaved with an abasic site-specific endonuclease (e.g., Endonucleoase IV or Endonuclease VIII). Releasable capture probes can be available for reaction once released. Thus, for example, an activatable capture probe can be activated by releasing the capture probes from a feature.

In some embodiments, the cleavage domain of the capture probe is a nucleotide sequence within the capture probe that is cleaved specifically, e.g., physically by light or heat, chemically or enzymatically. The location of the cleavage domain within the capture probe will depend on whether or not the capture probe is immobilized on the substrate such that it has a free 3' end capable of functioning as an extension primer (e.g. by its 5' or 3' end). For example, if the capture probe is immobilized by its 5' end, the cleavage domain will be located 5' to the spatial barcode and/or UMI, and cleavage of said domain results in the release of part of the capture probe including the spatial barcode and/or UMI and the sequence 3' to the spatial barcode, and optionally part of the cleavage domain, from a feature. Alternatively, if the capture probe is immobilized by its 3' end, the cleavage domain will be located 3' to the capture domain (and spatial barcode) and cleavage of said domain results in the release of part of the capture probe including the spatial barcode and the sequence 3' to the spatial barcode from a feature. In some embodiments, cleavage results in partial removal of the cleavage domain. In some embodiments, cleavage results in complete removal of the cleavage domain, particularly when the capture probes are immobilized via their 3' end as the presence of a part of the cleavage domain can interfere with the hybridization of the capture domain and the target nucleic acid and/or its subsequent extension.

In some embodiments, where the capture probe is immobilized to the substrate indirectly, e.g., via a surface probe defined below, the cleavage domain includes one or more mismatch nucleotides, so that the complementary parts of the surface probe and the capture probe are not 100% complementary (for example, the number of mismatched base pairs can one, two, or three base pairs). Such a mismatch is recognized, e.g., by the MutY and T7 endonuclease I enzymes, which results in cleavage of the nucleic acid molecule at the position of the mismatch.

In some embodiments, where the capture probe is immobilized to the feature indirectly, e.g., via a surface probe, the cleavage domain includes a nickase recognition site or sequence. In this respect, nickase enzymes cleave only one strand in a nucleic acid duplex. Nickases are endonucleases which cleave only a single strand of a DNA duplex. Thus, the cleavage domain can include a nickase recognition site close to the 5' end of the surface probe (and/or the 5' end of the capture probe) such that cleavage of the surface probe or capture probe destabilizes the duplex between the surface probe and capture probe thereby releasing the capture probe) from the feature.

Nickase enzymes can also be used in some embodiments where the capture probe is immobilized to the feature directly. For example, the substrate can be contacted with a nucleic acid molecule that hybridizes to the cleavage domain of the capture probe to provide or reconstitute a nickase recognition site, e.g., a cleavage helper probe. Thus, contact with a nickase enzyme will result in cleavage of the cleavage domain thereby releasing the capture probe from the feature. Such cleavage helper probes can also be used to provide or reconstitute cleavage recognition sites for other cleavage enzymes, e.g., restriction enzymes.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is herein incorporated by reference in its entirety. In general, any suitable nickase can be used to bind to a complementary nickase recognition site of a cleavage domain. Following use, the nickase enzyme can be removed from the assay or inactivated following release of the capture probes to prevent unwanted cleavage of the capture probes.

In some embodiments, a cleavage domain for separating spatial barcodes from a feature is absent from the capture probe. For example, a substrate having a capture probe lacking a cleavage domain can be used for spatial analysis (see, e.g., corresponding substrates and probes described Macosko et al., (2015) Cell 161, 1202-1214, the entire contents of which are incorporated herein by reference.

In some embodiments, the region of the capture probe corresponding to the cleavage domain can be used for some other function. For example, an additional region for nucleic acid extension or amplification can be included where the cleavage domain would normally be positioned. In such embodiments, the region can supplement the functional domain or even exist as an additional functional domain. In some embodiments, the cleavage domain is present but its use is optional.

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is barcoded directly via hybridization with capture probes or analyte capture agents hybridized, bound, or associated with either the cell surface, or introduced into the cell, as described above, sequencing can be performed on the intact sample. Alternatively, if the barcoded sample has been separated into fragments, cell groups, or individual cells, as described above, sequencing can be performed on individual fragments, cell groups, or cells. For analytes that have been barcoded via partitioning with beads, as described above, individual analytes (e.g., cells, or cellular contents following lysis of cells) can be extracted from the partitions by breaking the partitions, and then analyzed by sequencing to identify the analytes.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can directly be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule or it can be a molecule derived therefrom. For example, a first and/or second strand DNA molecule can be directly subjected to sequence analysis (e.g. sequencing), i.e., can directly take part in the sequence analysis reaction or process (e.g. the sequencing reaction or sequencing process, or be the molecule which is sequenced or otherwise identified). Alternatively, the barcoded nucleic acid molecule can be subjected to a step of second strand synthesis or amplification before sequence analysis (e.g. sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g. barcoded nucleic acid molecules) can be analyzed (e.g. sequenced). To perform single molecule sequencing, the nucleic acid strand can be modified at the 3' end.

Massively parallel sequencing techniques can be used for sequencing nucleic acids, as described above. In one embodiment, a massively parallel sequencing technique can be based on reversible dye-terminators. As an example, DNA molecules are first attached to primers on, e.g., a glass or silicon substrate, and amplified so that local clonal colonies are formed (bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

As another example, massively parallel pyrosequencing techniques can also be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., Anal. Biochem. 242(1), 84-9 (1996); Ronaghi, Genome Res. 11(1), 3-11 (2001); Ronaghi et al. Science 281 (5375), 363 (1998); and U.S. Pat. Nos. 6,210,891, 6,258,568, and 6,274,320, the entire contents of each of which are incorporated herein by reference.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, sequencing can be performed in-situ. In-situ sequencing methods are particularly useful, for example, when the biological sample remains intact after analytes on the sample surface (e.g., cell surface analytes) or within the sample (e.g., intracellular analytes) have been barcoded. In-situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in-situ sequencing are described, for example, in Mitra et al., (2003) Anal. Biochem. 320, 55-65, and Lee et al., (2014) Science, 343(6177), 1360-1363, the entire contents of each of which are incorporated herein by reference.

In addition, examples of methods and systems for performing in-situ sequencing are described in PCT Patent Application Publication Nos. WO2014/163886, WO2018/045181, WO2018/045186, and in U.S. Pat. Nos. 10,138,509 and 10,179,932, the entire contents of each of which are incorporated herein by reference. Example techniques for in-situ sequencing include, but are not limited to, STARmap (described for example in Wang et al., (2018) Science, 361(6499) 5691), MERFISH (described for example in Moffitt, (2016) Methods in Enzymology, 572, 1-49), and FISSEQ (described for example in U.S. Patent Application Publication No. 2019/0032121). The entire contents of each of the foregoing references are incorporated herein by reference.

For analytes that have been barcoded via partitioning, barcoded nucleic acid molecules or derivatives thereof (e.g., barcoded nucleic acid molecules to which one or more functional sequences have been added, or from which one or more features have been removed) can be pooled and processed together for subsequent analysis such as sequencing on high throughput sequencers. Processing with pooling can be implemented using barcode sequences. For example, barcoded nucleic acid molecules of a given partition can have the same barcode, which is different from barcodes of other spatial partitions. Alternatively, barcoded nucleic acid molecules of different partitions can be processed separately for subsequent analysis (e.g., sequencing).

In some embodiments, where capture probes do not contain a spatial barcode, the spatial barcode can be added after the capture probe captures analytes from a biological sample and before analysis of the analytes. When a spatial barcode is added after an analyte is captured, the barcode can be added after amplification of the analyte (e.g., reverse transcription and polymerase amplification of RNA). In some embodiments, analyte analysis uses direct sequencing of one or more captured analytes, such as direct sequencing of hybridized RNA. In some embodiments, direct sequencing is performed after reverse transcription of hybridized RNA. In some embodiments direct sequencing is performed after amplification of reverse transcription of hybridized RNA.

In some embodiments, direct sequencing of captured RNA is performed by sequencing-by-synthesis (SBS). In some embodiments, a sequencing primer is complementary to a sequence in one or more of the domains of a capture probe (e.g., functional domain). In such embodiments, sequencing-by-synthesis can include reverse transcription and/or amplification in order to generate a template sequence (e.g., functional domain) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid spots are present in a double stranded form these can be processed to provide single stranded nucleic acid templates using methods well known in the art, for example by denaturation, cleavage etc. The sequencing primers which are hybridized to the nucleic acid template and used for primer extension are preferably short oligonucleotides, for example, 15 to 25 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010,251, U.S. Patent App. Pub. No. 2012/0270305, U.S. Patent App. Pub. No. 2013/0260372, and U.S. Patent App. Pub. No. 2013/0079232, the entire contents of each of which are incorporated herein by reference.

In some embodiments, direct sequencing of captured RNA is performed by sequential fluorescence hybridization (e.g., sequencing by hybridization). In some embodiments, a hybridization reaction where RNA is hybridized to a capture probe is performed in situ. In some embodiments, captured RNA is not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of captured RNA using sequential fluorescence hybridization is performed in vitro. In some embodiments, captured RNA is amplified prior to hybridization with a sequencing probe (e.g., reverse transcription to cDNA and amplification of cDNA). In some embodiments, a capture probe containing captured RNA is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged. In some embodiments, a specific sequence of cDNA is resolved from an image of a sequencing reaction. In some embodiments, reverse transcription of captured RNA is performed prior to hybridization to the sequencing probe. In some embodiments, the sequencing probe is designed to target complementary sequences of the coding regions of RNA (e.g., targeting cDNA).

In some embodiments, a captured RNA is directly sequenced using a nanopore-based method. In some embodiments, direct sequencing is performed using nanopore direct RNA sequencing in which captured RNA is translocated through a nanopore. A nanopore current can be recorded and converted into a base sequence. In some embodiments, captured RNA remains attached to a substrate during nanopore sequencing. In some embodiments, captured RNA is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., Trends Biotechnol. 18, 14 7-151 (2000); Deamer et al., Acc. Chem. Res. 35:817-825 (2002); Li et al., Nat. Mater. 2:611-615 (2003); Soni et al., Clin. Chem. 53, 1996-2001 (2007); Healy et al., Nanomed. 2, 459-481 (2007); Cockroft et al., J. Am. Chem. Soc. 130, 818-820 (2008); and in U.S. Pat. No. 7,001,792. The entire contents of each of the foregoing references are incorporated herein by reference.

In some embodiments, direct sequencing of captured RNA is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina® sequencing (e.g., flow cell-based sequencing techniques), sequencing by synthesis using modified nucleotides (such as commercialized in TruSeq™ and HiSeg™ technology by Illumina, Inc., San Diego, CA), HeliScope™ by Helicos Biosciences Corporation, Cambridge, MA, and PacBio RS by Pacific Biosciences of California, Inc., Menlo Park, CA), sequencing by ion detection technologies (Ion Torrent, Inc., South San Francisco, CA), and sequencing of DNA nanoballs (Complete Genomics, Inc., Mountain View, CA).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes.

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181. The entire contents of each of the foregoing references are incorporated herein by reference herein.

In some embodiments, the methods described herein can be used to assess analyte levels and/or expression in a cell or a biological sample over time (e.g., before or after treatment with an agent or different stages of differentiation). In some examples, the methods described herein can be performed on multiple similar biological samples or cells obtained from the subject at a different time points (e.g., before or after treatment with an agent, different stages of differentiation, different stages of disease progression, different ages of the subject, or before or after development of resistance to an agent).

(h) Spatially Resolving Analyte Information

In some embodiments, a lookup table (LUT) can be used to associate one property with another property of a feature. These properties include, e.g., locations, barcodes (e.g., nucleic acid barcode molecules), spatial barcodes, optical labels, molecular tags, and other properties.

In some embodiments, a lookup table can associate the plurality of nucleic acid barcode molecules with the features. In some embodiments, the optical label of a feature can permit associating the feature with the biological particle (e.g., cell or nuclei). The association of the feature with the biological particle can further permit associating a nucleic acid sequence of a nucleic acid molecule of the biological particle to one or more physical properties of the biological particle (e.g., a type of a cell or a location of the cell). For example, based on the relationship between the barcode and the optical label, the optical label can be used to determine the location of a feature, thus associating the location of the feature with the barcode sequence of the feature. Subsequent analysis (e.g., sequencing) can associate the barcode sequence and the analyte from the sample. Accordingly, based on the relationship between the location and the barcode sequence, the location of the biological analyte can be determined (e.g., in a specific type of cell, in a cell at a specific location of the biological sample).

In some embodiments, the feature can have a plurality of nucleic acid barcode molecules attached thereto. The plurality of nucleic acid barcode molecules can include barcode sequences. The plurality of nucleic acid molecules attached to a given feature can have the same barcode sequences, or two or more different barcode sequences. Different barcode sequences can be used to provide improved spatial location accuracy.

As discussed above, analytes obtained from a sample, such as RNA, DNA, peptides, lipids, and proteins, can be further processed. In particular, the contents of individual cells from the sample can be provided with unique spatial barcode sequences such that, upon characterization of the analytes, the analytes can be attributed as having been derived from the same cell. More generally, spatial barcodes can be used to attribute analytes to corresponding spatial locations in the sample. For example, hierarchical spatial positioning of multiple pluralities of spatial barcodes can be used to identify and characterize analytes over a particular spatial region of the sample. In some embodiments, the spatial region corresponds to a particular spatial region of interest previously identified, e.g., a particular structure of cytoarchitecture previously identified. In some embodiments, the spatial region corresponds to a small structure or group of cells that cannot be seen with the naked eye. In some embodiments, a unique molecular identifier can be used to identify and characterize analytes at a single cell level.

The analyte can include a nucleic acid molecule, which can be barcoded with a barcode sequence of a nucleic acid barcode molecule. In some embodiments, the barcoded analyte can be sequenced to obtain a nucleic acid sequence. In some embodiments, the nucleic acid sequence can include genetic information associate with the sample. The nucleic acid sequence can include the barcode sequence, or a complement thereof. The barcode sequence, or a complement thereof, of the nucleic acid sequence can be electronically associated with the property (e.g., color and/or intensity) of the analyte using the LUT to identify the associated feature in an array.

In some embodiments, two- or three-dimensional spatial profiling of one or more analytes present in a biological sample can be performed using a proximity capture reaction, which is a reaction that detects two analytes that are spatially close to each other and/or interacting with each other. For example, a proximity capture reaction can be used to detect sequences of DNA that are close in space to each other, e.g., the DNA sequences can be within the same chromosome, but separated by about 700 bp or less. As another example, a proximity capture reaction can be used to detect protein associations, e.g., two proteins that interact with each other. A proximity capture reaction can be performed in situ to detect two analytes that are spatially close to each other and/or interacting with each other inside a cell. Non-limiting examples of proximity capture reactions include DNA nanoscopy, DNA microscopy, and chromosome conformation capture methods. Chromosome conformation capture (3C) and derivative experimental procedures can be used to estimate the spatial proximity between different genomic elements. Non-limiting examples of chromatin capture methods include chromosome conformation capture (3-C), conformation capture-on-chip (4-C), 5-C, ChIA-PET, Hi-C, targeted chromatin capture (T2C). Examples of such methods are described, for example, in Miele et al., Methods Mol Biol. (2009), 464, Simonis et al., Nat. Genet. (2006), 38(11): 1348-54, Raab et al., Embo. J. (2012), 31(2): 330-350, and Eagen et al., Trends Biochem. Sci. (2018) 43(6): 469-478, the entire contents of each of which is incorporated herein by reference.

In some embodiments, the proximity capture reaction includes proximity ligation. In some embodiments, proximity ligation can include using antibodies with attached DNA strands that can participate in ligation, replication, and sequence decoding reactions. For example, a proximity ligation reaction can include oligonucleotides attached to pairs of antibodies that can be joined by ligation if the antibodies have been brought in proximity to each oligonucleotide, e.g., by binding the same target protein (complex), and the DNA ligation products that form are then used to template PCR amplification, as described for example in Söderberg et al., Methods. (2008), 45(3): 227-32, the entire contents of which are incorporated herein by reference. In some embodiments, proximity ligation can include chromosome conformation capture methods. In some embodiments, the proximity capture reaction is performed on analytes within about 400 nm distance (e.g., about 300 nm, about 200 nm, about 150 nm, about 100 nm, about 50 nm, about 25 nm, about 10 nm, or about 5 nm) from each other. In general, proximity capture reactions can be reversible or irreversible.

III. General Spatial Cell-Based Analytical Methodology

(a) Barcoding Biological Sample

In some embodiments, provided herein are methods and materials for attaching and/or introducing a molecule (e.g., a nucleic acid molecule) having a barcode (e.g., a spatial barcode) to a biological sample (e.g., to a cell in a biological sample) for use in spatial analysis. In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis.

Figure 18:
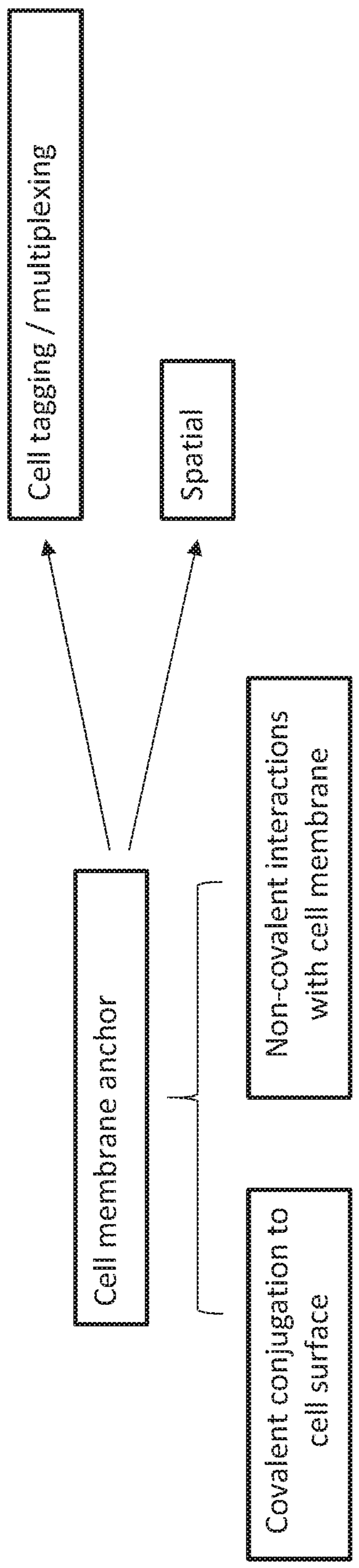
FIG. 18 is a schematic depicting cell tagging using either covalent conjugation of the analyte binding moiety to the cell surface or non-covalent interactions with cell membrane elements.

FIG. 18 is a schematic diagram depicting cell tagging using either covalent conjugation of the analyte binding moiety to the cell surface or non-covalent interactions with cell membrane elements. FIG. 18 lists non-exhaustive examples of a covalent analyte binding moiety/cell surface interactions, including protein targeting, amine conjugation using NHS chemistry, cyanuric chloride, thiol conjugation via maleimide addition, as well as targeting glycoproteins/glycolipids expressed on the cell surface via click chemistry. Non-exhaustive examples of non-covalent interactions with cell membrane elements include lipid modified oligos, biocompatible anchor for cell membrane (oleyl-PEG-NHS), lipid modified positive neutral polymer, and antibody to membrane proteins. The cell tag can be used in combination with an analyte capture agent and cleavable or non-cleavable spatially-barcoded capture probes for spatial and multiplexing applications.

In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis, wherein the plurality of molecules are introduced to the biological sample in an arrayed format. In some embodiments, a plurality of molecules (e.g., a plurality of nucleic acid molecules) having a plurality of barcodes are provided on a substrate (e.g., any of the variety of substrates described herein) in any of the variety of arrayed formats described herein, and the biological sample is contacted with the molecules on the substrate such that the molecules are introduced to the biological sample. In some embodiments, the molecules that are introduced to the biological sample are cleavably attached to the substrate, and are cleaved from the substrate and released to the biological sample when contacted with the biological sample. In some embodiments, the molecules that are introduced to the biological sample are attached to the substrate covalently prior to cleavage. In some embodiments, the molecules that are introduced to the biological sample are non-covalently attached to the substrate (e.g., via hybridization), and are released from the substrate to the biological sample when contacted with the biological sample.

In some embodiments, a plurality of molecules (e.g., a plurality of nucleic acid molecules) having a plurality of barcodes (e.g., a plurality of spatial barcodes) are migrated or transferred from a substrate to cells of a biological sample. In some embodiments, migrating a plurality of molecules from a substrate to cells of a biological sample includes applying a force (e.g., mechanical, centrifugal, or electrophoretic) to the substrate and/or the biological sample to facilitate migration of the plurality of molecules from the substrate to the biological sample.

In some embodiments of any of the spatial analysis methods described herein, physical force is used to facilitate attachment to or introduction of a molecule (e.g., a nucleic acid molecule) having a barcode (e.g., a spatial barcode) into a biological sample (e.g., a cell present in a biological sample). As used herein, "physical force" refers to the use of a physical force to counteract the cell membrane barrier in facilitating intracellular delivery of molecules. Examples of physical force instruments and methods that can be used in accordance with materials and methods described herein include the use of a needle, ballistic DNA, electroporation, sonoporation, photoporation, magnetofection, hydroporation, and combinations thereof.

In some embodiments, biological samples (e.g., cells in a biological sample) can be labelled using cell-tagging agents where the cell-tagging agents facilitate the introduction of the molecules (e.g., nucleic acid molecules) having barcodes (e.g., spatial barcodes) into the biological sample (e.g., into cells in a biological sample). As used herein, the term "cell-tagging agent" refers to a molecule having a moiety that is capable of attaching to the surface of a cell (e.g., thus attaching the barcode to the surface of the cell) and/or penetrating and passing through the cell membrane (e.g., thus introducing the barcode to the interior of the cell). In some embodiments, a cell-tagging agent includes a barcode (e.g., a spatial barcode). The barcode of a barcoded cell-tagging agent can be any of the variety of barcodes described herein. In some embodiments, the barcode of a barcoded cell-tagging agent is a spatial barcode. In some embodiments, a cell-tagging agent comprises a nucleic acid molecule that includes the barcode (e.g., the spatial barcode). In some embodiments, the barcode of a barcoded cell-tagging agent identifies the associated molecule, where each spatial barcode is associated with a particular molecule. In some embodiments, one or more molecules are applied to a sample. In some embodiments, a nucleic acid molecule that includes the barcode is covalently attached to the cell-tagging agent. In some embodiments, a nucleic acid molecule that includes the barcode is non-covalently attached to the cell-tagging agent. A non-limiting example of non-covalent attachment includes hybridizing the nucleic acid molecule that includes the barcode to a nucleic acid molecule on the cell-tagging agent (which nucleic acid molecule on the cell-tagging agent can be bound to the cell-tagging agent covalently or non-covalently). In some embodiments, a nucleic acid molecule that is attached to a cell-tagging agent that includes a barcode (e.g., a spatial barcode) also includes one or more additional domains. Such additional domains include, without limitation, a PCR handle, a sequencing priming site, a domain for hybridizing to another nucleic acid molecule, and combinations thereof.

In some embodiments, a cell-tagging agent attaches to the surface of a cell. When the cell-tagging agent includes a barcode (e.g., a nucleic acid that includes a spatial barcode), the barcode is also attached to the surface of the cell. In some embodiments of any of the spatial analysis methods described herein, a cell-tagging agent attaches covalently to the cell surface to facilitate introduction of the spatial profiling reagents. In some embodiments of any of the spatial analysis methods described herein, a cell-tagging agent attaches non-covalently to the cell surface to facilitate introduction of the spatial profiling reagents.

In some embodiments, once a cell or cells in a biological sample is spatially tagged with a cell-tagging agent(s), spatial analysis of analytes present in the biological sample is performed. In some embodiments, such spatial analysis includes dissociating the spatially-tagged cells of the biological sample (or a subset of the spatially-tagged cells of the biological sample) and analyzing analytes present in those cells on a cell-by-cell basis. Any of a variety of methods for analyzing analytes present in cells on a cell-by-cell basis can be used. Non-limiting examples include any of the variety of methods described herein and methods described in PCT Application Publication No. WO 2019/113533A1, the content of which is incorporated herein by reference in its entirety. For example, the spatially-tagged cells can be encapsulated with beads comprising one or more nucleic acid molecules having a barcode (e.g., a cellular barcode) (e.g., an emulsion). The nucleic acid present on the bead can have a domain that hybridizes to a domain on a nucleic acid present on the tagged cell (e.g., a domain on a nucleic acid that is attached to a cell-tagging agent), thus linking the spatial barcode of the cell to the cellular barcode of the bead. Once the spatial barcode of the cell and the cellular barcode of the bead are linked, analytes present in the cell can be analyzed using capture probes (e.g., capture probes present on the bead). This allows the nucleic acids produced (using these methods) from specific cells to be amplified and sequenced separately (e.g. within separate partitions or droplets).

In some embodiments, once a cell or cells in a biological sample is spatially tagged with a cell-tagging agent(s), spatial analysis of analytes present in the biological sample is performed in which the cells of the biological sample are not dissociated into single cells. In such embodiments, various methods of spatial analysis such as any of those provided herein can be employed. For example, once a cell or cells in a biological sample is spatially tagged with a cell-tagging agent(s), analytes in the cells can be captured and assayed. In some embodiments, cell-tagging agents include both a spatial barcode and a capture domain that can be used to capture analytes present in a cell. For example, cell-tagging agents that include both a spatial barcode and a capture domain can be introduced to cells of the biological sample in a way such that locations of the cell-tagging agents are known (or can be determined after introducing them to the cells). One non-limiting example of introducing cell-tagging agents to a biological sample is to provide the cell-tagging agents in an arrayed format (e.g., arrayed on a substrate such as any of the variety of substrates and arrays provided herein), where the positions of the cell-tagging agents on the array are known at the time of introduction (or can be determined after introduction). The cells can be permeabilized as necessary (e.g., using permeabilization agents and methods described herein), reagents for analyte analysis can be provided to the cells (e.g., a reverse transcriptase, a polymerase, nucleotides, etc., in the case where the analyte is a nucleic acid that binds to the capture probe), and the analytes can be assayed. In some embodiments, the assayed analytes (and/or copies thereof) can be released from the substrate and analyzed. In some embodiments, the assayed analytes (and/or copies thereof) are assayed in situ.

Introducing a Cell-Tagging Agent to the Surface of a Cell

Non-limiting examples of cell-tagging agents and systems that attach to the surface of a cell (e.g., thus introducing the cell-tagging agent and any barcode attached thereto to the exterior of the cell) that can be used in accordance with materials and methods provided herein for spatially profiling an analyte or analytes in a biological sample include: lipid tagged primers/lipophilic-tagged moieties, positive or neutral oligo-conjugated polymers, antibody-tagged primers, streptavidin-conjugated oligonucleotides, dye-tagged oligonucleotides, click-chemistry, receptor-ligand systems, covalent binding systems via amine or thiol functionalities, and combinations thereof.

Lipid Tagged Primers/Lipophilic-Tagged Moieties

In some embodiments of any of the spatial profiling methods described herein, a molecule (e.g., a nucleic acid molecule) having a barcode (e.g., a spatial barcode) is coupled to a lipophilic molecule. In some embodiments, the lipophilic molecule enables the delivery of the molecule to the cell membrane or the nuclear membrane. In some embodiments, a molecule (e.g., a nucleic acid molecule) having a barcode (e.g., a spatial barcode) coupled to a lipophilic molecule can associate with and/or insert into lipid membranes such as cell membranes and nuclear membranes. In some cases, the insertion can be reversible. In some cases, the association between the lipophilic molecule and the cell may be such that the cell retains the lipophilic molecule (e.g., and associated components, such as nucleic acid barcode molecules) during subsequent processing (e.g., partitioning, cell permeabilization, amplification, pooling, etc.). In some embodiments, a molecule (e.g., a nucleic acid molecule) having a barcode (e.g., a spatial barcode) coupled to a lipophilic molecule may enter into the intracellular space and/or a cell nucleus.

Non-limiting examples of lipophilic molecules that can be used in embodiments described herein include sterol lipids such as cholesterol, tocopherol, steryl, palmitate, lignoceric acid, and derivatives thereof. In some embodiments, the lipophilic molecules are neutral lipids that are conjugated to hydrophobic moieties (e.g., cholesterol, squalene, or fatty acids) (See Raouane et al. Bioconjugate Chem., 23(6):1091-1104 (2012) which is herein incorporated by reference in its entirety). In some embodiments, a molecule (e.g., a nucleic acid molecule) having a barcode (e.g., a spatial barcode) may be attached to the lipophilic moiety via a linker, such as a tetra-ethylene glycol (TEG) linker. Other exemplary linkers include, but are not limited to, Amino Linker C6, Amino Linker C12, Spacer C3, Spacer C6, Spacer C12, Spacer 9, and Spacer 18. In some embodiments, a molecule (e.g., a nucleic acid molecule) having a barcode (e.g., a spatial barcode) is indirectly coupled (e.g., via hybridization or ligand-ligand interactions, such as biotin-streptavidin) to a lipophilic molecule. Other lipophilic molecules that may be used in accordance with methods provided herein include amphiphilic molecules wherein the headgroup (e.g., charge, aliphatic content, and/or aromatic content) and/or fatty acid chain length (e.g., C12, C14, C16, or C18) can be varied. For instance, fatty acid side chains (e.g., C12, C14, C16, or C18) can be coupled to glycerol or glycerol derivatives (e.g., 3-t-butyldiphenylsilylglycerol), which can also comprise, e.g., a cationic head group. In some embodiments, a molecule (e.g., a nucleic acid molecule) having a barcode (e.g., a spatial barcode) disclosed herein can then be coupled (either directly or indirectly) to these amphiphilic molecules. In some embodiments, a molecule (e.g., a nucleic acid molecule) having a barcode (e.g., a spatial barcode) coupled to an amphiphilic molecule may associate with and/or insert into a membrane (e.g., a cell, cell bead, or nuclear membrane). In some cases, an amphiphilic or lipophilic moiety may cross a cell membrane and provide a molecule (e.g., a nucleic acid molecule) having a barcode (e.g., a spatial barcode) to an internal region of a cell and/or cell bead.

In some embodiments, wherein the molecule (e.g., with a nucleic acid sequence) has an amino group within the molecule, the molecule (e.g., a nucleic acid molecule) having a barcode (e.g., a spatial barcode) and an amino group can be coupled to an amine-reactive lipophilic molecule. For example, a molecule (e.g., a nucleic acid molecule) having a barcode (e.g., a spatial barcode) and an amino group can be conjugated to DSPE-PEG(2000)-cyanuric chloride (1,2-distearoyl-sn-glycero-3-phosphoethanolamine-N-[cyanur(polyethylene glycol)-2000]).

In some embodiments, a cell tagging agent can attach to a surface of a cell through a combination of lipophilic and covalent attachment. For example, a cell tagging agent can include an oligonucleotide attached to a lipid to target the oligonucleotide to a cell membrane, and an amine group that can be covalently linked to a cell surface protein(s) via any number of chemistries described herein. In these embodiments, the lipid can increase the surface concentration of the oligonucleotide and can promote the covalent reaction.

Positive or Neutral Oligo-Conjugated Polymers

In some embodiments of any of the spatial analysis methods described herein, a molecule (e.g., a nucleic acid molecule) having a barcode (e.g., a spatial barcode) can be coupled to a glycol chitosan derivative. The glycol chitosan derivative (e.g., glycol chitosan-cholesterol) can serve as a hydrophobic anchor (see Wang et al. J. Mater. Chem. B., 30:6165 (2015), which is herein incorporated by reference in its entirety). Non-limiting examples of chitosan derivatives that can be coupled to a molecule (e.g., a nucleic acid molecule) having a barcode (e.g., a spatial barcode) can be found in Cheung et al., Marine Drugs, 13(8): 5156-5186 (2015), which is herein incorporated by reference in its entirety.

Antibody-Tagged Primers

In some embodiments of any of the spatial analysis methods described herein, a molecule (e.g., a nucleic acid molecule) having a barcode (e.g., a spatial barcode) can be coupled to an antibody or antigen binding fragment thereof in a manner that facilitates attachment of the molecule (e.g., a nucleic acid molecule) having a barcode (e.g., a spatial barcode) to the surface of a cell. In some embodiments, facilitating attachment to the cell surface facilitates introduction of the molecule (e.g., a nucleic acid molecule) having a barcode (e.g., a spatial barcode) into the cell. In some embodiments, the molecule (e.g., a nucleic acid molecule) having a barcode (e.g., a spatial barcode) can be coupled to an antibody that is directed to an antigen that is present on the surface of a cell. In some embodiments, the molecule (e.g., a nucleic acid molecule) having a barcode (e.g., a spatial barcode) can be coupled to an antibody that is directed to an antigen that is present on the surface of a plurality of cells (e.g., a plurality of cells in a biological sample). In some embodiments, the molecule (e.g., a nucleic acid molecule) having a barcode (e.g., a spatial barcode) can be coupled to an antibody that is directed to an antigen that is present on the surface of all or substantially all the cells present in a biological sample. Any of the exemplary methods described herein of attaching a molecule (e.g., a nucleic acid molecule) having a barcode (e.g., a spatial barcode) to another molecule (e.g., a cell-tagging agent) can be used.

Streptavidin-Conjugated Oligonucleotides

In some embodiments of any of the spatial analysis methods described herein, a molecule (e.g., a nucleic acid molecule) having a barcode (e.g., a spatial barcode) can attach to the surface of a cell using biotin-streptavidin. In some embodiments, primary amines in the side chain of lysine residues of cell surface polypeptides are labelled with NETS-activated biotin reagents. For example, the N-terminus of a polypeptide can react with NETS-activated biotin reagents to form stable amide bonds. In some embodiments, cell-tagging agents include molecules (e.g., a nucleic acid molecule) having barcodes (e.g., a spatial barcode) conjugated to streptavidin. In some cases, streptavidin can be conjugated to the molecule (e.g., a nucleic acid molecule) having a barcode (e.g., a spatial barcode) using click chemistry (e.g., maleimide modification) as described herein. In some embodiments, a cell containing NHS-activated biotin incorporated into lysine side chains of a cell surface protein forms a non-covalent bond with the streptavidin conjugated to the molecule (e.g., a nucleic acid molecule) having a barcode (e.g., a spatial barcode). In some embodiments, the molecule (e.g., a nucleic acid molecule) having a barcode (e.g., a spatial barcode) conjugated to streptavidin is itself part of a cell-tagging agent.

Dye-Tagged Oligonucleotides

In some embodiments of any of the spatial analysis methods described herein, a molecule (e.g., a nucleic acid molecule) having a barcode (e.g., a spatial barcode) is directly linked to a fluorescent tag. In some embodiments, the physical properties of the fluorescent tags (e.g., hydrophobic properties) can overcome the hydrophilic nature of the molecule (e.g., a nucleic acid molecule) having a barcode (e.g., a spatial barcode). For example, in some embodiments, wherein the molecule is a nucleic acid molecule, a fluorescent tag (e.g., BODIPY, Cy3, Atto 647N, and Rhodamine Red C2) can be coupled to a 5' end of the nucleic acid molecule having a barcode (e.g., a spatial barcode). In some embodiments, wherein the molecule is a nucleic acid molecule, any fluorescent tag having hydrophobic properties can be coupled to the nucleic acid molecule having a barcode (e.g., a spatial barcode) in a manner that overcomes the hydrophilic nature of the nucleic acid molecule. Non-limiting examples of fluorescent tags with hydrophobic properties include BODIPY, Cy3, Atto 647N, and Rhodamine Red C2.

Click-Chemistry

In some embodiments of any of the spatial analysis methods described herein, molecules (e.g., a nucleic acid molecule) having barcodes (e.g., a spatial barcode) are coupled to click-chemistry moieties. As used herein, the term "click chemistry," generally refers to reactions that are modular, wide in scope, give high yields, generate only inoffensive byproducts, such as those that can be removed by nonchromatographic methods, and are stereospecific (but not necessarily enantioselective) (see, e.g., Angew. Chem. Int. Ed., 2001, 40(11):2004-2021, which is incorporated herein by reference in its entirety). In some cases, click chemistry can describe pairs of functional groups that can selectively react with each other in mild, aqueous conditions.

An example of a click chemistry reaction is the Huisgen 1,3-dipolar cycloaddition of an azide and an alkyne, i.e., copper-catalysed reaction of an azide with an alkyne to form the 5-membered heteroatom ring 1,2,3-triazole. The reaction is also known as a Cu(I)-Catalyzed Azide-Alkyne Cycloaddition (CuAAC), a Cu(I) click chemistry or a Cu+ click chemistry. Catalysts for the click chemistry include, but are not limited to, Cu(I) salts, or Cu(I) salts made in situ by reducing Cu(II) reagents to Cu(I) reagents with a reducing reagent (Pharm Res. 2008, 25(10): 2216-2230, which is incorporated herein by reference in its entirety). Known Cu(II) reagents for the click chemistry can include, but are not limited to, the Cu(II)-(TBTA) complex and the Cu(II) (THPTA) complex. TBTA, which is tris-[(1-benzyl-1H-1,2,3-triazol-4-yl)methyl]amine, also known as tris-(benzyltriazolylmethyl)amine, can be a stabilizing ligand for Cu(I) salts. THPTA, which is tris-(hydroxypropyltriazolylmethyl) amine, is another example of a stabilizing agent for Cu(I). Other conditions can also be used to construct the 1,2,3-triazole ring from an azide and an alkyne using copper-free click chemistry, such as the Strain-promoted Azide-Alkyne Click chemistry reaction (SPAAC) (see, e.g., Chem. Commun., 2011, 47:6257-6259 and Nature, 2015, 519(7544): 486-90, each of which is incorporated herein by reference in its entirety).

Receptor-Ligand Systems

In some embodiments of any of the spatial analysis methods described herein, a molecule (e.g., a nucleic acid molecule) having a barcode (e.g., a spatial barcode) can be coupled to a ligand, wherein the ligand is part of a receptor-ligand interaction on the surface of a cell. For example, a molecule (e.g., a nucleic acid molecule) having a barcode (e.g., a spatial barcode) can be coupled to a ligand that interacts selectively with a cell surface receptor thereby targeting the molecule (e.g., a nucleic acid molecule) having a barcode (e.g., a spatial barcode) to a specific cell. Non-limiting examples of receptor-ligand systems that can be used include integrin receptor-ligand interactions, GPCR receptor-ligand interactions, RTK receptor-ligand interactions, and TLR-ligand interactions (see Juliano, Nucleic Acids Res., 44(14): 6518-6548 (2016), which is incorporated herein by reference in its entirety). Any of the methods described herein for attaching a molecule (e.g., a nucleic acid molecule) having a barcode (e.g., a spatial barcode) to a ligand (e.g., any of the methods described herein relating to attaching a molecule (e.g., a nucleic acid molecule) having a barcode (e.g., a spatial barcode) to an antibody) can be used.

Covalent Binding Systems Via Amine or Thiol Functionalities

In some embodiments of any of the spatial analysis methods described herein, a molecule (e.g., a nucleic acid molecule) having a barcode (e.g., a spatial barcode) can incorporate reactive functional groups at sites within the molecule (e.g., with a nucleic acid sequence). In such cases, the reactive functional groups can facilitate conjugation to ligands and/or surfaces. In some embodiments, a molecule (e.g., a nucleic acid molecule) having a barcode (e.g., a spatial barcode) can include thiol modifiers that are designed to react with a broad array of activated accepting groups (e.g., maleimide and gold microspheres). For example, a molecule (e.g., a nucleic acid molecule) having a barcode (e.g., a spatial barcode) having thiol modifiers can interact with a maleimide-conjugated peptide thereby resulting in labelling of the peptide. In some embodiments, maleimide-conjugated peptides are present on the surface of a cell whereupon interaction with the thiol-modified molecule (e.g., a nucleic acid molecule) having a barcode (e.g., a spatial barcode), the molecule (e.g., a nucleic acid molecule) having a barcode (e.g., a spatial barcode) is coupled to the surface of the cell. Non-limiting examples of thiol modifiers include: 5' thiol modifier C6 S-S, 3' thiol modifier C3 S-S, dithiol, 3'thiol modifier oxa 6-S-S, and dithiol serinol.

In some embodiments of any of the spatial analysis methods described herein, a molecule (e.g., a nucleic acid molecule) having a barcode (e.g., a spatial barcode) can include amine modifiers, e.g., amine modifiers that are designed to attach to another molecule in the presence of an acylating agent. In some embodiments, a molecule (e.g., a nucleic acid molecule) having a barcode (e.g., a spatial barcode) can include amine modifiers that are designed to attach to a broad array of linkage groups (e.g., carbonyl amide, thiourea, sulfonamide, and carboxamide). For example, a molecule (e.g., a nucleic acid molecule) having a barcode (e.g., a spatial barcode) and an amine modifier can interact with a sulfonamide-conjugated peptide thereby resulting in labelling of the peptide. In some embodiments, sulfonamide-conjugated peptides are present on the surface of a cell whereupon interaction with the amine-modified molecule (e.g., a nucleic acid molecule) having a barcode (e.g., a spatial barcode), the molecule (e.g., a nucleic acid molecule) having a barcode (e.g., a spatial barcode) is coupled to the surface of the cell. Non-limiting example of amine modifiers include: DMS(O)MT-Amino-Modifier-C6, Amino-Modifier-C3-TFA, Amino-Modifier-C12, Amino-Modifier-C6-TFA, Amino-dT, Amino-Modifier-5, Amino-Modifier-C2-dT, Amino-Modifier-C6-dT, and 3'-Amino-Modifier-C7.

As another example, a molecule (e.g., a nucleic acid molecule) having a barcode (e.g., a spatial barcode) can incorporate reactive functional groups at sites within the molecule (e.g., with a nucleic acid sequence) such as N-hydroxysuccinimide (NHS). In some embodiments, amines (e.g., amine-containing peptides) are present on the surface of a cell whereupon interaction with the NETS-modified molecule (e.g., a nucleic acid molecule) having a barcode (e.g., a spatial barcode), the molecule (e.g., a nucleic acid molecule) having a barcode (e.g., a spatial barcode) is coupled to the surface of the cell. In some embodiments, a molecule (e.g., a nucleic acid molecule) having a barcode (e.g., a spatial barcode) is reacted with a bifunctional NETS linker to form an NETS-modified molecule (e.g., a nucleic acid molecule) having a barcode (e.g., a spatial barcode).

In some embodiments, a molecule (e.g., a nucleic acid molecule) having a barcode (e.g., a spatial barcode) can be coupled to a biocompatible anchor for cell membrane (BAM). For example, a BAM can include molecules that comprise an oleyl group and PEG. The oleyl group can facilitate anchoring the molecule (e.g., a nucleic acid molecule) having a barcode (e.g., a spatial barcode) to a cell, and the PEG can increase water solubility. In some embodiments, oleyl-PEG-NHS can be coupled to a molecule (e.g., a nucleic acid molecule) having a barcode (e.g., a spatial barcode) using NHS chemistry.

Azide-Based Systems

In some embodiments, wherein the molecule (e.g., with a nucleic acid sequence) incorporates reactive functional groups at sites within the molecule, a molecule (e.g., a nucleic acid molecule) having a barcode (e.g., a spatial barcode) can be coupled to an azide group on a cell surface. In some embodiments, the reactive functional group is an alkynyl group. In some embodiments, click chemistry as described herein can be used to attach the alkynyl-modified molecule (e.g., a nucleic acid molecule) having a barcode (e.g., a spatial barcode) to an azide group on the cell surface. An azide group can be attached to the cell surface through a variety of methods. For example, NHS chemistry can be used to attach an azide group to the cell surface. In some embodiments, N-azidoacetylmannosamine-tetraacylated (Ac4ManNAz), which contains an azide group, can react with sialic acid on the surface of a cell to attach azide to the cell surface. In some embodiments, azide is attached to the cell surface by bio-orthogonal expression of azide.

Lectin-Based Systems

In some embodiments of any of the spatial analysis methods described herein, a molecule (e.g., a nucleic acid molecule) having a barcode (e.g., a spatial barcode) can be coupled to a lectin that facilitates attachment of the molecule (e.g., a nucleic acid molecule) having a barcode (e.g., a spatial barcode) to a cell surface. Lectin can bind to glycans, e.g., glycans on the surface of cells. In some embodiments, the molecule (e.g., a nucleic acid molecule) having a barcode (e.g., a spatial barcode) has an incorporated reactive functional group such as an azide group. In some embodiments, the molecule (e.g., a nucleic acid molecule) having a barcode (e.g., a spatial barcode) and an azide group is reacted with a modified lectin, e.g., a lectin modified using NHS chemistry to introduce an azide reactive group. In some embodiments, a live cell is labelled with a lectin-modified molecule (e.g., a nucleic acid molecule) having a barcode (e.g., a spatial barcode). In some embodiments, a fixed cell is labelled with a lectin-modified molecule (e.g., a nucleic acid molecule) having a barcode (e.g., a spatial barcode). In some embodiments, a permeabilized cell is labelled with a lectin-modified molecule (e.g., a nucleic acid molecule) having a barcode (e.g., a spatial barcode). In some embodiments, organelles in the secretory pathway can be labelled with a lectin-modified molecule (e.g., a nucleic acid molecule) having a barcode (e.g., a spatial barcode).

(b) Introducing a Cell-Tagging Agent to the Interior of a Cell

Non-limiting examples of cell-tagging agents and systems that penetrate and/or pass through the cell membrane (e.g., thus introducing the cell-tagging agent and any barcode attached thereto to the interior of the cell) that can be used in accordance with materials and methods provided herein for spatially profiling an analyte or analytes in a biological sample include: a cell-penetrating agent (e.g., a cell-penetrating peptide), a nanoparticle, a liposome, a polymersome, a peptide-based chemical vector, electroporation, sonoporation, lentiviral vectors, retroviral vectors, and combinations thereof.

Figure 19:
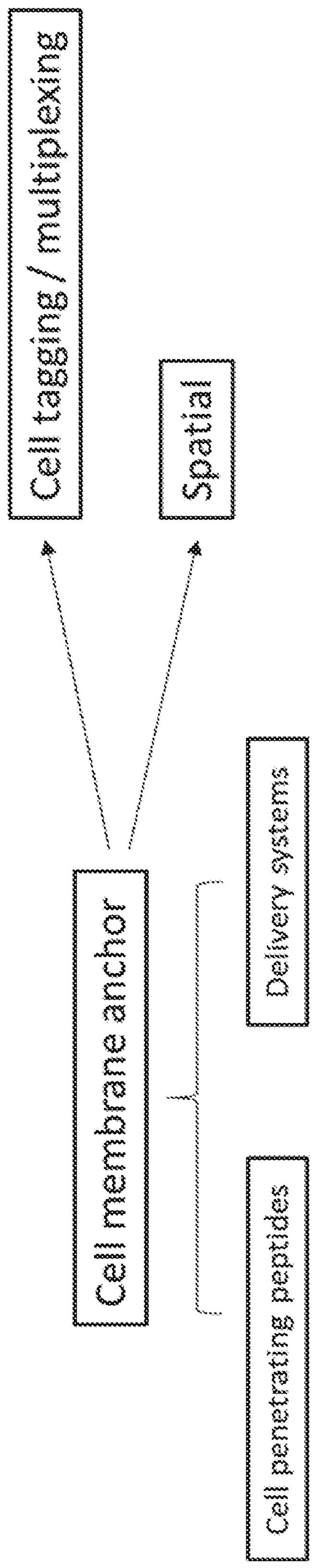
FIG. 19 is a schematic depicting cell tagging using either cell-penetrating peptides or delivery systems.

FIG. 19 is a schematic showing an exemplary cell tagging method. Non-exhaustive examples of oligo delivery vehicles may include a cell penetrating peptide or a nanoparticle. Non-exhaustive examples of the delivery systems can include lipid-based polymeric and metallic nanoparticles or oligos that can be conjugated or encapsulated within the delivery system. The cell tag can be used in combination with a capture agent barcode domain and a cleavable or non-cleavable spatially barcoded capture probes for spatial and multiplexing applications.

Cell-Penetrating Agent

In some embodiments of any of the spatial profiling methods described herein, capture of a biological analyte by a molecule (e.g., a nucleic acid molecule) having a barcode (e.g., a spatial barcode) and a capture domain is facilitated by a cell-penetrating agent. In some embodiments, a molecule (e.g., a nucleic acid molecule) having a barcode (e.g., a spatial barcode) and a capture domain is coupled to a cell-penetrating agent, and the cell-penetrating agent allows the molecule to interact with an analyte inside the cell. A "cell-penetrating agent" as used herein refers to an agent capable of facilitating the introduction of a molecule (e.g., a nucleic acid molecule) having a barcode (e.g., a spatial barcode) and a capture domain into a cell of a biological sample (see, e.g., Lovatt et al. Nat Methods. 2014 February; 11(2):190-6, which is incorporated herein by reference in its entirety). In some embodiments, a cell-penetrating agent is a cell-penetrating peptide. A "cell-penetrating peptide" as used herein refers to a peptide (e.g., a short peptide, e.g., a peptide not usually exceeding 30 residues) that has the capacity to cross cellular membranes.

In some embodiments of any of the spatial profiling methods described herein, a cell-penetrating peptide coupled to a molecule (e.g., a nucleic acid molecule) having a barcode (e.g., a spatial barcode) and a capture domain can cross a cellular membrane using an energy dependent or an energy independent mechanism. For example, a cell-penetrating peptide can cross a cellular membrane through direct translocation through physical perturbation of the plasma membrane, endocytosis, adaptive translocation, pore-formation, electroporation-like permeabilization, and/or entry at microdomain boundaries. Non-limiting examples of a cell-penetrating peptide include: penetratin, tat peptide, pVEC, transportan, MPG, Pep-1, a polyarginine peptide, MAP, R6W3, (D-Arg)9, Cys(Npys)-(D-Arg)9, Anti-BetaGamma (MPS-Phosducin-like protein C terminus), Cys(Npys) antennapedia, Cys(Npys)-(Arg)9, Cys(Npys)-TAT (47-57), HIV-1 Tat (48-60), KALA, mastoparan, penetratin-Arg, pep-1-cysteamine, TAT(47-57)GGG-Cys(Npys), Tat-NR2Bct, transdermal peptide, SynB1, SynB3, PTD-4, PTD-5, FHV Coat-(35-49), BMV Gag-(7-25), HTLV-II Rex-(4-16), R9-tat, SBP, FBP, MPG, MPG(ANLS), Pep-2, MTS, plsl, and a polylysine peptide (see, e.g., Bechara et al. FEBS Lett. 2013 Jun. 19; 587(12):1693-702, which is incorporated by reference herein in its entirety).

Nanoparticles

In some embodiments of any of the spatial profiling methods described herein, capture of a biological analyte by a molecule (e.g., a nucleic acid molecule) having a barcode (e.g., a spatial barcode) and a capture domain is facilitated by an inorganic particle (e.g., a nanoparticle). In some embodiments, a molecule (e.g., a nucleic acid molecule) having a barcode (e.g., a spatial barcode) and a capture domain is coupled to an inorganic particle (e.g., a nanoparticle), and the molecule (e.g., a nucleic acid molecule) having a barcode (e.g., a spatial barcode) and a capture domain uses the nanoparticle to get access to analytes inside the cell. Non-limiting examples of nanoparticles that can be used in embodiments herein to deliver a molecule (e.g., a nucleic acid molecule) having a barcode (e.g., a spatial barcode) and a capture domain into a cell and/or cell bead include inorganic nanoparticles prepared from metals, (e.g., iron, gold, and silver), inorganic salts, and ceramics (e.g., phosphate or carbonate salts of calcium, magnesium, or silicon). The surface of a nanoparticle can be coated to facilitate binding of the molecule (e.g., a nucleic acid molecule) having a barcode (e.g., a spatial barcode) and a capture domain, or the surface can be chemically modified to facilitate attachment of the molecule (e.g., a nucleic acid molecule) having a barcode (e.g., a spatial barcode) and a capture domain. Magnetic nanoparticles (e.g., supermagnetic iron oxide), fullerenes (e.g., soluble carbon molecules), carbon nanotubes (e.g., cylindrical fullerenes), quantum dots and supramolecular systems can also be used.

Liposomes

In some embodiments of any of the spatial analysis methods described herein, capture of a biological analyte by a molecule (e.g., a nucleic acid molecule) having a barcode (e.g., a spatial barcode) and a capture domain is facilitated by a liposome. Various types of lipids, including cationic lipids, can be used in liposome delivery. In some cases, a molecule (e.g., a nucleic acid molecule) having a barcode (e.g., a spatial barcode) and a capture domain is delivered to a cell via a lipid nano-emulsion. A lipid emulsion refers to a dispersion of one immiscible liquid in another stabilized by emulsifying agent. Labeling cells can comprise use of a solid lipid nanoparticle.

Polymersomes

In some embodiments of any of the spatial analysis methods described herein, capture of a biological analyte by a molecule (e.g., a nucleic acid molecule) having a barcode (e.g., a spatial barcode) and a capture domain is facilitated by a polymersome. In some embodiments, a molecule (e.g., a nucleic acid molecule) having a barcode (e.g., a spatial barcode) and a capture domain is contained in the polymersome, and the molecule (e.g., a nucleic acid molecule) having a barcode (e.g., a spatial barcode) and a capture domain uses the polymersome to get access to analytes inside the cell. A "polymersome" as referred to herein is an artificial vesicle. For example, a polymersome can be a vesicle similar to a liposome, but the membrane comprises amphiphilic synthetic block copolymers (see, e.g., Rideau et al. Chem. Soc. Rev., 2018, 47, 8572-8610, which is incorporated by reference herein in its entirety). In some embodiments, polymersomes comprise di-(AB) or tri-block copolymers (e.g., ABA or ABC), where A and C are a hydrophilic block and B is a hydrophobic block. In some embodiments, a polymersome comprises poly(butadiene)-b-poly(ethylene oxide), poly(ethyl ethylene)-b-poly(ethylene oxide), polystyrene-b-poly(ethylene oxide), poly(2-vinylpyridine)-b-poly(ethylene oxide), polydimethylsiloxane-b-poly(ethylene oxide), polydimethylsiloxane-g-poly(ethylene oxide), polycaprolactone-b-poly(ethylene oxide), polyisobutylene-b-poly(ethylene oxide), polystyrene-b-polyacrylic acid, polydimethylsiloxane-b-poly-2-methyl-2-oxazoline, or a combination thereof (wherein b=block and g=grafted).

Peptide-Based Chemical Vectors

In some embodiments of any of the spatial analysis methods described herein, capture of a biological analyte by a molecule (e.g., a nucleic acid molecule) having a barcode (e.g., a spatial barcode) and a capture domain is facilitated by a peptide-based chemical vector, e.g., a cationic peptide-based chemical vector. Cationic peptides can be rich in basic residues like lysine and/or arginine. In some embodiments of any of the spatial analysis methods described herein, capture of a biological analyte by a molecule (e.g., a nucleic acid molecule) having a barcode (e.g., a spatial barcode) and a capture domain is facilitated by a polymer-based chemical vector. Cationic polymers, when mixed with a molecule (e.g., a nucleic acid molecule) having a barcode (e.g., a spatial barcode) and a capture domain, can form nanosized complexes called polyplexes. Polymer based vectors can comprise natural proteins, peptides and/or polysaccharides. Polymer based vectors can comprise synthetic polymers. In some embodiments, a polymer-based vector comprises polyethylenimine (PEI). PEI can condense DNA into positively-charged particles, which bind to anionic cell surface residues and are brought into the cell via endocytosis. In some embodiments, a polymer-based chemical vector comprises poly(L)-lysine (PLL), poly (DL-lactic acid) (PLA), poly (DL-lactide-co-glycoside) (PLGA), polyornithine, polyarginine, histones, protamines, or a combination thereof. Polymer-based vectors can comprise a mixture of polymers, for example, PEG and PLL. Other non-limiting examples of polymers include dendrimers, chitosans, synthetic amino derivatives of dextran, and cationic acrylic polymers.

Electroporation

In some embodiments of any of the spatial analysis methods described herein, capture of a biological analyte by a molecule (e.g., a nucleic acid molecule) having a barcode (e.g., a spatial barcode) and a capture domain is facilitated by electroporation. With electroporation, a biological analyte by a molecule (e.g., a nucleic acid molecule) having a barcode (e.g., a spatial barcode) and a capture domain can enter a cell through one or more pores in the cellular membrane formed by applied electricity. The pore of the membrane can be reversible based on the applied field strength and pulse duration.

Sonoporation

In some embodiments of any of the spatial analysis methods described herein, capture of a biological analyte by a molecule (e.g., a nucleic acid molecule) having a barcode (e.g., a spatial barcode) and a capture domain is facilitated by sonoporation. Cell membranes can be temporarily permeabilized using sound waves, allowing cellular uptake of a biological analyte by a molecule (e.g., a nucleic acid molecule) having a barcode (e.g., a spatial barcode) and a capture domain.

Lentiviral Vectors and Retroviral Vectors

In some embodiments of any of the spatial analysis methods described herein, capture of a biological analyte by a molecule (e.g., a nucleic acid molecule) having a barcode (e.g., a spatial barcode) and a capture domain is facilitated by vectors. For example, a vector as described herein can be an expression vector where the expression vector includes a promoter sequence operably linked to the sequence encoding the molecule (e.g., a nucleic acid molecule) having a barcode (e.g., a spatial barcode) and a capture domain. Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, for example, include sufficient cis-acting elements for expression where other elements for expression can be supplied by the host mammalian cell or in an in vitro expression system. Skilled practitioners will be capable of selecting suitable vectors and mammalian cells for introducing any of spatial profiling reagents described herein.

Other Methods and Cell-Tagging Agents for Intracellular Introduction of a Molecule In some embodiments of any of the spatial analysis methods described herein, capture of a biological analyte by a molecule (e.g., a nucleic acid molecule) having a barcode (e.g., a spatial barcode) and a capture domain is facilitated by the use of a needle, for example for injection (e.g., microinjection), particle bombardment, photoporation, magnetofection, and/or hydroporation. For example, with particle bombardment, a molecule (e.g., a nucleic acid molecule) having a barcode (e.g., a spatial barcode) and a capture domain can be coated with heavy metal particles and delivered to a cell at a high speed. In photoporation, a transient pore in a cell membrane can be generated using a laser pulse, allowing cellular uptake of a molecule (e.g., a nucleic acid molecule) having a barcode (e.g., a spatial barcode) and a capture domain. In magnetofection, a molecule (e.g., a nucleic acid molecule) having a barcode (e.g., a spatial barcode) and a capture domain can be coupled to a magnetic particle (e.g., magnetic nanoparticle, nanowires, etc.) and localized to a target cell via an applied magnetic field. In hydroporation, a molecule (e.g., a nucleic acid molecule) having a barcode (e.g., a spatial barcode) and a capture domain can be delivered to a cell and/or cell bead via hydrodynamic pressure.

(c) Methods for Separating Sample into Single Cells or Cell Groups

Some embodiments of any of the methods described herein can include separating a biological sample into single cells, cell groups, types of cells, or a region or regions of interest. For example, a biological sample can be separated into single cells, cell groups, types of cells, or a region or regions of interest before being contacted with one or more capture probes. In other examples, a biological sample is first contacted with one or more capture probes, and then separated into single cells, cell groups, types of cells, or a region or regions of interest.

In some embodiments, a biological sample can be separated into chucks using pixelation. Pixelation can include the steps of providing a biological sample, and punching out one or more portions of the biological sample. The punched out portions of the biological sample can then be used to perform any of the methods described herein. In some embodiments, the punched-out portions of the biological sample can be in a random pattern or a designed pattern. In some embodiments, the punched-out portions of the biological sample can be focused on a region of interest or a subcellular structure in the biological sample.

Figure 20A:
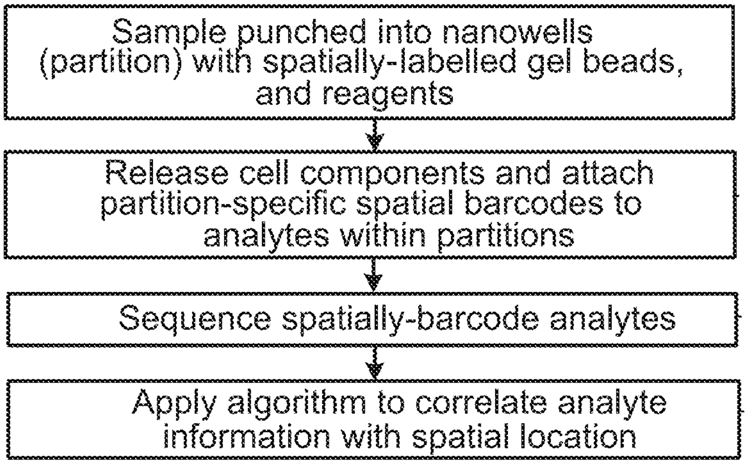
FIG. 20A is a workflow schematic illustrating exemplary, non-limiting, non-exhaustive steps for “pixelating” a sample, wherein the sample is cut, stamped, microdissected, or transferred by hollow-needle or microneedle, moving a small portion of the sample into an individual partition or well.

FIG. 20A is a workflow schematic illustrating exemplary, non-limiting, non-exhaustive steps for "pixelating" a sample, wherein the sample is cut, stamped, microdissected, or transferred by hollow-needle or microneedle, moving a small portion of the sample into an individual partition or well.

Figure 20B:
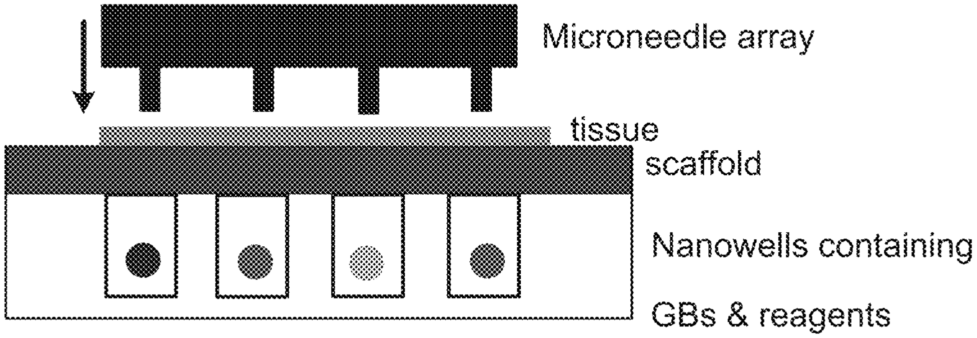
FIG. 20B is a schematic depicting multi-needle pixilation, wherein an array of needles punched through a sample on a scaffold and into nanowells containing gel beads and reagents below. Once the needle is in the nanowell, the cell(s) are ejected.

FIG. 20B is a schematic depicting multi-needle pixelation, wherein an array of needles punched through a sample on a scaffold and into nanowells containing gel beads and reagents below. Once the needle is in the nanowell, the cell(s) are ejected.

In some embodiments, a biological sample is divided into chucks before performance of any of the spatial analysis methods described herein. In some embodiments, the methods can include spatial barcoding of FFPE "chunks" via barcodes applied in spatially well-defined pattern (like in DNA microarray printing). The DNA barcode is either long so that it will not diffuse out in subsequent steps or is covalently applied to the FFPE sample. To enable barcodes to get embedded into an FFPE slide, the wax can be heated, barcodes can be added to the slide before cooling, and then the chunks can be cut. The cutting can be done in various ways such as using laser microdissection, or via mechanical or acoustic means. Other alternates are to embed some fluorophores/Qdots, etc. to preserve spatial information into the sample. The barcoding at this step enables massively parallel random encapsulation of chunks while retaining local spatial information (e.g., tumor vs normal cells).

In some embodiments, a biological sample can be divided or portioned using laser capture microdissection (e.g., highly-multiplexed laser capture microdissection).

(d) Release and Amplification of Analytes

In some embodiments, lysis reagents can be added to the sample to facilitate the release of analyte(s) from a sample. Examples of lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes. Other lysis agents can additionally or alternatively be co-partitioned with the biological sample to cause the release of the sample's contents into the partitions. In some embodiments, surfactant-based lysis solutions can be used to lyse cells, although these can be less desirable for emulsion-based systems where the surfactants can interfere with stable emulsions. Lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of biological materials that can be in addition to or in place of droplet partitioning, where any pore size of the encapsulate is sufficiently small to retain nucleic acid fragments of a given size, following cellular disruption.

In addition to the permeabilization agents, other reagents can also be added to interact with the biological sample, including, for example, DNase and RNase inactivating agents or inhibitors, such as proteinase K, chelating agents, such as EDTA, and other reagents to allow for subsequent processing of analytes from the sample.

Further reagents that can be added to a sample, include, for example, endonucleases to fragment DNA, DNA polymerase enzymes, and dNTPs used to amplify nucleic acids. Other enzymes that can also be added to the sample include, but are not limited to, polymerase, transposase, ligase, proteinase K, and DNAse, etc. Additional reagents can also include reverse transcriptase enzymes, including enzymes with terminal transferase activity, primers, and switch oligonucleotides. In some embodiments, template switching can be used to increase the length of a cDNA, e.g., by appending a predefined nucleic acid sequence to the cDNA.

If a tissue sample is not permeabilized sufficiently, the amount of analyte captured on the substrate can be too low to enable adequate analysis. Conversely, if the tissue sample is too permeable, the analyte can diffuse away from its origin in the tissue sample, such that the relative spatial relationship of the analytes within the tissue sample is lost. Hence, a balance between permeabilizing the tissue sample enough to obtain good signal intensity while still maintaining the spatial resolution of the analyte distribution in the tissue sample is desired.

In some embodiments, where the biological sample includes live cells, permeabilization conditions can be modified so that the live cells experience only brief permeabilization (e.g., through short repetitive bursts of electric field application), thereby allowing one or more analytes to migrate from the live cells to the substrate while retaining cellular viability. In some embodiments, after contacting a biological sample with a substrate that include capture probes, a removal step is performed to remove all or a portion of the biological sample from the substrate. In some embodiments, the removal step includes enzymatic or chemical degradation of the permeabilized cells of the biological sample. For example, the removal step can include treating the biological samples with an enzyme (e.g., proteinase K) to remove at least a portion of the biological sample from the first substrates. In some embodiments, the removal step can include ablation of the tissue (e.g., laser ablation).

In some embodiments, where RNA is captured from cells in a sample, one or more RNA species of interest can be selectively enriched. For example, one or more species of RNA of interest can be selected by addition of one or more oligonucleotides. One or more species of RNA can be selectively down-selected (e.g., removed) using any of a variety of methods. For example, probes can be administered to a sample that selectively hybridize to ribosomal RNA (rRNA), thereby reducing the pool and concentration of rRNA in the sample. Subsequent application of the capture probes to the sample can result in improved RNA capture due to the reduction in non-specific RNA present in the sample. In some embodiments, the additional oligonucleotide is a sequence used for priming a reaction by a polymerase. For example, one or more primer sequences with sequence complementarity to one or more RNAs of interest, can be used to amplify the one or more RNAs of interest, thereby selectively enriching these RNAs. In some embodiments, an oligonucleotide with sequence complementarity to the complementary strand of captured RNA (e.g., cDNA) can bind to the cDNA. In one non-limiting example, biotinylated oligonucleotides with sequence complementary to one or more cDNA of interest binds to the cDNA and can be selected using biotinylation-strepavidin affinity in any number of methods known to the field (e.g., streptavidin beads).

Nucleic acid analytes can be amplified using a polymerase chain reaction (e.g., digital PCR, quantitative PCR, or real time PCR), or isothermal amplification, or any of the nucleic acid amplification or extension reactions described herein.

(e) Partitioning

As discussed above, in some embodiments, the sample can optionally be separated into single cells, cell groups, or other fragments/pieces that are smaller than the original, unfragmented sample. Each of these smaller portions of the sample can be analyzed to obtain spatially-resolved analyte information from the sample. Non-limiting partitioning methods are described herein.

For samples that have been separated into smaller fragments—and particularly, for samples that have been disaggregated, dissociated, or otherwise separated into individual cells—one method for analyzing the fragments involves partitioning the fragments into individual partitions (e.g., fluid droplets), and then analyzing the contents of the partitions. In general, each partition maintains separation of its own contents from the contents of other partitions. For example, the partition can be a droplet in an emulsion.

In addition to analytes, a partition can include additional components, and in particular, one or more beads. A partition can include a single gel bead, a single cell bead, or both a single cell bead and single gel bead.

A partition can also include one or more reagents. Unique identifiers, such as barcodes, can be injected into the droplets previous to, subsequent to, or concurrently with droplet generation, such as via a microcapsule (e.g., bead). Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids.

The partitions can be flowable within fluid streams. The partitions can include, for example, micro-vesicles that have an outer barrier surrounding an inner fluid center or core. In some cases, the partitions can include a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions can be provided in a water-in-oil emulsion or oil-in-water emulsion. A variety of different vessels are described in, for example, U.S. Patent Application Publication No. 2014/0155295, the entire contents of which are incorporated herein by reference. Emulsion systems for creating stable droplets in non-aqueous or oil continuous phases are described, for example, in U.S. Patent Application Publication No. 2010/0105112, the entire contents of which are incorporated herein by reference.

For droplets in an emulsion, allocating individual particles to discrete partitions can be accomplished, for example, by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters can be adjusted to control the occupancy of the resulting partitions (e.g., number of analytes per partition, number of beads per partition, etc.) For example, partition occupancy can be controlled by providing the aqueous stream at a certain concentration and/or flow rate of analytes.

To generate single analyte partitions, the relative flow rates of the immiscible fluids can be selected such that, on average, the partitions can contain less than one analyte per partition to ensure that those partitions that are occupied are primarily singly occupied. In some cases, partitions among a plurality of partitions can contain at most one analyte. In some embodiments, the various parameters (e.g., fluid properties, particle properties, microfluidic architectures, etc.) can be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

The channel segments described herein can be coupled to any of a variety of different fluid sources or receiving components, including reservoirs, tubing, manifolds, or fluidic components of other systems. As will be appreciated, the microfluidic channel structure can have a variety of geometries. For example, a microfluidic channel structure can have one or more than one channel junction. As another example, a microfluidic channel structure can have 2, 3, 4, or 5 channel segments each carrying particles that meet at a channel junction. Fluid can be directed to flow along one or more channels or reservoirs via one or more fluid flow units. A fluid flow unit can include compressors (e.g., providing positive pressure), pumps (e.g., providing negative pressure), actuators, and the like to control flow of the fluid. Fluid can also or otherwise be controlled via applied pressure differentials, centrifugal force, electrokinetic pumping, vacuum, capillary, and/or gravity flow.

A partition can include one or more unique identifiers, such as barcodes. Barcodes can be previously, subsequently, or concurrently delivered to the partitions that hold the compartmentalized or partitioned biological particle. For example, barcodes can be injected into droplets previous to, subsequent to, or concurrently with droplet generation. The delivery of the barcodes to a particular partition allows for the later attribution of the characteristics of the individual biological particle to the particular partition. Barcodes can be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can include a bead.

In some embodiments, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus can disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

In some embodiments, one more barcodes (e.g., spatial barcodes, UMIs, or a combination thereof) can be introduced into a partition as part of the analyte. As described previously, barcodes can be bound to the analyte directly, or can form part of a capture probe or analyte capture agent that is hybridized to, conjugated to, or otherwise associated with an analyte, such that when the analyte is introduced into the partition, the barcode(s) are introduced as well.

Figure 21:
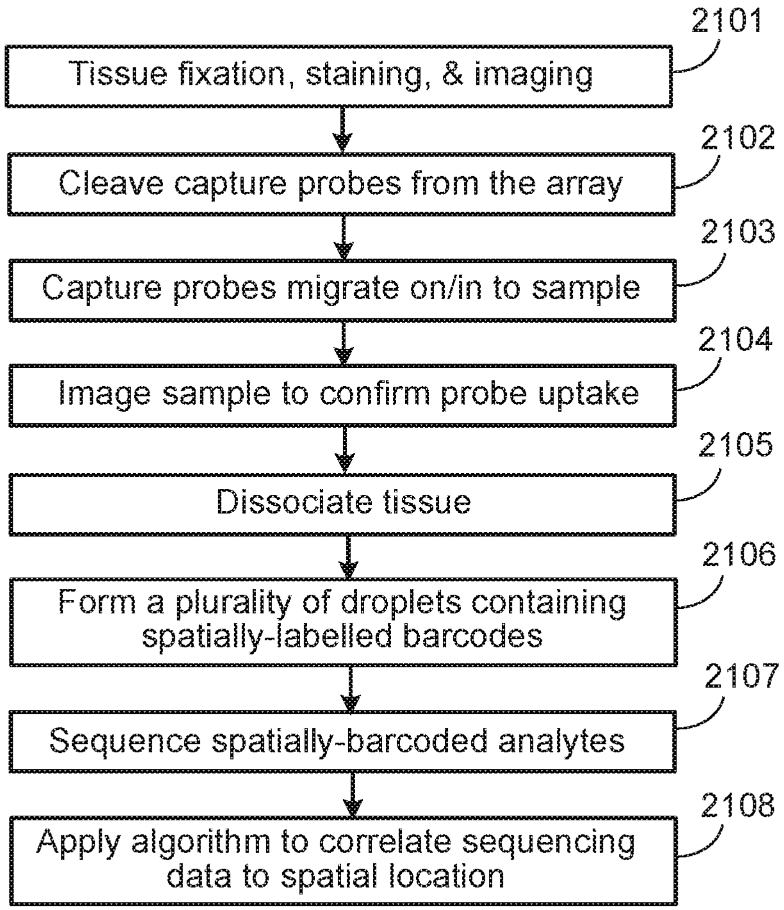
FIG. 21 shows a workflow schematic illustrating exemplary, non-limiting, non-exhaustive steps for dissociating a spatially-barcoded sample for analysis via droplet or flow cell analysis methods.

FIG. 21 depicts an exemplary workflow, where a sample is contacted with a spatially-barcoded capture probe array and the sample is fixed, stained, and imaged 2101, as described elsewhere herein. The capture probes can be cleaved from the array 2102 using any method as described herein. The capture probes can diffuse toward the cells by either passive or active migration as described elsewhere herein. The capture probes may then be introduced to the sample 2103 as described elsewhere herein, wherein the capture probe is able to gain entry into the cell in the absence of cell permeabilization, using one of the cell penetrating peptides or lipid delivery systems described herein. The sample can then be optionally imaged in order to confirm probe uptake, via a reporter molecule incorporated within the capture probe 2104. The sample can then be separated from the array and undergo dissociation 2105, wherein the sample is separated into single cells or small groups of cells. Once the sample is dissociated, the single cells can be introduced to an oil-in water droplet 2106, wherein a single cell is combined with reagents within the droplet and processed so that the spatial barcode that penetrated the cell labels the contents of that cell within the droplet. Other cells undergo separately partitioned reactions concurrently. The contents of the droplet is then sequenced 2107 in order to associate a particular cell or cells with a particular spatial location within the sample 2108.

As described above, FIG. 16 shows an example of a microfluidic channel structure for partitioning individual analytes (e.g., cells) into discrete partitions. FIGS. 17A and 17C also show other examples of microfluidic channel structures that can be used for delivering beads to droplets.

A variety of different beads can be incorporated into partitions as described above. In some embodiments, for example, non-barcoded beads can be incorporated into the partitions. For example, where the biological particle (e.g., a cell) that is incorporated into the partitions carries one or more barcodes (e.g., spatial barcode(s), UMI(s), and combinations thereof), the bead can be a non-barcoded bead.

In some embodiments, a barcode carrying bead can be incorporated into partitions. For example, a nucleic acid molecule, such as an oligonucleotide, can be coupled to a bead by a releasable linkage, such as, for example, a disulfide linker. The same bead can be coupled (e.g., via releasable linkage) to one or more other nucleic acid molecules. The nucleic acid molecule can be or include a barcode. As noted elsewhere herein, the structure of the barcode can include a number of sequence elements.

The nucleic acid molecule can include a functional domain that can be used in subsequent processing. For example, the functional domain can include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule can include a barcode sequence for use in barcoding the sample (e.g., DNA, RNA, protein, etc.). In some cases, the barcode sequence can be bead-specific such that the barcode sequence is common to all nucleic acid molecules coupled to the same bead. Alternatively or in addition, the barcode sequence can be partition-specific such that the barcode sequence is common to all nucleic acid molecules coupled to one or more beads that are partitioned into the same partition. The nucleic acid molecule can include a specific priming sequence, such as an mRNA specific priming sequence (e.g., poly (T) sequence), a targeted priming sequence, and/or a random priming sequence. The nucleic acid molecule can include an anchoring sequence to ensure that the specific priming sequence hybridizes at the sequence end (e.g., of the mRNA). For example, the anchoring sequence can include a random short sequence of nucleotides, such as a 1-mer, 2-mer, 3-mer or longer sequence, which can ensure that a poly(T) segment is more likely to hybridize at the sequence end of the poly(A) tail of the mRNA.

The nucleic acid molecule can include a unique molecular identifying sequence (e.g., unique molecular identifier (UMI)). In some embodiments, the unique molecular identifying sequence can include from about 5 to about 8 nucleotides. Alternatively, the unique molecular identifying sequence can include less than about 5 or more than about 8 nucleotides. The unique molecular identifying sequence can be a unique sequence that varies across individual nucleic acid molecules coupled to a single bead.

In some embodiments, the unique molecular identifying sequence can be a random sequence (e.g., such as a random N-mer sequence). For example, the UMI can provide a unique identifier of the starting mRNA molecule that was captured, in order to allow quantitation of the number of original expressed RNA.

In general, an individual bead can be coupled to any number of individual nucleic acid molecules, for example, from one to tens to hundreds of thousands or even millions of individual nucleic acid molecules. The respective barcodes for the individual nucleic acid molecules can include both common sequence segments or relatively common sequence segments and variable or unique sequence segments between different individual nucleic acid molecules coupled to the same bead.

Within any given partition, all of the cDNA transcripts of the individual mRNA molecules can include a common barcode sequence segment. However, the transcripts made from the different mRNA molecules within a given partition can vary at the unique molecular identifying sequence segment (e.g., UMI segment). Beneficially, even following any subsequent amplification of the contents of a given partition, the number of different UMIs can be indicative of the quantity of mRNA originating from a given partition. As noted above, the transcripts can be amplified, cleaned up and sequenced to identify the sequence of the cDNA transcript of the mRNA, as well as to sequence the barcode segment and the UMI segment. While a poly(T) primer sequence is described, other targeted or random priming sequences can also be used in priming the reverse transcription reaction. Likewise, although described as releasing the barcoded oligonucleotides into the partition, in some cases, the nucleic acid molecules bound to the bead can be used to hybridize and capture the mRNA on the solid phase of the bead, for example, in order to facilitate the separation of the RNA from other cell contents.

In some embodiments, precursors that include a functional group that is reactive or capable of being activated such that it becomes reactive can be polymerized with other precursors to generate gel beads that include the activated or activatable functional group. The functional group can then be used to attach additional species (e.g., disulfide linkers, primers, other oligonucleotides, etc.) to the gel beads. For example, some precursors featuring a carboxylic acid (COOH) group can co-polymerize with other precursors to form a bead that also includes a COOH functional group. In some cases, acrylic acid (a species comprising free COOH groups), acrylamide, and bis(acryloyl)cystamine can be co-polymerized together to generate a bead with free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead. In some embodiments, a degradable bead can be introduced into a partition, such that the bead degrades within the partition and any associated species (e.g., oligonucleotides) are released within the droplet when the appropriate stimulus is applied. The free species (e.g., oligonucleotides, nucleic acid molecules) can interact with other reagents contained in the partition. For example, a polyacrylamide bead featuring cystamine and linked, via a disulfide bond, to a barcode sequence, can be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet with a bead-bound barcode sequence in basic solution can also result in bead degradation and release of the attached barcode sequence into the aqueous, inner environment of the droplet.

Any suitable number of species (e.g., primer, barcoded oligonucleotide) can be associated with a bead such that, upon release from the bead, the species (e.g., primer, e.g., barcoded oligonucleotide) are present in the partition at a pre-defined concentration. Such pre-defined concentration can be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

A degradable bead can include one or more species with a labile bond such that, when the bead/species is exposed to the appropriate stimulus, the bond is broken and the bead degrades. The labile bond can be a chemical bond (e.g., covalent bond, ionic bond) or can be another type of physical interaction (e.g., van der Waals interactions, dipole-dipole interactions, etc.). In some embodiments, a crosslinker used to generate a bead can include a labile bond. Upon exposure to the appropriate conditions, the labile bond can be broken and the bead degraded. For example, upon exposure of a polyacrylamide gel bead that includes cystamine crosslinkers to a reducing agent, the disulfide bonds of the cystamine can be broken and the bead degraded.

A degradable bead can be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a barcode sequence can be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above description, while referred to as degradation of a bead, in many embodiments, degradation can refer to the disassociation of a bound or entrained species from a bead, both with and without structurally degrading the physical bead itself. For example, entrained species can be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In some embodiments, osmotic shrinking of a bead can cause a bead to better retain an entrained species due to pore size contraction.

Numerous chemical triggers can be used to trigger the degradation of beads within partitions. Examples of these chemical changes can include, but are not limited to pH-mediated changes to the integrity of a component within the bead, degradation of a component of a bead via cleavage of cross-linked bonds, and depolymerization of a component of a bead.

In some embodiments, a bead can be formed from materials that include degradable chemical cross-linkers, such as BAC or cystamine. Degradation of such degradable cross-linkers can be accomplished through a number of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof. A reducing agent can degrade the disulfide bonds formed between gel precursors forming the bead, and thus, degrade the bead.

In certain embodiments, a change in pH of a solution, such as an increase in pH, can trigger degradation of a bead. In other embodiments, exposure to an aqueous solution, such as water, can trigger hydrolytic degradation, and thus degradation of the bead. In some cases, any combination of stimuli can trigger degradation of a bead. For example, a change in pH can enable a chemical agent (e.g., DTT) to become an effective reducing agent.

Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In other cases, heat can increase the internal pressure of the bead components such that the bead ruptures or explodes. Heat can also act upon heat-sensitive polymers used as materials to construct beads.

In addition to beads and analytes, partitions that are formed can include a variety of different reagents and species. For example, when lysis reagents are present within the partitions, the lysis reagents can facilitate the release of analytes within the partition. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St. Louis, MO), as well as other commercially available lysis enzymes. Other lysis agents can additionally or alternatively be co-partitioned to cause the release analytes into the partitions. For example, in some cases, surfactant-based lysis solutions can be used to lyse cells, although these can be less desirable for emulsion based systems where the surfactants can interfere with stable emulsions. In some embodiments, lysis solutions can include non-ionic surfactants such as, for example, TritonX-100 and Tween 20. In some embodiments, lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of analytes that can be in addition to or in place of droplet partitioning, where any pore size of the encapsulate is sufficiently small to retain nucleic acid fragments of a given size, following cellular disruption.

Examples of other species that can be co-partitioned with analytes in the partitions include, but are not limited to, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. Additional reagents can also be co-partitioned, including endonucleases to fragment DNA, DNA polymerase enzymes and dNTPs used to amplify nucleic acid fragments and to attach the barcode molecular tags to the amplified fragments.

Additional reagents can also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some embodiments, template switching can be used to increase the length of a cDNA. Template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., poly(C), to the cDNA in a template independent manner. Switch oligos can include sequences complementary to the additional nucleotides, e.g., poly(G). The additional nucleotides (e.g., poly(C)) on the cDNA can hybridize to the additional nucleotides (e.g., poly(G)) on the switch oligo, whereby the switch oligo can be used by the reverse transcriptase as template to further extend the cDNA.

Template switching oligonucleotides can include a hybridization region and a template region. The hybridization region can include any sequence capable of hybridizing to the target. In some cases, the hybridization region includes a series of G bases to complement the overhanging C bases at the 3' end of a cDNA molecule. The series of G bases can include 1 G base, 2 G bases, 3 G bases, 4 G bases, 5 G bases or more than 5 G bases. The template sequence can include any sequence to be incorporated into the cDNA. In some cases, the template region includes at least 1 (e.g., at least 2, 3, 4, 5 or more) tag sequences and/or functional sequences. Switch oligos can include deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), and combinations of the foregoing.

In some embodiments, beads that are partitioned with the analyte can include different types of oligonucleotides bound to the bead, where the different types of oligonucleotides bind to different types of analytes. For example, a bead can include one or more first oligonucleotides (which can be capture probes, for example) that can bind or hybridize to a first type of analyte, such as mRNA for example, and one or more second oligonucleotides (which can be capture probes, for example) that can bind or hybridize to a second type of analyte, such as gDNA for example. Partitions can also include lysis agents that aid in releasing nucleic acids from the co-partitioned cell, and can also include an agent (e.g., a reducing agent) that can degrade the bead and/or break covalent linkages between the oligonucleotides and the bead, releasing the oligonucleotides into the partition. The released barcoded oligonucleotides (which can also be barcoded) can hybridize with mRNA released from the cell and also with gDNA released from the cell.

Barcoded constructs thus formed from hybridization can include a first type of construct that includes a sequence corresponding to an original barcode sequence from the bead and a sequence corresponding to a transcript from the cell, and a second type of construct that includes a sequence corresponding to the original barcode sequence from the bead and a sequence corresponding to genomic DNA from the cell. The barcoded constructs can then be released/removed from the partition and, in some embodiments, further processed to add any additional sequences. The resulting constructs can then be sequenced, the sequencing data processed, and the results used to spatially characterize the mRNA and the gDNA from the cell.

In another example, a partition includes a bead that includes a first type of oligonucleotide (e.g., a first capture probe) with a first barcode sequence, a poly(T) priming sequence that can hybridize with the poly(A) tail of an mRNA transcript, and a UMI barcode sequence that can uniquely identify a given transcript. The bead also includes a second type of oligonucleotide (e.g., a second capture probe) with a second barcode sequence, a targeted priming sequence that is capable of specifically hybridizing with a third barcoded oligonucleotide (e.g., an analyte capture agent) coupled to an antibody that is bound to the surface of the partitioned cell. The third barcoded oligonucleotide includes a UMI barcode sequence that uniquely identifies the antibody (and thus, the particular cell surface feature to which it is bound).

In this example, the first and second barcoded oligonucleotides include the same spatial barcode sequence (e.g., the first and second barcode sequences are the same), which permits downstream association of barcoded nucleic acids with the partition. In some embodiments, however, the first and second barcode sequences are different.

The partition also includes lysis agents that aid in releasing nucleic acids from the cell and can also include an agent (e.g., a reducing agent) that can degrade the bead and/or break a covalent linkage between the barcoded oligonucleotides and the bead, releasing them into the partition. The first type of released barcoded oligonucleotide can hybridize with mRNA released from the cell and the second type of released barcoded oligonucleotide can hybridize with the third type of barcoded oligonucleotide, forming barcoded constructs.

The first type of barcoded construct includes a spatial barcode sequence corresponding to the first barcode sequence from the bead and a sequence corresponding to the UMI barcode sequence from the first type of oligonucleotide, which identifies cell transcripts. The second type of barcoded construct includes a spatial barcode sequence corresponding to the second barcode sequence from the second type of oligonucleotide, and a UMI barcode sequence corresponding to the third type of oligonucleotide (e.g., the analyte capture agent) and used to identify the cell surface feature. The barcoded constructs can then be released/removed from the partition and, in some embodiments, further processed to add any additional sequences. The resulting constructs are then sequenced, sequencing data processed, and the results used to characterize the mRNA and cell surface feature of the cell.

The foregoing discussion involves two specific examples of beads with oligonucleotides for analyzing two different analytes within a partition. More generally, beads that are partitioned can have any of the structures described previously, and can include any of the described combinations of oligonucleotides for analysis of two or more (e.g., three or more, four or more, five or more, six or more, eight or more, ten or more, 12 or more, 15 or more, 20 or more, 25 or more, 30 or more, 40 or more, 50 or more) different types of analytes within a partition. Examples of beads with combinations of different types of oligonucleotides (e.g., capture probes) for concurrently analyzing different combinations of analytes within partitions include, but are not limited to: (a) genomic DNA and cell surface features (e.g., using the analyte capture agents described herein); (b) mRNA and a lineage tracing construct; (c) mRNA and cell methylation status; (d) mRNA and accessible chromatin (e.g., ATAC-seq, DNase-seq, and/or MNase-seq); (e) mRNA and cell surface or intracellular proteins and/or metabolites; (f) a barcoded analyte capture agent (e.g., the MHC multimers described herein) and a V(D)J sequence of an immune cell receptor (e.g., T-cell receptor); and (g) mRNA and a perturbation agent (e.g., a CRISPR crRNA/sgRNA, TALEN, zinc finger nuclease, and/or antisense oligonucleotide as described herein).

(f) Sequencing Analysis

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is barcoded directly via hybridization with capture probes or analyte capture agents hybridized, bound, or associated with either the cell surface, or introduced into the cell, as described above, sequencing can be performed on the intact sample. Alternatively, if the barcoded sample has been separated into fragments, cell groups, or individual cells, as described above, sequencing can be performed on individual fragments, cell groups, or cells. For analytes that have been barcoded via partitioning with beads, as described above, individual analytes (e.g., cells, or cellular contents following lysis of cells) can be extracted from the partitions by breaking the partitions, and then analyzed by sequencing to identify the analytes.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can directly be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule or it can be a molecule derived therefrom. For example, a first and/or second strand DNA molecule can be directly subjected to sequence analysis (e.g. sequencing), i.e., can directly take part in the sequence analysis reaction or process (e.g. the sequencing reaction or sequencing process, or be the molecule which is sequenced or otherwise identified). Alternatively, the barcoded nucleic acid molecule can be subjected to a step of second strand synthesis or amplification before sequence analysis (e.g. sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g. barcoded nucleic acid molecules) can be analyzed (e.g. sequenced). To perform single molecule sequencing, the nucleic acid strand can be modified at the 3' end.

Massively parallel sequencing techniques can be used for sequencing nucleic acids, as described above. In one embodiment, a massively parallel sequencing technique can be based on reversible dye-terminators. As an example, DNA molecules are first attached to primers on, e.g., a glass or silicon substrate, and amplified so that local clonal colonies are formed (bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

As another example, massively parallel pyrosequencing techniques can also be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., Anal. Biochem. 242(1), 84-9 (1996); Ronaghi, Genome Res. 11(1), 3-11 (2001); Ronaghi et al. Science 281 (5375), 363 (1998); and U.S. Pat. Nos. 6,210,891, 6,258,568, and 6,274,320, the entire contents of each of which are incorporated herein by reference.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, sequencing can be performed in-situ. In-situ sequencing methods are particularly useful, for example, when the biological sample remains intact after analytes on the sample surface (e.g., cell surface analytes) or within the sample (e.g., intracellular analytes) have been barcoded. In-situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in-situ sequencing are described, for example, in Mitra et al., (2003) Anal. Biochem., 320, 55-65, and Lee et al., (2014) Science, 343(6177), 1360-1363, the entire contents of each of which are incorporated herein by reference.

In addition, examples of methods and systems for performing in-situ sequencing are described in PCT Patent Application Publication Nos. WO2014/163886, WO2018/045181, WO2018/045186, and in U.S. Pat. Nos. 10,138,509 and 10,179,932, the entire contents of each of which are incorporated herein by reference. Example techniques for in-situ sequencing include, but are not limited to, STARmap (described for example in Wang et al., (2018) Science, 361(6499) 5691), MERFISH (described for example in Moffitt, (2016) Methods in Enzymology, 572, 1-49), and FISSEQ (described for example in U.S. Patent Application Publication No. 2019/0032121). The entire contents of each of the foregoing references are incorporated herein by reference.

For analytes that have been barcoded via partitioning, barcoded nucleic acid molecules or derivatives thereof (e.g., barcoded nucleic acid molecules to which one or more functional sequences have been added, or from which one or more features have been removed) can be pooled and processed together for subsequent analysis such as sequencing on high throughput sequencers. Processing with pooling can be implemented using barcode sequences. For example, barcoded nucleic acid molecules of a given partition can have the same barcode, which is different from barcodes of other spatial partitions. Alternatively, barcoded nucleic acid molecules of different partitions can be processed separately for subsequent analysis (e.g., sequencing).

In some embodiments, where capture probes do not contain a spatial barcode, the spatial barcode can be added after the capture probe captures analytes from a biological sample and before analysis of the analytes. When a spatial barcode is added after an analyte is captured, the barcode can be added after amplification of the analyte (e.g., reverse transcription and polymerase amplification of RNA). In some embodiments, analyte analysis uses direct sequencing of one or more captured analytes, such as direct sequencing of hybridized RNA. In some embodiments, direct sequencing is performed after reverse transcription of hybridized RNA. In some embodiments direct sequencing is performed after amplification of reverse transcription of hybridized RNA.

In some embodiments, direct sequencing of captured RNA is performed by sequencing-by-synthesis (SBS). In some embodiments, a sequencing primer is complementary to a sequence in one or more of the domains of a capture probe (e.g., functional domain). In such embodiments, sequencing-by-synthesis can include reverse transcription and/or amplification in order to generate a template sequence (e.g., functional domain) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid spots are present in a double stranded form these can be processed to provide single stranded nucleic acid templates using methods well known in the art, for example by denaturation, cleavage etc. The sequencing primers which are hybridized to the nucleic acid template and used for primer extension are preferably short oligonucleotides, for example, 15 to 25 nucleotides in length. The sequencing primers can be greater than 25 nucleotides in length as well. For example, sequencing primers can be about 20 to about 60 nucleotides in length, or more than 60 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010,251, U.S. Patent App. Pub. No. 2012/0270305, U.S. Patent App. Pub. No. 2013/0260372, and U.S. Patent App. Pub. No. 2013/0079232, the entire contents of each of which are incorporated herein by reference.

In some embodiments, direct sequencing of captured RNA is performed by sequential fluorescence hybridization (e.g., sequencing by hybridization). In some embodiments, a hybridization reaction where RNA is hybridized to a capture probe is performed in situ. In some embodiments, captured RNA is not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of captured RNA using sequential fluorescence hybridization is performed in vitro. In some embodiments, captured RNA is amplified prior to hybridization with a sequencing probe (e.g., reverse transcription to cDNA and amplification of cDNA). In some embodiments, a capture probe containing captured RNA is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged. In some embodiments, a specific sequence of cDNA is resolved from an image of a sequencing reaction. In some embodiments, reverse transcription of captured RNA is performed prior to hybridization to the sequencing probe. In some embodiments, the sequencing probe is designed to target complementary sequences of the coding regions of RNA (e.g., targeting cDNA).

In some embodiments, a captured RNA is directly sequenced using a nanopore-based method. In some embodiments, direct sequencing is performed using nanopore direct RNA sequencing in which captured RNA is translocated through a nanopore. A nanopore current can be recorded and converted into a base sequence. In some embodiments, captured RNA remains attached to a substrate during nanopore sequencing. In some embodiments, captured RNA is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., Trends Biotechnol. 18, 14 7-151 (2000); Deamer et al., Acc. Chem. Res. 35:817-825 (2002); Li et al., Nat. Mater. 2:611-615 (2003); Soni et al., Clin. Chem. 53, 1996-2001 (2007); Healy et al., Nanomed. 2, 459-481 (2007); Cockroft et al., J. Am. Chem. Soc. 130, 818-820 (2008); and in U.S. Pat. No. 7,001,792. The entire contents of each of the foregoing references are incorporated herein by reference.

In some embodiments, direct sequencing of captured RNA is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina® sequencing (e.g., flow cell-based sequencing techniques), sequencing by synthesis using modified nucleotides (such as commercialized in TruSeq™ and HiSeg™ technology by Illumina, Inc., San Diego, CA), HeliScope™ by Helicos Biosciences Corporation, Cambridge, MA, and PacBio RS by Pacific Biosciences of California, Inc., Menlo Park, CA), sequencing by ion detection technologies (Ion Torrent, Inc., South San Francisco, CA), and sequencing of DNA nanoballs (Complete Genomics, Inc., Mountain View, CA).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes. The entire contents of each of the foregoing references are incorporated herein by reference.

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181. The entire contents of each of the foregoing references are herein incorporated by reference.

IV. Multiplexing

(a) Multiplexing Generally

In various embodiments of spatial analysis as described herein, features can include different types of capture probes for analyzing both intrinsic and extrinsic information for individual cells. For example, a feature can include one or more of the following: 1) a capture probe featuring a capture domain that binds to one or more endogenous nucleic acids in the cell; 2) a capture probe featuring a capture domain that binds to one or more exogenous nucleic acids in the cell (e.g., nucleic acids from a microorganism (e.g., a virus, a bacterium)) that infects the cell, nucleic acids introduced into the cell (e.g., such as plasmids or nucleic acid derived therefrom), nucleic acids for gene editing (e.g., CRISPR-related RNA such as crRNA, guide RNA); 3) a capture probe featuring a capture domain that binds to a analyte capture agent (e.g., an antibody coupled to a oligonucleotide that includes a capture agent barcode domain having an analyte capture sequence that binds the capture domain), and 4) a capture moiety featuring a domain that binds to a protein (e.g., an exogenous protein expressed in the cell, a protein from a microorganism (e.g., a virus, a bacterium)) that infects the cell, or a binding partner for a protein of the cell (e.g., an antigen for an immune cell receptor).

In some embodiments of any of the spatial analysis methods as described herein, spatial profiling includes concurrent analysis of two different types of analytes. A feature can be a gel bead, which is coupled (e.g., reversibly coupled) to one or more capture probes. The capture probes can include a spatial barcode sequence and a poly (T) priming sequence that can hybridize with the poly (A) tail of an mRNA transcript. The capture probe can also include a UMI sequence that can uniquely identify a given transcript. The capture probe can also include a spatial barcode sequence and a random N-mer priming sequence that is capable of randomly hybridizing with gDNA. In this configuration, capture probes can include the same spatial barcode sequence, which permits association of downstream sequencing reads with the feature.

In some embodiments of any of the spatial analysis methods as described herein, a feature can be a gel bead, which is coupled (e.g., reversibly coupled) to capture probes. The Capture probe can include a spatial barcode sequence and a poly(T) priming sequence 614 that can hybridize with the poly(A) tail of an mRNA transcript. The capture probe can also include a UMI sequence that can uniquely identify a given transcript. The capture probe can include a spatial barcode sequence and a capture domain that is capable of specifically hybridizing with an analyte capture agent. The analyte capture agent can includes an oligonucleotide that includes an analyte capture sequence that interacts with the capture domain coupled to the feature. The oligonucleotide of the analyte capture agent can be coupled to an antibody that is bound to the surface of a cell. The oligonucleotide includes a barcode sequence (e.g., an analyte binding moiety barcode) that uniquely identifies the antibody (and thus, the particular cell surface feature to which it is bound). In this configuration, the capture probes include the same spatial barcode sequence, which permit downstream association of barcoded nucleic acids with the location on the spatial array. In some embodiments of any of the spatial profiling methods described herein, the analyte capture agents can be can be produced by any suitable route, including via example coupling schemes described elsewhere herein.

In some embodiments of any of the spatial analysis methods described herein, other combinations of two or more biological analytes that can be concurrently measured include, without limitation: (a) genomic DNA and cell surface features (e.g., via analyte capture agents that bind to a cell surface feature), (b) mRNA and a lineage tracing construct, (c) mRNA and cell methylation status, (d) mRNA and accessible chromatin (e.g., ATAC-seq, DNase-seq, and/or MNase-seq), (e) mRNA and cell surface or intracellular proteins and/or metabolites, (f) mRNA and chromatin (spatial organization of chromatin in a cell), (g) an analyte capture agent (e.g., any of the MEW multimers described herein) and a V(D)J sequence of an immune cell receptor (e.g., T-cell receptor), (h) mRNA and a perturbation agent (e.g., a CRISPR crRNA/sgRNA, TALEN, zinc finger nuclease, and/or antisense oligonucleotide as described herein), (i) genomic DNA and a perturbation agent, (j) an analyte capture agent and a perturbation reagents, (k) accessible chromatin and a perturbation reagent, (l) chromatin (e.g., spatial organization of chromatin in a cell) and a perturbation reagent, and (m) cell surface or intracellular proteins and/or metabolites and a perturbation reagent, or any combination thereof.

In some embodiments of any of the spatial analysis methods described herein, the first analyte can include a nucleic acid molecule with a nucleic acid sequence (e.g., mRNA, complementary DNA derived from reverse transcription of mRNA) encoding at least a portion of a V(D)J sequence of an immune cell receptor (e.g., a TCR or BCR). In some embodiments, the nucleic acid molecule with a nucleic acid sequence encoding at least a portion of a V(D)J sequence of an immune cell receptor is cDNA first generated from reverse transcription of the corresponding mRNA, using a poly(T) containing primer. The cDNA that is generated can then be barcoded using a primer, featuring a spatial barcode sequence (and optionally, a UMI sequence) that hybridizes with at least a portion of the cDNA that is generated. In some embodiments, a template switching oligonucleotide in conjunction a terminal transferase or a reverse transcriptase having terminal transferase activity can be employed to generate a priming region on the cDNA to which a barcoded primer can hybridize during cDNA generation. Terminal transferase activity can, for example, add a poly(C) tail to a 3' end of the cDNA such that the template switching oligonucleotide can bind via a poly(G) priming sequence and the 3' end of the cDNA can be further extended. The original mRNA template and template switching oligonucleotide can then be denatured from the cDNA and the barcoded primer comprising a sequence complementary to at least a portion of the generated priming region on the cDNA can then hybridize with the cDNA and a barcoded construct comprising the barcode sequence (and any optional UMI sequence) and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described, for example, in PCT Patent Application Publication No. WO 2018/075693, and in U.S. Patent Application Publication No. 2018/0105808, the entire contents of each of which are incorporated herein by reference.

In some embodiments, V(D)J analysis can be performed using methods similar to those described herein. For example, V(D)J analysis can be completed with the use of one or more analyte capture agents that bind to particular surface features of immune cells and are associated with barcode sequences (e.g., analyte binding moiety barcodes). The one or more analyte capture agents can include an MEW or MEW multimer. A barcoded oligonucleotide coupled to a bead that can be used for V(D)J analysis. The oligonucleotide is coupled to a bead by a releasable linkage, such as a disulfide linker. The oligonucleotide can include functional sequences that are useful for subsequent processing, such as functional sequence, which can include a sequencer specific flow cell attachment sequence, e.g., a P5 sequence, as well as functional sequence, which can include sequencing primer sequences, e.g., a R1 primer binding site. In some embodiments, the sequence can include a P7 sequence and a R2 primer binding site. A barcode sequence can be included within the structure for use in barcoding the template polynucleotide. The functional sequences can be selected for compatibility with a variety of different sequencing systems, e.g., 454 Sequencing, Ion Torrent Proton or PGM, Illumina X10, etc., and the requirements thereof. In some embodiments, the barcode sequence, functional sequences (e.g., flow cell attachment sequence) and additional sequences (e.g., sequencing primer sequences) can be common to all of the oligonucleotides attached to a given bead. The barcoded oligonucleotide can also include a sequence to facilitate template switching (e.g., a poly(G) sequence). In some embodiments, the additional sequence provides a unique molecular identifier (UMI) sequence segment, as described elsewhere herein.

In an exemplary method of cellular polynucleotide analysis using a barcode oligonucleotide, a cell is co-partitioned along with a bead bearing a barcoded oligonucleotide and additional reagents such as a reverse transcriptase, primers, oligonucleotides (e.g., template switching oligonucleotides), dNTPs, and a reducing agent into a partition (e.g., a droplet in an emulsion). Within the partition, the cell can be lysed to yield a plurality of template polynucleotides (e.g., DNA such as genomic DNA, RNA such as mRNA, etc.).

A reaction mixture featuring a template polynucleotide from a cell and (i) the primer having a sequence towards a 3' end that hybridizes to the template polynucleotide (e.g., poly(T)) and (ii) a template switching oligonucleotide that includes a first oligonucleotide towards a 5' end can be subjected to an amplification reaction to yield a first amplification product. In some embodiments, the template polynucleotide is an mRNA with a poly(A) tail and the primer that hybridizes to the template polynucleotide includes a poly(T) sequence towards a 3' end, which is complementary to the poly(A) segment. The first oligonucleotide can include at least one of an adaptor sequence, a barcode sequence, a unique molecular identifier (UMI) sequence, a primer binding site, and a sequencing primer binding site or any combination thereof. In some cases, a first oligonucleotide is a sequence that can be common to all partitions of a plurality of partitions. For example, the first oligonucleotide can include a flow cell attachment sequence, an amplification primer binding site, or a sequencing primer binding site and the first amplification reaction facilitates the attachment the oligonucleotide to the template polynucleotide from the cell. In some embodiments, the first oligonucleotide includes a primer binding site. In some embodiments, the first oligonucleotide includes a sequencing primer binding site.

The sequence towards a 3' end (e.g., poly(T)) of the primer hybridizes to the template polynucleotide. In a first amplification reaction, extension reaction reagents, e.g., reverse transcriptase, nucleoside triphosphates, co-factors (e.g., $Mg^{2+}$ or $Mn^{2+}$), that are also co-partitioned, can extend the primer sequence using the cell's nucleic acid as a template, to produce a transcript, e.g., cDNA, having a fragment complementary to the strand of the cell's nucleic acid to which the primer annealed. In some embodiments, the reverse transcriptase has terminal transferase activity and the reverse transcriptase adds additional nucleotides, e.g., poly(C), to the cDNA in a template independent manner.

The template switching oligonucleotide, for example a template switching oligonucleotide which includes a poly (G) sequence, can hybridize to the cDNA and facilitate template switching in the first amplification reaction. The transcript, therefore, can include the sequence of the primer, a sequence complementary to the template polynucleotide from the cell, and a sequence complementary to the template switching oligonucleotide.

In some embodiments of any of the spatial analysis methods described herein, subsequent to the first amplification reaction, the first amplification product or transcript can be subjected to a second amplification reaction to generate a second amplification product. In some embodiments, additional sequences (e.g., functional sequences such as flow cell attachment sequence, sequencing primer binding sequences, barcode sequences, etc.) are attached. The first and second amplification reactions can be performed in the same volume, such as for example in a droplet. In some embodiments, the first amplification product is subjected to a second amplification reaction in the presence of a barcoded oligonucleotide to generate a second amplification product having a barcode sequence. The barcode sequence can be unique to a partition, that is, each partition can have a unique barcode sequence. The barcoded oligonucleotide can include a sequence of at least a segment of the template switching oligonucleotide and at least a second oligonucleotide. The segment of the template switching oligonucleotide on the barcoded oligonucleotide can facilitate hybridization of the barcoded oligonucleotide to the transcript, e.g., cDNA, to facilitate the generation of a second amplification product. In addition to a barcode sequence, the barcoded oligonucleotide can include a second oligonucleotide such as at least one of an adaptor sequence, a unique molecular identifier (UMI) sequence, a primer binding site, and a sequencing primer binding site, or any combination thereof.

In some embodiments of any of the spatial analysis methods described herein, the second amplification reaction uses the first amplification product as a template and the barcoded oligonucleotide as a primer. In some embodiments, the segment of the template switching oligonucleotide on the barcoded oligonucleotide can hybridize to the portion of the cDNA or complementary fragment having a sequence complementary to the template switching oligonucleotide or that which was copied from the template switching oligonucleotide. In the second amplification reaction, extension reaction reagents, e.g., polymerase, nucleoside triphosphates, co-factors (e.g., $Mg^{2+}$ or $Mn^{2+}$), that are also co-partitioned, can extend the primer sequence using the first amplification product as template. The second amplification product can include a second oligonucleotide, a sequence of a segment of the template polynucleotide (e.g., mRNA), and a sequence complementary to the primer.

In some embodiments of any of the spatial analysis methods described herein, the second amplification product uses the barcoded oligonucleotide as a template and at least a portion of the first amplification product as a primer. The segment of the first amplification product (e.g., cDNA) having a sequence complementary to the template switching oligonucleotide can hybridize to the segment of the barcoded oligonucleotide comprising a sequence of at least a segment of the template switching oligonucleotide. In the second amplification reaction, extension reaction reagents, e.g., polymerase, nucleoside triphosphates, co-factors (e.g., Mg' or Mn'), that are also co-partitioned, can extend the primer sequence (e.g., first amplification product) using the barcoded oligonucleotide as template. The second amplification product can include the sequence of the primer, a sequence which is complementary to the sequence of the template polynucleotide (e.g., mRNA), and a sequence complementary to the second oligonucleotide.

In some embodiments of any of the spatial analysis methods described herein, three or more classes of biological analytes can be concurrently measured. For example, a feature can include capture probes that can participate in an assay of at least three different types of analytes via three different capture domains. A bead can be coupled to a barcoded oligonucleotide that includes a capture domain that includes a poly(T) priming sequence for mRNA analysis; a barcoded oligonucleotide that includes a capture domain that includes a random N-mer priming sequence for gDNA analysis; and a barcoded oligonucleotide that includes a capture domain that can specifically bind a an analyte capture agent (e.g., an antibody with a spatial barcode), via its analyte capture sequence.

In some embodiments of any of the spatial analysis methods described herein, other combinations of three or more biological analytes that can be concurrently measured include, without limitation: (a) mRNA, a lineage tracing construct, and cell surface and/or intracellular proteins and/or metabolites; (b) mRNA, accessible chromatin (e.g., ATAC-seq, DNase-seq, and/or MNase-seq), and cell surface and/or intracellular proteins and/or metabolites; (c) mRNA, genomic DNA, and a perturbation reagent (e.g., a CRISPR crRNA/sgRNA, TALEN, zinc finger nuclease, and/or antisense oligonucleotide as described herein); (d) mRNA, accessible chromatin, and a perturbation reagent; (e) mRNA, an analyte capture agent (e.g., any of the MEW multimers described herein), and a perturbation reagent; (f) mRNA, cell surface and/or intracellular proteins and/or metabolites, and a perturbation agent; (g) mRNA, a V(D)J sequence of an immune cell receptor (e.g., T-cell receptor), and a perturbation reagent; (h) mRNA, an analyte capture agent, and a V(D)J sequence of an immune cell receptor; (i) cell surface and/or intracellular proteins and/or metabolites, a an analyte capture agent (e.g., the MEW multimers described herein), and a V(D)J sequence of an immune cell receptor; (j)

methylation status, mRNA, and cell surface and/or intracellular proteins and/or metabolites; (k) mRNA, chromatin (e.g., spatial organization of chromatin in a cell), and a perturbation reagent; (1) a V(D)J sequence of an immune cell receptor, chromatin (e.g., spatial organization of chromatin in a cell); and a perturbation reagent; and (m) mRNA, a V(D)J sequence of an immune cell receptor, and chromatin (e.g., spatial organization of chromatin in a cell), or any combination thereof.

In some embodiments of any of the spatial analysis methods described herein, four or more classes biological analytes can be concurrently measured. A feature can be a bead that is coupled to barcoded primers that can each participate in an assay of a different type of analyte. The feature is coupled (e.g., reversibly coupled) to a capture probe that includes a capture domain that includes a poly(T) priming sequence for mRNA analysis and is also coupled (e.g., reversibly coupled) to capture probe that includes a capture domain that includes a random N-mer priming sequence for gDNA analysis. Moreover, the feature is also coupled (e.g., reversibly coupled) to a capture probe that binds an analyte capture sequence of an analyte capture agent via its capture domain. The feature can also be coupled (e.g., reversibly coupled) to a capture probe that can specifically bind a nucleic acid molecule that can function as a perturbation agent (e.g., a CRISPR crRNA/sgRNA, TALEN, zinc finger nuclease, and/or antisense oligonucleotide as described herein), via its capture domain.

In some embodiments of any of the spatial analysis methods described herein, each of the various spatially barcoded capture probes present at a given feature or on a given bead include the same spatial barcode sequence. In some embodiments, each barcoded capture probe can be released from the feature in a manner suitable for analysis of its respective analyte. For example, barcoded constructs A, B, C and D can be generated as described elsewhere herein and analyzed. Barcoded construct A can include a sequence corresponding to the barcode sequence from the bead (e.g., a spatial barcode) and a DNA sequence corresponding to a target mRNA. Barcoded construct B can include a sequence corresponding to the barcode sequence from the bead (e.g., a spatial barcode) and a sequence corresponding to genomic DNA. Barcoded construct C can include a sequence corresponding to the barcode sequence from the bead (e.g., a spatial barcode) and a sequence corresponding to barcode sequence associated with an analyte capture agent (e.g., an analyte binding moiety barcode). Barcoded construct D can include a sequence corresponding to the barcode sequence from the bead (e.g., a spatial barcode) and a sequence corresponding to a CRISPR nucleic acid (which, in some embodiments, also includes a barcode sequence). Each construct can be analyzed (e.g., via any of a variety of sequencing methods) and the results can be associated with the given cell from which the various analytes originated. Barcoded (or even non-barcoded) constructs can be tailored for analyses of any given analyte associated with a nucleic acid and capable of binding with such a construct.

In some embodiments of any of the spatial analysis methods described herein, other combinations of four or more biological analytes that can be concurrently measured include, without limitation: (a) mRNA, a lineage tracing construct, cell surface and/or intracellular proteins and/or metabolites, and gDNA; (b) mRNA, accessible chromatin (e.g., ATAC-seq, DNase-seq, and/or MNase-seq), cell surface and/or intracellular proteins and/or metabolites, and a perturbation agent (e.g., a CRISPR crRNA/sgRNA, TALEN, zinc finger nuclease, and/or antisense oligonucleotide as described herein); (c) mRNA, cell surface and/or intracellular proteins and/or metabolites, an analyte capture agent (e.g., the MHC multimers described herein), and a V(D)J sequence of an immune cell receptor (e.g., T-cell receptor); (d) mRNA, genomic DNA, a perturbation reagent, and accessible chromatin; (e) mRNA, cell surface and/or intracellular proteins and/or metabolites, an analyte capture agent (e.g., the MHC multimers described herein), and a perturbation reagent; (f) mRNA, cell surface and/or intracellular proteins and/or metabolites, a perturbation reagent, and a V(D)J sequence of an immune cell receptor (e.g., T-cell receptor); (g) mRNA, a perturbation reagent, an analyte capture agent (e.g., the MHC multimers described herein), and a V(D)J sequence of an immune cell receptor (e.g., T-cell receptor); (h) mRNA, chromatin (e.g., spatial organization of chromatin in a cell), and a perturbation reagent; (i) a V(D)J sequence of an immune cell receptor, chromatin (e.g., spatial organization of chromatin in a cell); and a perturbation reagent; (j) mRNA, a V(D)J sequence of an immune cell receptor, chromatin (e.g., spatial organization of chromatin in a cell), and genomic DNA; (k) mRNA, a V(D)J sequence of an immune cell receptor, chromatin (e.g., spatial organization of chromatin in a cell), and a perturbation reagent, or any combination thereof.

(b) Construction of Spatial Arrays for Multi-Analyte Analysis

This disclosure also provides methods and materials for constructing a spatial array capable of multi-analyte analysis. In some embodiments, a spatial array includes a plurality of features on a substrate where one or more members of the plurality of features include a plurality of oligonucleotides having a first type functional sequence and oligonucleotides having a second, different type of functional sequence. In some embodiments, a feature can include oligonucleotides with two types of functional sequences. A feature can be coupled to oligonucleotides comprising a TruSeq functional sequence and also to oligonucleotides comprising a Nextera functional sequence. In some embodiments, one or more members of the plurality of features comprises both types of functional sequences. In some embodiments, one or more members of the plurality features includes a first type of functional sequence. In some embodiments, one or more members of the plurality of features includes a second type of functional sequence. In some embodiments, an additional oligonucleotide can be added to the functional sequence to generate a full oligonucleotide where the full oligonucleotide includes a spatial barcode sequence, an optional UMI sequence, a priming sequence, and a capture domain. Attachment of these sequences can be via ligation (including via splint ligation as is described in U.S. Patent Application Publication No. 20140378345, the entire contents of which are incorporated herein by reference), or any other suitable route. As discussed herein, oligonucleotides can be hybridized with splint sequences that can be helpful in constructing complete full oligonucleotides (e.g., oligonucleotides that are capable of spatial analysis).

In some embodiments, the oligonucleotides that hybridize to the functional sequences (e.g., TruSeq and Nextera) located on the features include capture domains capable of capturing different types of analytes (e.g., mRNA, genomic DNA, cell surface proteins, or accessible chromatin). In some examples, oligonucleotides that can bind to the TruSeq functional sequences can include capture domains that include poly(T) capture sequences. In addition to the poly (T) capture sequences, the oligonucleotides that can bind the TruSeq functional groups can also include a capture domain that includes a random N-mer sequence for capturing genomic DNA (e.g., or any other sequence or domain as described herein capable of capturing any of the biological analytes described herein). In such cases, the spatial arrays can be constructed by applying ratios of TruSeq-poly(T) and TruSeq-N-mer oligonucleotides to the features comprising the functional TruSeq sequences. This can produce spatial arrays where a portion of the oligonucleotides can capture mRNA and a different portion of oligonucleotides can capture genomic DNA. In some embodiments, one or more members of a plurality of features include both TruSeq and Nextera functional sequences. In such cases, a feature including both types of functional sequences is capable of binding oligonucleotides specific to each functional sequence. For example, an oligonucleotide capable of binding to a TruSeq functional sequence could be used to deliver an oligonucleotide including a poly(T) capture domain and an oligonucleotide capable of binding to a Nextera functional sequence could be used to deliver an oligonucleotide including an N-mer capture domain for capturing genomic DNA. It will be appreciated by a person of ordinary skill in the art that any combination of capture domains (e.g., capture domains having any of the variety of capture sequences described herein capable of binding to any of the different types of analytes as described herein) could be combined with oligonucleotides capable of binding to TruSeq and Nextera functional sequences to construct a spatial array.

In some embodiments, an oligonucleotide that includes a capture domain (e.g., an oligonucleotide capable of coupling to an analyte) or an analyte capture agent can include an oligonucleotide sequence that is capable of binding or ligating to an assay primer. The adapter can allow the capture probe or the analyte capture agent to be attached to any suitable assay primers and used in any suitable assays. The assay primer can include a priming region and a sequence that is capable of binding or ligating to the adapter. In some embodiments, the adapter can be a non-specific primer (e.g., a 5' overhang) and the assay primer can include a 3' overhang that can be ligated to the 5' overhang. The priming region on the assay primer can be any primer described herein, e.g., a poly (T) primer, a random N-mer primer, a target-specific primer, or an analyte capture agent capture sequence.

In some examples, an oligonucleotide can includes an adapter, e.g., a 5' overhang with 10 nucleotides. The adapter can be ligated to assay primers, each of which includes a 3' overhang with 10 nucleotides that complementary to the 5' overhang of the adapter. The capture probe can be used in any assay by attaching to the assay primer designed for that assay.

Adapters and assay primers can be used to allow the capture probe or the analyte capture agent to be attached to any suitable assay primers and used in any suitable assays. A capture probe that includes a spatial barcode can be attached to a bead that includes a poly(dT) sequence. A capture probe including a spatial barcode and a poly(T) sequence can be used to assay multiple biological analytes as generally described herein (e.g., the biological analyte includes a poly(A) sequence or is coupled to or otherwise is associated with an analyte capture agent comprising a poly (A) sequence as the analyte capture sequence).

A splint oligonucleotide with a poly(A) sequence can be used to facilitate coupling to a capture probe that includes a spatial barcode and a second sequence that facilitates coupling with an assay primer. Assay primers include a sequence complementary to the splint oligo second sequence and an assay-specific sequence that determines assay primer functionality (e.g., a poly(T) primer, a random N-mer primer, a target-specific primer, or an analyte capture agent capture sequence as described herein).

In some embodiments of any of the spatial profiling methods described herein, a feature can include a capture probe that includes a spatial barcode comprising a switch oligonucleotide, e.g., with a 3' end 3rG. For example, a feature (e.g., a gel bead) with a spatial barcode functionalized with a 3rG sequence can be used that enables template switching (e.g., reverse transcriptase template switching), but is not specific for any particular assay. In some embodiments, the assay primers added to the reaction can determine which type of analytes are analyzed. For example, the assay primers can include binding domains capable of binding to target biological analytes (e.g., poly (T) for mRNA, N-mer for genomic DNA, etc.). A capture probe (e.g., an oligonucleotide capable of spatial profiling) can be generated by using a reverse transcriptase enzyme/polymerase to extend, which is followed by template switching onto the barcoded adapter oligonucleotide to incorporate the barcode and other functional sequences. In some embodiments, the assay primers include capture domains capable of binding to a poly(T) sequence for mRNA analysis, random primers for genomic DNA analysis, or a capture sequence that can bind a nucleic acid molecule coupled to an analyte binding moiety (e.g., a an analyte capture sequence of an analyte capture agent) or a nucleic acid molecule that can function in as a perturbation reagent (e.g., a CRISPR crRNA/sgRNA, TALEN, zinc finger nuclease, and/or antisense oligonucleotide as described herein).

V. Systems for Sample Analysis

The methods described above for analyzing biological samples can be implemented using a variety of hardware components. In this section, examples of such components are described. However, it should be understood that in general, the various steps and techniques discussed herein can be performed using a variety of different devices and system components, not all of which are expressly set forth.

Figure 26A:
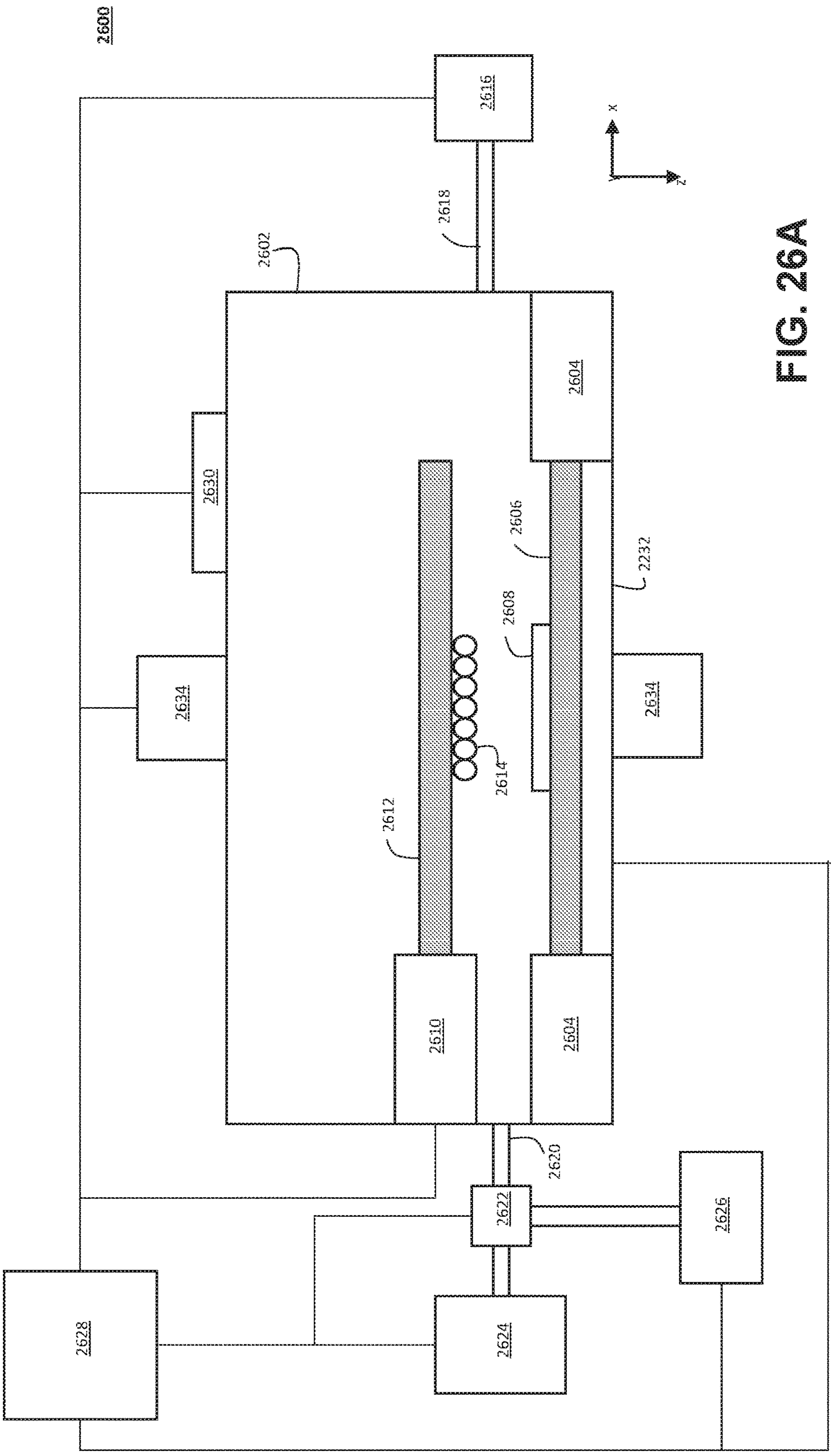
FIG. 26A is a schematic diagram showing an example sample handling apparatus that can be used to implement various steps and methods described herein.

FIG. 26A is a schematic diagram showing an example sample handling apparatus 2600. Sample handling apparatus 2600 includes a sample chamber 2602 that, when closed or sealed, is fluid-tight. Within chamber 2602, a first holder 2604 holds a first substrate 2606 on which a sample 2608 is positioned. Sample chamber 2602 also includes a second holder 2610 that holds a second substrate 2612 with an array of features 2614, as described above.

A fluid reservoir 2616 is connected to the interior volume of sample chamber 2602 via a fluid inlet 2618. Fluid outlet 2620 is also connected to the interior volume of sample chamber 2602, and to valve 2622. In turn, valve 2622 is connected to waste reservoir 2624 and, optionally, to analysis apparatus 2626. A control unit 2628 is electrically connected to second holder 2610, to valve 2622, to waste reservoir 2624, and to fluid reservoir 2616.

During operation of apparatus 2600, any of the reagents, solutions, and other biochemical components described above can be delivered into sample chamber 2602 from fluid reservoir 2616 via fluid inlet 2618. Control unit 2628, connected to fluid reservoir 2616, can control the delivery of reagents, solutions, and components, and adjust the volumes and flow rates according to programmed analytical protocols for various sample types and analysis procedures. In some embodiments, fluid reservoir 2616 includes a pump, which can be controlled by control unit 2628, to facilitate delivery of substances into sample chamber 2602.

In certain embodiments, fluid reservoir 2616 includes a plurality of chambers, each of which is connected to fluid inlet 2618 via a manifold (not shown). Control unit 2628 can selectively deliver substances from any one or more of the multiple chambers into sample chamber 2602 by adjusting the manifold to ensure that the selected chambers are fluidically connected to fluid inlet 2618.

In general, control unit 2628 can be configured to introduce substances from fluid reservoir 2616 into sample chamber 2602 before, after, or both before and after, sample 2608 on first substrate 2606 has interacted with the array of features 2614 on first substrate 2612. Many examples of such substances have been described previously. Examples of such substances include, but are not limited to, permeabilizing agents, buffers, fixatives, staining solutions, washing solutions, and solutions of various biological reagents (e.g., enzymes, peptides, oligonucleotides, primers).

To initiate interaction between sample 2608 and feature array 2614, the sample and array are brought into spatial proximity. To facilitate this step, second holder 2610—under the control of control unit 2628—can translate second substrate 2612 in any of the x-, y-, and z-coordinate directions. In particular, control unit 2628 can direct second holder 2610 to translate second substrate 2612 in the z-direction so that sample 2608 contacts, or nearly contacts, feature array 2614.

In some embodiments, apparatus 2600 can optionally include an alignment sub-system 2630, which can be electrically connected to control unit 2628. Alignment sub-system 2630 functions to ensure that sample 2608 and feature array 2614 are aligned in the x-y plane prior to translating second substrate 2612 in the z-direction so that sample 2608 contacts, or nearly contacts, feature array 2614.

Alignment sub-system 2630 can be implemented in a variety of ways. In some embodiments, for example, alignment sub-system 2630 includes an imaging unit that obtains one or more images showing fiducial markings on first substrate 2606 and/or second substrate 2612. Control unit 2618 analyzes the image(s) to determine appropriate translations of second substrate 2612 in the x- and/or y-coordinate directions to ensure that sample 2608 and feature array 2614 are aligned prior to translation in the z-coordinate direction.

In certain embodiments, control unit 2628 can optionally regulate the removal of substances from sample chamber 2602. For example, control unit 2628 can selectively adjust valve 2622 so that substances introduced into sample chamber 2602 from fluid reservoir 2616 are directed into waste reservoir 2624. In some embodiments, waste reservoir 2624 can include a reduced-pressure source (not shown) electrically connected to control unit 2628. Control unit 2628 can adjust the fluid pressure in fluid outlet 2620 to control the rate at which fluids are removed from sample chamber 2602 into waste reservoir 2624.

In some embodiments, analytes from sample 2608 or from feature array 2614 can be selectively delivered to analysis apparatus 2626 via suitable adjustment of valve 2622 by control unit 2628. As described above, in some embodiments, analysis apparatus 2626 includes a reduced-pressure source (not shown) electrically connected to control unit 2628, so that control unit 2628 can adjust the rate at which analytes are delivered to analysis apparatus 2626. As such, fluid outlet 2620 effectively functions as an analyte collector, while analysis of the analytes is performed by analysis apparatus 2626. It should be noted that not all of the workflows and methods described herein are implemented via analysis apparatus 2626. For example, in some embodiments, analytes that are captured by feature array 2614 remain bound to the array (i.e., are not cleaved from the array), and feature array 2614 is directly analyzed to identify specifically-bound sample components.

In addition to the components described above, apparatus 2600 can optionally include other features as well. In some embodiments, for example, sample chamber 2602 includes a heating sub-system 2632 electrically connected to control unit 2628. Control unit 2628 can activate heating sub-system 2632 to heat sample 2608 and/or feature array 2614, which can help to facilitate certain steps of the methods described herein.

In certain embodiments, sample chamber 2602 includes an electrode 2634 electrically connected to control unit 2628. Control unit 2628 can optionally activate electrode 2634, thereby establishing an electric field between the first and second substrates. Such fields can be used, for example, to facilitate migration of analytes from sample 2608 toward feature array 2614.

Figure 26B:
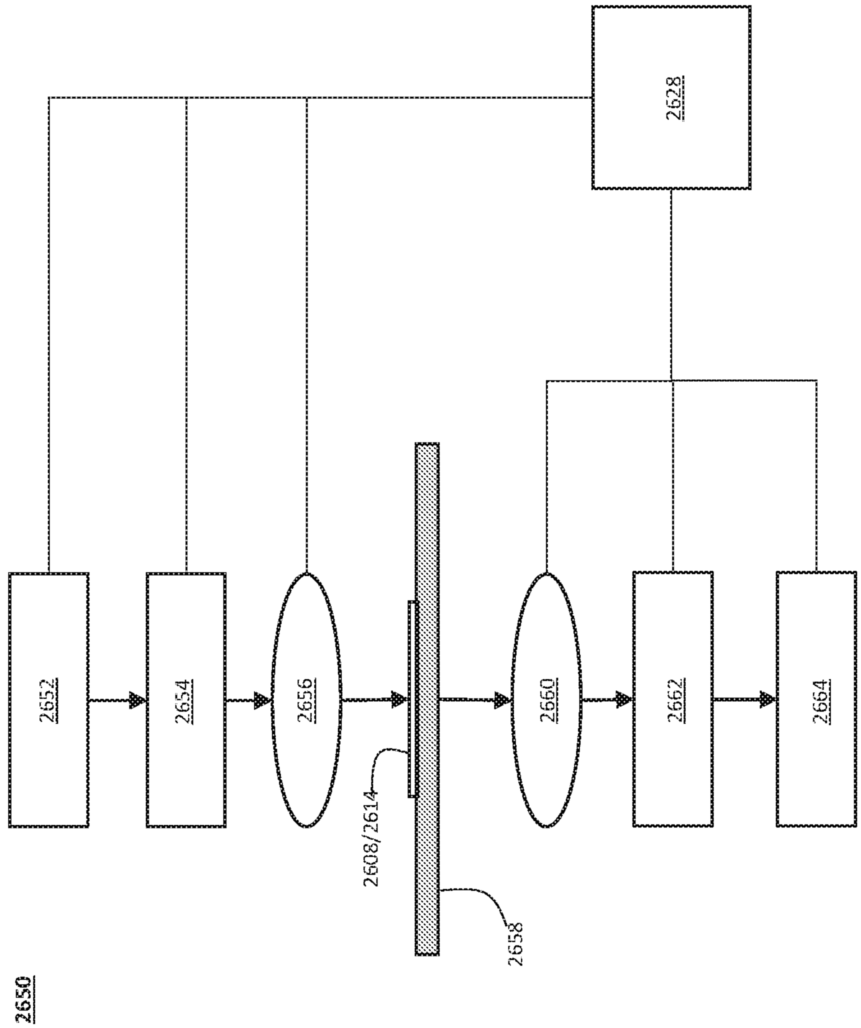
FIG. 26B is a schematic diagram showing an example imaging apparatus that can be used to obtain images of biological samples, analytes, and arrays of features.

In some of the methods described herein, one or more images of a sample and/or a feature array are acquired. Imaging apparatus that is used to obtain such images can generally be implemented in a variety of ways. FIG. 26B shows one example of an imaging apparatus 2650. Imaging apparatus 2650 includes a light source 2652, light conditioning optics 2654, light delivery optics 2656, light collection optics 2660, light adjusting optics 2662, and a detection sub-system 2664. Each of the foregoing components can optionally be connected to control unit 2628, or alternatively, to another control unit. For purposes of explanation below, it will be assumed that control unit 2628 is connected to the components of imaging apparatus 2650.

During operation of imaging apparatus 2650, light source 2652 generates light. In general, the light generated by source 2652 can include light in any one or more of the ultraviolet, visible, and/or infrared regions of the electromagnetic spectrum. A variety of different light source elements can be used to generate the light, including (but not limited to) light emitting diodes, laser diodes, laser sources, fluorescent sources, incandescent sources, and glow-discharge sources.

The light generated by light source 2652 is received by light conditioning optics 2654. In general, light conditioning optics 2654 modify the light generated by light source 2652 for specific imaging applications. For example, in some embodiments, light conditioning optics 2654 modify the spectral properties of the light, e.g., by filtering out certain wavelengths of the light. For this purpose, light conditioning optics 2654 can include a variety of spectral optical elements, such as optical filters, gratings, prisms, and chromatic beam splitters.

In certain embodiments, light conditioning optics 2654 modify the spatial properties of the light generated by light source 2652. Examples of components that can be used for this purpose include (but are not limited to) apertures, phase masks, apodizing elements, and diffusers.

After modification by light conditioning optics 2654, the light is received by light delivery optics 2656 and directed onto sample 2608 or feature array 2614, either of which is positioned on a mount 2658. Light conditioning optics 2654 generally function to collect and direct light onto the surface of the sample or array. A variety of different optical elements can be used for this purpose, and examples of such elements include, but are not limited to, lenses, mirrors, beam splitters, and various other elements having non-zero optical power.

Light emerging from sample 2608 or feature array 2614 is collected by light collection optics 2660. In general, light collection optics 2660 can include elements similar to any of those described above in connection with light delivery optics 2656. The collected light can then optionally be modified by light adjusting optics 2662, which can generally include any of the elements described above in connection with light conditioning optics 2654.

The light is then detected by detection sub-system 2664. Generally, detection sub-system 2664 functions to generate one or more images of sample 2608 or feature array 2614 by detecting light from the sample or feature array. A variety of different imaging elements can be used in detection sub-system 2664, including CCD detectors and other image capture devices.

Each of the foregoing components can optionally be connected to control unit 2628 as shown in FIG. 26B, so that control unit 2628 can adjust various properties of the imaging apparatus. For example, control unit 2628 can adjust the position of sample 2608 or feature array 2614 relative to the position of the incident light, and also with respect to the focal plane of the incident light (if the incident light is focused). Control unit 2628 can also selectively filter both the incident light and the light emerging from the sample.

Imaging apparatus 2650 can typically obtain images in a variety of different imaging modalities. In some embodiments, for example, the images are transmitted light images, as shown in FIG. 26B. In certain embodiments, apparatus 2650 is configured to obtain reflection images. In some embodiments, apparatus 2650 can be configured to obtain birefringence images, fluorescence images, phosphorescence images, multiphoton absorption images, and more generally, any known image type.

In general, control unit 2628 can perform any of the method steps described herein that do not expressly require user intervention by transmitting suitable control signals to the components of sample handling apparatus 2600 and/or imaging apparatus 2650. To perform such steps, control unit 2628 generally includes software instructions that, when executed, cause control unit 2628 to undertake specific steps. In some embodiments, control unit 2628 includes an electronic processor and software instructions that are readable by the electronic processor, and cause the processor to carry out the steps describe herein. In certain embodiments, control unit 2628 includes one or more application-specific integrated circuits having circuit configurations that effectively function as software instructions.

Figure 26C:
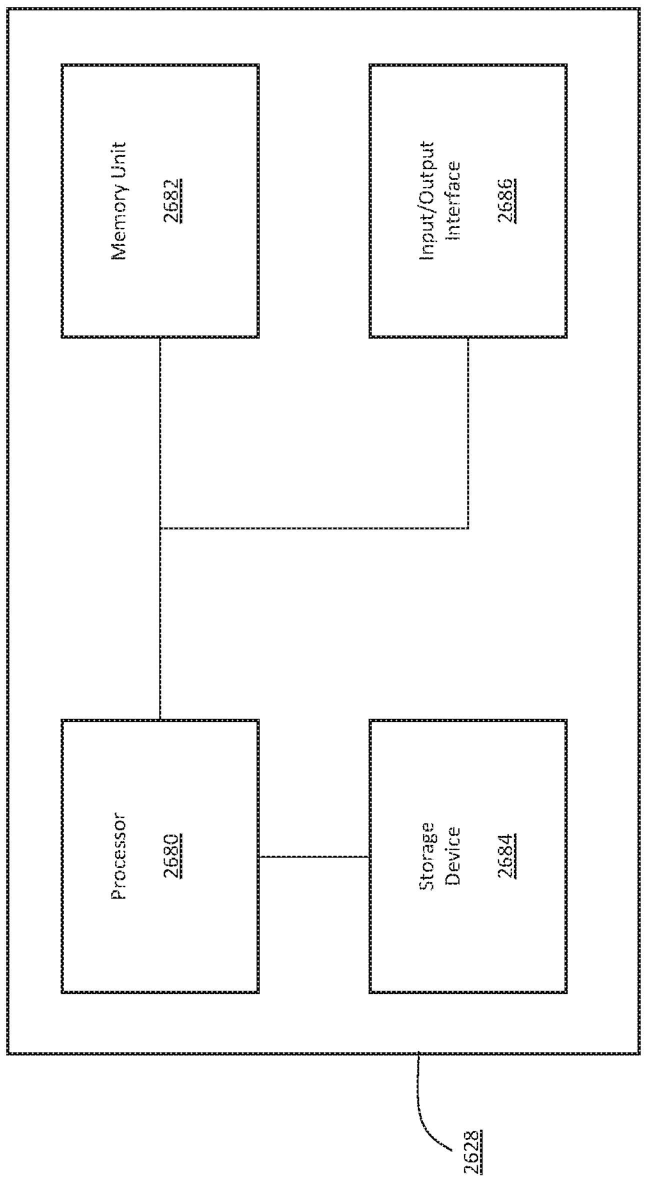
FIG. 26C is a schematic diagram of an example of a control unit of the apparatus of FIGS. 26A and 26B.

Control unit 2628 can be implemented in a variety of ways. FIG. 26C is a schematic diagram showing one example of control unit 2628, including an electronic processor 2680, a memory unit 2682, a storage device 2684, and an input/output interface 2686. Processor 2680 is capable of processing instructions stored in memory unit 2682 or in storage device 2684, and to display information on input/output interface 2686.

Memory unit 2682 stores information. In some embodiments, memory unit 2682 is a computer-readable medium. Memory unit 2682 can include volatile memory and/or non-volatile memory. Storage device 2684 is capable of providing mass storage, and in some embodiments, is a computer-readable medium. In certain embodiments, storage device 2684 may be a floppy disk device, a hard disk device, an optical disk device, a tape device, a solid state device, or another type of writeable medium.

The input/output interface 2686 implements input/output operations. In some embodiments, the input/output interface 2686 includes a keyboard and/or pointing device. In some embodiments, the input/output interface 2686 includes a display unit for displaying graphical user interfaces and/or display information.

Instructions that are executed and cause control unit 2628 to perform any of the steps or procedures described herein can be implemented in digital electronic circuitry, or in computer hardware, firmware, or in combinations of these. The instructions can be implemented in a computer program product tangibly embodied in an information carrier, e.g., in a machine-readable storage device, for execution by a programmable processor (e.g., processor 2680). The computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

Processor 2680 can include any one or more of a variety of suitable processors. Suitable processors for the execution of a program of instructions include, by way of example, both general and special purpose microprocessors, and the sole processor or one of multiple processors of any kind of computer or computing device.

VI. Resolving Spatial Arrays

Spatial analysis involves associating analyte measurements with specific locations in a sample to provide a complete picture of sample biochemical function. This disclosure features methods for associating spatial array features and capture probes linked to the features which bind to specific sample analytes, with spatial locations in the array. In this manner, when an analyte is extracted and detected from a biological sample, the analyte's spatial location information within the sample is preserved, enabling spatially-resolved measurements to be performed for a wide variety of analytes at high resolution.

(i) Capture Probes

Figure 22A:
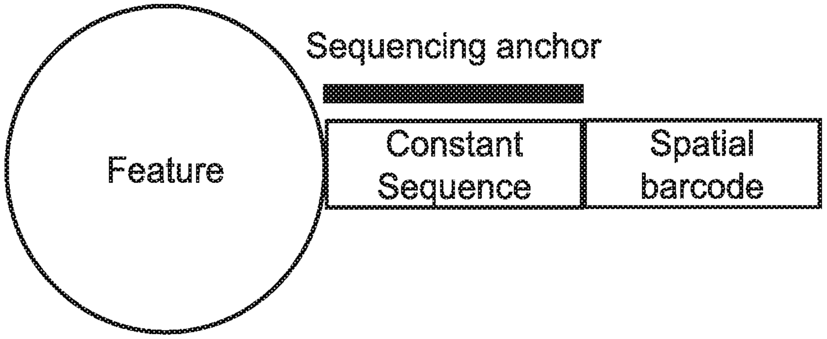
FIGS. 22A-B are schematic diagrams showing example capture probes featuring a constant sequence and one or more spatial barcodes and a sequencing anchor.
Figure 22B:
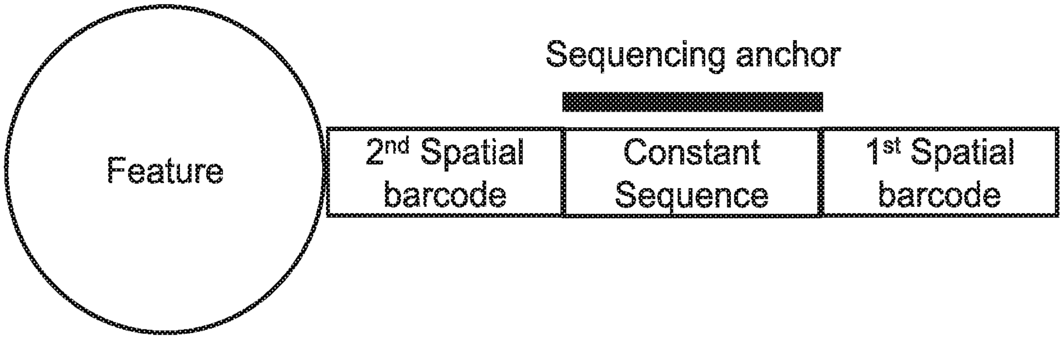

This disclosure features methods and systems for determining sequences of spatial barcodes that are part of capture probes in a spatial array of features, and associating each capture probe with a specific location on a substrate (i.e, the substrate that supports the array of features). FIGS. 22A and 22B are schematic diagrams showing examples of capture probes attached to array features. In some embodiments of the spatial analysis methods described herein, one or more capture probes includes a unique spatial barcode and a constant sequence (FIG. 22A). For example, a capture probe can include, from the 5' end to the 3' end, a cleavage domain, a constant sequence, a unique spatial barcode, and a capture domain. In some embodiments, the capture probe also includes a UMI. For example, a capture probe can include from 5' to 3' a cleavage domain, a constant sequence, a unique spatial barcode, a UMI, and a capture domain.

In some embodiments, one or more capture probes includes a capture probe with a first unique spatial barcode and a second unique spatial barcode (FIG. 22B). For example, a capture probe can include from 5' to 3' a cleavage domain, a second unique spatial barcode, a constant sequence, a first unique spatial barcode and a capture domain. In some embodiments, the capture probe also includes a UMI. For example, a capture probe can include from 5' to 3' a cleavage domain, a second unique spatial barcode, a constant sequence, a first unique spatial barcode, a UMI, and a capture domain.

In some embodiments, an oligonucleotide (e.g., a capture probe) includes a constant sequence. As used herein, a "constant sequence" refers to a sequence that is identical for all oligonucleotides (e.g., capture probes) within a plurality of oligonucleotides (e.g., capture probes). For example, a spatial array with a feature or plurality of features where the feature or plurality of features includes a plurality of capture probes and the capture probes include a constant sequence, the constant sequence will be identical for all capture probes. In some embodiments, a spatial array having a feature or plurality of features where the feature or plurality of features having a plurality of capture probes and the capture probes include a constant sequence, the capture probes can have constant sequences that are at least 70% identical (e.g., at least 75% identical, at least 80% identical, at least 85% identical, at least 90% identical, at least 95% identical, or at least 99% identical). In some embodiments, the constant sequence includes a sequence that is used for initiating a sequencing reaction. For example, an oligonucleotide (e.g., sequencing anchor) can bind to the constant sequence and serve as the substrate for a sequencing reaction. In some embodiments, the constant sequence includes a sequence that is complementary to a sequencing anchor. For example, the sequencing anchor has enough complementarity with the constant sequence so as to facilitate binding and serve as a substrate for a sequencing by hybridization (e.g., sequencing by ligation) reaction.

In some embodiments, the constant sequence can bind to a priming oligonucleotide (e.g., a primer capable of binding to and serving as a substrate for a nucleic acid extension reaction). In such cases, the priming oligonucleotide can amplify the portion of the capture probe that is downstream (3') of the constant sequence. Amplification can be done using isothermal or non-isothermal amplification reactions. Amplification can be done prior to a sequencing by hybridization action. In some embodiments, amplification of the capture probe is done by rolling circle amplification, where the subsequent sequencing by hybridization uses the amplified capture probe as a template.

(ii) Analyte Capture

A spatial array that includes a plurality of features, with at least some of the features including one or more capture probes (e.g., the capture probes shown in FIGS. 22A and 22B) can be fabricated using any of the methods described herein. Following fabrication of the array, a biological sample is brought into contact with the array features and, for example, one or more analytes bind to the capture probes attached to the array features. Migration of the analytes from the sample to the capture probes occurs in spatially-resolved fashion—that is, the relative spatial relationships among the analytes in the sample are preserved—so that the spatial relationships of the analytes bound to the capture probes of the array is representative of the spatial relationships among the analytes in the sample.

(iii) Sequence and Location Determination for Spatial Barcodes

Following the capture of analytes from the sample by specific array features, the locations of the array features are determined within the array, so that specific captured analytes can be associated with specific locations within the sample.

Figure 23:
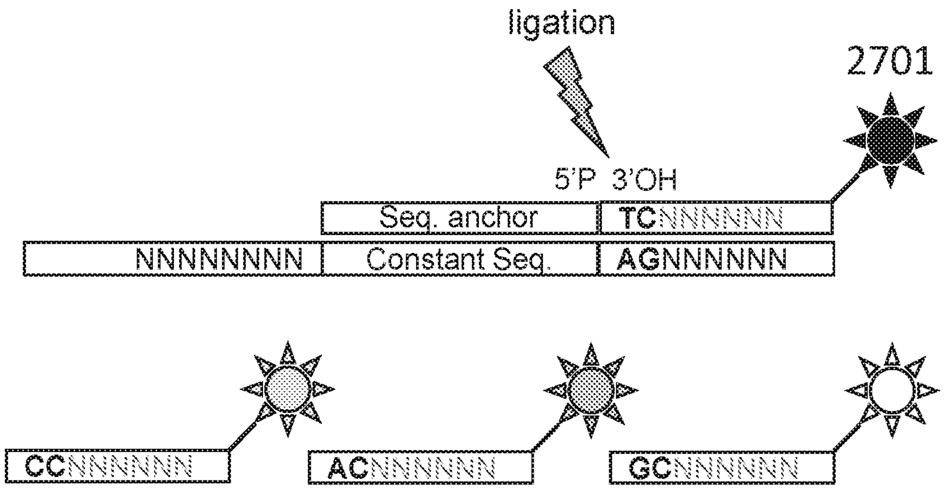
FIG. 23 is a schematic diagram showing sequencing by ligation of a spatial barcode using (1) the 5' phosphate of the sequencing anchor, (2) the 3' OH of the sequencing probe and (3) the complementarity between the nucleic acid at the first 3' position of the sequencing probe and the spatial barcode sequence as substrates in a ligation reaction.

To determine the location of the feature on the array, a sequencing anchor can be hybridized to the constant sequence of a capture probe linked to the feature. Then, the feature (i.e., the capture probe) is contacted with a composition that includes multiple different sequencing probes. In general, the sequencing probes are of the same length, but include different nucleic acids in at least one non-degenerate position in each sequence. FIG. 23 is a schematic diagram that shows one example of a sequencing procedure that can be used to determine both the sequence of a spatial barcode of a capture probe, and a location of the capture probe (and the feature to which the capture probe is attached) within a spatial array.

In FIG. 23, the composition includes four different sequencing probes, each of which has a different nucleic acid in the first sequence position adjacent the 3' end. The sequencing probe that is complementary to the spatial barcode at the non-degenerate position is ligated to the sequencing anchor, and hybridizes to the spatial barcode. The non-hybridized sequencing probes are removed (e.g., washed away). Then, an image of the first label 2701 of the hybridized sequencing probe is obtained.

The label can be, for example, an optical label, a radioactive label, a fluorescent label, an enzymatic label, a chemiluminescent label, a bioluminescent label, a dye, or any of the other optical labels described herein. The image of the first label provides a spatial location of the first label in the image relative to other features of the array, such as a fiducial mark positioned on a substrate that supports the array. Because the first label corresponds to the location of the capture probe and the feature to which it is attached, the feature is then associated with a location in the spatial array, e.g., by reference to the feature's location relative to a reference location such as a fiducial mark or another mark associated with the array. That is, the feature location corresponds to the label location in the array, as determined from the image.

In addition, because each sequencing probe in the composition has a different label, measurement of spectrally resolved absorption or emission of radiation from the hybridized sequencing probe reveals the identity of the nucleic acid at the non-degenerate position in the probe's sequence. The nucleic acid is complementary to the nucleic acid at the corresponding location in the spatial barcode sequence, and so the image of the label reveals the identity of the nucleic acid at the corresponding location in the spatial barcode sequence.

The capture probe can then be contacted with successive compositions of sequencing probes in similar fashion. Each successive composition includes sequencing probes having different nucleic acids in one or more non-degenerate positions, and degenerate bases in the remaining positions. For example, the second sequencing probe that hybridizes to the spatial barcode in FIG. 23 can include a known nucleic acid in the second position from the 3' end, and with degenerate bases in the remaining positions. Imaging the label of the second sequencing probe reveals the identity of the nucleic acid at the corresponding second location in the spatial barcode sequence. In this manner, exposure of the capture probe and its spatial barcode to successive compositions allows step-wise determination of the sequence of the spatial barcode of the capture probe attached to the feature.

The foregoing process can be repeated for multiple features in a spatial array, to determine sequences of capture probes linked to each of the multiple features, and to associate each of the multiple features with a different spatial location in the spatial array, relative to one or more reference locations such as fiducial marks.

In some embodiments, the complete sequence of the spatial barcode is determined. In some embodiments, only a portion of the complete sequence of the spatial barcode is determined. For example, to uniquely distinguish among the spatial barcodes of the capture probes in the array, it may be sufficient to determine only a portion of the complete sequence of each spatial barcode. Accordingly, the sequencing process can be terminated when a sufficient portion of each spatial barcode has been sequenced to unambiguously distinguish the spatial barcodes from one another.

In some embodiments, as shown in FIG. 23, among sequencing probes in a composition, the sequencing probe nucleic acid sequences differ at only a single non-degenerate nucleic acid position. Accordingly, each sequencing step determines the sequence of the spatial barcode at a single position in the spatial barcode sequence.

In some embodiments, the sequencing probes in a composition differ at two (or more) non-degenerate positions. Each sequencing step therefore determines the sequence of the spatial barcode at two positions in the spatial barcode sequence. The two non-degenerate positions can be adjacent or non-adjacent in the sequences of the sequencing probes, and consequently, the sequence of the spatial barcode can be determined at sequential or non-sequential positions using such compositions.

After each sequencing probe has been hybridized and the sequence of a portion of the spatial barcode determined, the hybridized sequencing probe can be removed, e.g., via nuclease cleaveage. To facilitate cleaveage, in some embodiments, sequencing probes include a nuclease recognition site.

In some embodiments, cleavage of the sequencing probe removes the probe entirely from the spatial barcode. In some embodiments, cleavage of the sequencing probe removes only a first portion of the probe, and leaves a second portion of the sequencing probe hybridized to the spatial barcode. However, provided the second portion of the probe provides an appropriate ligation site, a successive sequencing probe can be ligated to the remaining second portion of the probe, and can hybridize to the spatial barcode to extend the sequencing procedure. In some embodiments, the removed first portion of the sequencing probe includes the label.

In some embodiments, determining the complete sequence of the spatial barcode includes sequentially hybridizing three or more (e.g., four or more, five or more, six or more, eight or more, ten or more, 12 or more, 15 or more, 20 or more) sequencing probes to the spatial barcode, each of which determines a portion of the spatial barcode sequence. The spatial barcode sequence typically includes 3 or more (e.g., 4 or more, 5 or more, 6 or more, 7 or more, 8 or more, 9 or more, 10 or more, 11 or more, 12 or more, 13 or more, 14 or more, 15 or more, 20 or more) nucleic acids. In some embodiments, the spatial barcode sequence includes between 5 and 15 (e.g., between 6 and 12, between 6 and 10) nucleic acids.

More generally, the spatial barcode can include N nucleic acids (where N corresponds to any of the examples above), and the complete sequence of the spatial barcode can be determined by sequentially hybridizing N different sequencing probes to the spatial barcode, in which case the spatial barcode sequence is determined stepwise, one nucleic acid at a time. Alternatively, the complete sequence of the spatial barcode can be determined by sequentially hybridizing fewer than N different sequencing probes to the spatial barcode. In such a case, at least one of the sequencing probes, or more than one of the sequencing probes, determines more than one nucleic acid of the spatial barcode sequence.

In some embodiments, successively hybridized sequencing probes have the same sequence length. In some embodiments, successively hybridized sequencing probes have different lengths. For example, for a spatial barcode sequence of length N as described above, a hybridized sequencing probe can be from 1 nucleic acid in length to any length, including lengths of N nucleic acids or more.

In some embodiments, successive sequencing probes hybridize to a common region of the spatial barcode sequence, which can be the entire spatial barcode sequence, or only a subset of the entire sequence. In certain embodiments, successive sequencing probes hybridize to different portions of the spatial barcode sequence.

In some embodiments, successive sequencing probes are used to determine the sequence of the spatial barcode at successive positions in the sequence. For example, the first sequencing probe determines the spatial barcode sequence at the first position, the second sequencing probe determines the spatial barcode sequence at the second position, and so on in consecutive fashion. In some embodiments, the sequence of the spatial barcode is determined at least partly at non-successive locations. The locations at which the sequence is determined can be selected, for example, based on the compositions of the sequencing probes and the non-degenerate sequence positions for the probes in a particular composition.

In some embodiments, as discussed above, the capture probe can include a second spatial barcode, such that the first and second barcodes are unique relative to one another. In general, the sequence of the second spatial barcode can be determined in a manner analogous to the determination of the first spatial barcode, and all of the aspects discussed above apply in analogous fashion to the determination of the second spatial barcode sequence.

In some embodiments, all or a portion of the sequence of the first unique spatial barcode is determined prior to determination of all or a portion of the sequence of the second unique spatial barcode. In some embodiments where the first unique spatial barcode is determined using any of the methods described herein, the sequencing anchor is not removed prior to determining all or a portion of the sequence of the second unique spatial barcode. For example, the methods described herein are repeated until as much of the sequence of the first unique spatial barcode that can be determined is determined without having to remove the sequencing anchor.

In some embodiments, all or a portion of the sequence of the second unique spatial barcode is determined prior to determination of all or a portion of the sequence of the first unique spatial barcode. In some embodiments where the second unique spatial barcode is determined using any of the methods described herein, the sequencing anchor is not removed prior to determining all or a portion of the sequence of the first unique spatial barcode. For example, the methods described herein are repeated until as much of the sequence of the second unique spatial barcode that can be determined is determined without having to remove the sequencing anchor.

Figure 24:
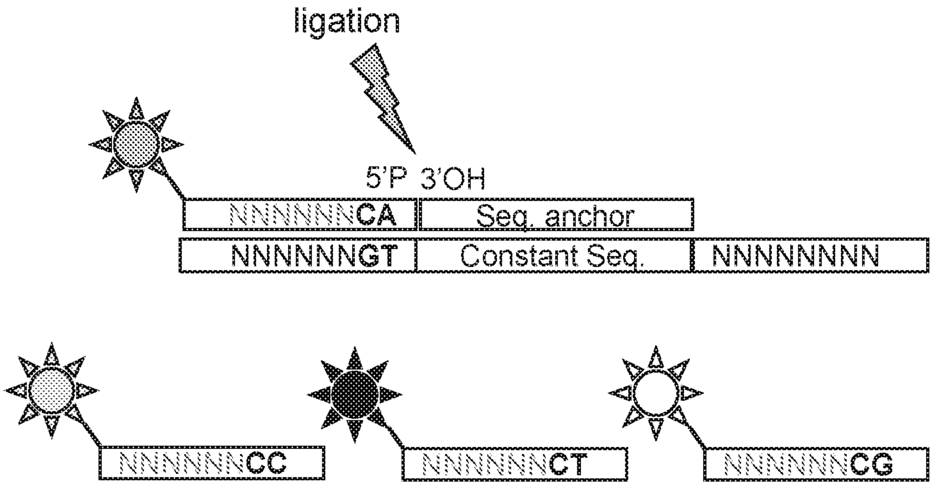
FIG. 24 is a schematic diagram showing sequencing by ligation of a spatial barcode using (1) the 3' OH of the sequencing anchor, (2) the 5' phosphate of the sequencing probe, and (3) the complementarity between the nucleic acid at the first 5' position of the sequencing probe and the spatial barcode sequence as substrates in a ligation reaction.

The sequencing methodology described above can generally be implemented in a variety of different ways. As discussed above, a sequencing anchor binds to the constant sequence of the capture probe and serves as a substrate for a sequencing by hybridization reaction. In some embodiments, the sequencing by hybridization reaction relies in part on the ligation of a sequencing probe to either the 5' phosphate or the 3' OH of a sequencing anchor (e.g., a sequencing anchor hybridized to the constant sequence) (see the examples shown schematically in FIG. 23 and FIG. 24, respectively).

In some embodiments, the sequencing anchor includes a free 5' phosphate that serves as a substrate for a ligation reaction. In such cases, the 3' OH is provided by the sequencing probe. The sequencing anchor's free 5' phosphate can be dephosphorylated by any variety of phosphatases known in the art (e.g., shrimp alkaline phosphatase). In some embodiments, the sequencing anchor does not include a free 5' phosphate group. In such cases, the 5' phosphate can be provided by any variety of kinases known in the art (e.g., T4 polynucleotide kinase). In some embodiments, a sequencing anchor includes a 3' OH that serves as a substrate for a ligation reaction. In such cases, the 5' phosphate is provided by a sequencing probe. In some embodiments, the sequencing anchor is at least at least 70% identical (e.g., at least 75% identical, at least 80% identical, at least 85% identical, at least 90% identical, at least 95% identical, or at least 99% identical) to the complementary sequence of the constant sequence.

In some embodiments, a sequencing anchor has a sequence that is n−1 bases different from the original sequence anchor. For example, a sequencing anchor having a sequence of 3'-ACTGTCCGATAGTTAGACTG-5' can have an n−1 sequence of 3'-ACTGTCCGATAGTTAGACT-5', wherein the 5' G is removed. In cases where the sequence to be determined is located 5' to the sequencing anchor, the nucleic acids to be removed in an n−1 sequencing anchor will be removed from the 5' of the sequencing anchor. In some embodiments, the sequencing anchor is n−1 bases different from the original sequencing anchor but includes an additional one or more bases. For example, the sequencing anchor that is n−1 of the original sequencing anchor includes a nucleic acid that is immediately 3' of the original constant sequence (e.g., the base is complementary to the base immediately 5' to the constant sequence in the capture probe). In some embodiments where the sequence to be determined is located 3' to the sequencing anchor, the nucleic acids to be removed in an n−1 sequencing anchor will be removed from the 3' end of the sequencing anchor.

In some embodiments, a sequencing anchor has a sequence that is n−2 bases different from the original sequencing anchor. For example, a sequencing anchor having a sequence of 3'-ACTGTCCGATAGTTAGACTG-5' can have an n−2 sequence of 3'-ACTGTCCGATAGTTAGAC-5', wherein the 5' TG is removed. In cases where the sequence to be determined is located 5' to the sequencing anchor, the nucleic acids to be removed in an n−2 sequencing anchor will be removed from the 5' of the sequencing anchor. In some embodiments, the sequencing anchor is n−2 bases different from the original sequencing anchor but includes an additional one or more bases. For example, the sequencing anchor that is n−2 of the original sequencing anchor includes one or more nucleic acids that are immediately 3' of the original constant sequence (e.g., the one or more bases are complementary to the bases immediately 5' to the constant sequence in the capture probe). In some embodiments, where the sequence to be determined is located 3' to the sequencing anchor, the nucleic acids to be removed in an n−2 sequencing anchor will be removed from the 3' end of the sequencing anchor.

The sequencing probes described herein each generally include (1) at least one base pair that is known prior to contacting the capture probe, and (2) a label that corresponds to the identity (e.g., A, G, C, or T) of the at least one base pair having a known sequence. For example, the when a sequencing probe is complementary to the sequence of the unique spatial barcode the sequencing probe will hybridize (e.g., Watson-Crick base pairing) with the unique spatial barcode and the label will be detectable upon interrogation.

In some embodiments, the sequencing probes can range in length from 6 nucleic acids to about 12 nucleic acids, from about 6 nucleic acids to about 11 nucleic acids, from about 6 nucleic acids to about 10 nucleic acids, from about 6 nucleic acids to about 9 nucleic acids, form about 6 nucleic acids to about 8 nucleic acids, form about 6 nucleic acids to about 7 nucleic acids, from about 7 nucleic acids to about 12 nucleic acids, from about 7 nucleic acids to about 10 nucleic acids, from about 7 nucleic acids to about 9 nucleic acids, from about 7 nucleic acids to about 8 nucleic acids, from about 8 nucleic acids to about 12 nucleic acids, from about 8 nucleic acids to about 11 nucleic acids, from about 8 nucleic acids to about 10 nucleic acids, from about 8 nucleic acids to about 9 nucleic acids, from about 9 nucleic acids to about 12 nucleic acids, from about 9 nucleic acids to about 11 nucleic acids, from about 9 nucleic acids to about 10 nucleic acids, from about 10 nucleic acids to about 12 nucleic acids, from about 10 nucleic acids to about 11 nucleic acids, or from about 11 nucleic acids to about 12 nucleic acids. In some embodiments, the sequencing probes can be 8 nucleic acids in length.

In some embodiments, the sequencing probes include a known nucleic acid sequence located in at least one location within the sequencing probe. For example, the sequencing probe can include a sequence where it is known that an A, G, C, or T is located at the first position in the 3' to 5' orientation sequencing probed. The first position in the 3' to 5' sequence orientation of the sequencing probe can be an A. The first position in the 3' to 5' sequence orientation of the sequencing probe can be a G. The first position in the 3' to 5' sequence orientation of the sequencing probe can be a C. The first position in the 3' to 5' sequence orientation of the sequencing probe can be a T. In cases where the first position of the sequencing probe includes a known sequence, the remaining nucleic acids include a degenerate sequence (e.g., universal bases).

In some embodiments, the sequencing probe can include a sequence where it is known that an A, G, C or T is located at the second position in the 3' to 5' orientation of the sequencing probe. For example, the second position in the 3' to 5' sequence orientation of the sequencing probe can be an A. The second position in the 3' to 5' sequence orientation of the sequencing probe can be a G. The second position in the 3' to 5' sequence orientation of the sequencing probe can be a C. The second position in the 3' to 5' sequence orientation of the sequencing probe can be a T. In cases where, the second position of the sequencing probe includes a known sequence, the remaining nucleic acids include a degenerate sequence (e.g., universal bases).

In some embodiments, the sequencing probe can include a sequence where it is known that an A, G, C, or T is located at the first position in the 5' to 3' orientation of the sequencing probe. The first position in the 5' to 3' sequence orientation of the sequencing probe can be an A. The first position in the 5' to 3' sequence orientation of the sequencing probe can be a G. The first position in the 5' to 3' sequence orientation of the sequencing probe can be a C. The first position in the 5' to 3' sequence orientation of the sequencing probe can be a T. In cases where the first position of the sequencing probe includes a known sequence, the remaining nucleic acids include a degenerate sequence (e.g., universal bases).

In some embodiments, the sequencing probe can include a sequence where it is known that an A, G, C or T is located at the second position in the 5' to 3' orientation of the sequencing probe. For example, the second position in the 5' to 3' sequence orientation of the sequencing probe can be an A. The second position in the 5' to 3' sequence orientation of the sequencing probe can be a G. The second position in the 5' to 3' sequence orientation of the sequencing probe can be a C. The second position in the 5' to 3' sequence orientation of the sequencing probe can be a T. In cases where, the second position of the sequencing probe includes a known sequence, the remaining nucleic acids include a degenerate sequence (e.g., universal bases). In some embodiments, where a sequencing probe includes a first known nucleic acid at a first position (e.g., the first nucleic acid at the 3' end or first nucleic acid at the 5' end) and a second known nucleic acid at a second position (e.g., the second nucleic acid from the 3' end or second nucleic acid at the 5' end), there are 16 possible dinucleotide combinations. For example, the 16 possible dinucleotide combinations include: TA, CG, GC, TA, AC, AA, GA, CA, CC, TC, GT, GG, AG, TG, TT, and CT.

In some embodiments, the sequencing probe can include a sequence where it is known that an A, G, C, or T is present at any of the positions in a 3' to 5' orientation. In some embodiments, the sequencing probe can include a sequence where it is known that an A, G, C, or T is present at any of the positions in a 5' to 3' orientation.

In some embodiments, the nucleic acids included in a sequencing probe and/or a sequencing anchor can be non-natural nucleic acids, modified nucleic acids (e.g., 5' Methyl group, 2' Fluoro) or any of a variety of different nucleic acids that can facilitate the sequencing methods described above. Additional examples of such nucleic acids have been described previously.

In some embodiments, some or all of the sequencing steps described above can be implemented using ABI SOLiD v2.0 sequencing chemistry. The SOLiD v2.0 sequencing chemistry uses a mixture of labeled sequencing probes and queries the input strand with ligase in order to resolve the sequence of interest. The SOLiD v.2.0 chemistry utilizes 1/2 encoding where the nucleic acids at the first two positions of the sequencing primer are known and are associated with a particular fluorescent dye. Each sequencing probe (numbered from the 3' end) includes universal bases at bases 3-5 and one of sixteen specific dinucleotides at positions 1-2 (e.g., known nucleic acid). Positions 6-8 include universal bases and are coupled to one of four fluorescent dyes. In some embodiments, sequencing by hybridization involves providing a spatial array that includes features comprising at least capture probe having a spatial barcode and contacting the capture probe on the spatial array with a sequencing anchor.

In some embodiments, the sequencing anchor is complementary to the constant sequence and provides a 5' phosphate that can be used as a substrate in a ligation reaction. The capture probes, with the sequencing anchor bound, are contacted with a mixture of sequencing probes. If the sequencing probe contains a dinucleotide combination at the 3' end of the sequencing probe that is complementary to the capture probe (e.g., the spatial barcode sequence within the capture probe), then a ligation reaction occurs and the sequencing probe is ligated onto the capture probe (as shown schematically in FIG. 23). The fluorescent dye (or other optical label) associated with that dinucleotide is detectable upon interrogation.

In some embodiments, the sequencing anchor is complementary to the constant sequence and provides a 3' OH that can be used as a substrate in a ligation reaction. The capture probes, with the sequencing anchor bound, are contacted with a mixture of sequencing probes. If the sequencing probe contains a dinucleotide combination at the 5' end of the sequencing probe that is complementary to the capture probe (e.g., the spatial barcode sequence within the capture probe), then a ligation reaction occurs and the sequencing probe is ligated onto the capture probe (as shown schematically in FIG. 24). The fluorescent dye (or other optical label) associated with that dinucleotide is detectable upon interrogation. As described herein, the non-selective nature of the universal bases allows ligation where there is complementarity between the dinucleotides and the capture probe.

Before detection of the fluorescent dye or other optical label, un-bound sequencing probes are washed away and un-extended fragments are capped and treated with phosphatase to prevent un-extended strands from contributing to out of phase ligation events. After one or more images of the capture probes being sequenced have been obtained to obtain fluorescence or other optical information that can be used to identify dinucleotide combinations during sequencing, the fluorescent dye (or other optical label) is removed using a two-step chemical cleavage of the three 5' bases or three 3' bases of the sequencing probe that leaves behind a sequencing probe, including the five most 3' bases or five most 5' bases of the original sequence, which includes a 5' phosphate or a 3' OH.

In some embodiments, the method is repeated with interrogation focusing on bases 6-7 of the template (e.g., bases 6-7 of the unique spatial barcode of the probe). After the first "repeat" (e.g., two runs through the method), a "reset" is performed wherein the sequencing anchor and ligated sequencing probes are removed from the template. A new sequencing anchor that is n−1 nucleic acids different than the sequencing probe used in the first two runs through the method is contacted to the constant sequence. The method is then repeated with the same mixture of sequencing probes, wash, detection, and cleaving steps performed until all or a portion of the sequence of the spatial barcode is determined. In some embodiments where the sequence of a second unique spatial barcode is determined, the method as described herein can be used. In some embodiments, the use of four fluorescent dyes or other distinguishable optical labels means there are four dinucleotide combinations for each label. In order to resolve the sequence of interest following hybridization of these sequencing probes, dibase encoding is used to base call the template sequence (see Applied Biosystems, "Application Note: Principles of Di-Base Sequencing and the Advantages of Color Space Analysis in the SOLiD System" (2008), available from http://biol.wwu.edu/young/470/stuff/abi-solid.pdf, the entire contents of which are incorporated herein by reference.

In some embodiments, the sequencing probe includes universal bases. As used herein, a "universal base" refers to a nucleobase analog that can hybridize non-selectively to each of the native bases (e.g., A, C, G, or T). (See Berger et al., *Nucleic Acid Res.,* 28(15): 2911-2914 (2000), the entire contents of which are incorporated herein by reference.

A sequencing probe that includes a sequence of 3'-ANNNNNNNN-5', where A is a known nucleic acid at a first position and N represents a universal base located at positions two through eight will hybridize to a complementarity sequence only when a T is at the first position on the 5' end (e.g., 5'-TNNNNNNN-3'). The non-selective nature of the universal bases allows ligation where there is complementarity between the known one or more nucleic acids and the complementary strand (e.g., unique spatial barcode sequence). In some embodiments, where there are there are two known nucleic acids in the sequence, ligation occurs between the sequencing probe and the complementary sequence when there is complementarity between the two known nucleic acids and two corresponding nucleic acids in the complementary sequence.

In some embodiments, the sequencing procedure includes a removing step where the sequencing probe is cleaved. Cleavage can result in the release of the portion of the sequencing probe that does not contain complementarity with the template. In some embodiments, complementarity between the sequencing probe and the capture probe occur either at the first one or two nucleic acids at the 3' end of the sequencing probe or at the first one or two nucleic acids at the 5' end of the sequencing probe. For example, when the sequence of interest is downstream (3') of the constant sequence on the template and a sequencing anchor is hybridized to the constant sequence, the sequencing anchor can provide a free 5' phosphate as a substrate for a ligation reaction and the sequencing probes can provide the 3' OH. In such circumstances, the sequencing probe will include nucleic acids with known sequences at the 3' end of the sequencing probe.

When a sequencing probe contains one or two nucleic acids at the 3' end that are complementary to the template, the sequencing probe can be ligated onto the template. In this circumstance, cleavage of the sequencing probe will result in the release (e.g., removal) of the nucleic acids at the 5' positions of the sequencing probe. The cleaved sequencing probe can now serve as a substrate in a new ligation reaction, if following the cleavage step, the sequencing probe retains a free 5' phosphate.

In some embodiments, removal of the sequencing probe occurs by enzymatic cleavage. For example, the sequencing probe can be cleaved by a nuclease. To facilitate cleavage, in some embodiments, the sequencing probe can include a nuclease recognition site, or a recognition site for another cleavage enzyme.

In some examples in the foregoing description, analytes are transferred from the sample to capture probes bound to an array of features, and sequencing of spatial barcodes of the capture probes yields optical information that is also used to determine the spatial locations of the capture probes within the array, and to associate captured analytes with specific locations in the array and sample. In some embodiments, however, capture probes are cleaved from the array and transferred to the sample, where they bind to specific analytes in the sample.

To facilitate spatially resolved sample analysis in this manner, capture probes bound to array features are sequenced as described above prior to capturing analytes. That is, sequencing by hybridization or ligation is performed to determine the individual sequences of the spatial barcodes and to determine the locations of each of the spatial barcodes and the capture probes and features to which they are bound, using the methods described above. After the capture probes and features of the array have been associated with particular spatial locations within the array, the capture probes are cleaved (using any of the methods discussed previously) and transferred to the sample, where they bind sample analytes. Analysis (i.e., sequencing) of the spatial and molecular barcodes following analyte binding according to any of the methods described previously permits determination of the nature of the analytes and their spatial locations within the sample, as physical locations associated with the spatial barcodes have already been determined prior to cleavage of the capture probes from the array of features.

(iv) Fabrication of Spatial Arrays

In some embodiments, spatial arrays with relatively high spatial densities of capture probes can be fabricated from spatial arrays with lower densities of oligonucleotides. Referring to methods shown schematically in FIGS. 25A-25C, a spatial array with a relatively low spatial density of oligonucleotides 2501 is first fabricated using any of the methods described herein.

The oligonucleotides can include a variety of structural features. In some embodiments, at least one oligonucleotide 2501 in the array includes a spatial barcode 2505, a constant sequence 2503, and a capture domain 2507. The location of the oligonucleotide in the spatial array and the sequence of the oligonucleotide can then be determined using the methods discussed above.

Next, a feature 2509 (e.g., a bead) that includes a plurality of capture probes 2511 can be attached to the substrate by coupling the feature to the oligonucleotide. For example, in some embodiments, the bead includes one or more surface-linked moieties that bind to the capture domain of the oligonucleotide. The location of the feature in the spatial array is determined by coupling to the oligonucleotide; the feature location is the same as the location of the oligonucleotide.

If the feature includes a capture probe, the spatial barcode can be sequenced using any of the methods described herein, and the spatial barcode sequence for the feature's capture probe associated with the feature location on the spatial array, so that an analyte that binds to the capture probe can be spatially resolved relative to the spatial array and to a location in the sample. Alternatively, in some embodiments, the feature does not include capture probes with spatial barcodes, and captured analyte locations are determined based on the feature location in the array.

In some embodiments, capture probes on the feature can include primer sequences for assays (e.g., reverse transcription primers). In such cases, the oligonucleotides can optionally include template sequences for the assays. The assays can include any of the sequencing techniques described herein, for example.

Other Embodiments

Figure 25A:
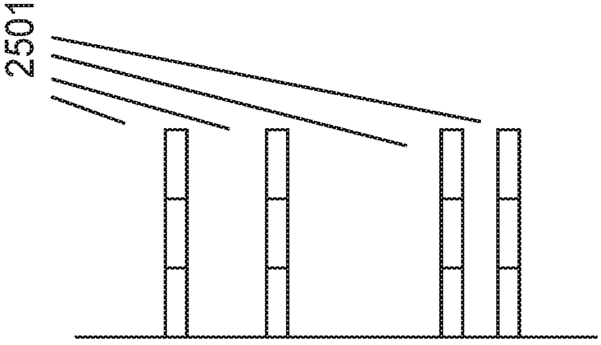
FIGS. 25A-C are schematic drawings showing fabrication of a high resolution spatial array.
Figure 25B:
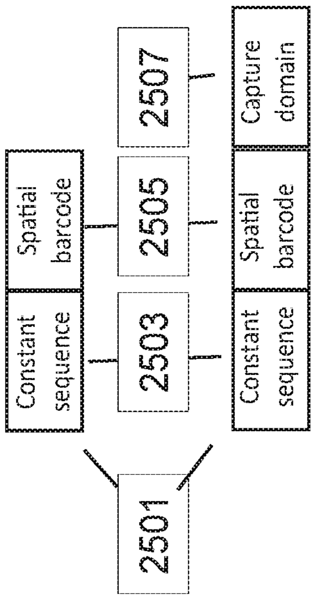
Figure 25C:
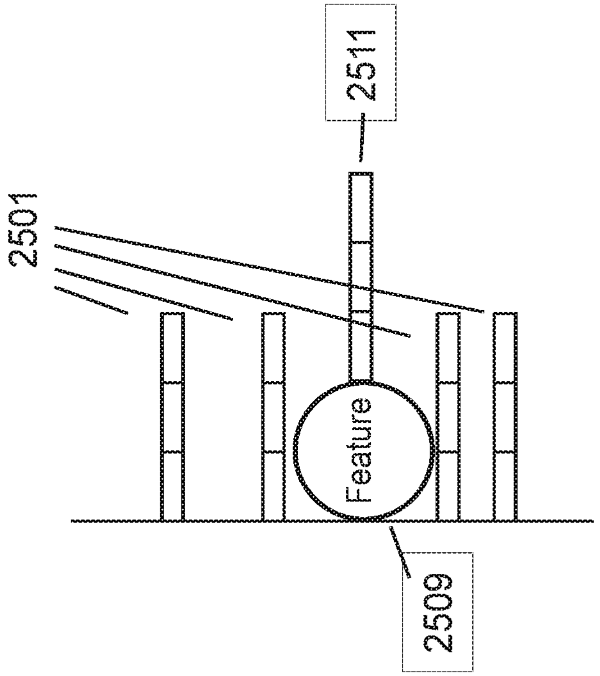

FIG. 25A shows oligonucleotides 2501 printed onto the array in an irregular pattern. In some embodiments as shown in FIG. 25B, the oligonucleotides include at least a constant sequence 2503 and a spatial barcode 2505. In some embodiments, the oligonucleotides include a constant sequence 2503, a spatial barcode 2505, and a capture domain 2507. In some embodiments as shown in FIG. 25C, a plurality of features 2509 where the features include a plurality of capture probes 2511 are delivered onto the array containing the oligonucleotides 2501. In some embodiments, the capture probes 2511 include at least a spatial barcode and a capture domain. In some embodiments, the features are coupled to the oligonucleotides through interaction of the capture domain on the oligonucleotide (e.g., a poly-A sequence) with the capture domain on the capture probe (e.g., a poly-T sequence). In some embodiments, oligonucleotides on the array can act as a template for the capture probes on the features. For example, when an oligonucleotide is coupled to a capture probe through the interaction of the capture domains (e.g., a poly-A sequence on the oligonucleotide interacts with a poly-T sequence on the capture probe), the oligonucleotide can serve as a template in a primer extension reaction. This allows a copy of the spatial barcode from the oligonucleotide to be associated with the capture probe on the feature. This imparts the spatial location from the oligonucleotide onto the capture probe and onto the feature. Overall, this strategy uses features to provide many more capture probes in given area then just through printing alone and uses the oligonucleotides to convey spatial location information.

In some embodiments, oligonucleotides on a substrate are used as a vehicle to deliver gel beads (e.g., or any other feature described herein) containing a plurality of capture probes to small area on the array. In some embodiments, high diversity gel beads (e.g., or any other feature described herein) are added onto a substrate and are used as a vehicle to deliver high-diversity oligonucleotides with high oligonucleotide density in small area on the array. In some embodiments, the pattern of the array can be irregular with regard to the spatial location of the oligonucleotide or gel bead (e.g., or any other feature described herein) on the substrate. In some embodiments, sequencing by hybridization is used to determine the location of the gel beads (e.g., or any other feature described herein) or the oligonucleotides. In such cases, the location of the gel bead (e.g., or any other feature described herein) or the oligonucleotide can serve as an indicator of spatial location on the array for any other oligonucleotide or feature described herein. For example, when an array includes a plurality of oligonucleotides and the location of the oligonucleotides are resolved using sequencing by hybridization and a plurality of features are then delivered onto the array, the location of the oligonucleotides can be used to resolve the location of one or members of the plurality of features.

In some embodiments, multiple rounds of hybridization of sequencing probes having different fluorophores is performed until all or a portion of the spatial barcode of the oligonucleotide is determined. In some embodiments, multiple rounds of hybridization of sequencing probes having different fluorophores is performed until all or a portion of the spatial barcode on the feature is determined. In some embodiments, strategic selection of sequencing probes can reduce the number of hybridization rounds needed to determine the sequence of oligonucleotides or the sequence of the capture probes. For example, by placing the known nucleic acids at different positions in the sequencing probe, the number of cycles of sequencing by hybridization needed to resolve the sequence of the spatial barcode can be reduced. In some embodiments, detection of the label associated with a ligated sequencing probe could be performed at the time of manufacturing. In some embodiments, detection of the label associated with a ligated sequencing probe can be performed after preparation of the array. In some embodiments, multiple arrays could be used in a batch for parallel imaging.

In some embodiments, determination of the location (e.g., determination of the sequence) of the oligonucleotide and/or the feature can be performed before, contemporaneously with, or after the spatial analysis methods described herein. For example, determination of the sequence of the spatial barcode of the oligonucleotide can be performed contemporaneously with the determination of the sequence of the target biological analyte specifically bound to the capture probe. In another example, determination of the sequence of the spatial barcode of the oligonucleotide can be performed contemporaneously with the determination of the sequence of the spatial barcode located on the capture probe that is coupled to the feature.

Methods for determining locations of a plurality of beads on an array can include: (a) providing an array with a plurality of beads, wherein members of the plurality of beads are coupled to a nucleotide sequence comprising a constant domain and a spatial domain; and (b) determining the sequence of the spatial domain on the one or more beads, thereby determining the locations of the beads on the array. The methods include determining the sequence of the spatial domain by sequential hybridization and detection with a plurality of labelled probes. The methods can include determining the sequence of the spatial domain on the beads by: (1) contacting the plurality of beads with a sample comprising one or more oligonucleotide sequences that are complementary to a sequence in the constant domain of one or more beads; (2) contacting the plurality of beads with a mixture comprising four probes, each of which comprises either A, C, G, or T at one terminus, a degenerate nucleotide sequence of 5 to 11 nucleotides in length, and a label that is different from each other among the four probes; and (3) detecting the label of the probes on the array and recording the location of the label, thereby determining the sequence at one position of the spatial domain. The methods can also include removing the oligonucleotide sequences and probes from the plurality of beads; and repeating the steps of (1)-(3), thereby determining the sequence at a second position of the spatial domain. The label can be selected from the group consisting of: a radioactive molecule, a fluorescent molecule, and an enzyme. The label can be an optical label. The nucleotide sequence coupled to the beads can include a capture domain.

Methods for spatially detecting a biological analyte of interest in a sample can include: (a) performing any of the methods described herein to determine the locations of the plurality of beads on the array; (b) contacting the array with a sample comprising a plurality of biological analytes; and (c) associating the biological analyte of interest from the plurality of biological analytes to one or more beads on the array.

What is claimed is:

1. A method of determining a location of a feature in a spatial array, the method comprising:

(a) providing the spatial array comprising a plurality of features on a substrate, wherein the substrate of the spatial array comprises both:

(i) a plurality of oligonucleotides on the substrate, wherein an oligonucleotide of the plurality of oligonucleotides is attached to a first site of the substrate and comprises: a first spatial barcode and a first capture domain; and (ii) the plurality of features randomly affixed on the substrate, wherein the feature of the plurality of features is affixed to the first site and comprises a plurality of capture probes, wherein a capture probe of the plurality of capture probes comprises: a second spatial barcode and a second capture domain;

(b) determining a nucleotide sequence of the first spatial barcode, thereby determining the location of the oligonucleotide on the substrate;

(c) hybridizing the first capture domain of the oligonucleotide attached to the first site to the second capture domain of the capture probe of the feature affixed to the first site, thereby producing a second capture probe comprising the first spatial barcode of the oligonucleotide and the second spatial barcode of the capture probe, wherein the first spatial barcode and second spatial barcode comprise different sequences;

(d) determining: (i) the sequence of the first spatial barcode of the second capture probe, or a complement thereof; and (ii) the sequence of the second spatial barcode of the second capture probe, or a complement thereof; and (e) associating the second spatial barcode of the second capture probe with the first spatial barcode of the oligonucleotide having a known location on the substrate, thereby determining the location of the feature in the spatial array of the plurality of features randomly affixed to the substrate.

2. The method of claim 1, wherein the plurality of features comprises a plurality of beads.

3. The method of claim 1, wherein the first capture domain comprises a poly (A) sequence.

4. The method of claim 1, wherein the second capture domain comprises a poly (T) sequence.

5. The method of claim 1, wherein the determining in (b) comprises sequencing.

6. The method of claim 1, wherein the oligonucleotide further comprises a constant sequence for initiating a sequencing reaction.

7. The method of claim 6, further comprising hybridizing a sequencing anchor to the constant sequence prior to hybridizing a sequencing probe to the oligonucleotide downstream of the sequencing anchor.

8. The method of claim 1, wherein the determining in (d) comprises sequencing.

9. The method of claim 1, wherein the capture probe further comprises a constant sequence for initiating a sequencing reaction.

10. The method of claim 9, further comprising hybridizing a sequencing anchor to the constant sequence prior to hybridizing a sequencing probe to the capture probe downstream of the sequencing anchor.

11. The method of claim 1, wherein the capture probe further comprises one or more functional domains, a unique molecular identifier, a cleavage domain, or combinations thereof.

12. The method of claim 1, wherein, further comprising extending the oligonucleotide using the capture probe as a template, and optionally, extending the capture probe using the oligonucleotide as a template.

13. The method of claim 1, wherein the second spatial barcode of the capture probe on the feature is unique relative to the second spatial barcode of capture probes on other features in the spatial array.

* * * * *